United States Patent
Crooke et al.

(10) Patent No.: US 9,884,072 B2
(45) Date of Patent: Feb. 6, 2018

(54) METHODS AND COMPOSITIONS FOR MODULATING APOLIPOPROTEIN (A) EXPRESSION

(71) Applicant: Ionis Pharmaceuticals, Inc., Carlsbad, CA (US)

(72) Inventors: Rosanne M. Crooke, Carlsbad, CA (US); Mark J. Graham, San Clemente, CA (US); Susan M. Freier, San Diego, CA (US); Marc Lim, Oceanside, CA (US); Andrew Dibble, Vista, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/401,914

(22) Filed: Jan. 9, 2017

(65) Prior Publication Data

US 2017/0182084 A1    Jun. 29, 2017

Related U.S. Application Data

(60) Division of application No. 14/552,436, filed on Nov. 24, 2014, now Pat. No. 9,574,193, which is a continuation of application No. PCT/US2013/042532, filed on May 23, 2013, said application No. 14/552,436 is a continuation-in-part of application No. 14/401,761, filed as application No. PCT/US2013/041701 on May 17, 2013, now abandoned.

(60) Provisional application No. 61/651,539, filed on May 24, 2012, provisional application No. 61/648,556, filed on May 17, 2012.

(51) Int. Cl.
*A61K 31/7115* (2006.01)
*A61K 31/712* (2006.01)
*A61K 31/7125* (2006.01)

(52) U.S. Cl.
CPC ........ *A61K 31/7115* (2013.01); *A61K 31/712* (2013.01); *A61K 31/7125* (2013.01)

(58) Field of Classification Search
None
See application file for complete search history.

(56) References Cited

U.S. PATENT DOCUMENTS

2011/0251130 A1* 10/2011 Robertson .............. C07K 14/82
                                                                514/16.7
2011/0313019 A1* 12/2011 Swayze .................. C07H 21/00
                                                                514/44 A

* cited by examiner

*Primary Examiner* — Tracy Vivlemore
(74) *Attorney, Agent, or Firm* — Grant IP

(57) ABSTRACT

Disclosed herein are antisense compounds and methods for decreasing apo(a) to treat, prevent, or ameliorate diseases, disorders or conditions related to apo(a) or Lp(a). Certain diseases, disorders or conditions related to apo(a) or Lp(a) include inflammatory, cardiovascular and/or metabolic diseases, disorders or conditions. The antisense compounds disclosed herein can be used to treat such diseases, disorders or conditions in an individual in need thereof.

23 Claims, No Drawings

METHODS AND COMPOSITIONS FOR MODULATING APOLIPOPROTEIN (A) EXPRESSION

SEQUENCE LISTING

The present application is being filed along with a Sequence Listing in electronic format. The Sequence Listing is provided as a file entitled BIOL0177USD1SEQ_ST25.txt created Jan. 4, 2017, which is 424 Kb in size. The information in the electronic format of the sequence listing is incorporated herein by reference in its entirety.

FIELD

Embodiments described herein provide methods, compounds, and compositions for reducing expression of apolipoprotein (a) mRNA and protein in an animal. Such methods, compounds, and compositions are useful to treat, prevent, or ameliorate cardiovascular and/or metabolic diseases, disorders or conditions.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver.

Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008;117:176-84). Further, in the recent Precocious Coronary Artery Disease (PROCARDIS) study, Clarke et al. (Clarke et al., NEJM (2009)361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; U.S. Pat. No. 8,138,328; Merki et al., J Am Coll Cardiol 2011; 57:1611-1621) have been developed, but none of the compounds directly targeting apo(a) are currently used in the clinic.

Thus, there remains a clear unmet medical need for novel agents which can potently and selectively reduce apo(a) levels in patients at enhanced risk for cardiovascular events due to chronically elevated plasma Lp(a) levels.

SUMMARY

Provided herein are compositions and methods for modulating expression of apo(a) mRNA and protein. In certain embodiments, the apo(a) specific inhibitor decreases expression of apo(a) mRNA and protein.

In certain embodiments, the composition is an apo(a) specific inhibitor. In certain embodiments, the apo(a) specific inhibitor is a nucleic acid, protein, or small molecule. In certain embodiments, the apo(a) specific inhibitor is an antisense oligonucleotide targeting apo(a). In certain embodiments, the apo(a) specific inhibitor is a modified oligonucleotide consisting of 12 to 30 linked nucleosides and comprising a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 1-130, 133, 134. In certain embodiments, the apo(a) specific inhibitor is a modified oligonucleotide consisting of 20 linked nucleosides and having a nucleobase sequence comprising at least 8 contiguous nucleobases of any of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a composition comprising a compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. Such reduction may occur in a time-dependent or in a dose-dependent manner.

Certain embodiments provide compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or", unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE, MOE, 2'-O(CH$_2$)$_2$—OCH$_3$ and 2'-O-(2-methoxyethyl)) refers to an O-methoxyethyl modification of the 2' position of a furanosyl ring. A 2'-O-methoxyethyl modified sugar is a modified sugar.

"2'-deoxyribonucleoside" means a nucleoside comprising 2'-H furanosyl sugar moiety, as found in naturally occurring deoxyribonucleosides (DNA).

"2'-MOE nucleoside" (also 2'-O-methoxyethyl nucleoside) means a nucleoside comprising a 2'-MOE modified sugar moiety. "2'-O-methoxyethyl nucleotide" means a nucleotide comprising a 2'-O-methoxyethyl modified sugar moiety.

"3'-fluoro-HNA" (also "F-HNA" or "3'-F-HNA") means the sugar moiety of a nucleoside having the following structure:

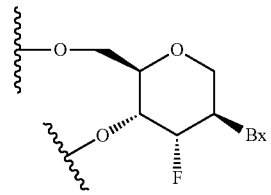

wherein Bx is a nucleobase.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to apo(a) is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

"Agent" means an active substance that can provide a therapeutic benefit when administered to an animal. "First Agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo(a) therapeutic compound.

"Amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody can refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats. As used herein, the term "antisense compound" encompasses pharmaceutically acceptable derivatives of the compounds described herein.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"Apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

"Apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

"Apo(a) mRNA" means a mRNA encoding an apo(a) protein.

"Apo(a) protein" means any protein sequence encoding Apo(a).

"Apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-estrified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Constrained ethyl" or "cEt" refers to a bicyclic nucleoside having a furanosyl sugar that comprises a methyl (methyleneoxy) (4'-CH(CH$_3$)—O-2') bridge between the 4' and the 2' carbon atoms.

"Constrained ethyl nucleoside" (also cEt nucleoside) means a nucleoside comprising a bicyclic sugar moiety comprising a 4'-CH(CH$_3$)—O-2' bridge.

"Contiguous nucleobases" means nucleobases immediately adjacent to each other.

"Cross-reactive" means an oligomeric compound targeting one nucleic acid sequence can hybridize to a different nucleic acid sequence. For example, in some instances an antisense oligonucleotide targeting human apo(a) can cross-react with an apo(a) from another species. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides can be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides (TG), and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Furanosyl" means a structure comprising a 5-membered ring comprising four carbon atoms and one oxygen atom.

"Gapmer" means a chimeric antisense compound in which an internal region having a plurality of nucleosides that support RNaseH cleavage is positioned between external regions having one or more nucleosides, wherein the nucleosides comprising the internal region are chemically distinct from the nucleoside or nucleosides comprising external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120).

"Identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia. "Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Individual in need thereof" refers to a human or non-human animal selected for treatment or therapy that is in need of such treatment or therapy.

"Induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

"Inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time. "Lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

"Lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

"Lp(a)" comprises apo(a) and a LDL like particle containing apoB. The apo(a) is linked to the apoB by a disulfide bond.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond). For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide. "Modified sugar" refers to a substitution or change from a natural sugar. For example, a 2'-O-methoxyethyl modified sugar is a modified sugar.

"MOE nucleoside" means a nucleoside comprising a 2'-substituted sugar moiety comprising MOE at the 2'-position.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to apo(a) is a pharmaceutical agent.

"Pharmaceutical composition" or "composition" means a mixture of substances suitable for administering to an individual. For example, a pharmaceutical composition can comprise one or more active agents and a pharmaceutical carrier e.g., a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage. "Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Subject" means a human or non-human animal selected for treatment or therapy.

"Sugar moiety" means a naturally occurring sugar moiety or a modified sugar moiety of a nucleoside.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutically effective amount" means an amount of a pharmaceutical agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" or "treating" refers to administering a compound described herein to effect an alteration or improvement of a disease, disorder, or condition.

"Triglyceride" or "TG" means a lipid or neutral fat consisting of glycerol combined with three fatty acid molecules. "Type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a).

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a).

Certain embodiments provide a compound comprising a modified oligonucleotide targeting apo(a) consisting of 12 to 30 linked nucleosides. In certain embodiments, the modified oligonucleotide consists of 15 to 30, 18 to 24, 19 to 22, 13 to 25, 14 to 25, 15 to 25 linked nucleosides. In certain embodiments, the modified oligonucleotide comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide consists of 20 linked nucleosides.

Certain embodiments provide a compound comprising a modified oligonucleotide targeting apo(a) comprising at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4. Certain embodiments provide a compound comprising a modified oligonucleotide targeting an apo(a) segment comprising at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in Tables 3-13 and 28-30. In the tables, the "Start Site" refers to the 5'-most nucleotide of a target segment and "Stop Site" refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 5, a target segment can range from 3901-3920, the start site to the stop site of SEQ ID NO: 58. In another example, as shown in Table 5, a target segment can range from 3900-3923, the start site of SEQ ID NO: 57 to the stop site of SEQ ID NO: 61.

Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of the target segments shown in Tables 3-13 and 28-30.

Certain embodiments provide a compound comprising a modified oligonucleotide targeting apo(a) consisting of 12 to 30 linked nucleosides and comprising a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 111, 114-121, 123-129.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 17, 18, 26-28, 39, 71, 106-107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 26-29, 39-40, 82.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 16-18.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 26-27,107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28-29, 39-40, 47.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28, 93, 104, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 58.

In certain embodiments, the modified oligonucleotide has a nucleobase sequence comprising at least 8 contiguous nucleobases of the nucleobase sequence of SEQ ID NO: 58.

Certain embodiments provide a compound comprising a modified oligonucleotide targeting apo(a), wherein the modified oligonucleotide is single-stranded.

Certain embodiments provide a compound comprising a modified oligonucleotide targeting apo(a), wherein at least one internucleoside linkage is a modified internucleoside linkage. In certain embodiments, each internucleoside linkage is a phosphorothioate internucleoside linkage.

Certain embodiments provide a compound comprising a modified oligonucleotide targeting apo(a), wherein at least one nucleoside comprises a modified nucleobase. In certain embodiments, the modified nucleobase is a 5-methylcytosine.

Certain embodiments provide a compound comprising a modified oligonucleotide targeting apo(a), wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-$(CH_2)_n$—O-2' bridge, wherein n is 1 or 2.

Certain embodiments provide a compound comprising a modified oligonucleotide targeting apo(a), wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a), wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a modified oligonucleotide targeting apo(a), wherein the modified oligonucleotide consists of 20 linked nucleosides with the nucleobase sequence of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the compound is in a salt form. In further embodiments, the compound further comprises of a pharmaceutically acceptable carrier or diluent. In certain embodiments, the compound comprising a modified oligonucleotide targeting apo(a), or a salt thereof, and a pharmaceutically acceptable carrier or diluent.

Certain embodiments provide a composition comprising a compound as described herein, wherein the viscosity level of the compound is less than 40 centipoise (cP). In certain embodiments, the antisense compounds as described herein are efficacious by virtue of having a viscosity of less than 40 cP, less than 35 cP, less than 30 cP, less than 25 cP, less than 20 cP or less than 15 cP when measured by the parameters as described in Example 13.

Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the modified oligonucleotide targeting apo(a), is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include cardiovascular and/or metabolic diseases, disorders, and conditions. Certain such cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, coronary artery disease (CAD), Alzheimer's Disease and thromboembolic diseases, disorder or conditions. Certain thromboembolic diseases, disorders or conditions include, but are not limited to, stroke, thrombosis (e.g., venous thromboembolism), myocardial infarction and peripheral vascular disease.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the compound is parenterally administered. In further embodiments, the parenteral administration is subcutaneous.

In certain embodiments, the compound is co-administered with a second agent or therapy. In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a compound targeted to apo(a) for decreasing apo(a) levels in an animal. Certain embodiments provide use of a compound targeted to apo(a) for decreasing Lp(a) levels in an animal. Certain embodiments provide use of a compounds targeted to apo(a) for the treatment, prevention, or amelioration of a disease, disorder, or condition associated with apo(a). Certain embodiments provide use of a compounds targeted to apo(a) for the treatment, prevention, or amelioration of a disease, disorder, or condition associated with Lp(a).

Certain embodiments provide use of a compound targeted to apo(a) in the preparation of a medicament for decreasing apo(a) levels in an animal. Certain embodiments provide use of a compound targeted to apo(a) in the preparation of a medicament for decreasing Lp(a) levels in an animal. Certain embodiments provide use of a compound for the preparation of a medicament for the treatment, prevention, or amelioration of a disease, disorder, or condition associated with apo(a). Certain embodiments provide use of a compound for the preparation of a medicament for the treatment, prevention, or amelioration of a disease, disorder, or condition associated with Lp(a).

Certain embodiments provide a kit for treating, preventing, or ameliorating a disease, disorder or condition as described herein wherein the kit comprises: (i) an apo(a) specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

Antisense Compounds

Oligomeric compounds include, but are not limited to, oligonucleotides, oligonucleosides, oligonucleotide analogs, oligonucleotide mimetics, antisense compounds, antisense oligonucleotides, ribozymes, microRNAs and siRNAs. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an apo(a) nucleic acid is 12 to 30 subunits in length. In other words, such antisense compounds are from 12 to 30 linked subunits. In other embodiments, the antisense compound is 8 to 80, 10 to 80, 12 to 50, 15 to 30, 18 to 24, 19 to 22, 13 to 25, 14 to 25 or 15 to 25 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain such embodiments, the antisense compounds are 8 linked subunits in length. In some embodiments the antisense compound is an antisense oligonucleotide. In some embodiments, the linked subunits are nucleosides.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the central portion, 5' or 3' end of the oligonucleotide. When two or more additional nucleosides are present, the added nucleosides can be adjacent to each other, for example, in an oligonucleotide having two nucleosides added to the central portion, to the 5' end (5' addition), or alternatively to the 3' end (3' addition), of the oligonucleotide. Alternatively, the added nucleosides can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358,1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an apo(a) nucleic acid have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA: DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-12-2, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an apo(a) nucleic acid possess a 5-10-5 gapmer motif.

In certain embodiments, an antisense compound targeted to an apo(a) nucleic acid has a gap-widened motif.

Target Nucleic Acids, Target Regions and Nucleotide Sequences

Nucleotide sequences that encode the apo(a) target sequence include, without limitation, the following: GENBANK Accession No. NM_005577.2, incorporated herein as SEQ ID NO: 1; GENBANK Accession No. NT —007422.12 truncated from nucleotides 3230000 to 3380000, incorporated herein as SEQ ID NO: 2; GENBANK Accession No. NT —025741.15 truncated from nucleotides 65120000 to 65258000, designated herein as SEQ ID NO: 3; and GENBANK Accession No. NM_005577.1, incorporated herein as SEQ ID NO: 4.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage or a nucleobase. Antisense compounds described by Isis Number (Isis No.) indicate a combination of nucleobase sequence and motif In certain embodiments, a "target region" is a structurally defined region of the target nucleic acid. For example, a target region can encompass a 3' UTR, a 5' UTR, an exon, an intron, an exon/intron junction, a coding region, a translation initiation region, a translation termination region, or other defined nucleic acid region. The structurally defined regions for apo(a) can be obtained by accession number from sequence databases such as NCBI and such information is incorporated herein by reference. In certain embodiments, a target region can encompass the sequence from a 5' target site of one target segment within the target region to a 3' target site of another target segment within the same target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region, such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in apo(a) mRNA levels can be indicative of inhibition of apo(a) expression. Reductions in levels of an apo(a) protein can be indicative of inhibition of target mRNA expression. Further, phenotypic changes can be indicative of inhibition of apo(a) expression. For example, an increase in HDL levels, decrease in LDL levels, decrease in cholesterol levels or decrease in triglyceride levels, are among phenotypic changes that can be assessed for inhibition of apo(a) expression. Other phenotypic indications, e.g., symptoms associated with a cardiovascular disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an apo(a) nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, 3$^{rd}$ Ed., 2001). In certain embodiments, the antisense compounds provided herein are specifically hybridizable with an apo(a) nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an apo(a) nucleic acid).

Noncomplementary nucleobases between an antisense compound and an apo(a) nucleic acid can be tolerated provided that the antisense compound remains able to specifically hybridize to a target nucleic acid. Moreover, an antisense compound can hybridize over one or more segments of an apo(a) nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an apo(a) nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an apo(a) nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an apo(a) nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an apo(a) nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an apo(a) nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups), bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—$C(=O)$—$N(R_m)(R_n)$, and O—$CH_2$—$C(=O)$—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2'; 4'-$(CH_2)_2$—O-2' (ENA); 4'-$CH(CH_3)$—O-2' and 4'-CH($CH_2OCH_3$)—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—($=CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U. S. A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —$C(=O)$—, —$C(=NR_a)$—, —$C(=S)$—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

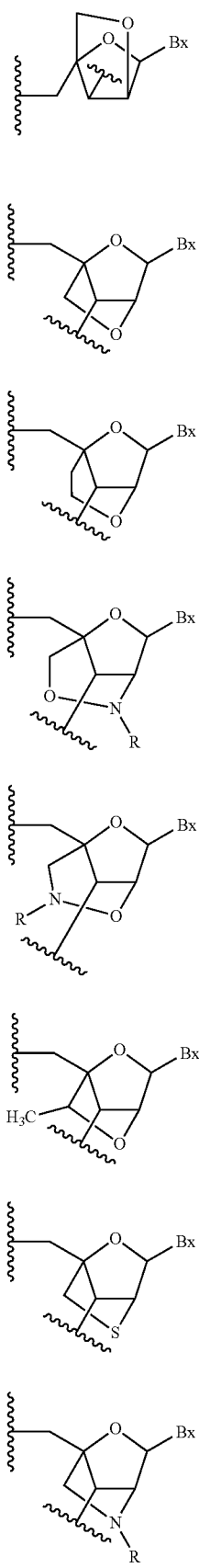

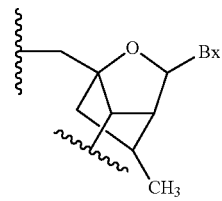

(A)

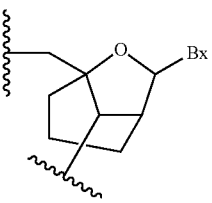

(B)

(C)

(D)

(E)

(F)

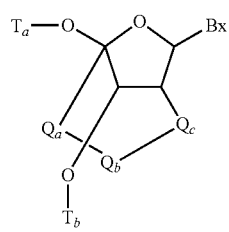

(G)

(H)

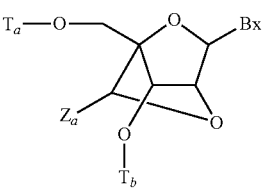

(I)

(J)

wherein Bx is the base moiety and R is independently H, a protecting group or $C_1$-$C_{12}$ alkyl.

In certain embodiments, bicyclic nucleosides are provided having Formula I:

I wherein:

Bx is a heterocyclic base moiety;

-$Q_a$-$Q_b$-$Q_c$- is —$CH_2$—$N(R_c)$—$CH_2$—, —$C(=O)$—$N(R_c)$—$CH_2$—, —$CH_2$—O—$N(R_c)$—, —$CH_2$—$N(R_c)$—O— or —$N(R_c)$—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

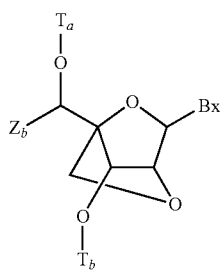

III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)-).

In certain embodiments, bicyclic nucleosides are provided having Formula IV:

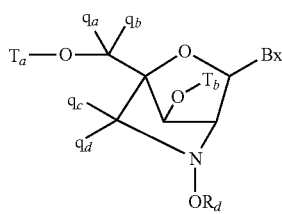

IV wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

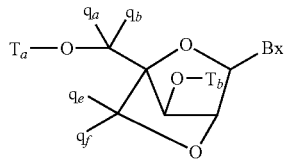

V wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium; $q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported. In certain embodiments, bicyclic nucleosides are provided having Formula VI:

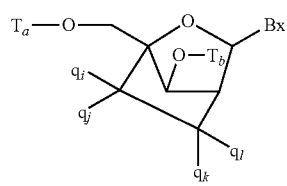

VI wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_i$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

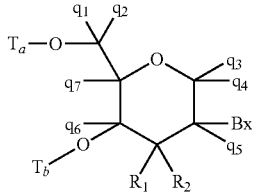

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group; $q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, subsitituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, q3, q4, q5, q6 and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H. In certain embodiments, $R_1$ is H and $R_2$ is fluoro; $R_1$ is H and $R_2$ is methoxy, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N(R$_m$)(R$_n$), where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an apo(a) nucleic acid comprise one or more modified nucleobases. In certain embodiments, gap-widened antisense oligonucleotides targeted to an apo(a) nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an apo(a) nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an apo(a) nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3' terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602, published on Jan. 16, 2003.

Cell Culture and Antisense Compounds Treatment

The effects of antisense compounds on the level, activity or expression of apo(a) nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g., Invitrogen Life Technologies, Carlsbad, Calif.). Illustrative cell types include, but are not limited to, HepG2 cells, Hep3B cells, Huh? (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEMTM-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrooke and Russell in *Molecular Cloning. A Laboratory Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrooke and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrooke and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000®(Invitrogen, Carlsbad, Calif.), Lipofectin® (Invitrogen, Carlsbad, Calif.) or Cytofectin (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrooke and Russell in *Molecular Cloning. A Laboratory Manual*. Third Edition. Cold Spring Harbor Laboratory Press, Cold Spring Harbor, N.Y. 2001). For example, RNA can be prepared using TRIZOL® (Invitrogen, Carlsbad, Calif.) according to the manufacturer's recommended protocols.

Analysis of Inhibition of Target Levels or Expression

Inhibition of levels or expression of an apo(a) nucleic acid can be assayed in a variety of ways known in the art (Sambrooke and Russell in *Molecular Cloning. A Laboratory Manual*. Third Edition. Cold Spring Harbor Laboratory Press, Cold Spring Harbor, N.Y., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems (Foster City, Calif.) and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GAPDH, or by quantifying total RNA using RIBOGREEN® (Invitrogen, Inc. Carlsbad, Calif.). Cyclophilin A or GAPDH expression can be quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers can be designed to hybridize to an apo(a) nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of apo(a) nucleic acids can be assessed by measuring apo(a) protein levels. Protein levels of apo(a) can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of apo(a) are commercially available.

In Vivo Testing of Antisense Compounds

Antisense compounds, for example, antisense oligonucleotides, are tested in animals to assess their ability to inhibit expression of apo(a) and produce phenotypic changes. Testing can be performed in normal animals, or in experimental disease models. For administration to animals, antisense oligonucleotides are formulated in a pharmaceutically acceptable diluent, such as saline or phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in apo(a) nucleic acid expression are measured. Changes in apo(a) protein levels are also measured.

Certain Indications

In certain embodiments, provided herein are methods of treating an individual comprising administering one or more pharmaceutical compositions as described herein. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administrion of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, coronary artery disease (CAD), Alzheimer's Disease and thromboembolic diseases, disorders or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15, 20, 25, 30, 35, 40, 45, 50, 55, 60, 65, 70, 75, 80, 85, 90, 95 or 99%, or a range defined by any two of these values. In certain embodiments, apo(a) expression is reduced to ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to apo(a) are used for the preparation of a medicament for treating a patient suffering or susceptible to an inflammatory, cardiovascular and/or a metabolic disease, disorder or condition.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of apo(a) or the prevention, reduction, amelioration or slowing the progression of a disease or condition associated with apo(a).

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg -1000 mg dosing, and may be given once or more daily, weekly, monthly or yearly, or even once every 2 to 20 years. Following successful treatment, it can be desirable to have the patient undergo maintenance therapy to prevent the recurrence of the disease state, wherein the oligonucleotide is administered in maintenance doses, ranging from 0.01 µg to 100 mg per kg of body weight or ranging from 0.001 mg to 1000 mg dosing, once or more daily, weekly, monthly, yearly to once every 2 to 20 years.

Certain Combination Therapies

In certain embodiments, a first agent comprising the compound described herein is co-administered with one or more secondary agents or therapy. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, an apo(a) lowering agent, a Lp(a) lowering agent, an agent for treating Azheimer's Disease, an agent to reduce thromboembolism formation, a cholesterol lowering agent, a non-HDL lipid lowering (e.g., LDL) agent, a HDL raising agent, fish oil, niacin, nicotinic acid, a fibrate, a statin, DCCR (salt of diazoxide), a glucose-lowering agent, an anti-inflammatory agent and/or an anti-diabetic agent. In certain embodiments, the first agent is administered in combination with the maximally tolerated dose of the second agent. In certain embodiments, the first agent is administered to a subject that fails to respond to a maximally tolerated dose of the second agent.

Examples of apo(a) lowering agents include an apo(a) antisense oligonucleotide different from the first agent, niacin, nicotinic acid, or an apoB antisense oligonucleotide (i.e. Mipomersen). An example of an apo(a) lowering therapy is Lp(a) apheresis.

Examples of glucose-lowering and/or anti-diabetic agents include, but are not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

Examples of cholesterol or lipid lowering therapy include, but are not limited to, a therapeutic lifestyle change, statins, bile acids sequestrants, niacin, nicotinic acid, CETP inhibitors and peroxisome proliferation activated receptor agonists such as fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The CETP inhibitor can be a CETP antisense oligonucleotide or Torcetrapib.

Certain Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has elevated apo(a) levels ≥30 mg/dL, ≥40 mg/dL, ≥50 mg/dL, ≥60 mg/dL, ≥70 mg/dL, ≥80 mg/dL, ≥90 mg/dL or ≥100 mg/dL.

Certain Compounds

Selected gapmer antisense oligonucleotides from PCT application WO2005/000201 (incorporated by reference in its entirety herein) were assessed (Example 1) and the most potent compound, ISIS 144367, was used as a benchmark comparison for the newly designed antisense oligonucleotides described herein.

About 90 of the newly designed antisense oligonucleotides were found to be more potent than the benchmark, ISIS 144367, as assessed by single dose in vitro studies (Examples 2-3, 5). Of the about 90 antisense oligonucleotides, about 83 were selected for in vitro multi-dose response studies and 64 antisense oligonucleotides were found to be more potent than the benchmark (Examples 4, 6).

About 32 antisense oligonucleotides were further selected for in vivo studies in human apo(a) transgenic mice (Example 7). Multiple antisense oligonucleotides were identified that were more potent than the benchmark in vivo.

About 24 antisense oligonucleotides were further selected for viscosity testing in vitro (Example 13). Antisense oligonucleotides that were viscous were not carried forward in further studies.

About 14 antisense oligonucleotides were further selected for in vivo studies in rodent tolerability and pharmacokinetics (Examples 8-10). The studies indicated that ISIS 494372 was the best tolerated antisense oligonucleotide.

ISIS 494283, 494284, 494286, 494301, 494302 and 494372 were tested in cynomolgus monkeys (Examples 11-12). The studies indicated that ISIS 494372 was well tolerated and potent in monkeys.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Dose-Dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, N.J.) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTACCAGCTATGCCAAACCTT, designated herein as SEQ ID NO: 7) was used to measure mRNA levels. Additionally, mRNA levels were also measured using human apo(a) primer probe set hAPO(a)12kB (forward sequence CCACAGTGGCCCCGGT, designated herein as SEQ ID NO: 8; reverse sequence ACAGGGCTTTTCTCAGGTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in Table 1 as percent inhibition of apo(a), relative to untreated control cells.

TABLE 1

Antisense inhibition of human apo(a) in human primary hepatocytes

| ISIS No | % inhibition (hAPO(a)3' PPset) | % inhibition (hAPO(a)12 kB PPset) |
|---|---|---|
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |
| 144383 | 63 | 79 |
| 144384 | 38 | 0 |
| 144385 | 40 | 94 |
| 144386 | 47 | 61 |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in Table 2 below. After a treatment period of approximately 16 hours, RNA was isolated from the cells and apo(a) mRNA levels were measured by quantitative real-time PCR. Human apo(a) primer probe set hAPO(a)3' was used to measure mRNA levels. Apo(a) mRNA levels were normalized to GAPDH mRNA expression. Results are presented as percent inhibition of apo(a), relative to untreated control cells.

TABLE 2

Dose-dependent antisense inhibition of human apo(a) in human primary hepatocytes, as measured with hAPO(a)3'

| ISIS No | 25 nM | 50 nM | 150 nM | 300 nM |
|---|---|---|---|---|
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 2

Antisense Inhibition of Human Apo(a) in Transgenic Mouse Primary Hepatocytes

Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 3

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 494157 | 238 | 257 | CCTGTGACAGTGGTGGAGTA | 95 | 21199 | 21218 | 12 |
|  | 580 | 599 |  |  | 26690 | 26709 |  |
|  | 922 | 941 |  |  | 32237 | 32256 |  |
|  | 1606 | 1625 |  |  | 43330 | 43349 |  |
|  | 1948 | 1967 |  |  | 48874 | 48893 |  |
|  | 2290 | 2309 |  |  | 54420 | 54439 |  |
|  | 3316 | 3335 |  |  | 72037 | 72056 |  |
| 494158 | 239 | 258 | TCCTGTGACAGTGGTGGAGT | 95 | 21200 | 21219 | 13 |
|  | 581 | 600 |  |  | 26691 | 26710 |  |
|  | 923 | 942 |  |  | 32238 | 32257 |  |
|  | 1607 | 1626 |  |  | 43331 | 43350 |  |
|  | 1949 | 1968 |  |  | 48875 | 48894 |  |
|  | 2291 | 2310 |  |  | 54421 | 54440 |  |
|  | 3317 | 3336 |  |  | 72038 | 72057 |  |
| 494159 | 241 | 260 | CTTCCTGTGACAGTGGTGGA | 97 | 21202 | 21221 | 14 |
|  | 583 | 602 |  |  | 26693 | 26712 |  |
|  | 925 | 944 |  |  | 32240 | 32259 |  |
|  | 1609 | 1628 |  |  | 43333 | 43352 |  |
|  | 1951 | 1970 |  |  | 48877 | 48896 |  |
|  | 2293 | 2312 |  |  | 54423 | 54442 |  |
|  | 3319 | 3338 |  |  | 72040 | 72059 |  |
|  | 4663 | 4682 |  |  | 94404 | 94423 |  |
|  | 5005 | 5024 |  |  | 115515 | 115534 |  |

TABLE 3-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494160 | 242 | 261 | CCTTCCTGTGACAGTGGTGG | 97 | 21203 | 21222 | 15 |
|  | 4664 | 4683 |  |  | 94405 | 94424 |  |
|  | 5006 | 5025 |  |  | 115516 | 115535 |  |
| 494161 | 243 | 262 | TCCTTCCTGTGACAGTGGTG | 96 | 21204 | 21223 | 16 |
|  | 4665 | 4684 |  |  | 94406 | 94425 |  |
|  | 5007 | 5026 |  |  | 115517 | 115536 |  |
| 494162 | 244 | 263 | GTCCTTCCTGTGACAGTGGT | 95 | 21205 | 21224 | 17 |
|  | 3664 | 3683 |  |  | 77585 | 77604 |  |
|  | 4666 | 4685 |  |  | 94407 | 94426 |  |
|  | 5008 | 5027 |  |  | 115518 | 115537 |  |
| 494163 | 245 | 264 | GGTCCTTCCTGTGACAGTGG | 96 | 21206 | 21225 | 18 |
|  | 4667 | 4686 |  |  | 94408 | 94427 |  |
| 494164 | 246 | 265 | AGGTCCTTCCTGTGACAGTG | 93 | 21207 | 21226 | 19 |
|  | 4668 | 4687 |  |  | 94409 | 94428 |  |
| 494165 | 247 | 266 | CAGGTCCTTCCTGTGACAGT | 91 | 21208 | 21227 | 20 |
|  | 4669 | 4688 |  |  | 94410 | 94429 |  |
| 494166 | 248 | 267 | GCAGGTCCTTCCTGTGACAG | 89 | 21209 | 21228 | 21 |
| 494167 | 250 | 269 | TGGCAGGTCCTTCCTGTGAC | 92 | 21211 | 21230 | 22 |
| 494168 | 251 | 270 | TTGGCAGGTCCTTCCTGTGA | 89 | 21212 | 21231 | 23 |
| 494169 | 252 | 271 | CTTGGCAGGTCCTTCCTGTG | 92 | 21213 | 21232 | 24 |
| 494170 | 253 | 272 | GCTTGGCAGGTCCTTCCTGT | 88 | 21214 | 21233 | 25 |

TABLE 4

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 84 | 21210 | 21229 | 11 |
| 494283 | 584 | 603 | TCTTCCTGTGACAGTGGTGG | 93 | 26694 | 26713 | 26 |
|  | 926 | 945 |  |  | 32241 | 32260 |  |
|  | 1610 | 1629 |  |  | 43334 | 43353 |  |
|  | 1952 | 1971 |  |  | 48878 | 48897 |  |
|  | 2294 | 2313 |  |  | 54424 | 54443 |  |
|  | 3320 | 3339 |  |  | 72041 | 72060 |  |
| 494284 | 585 | 604 | TTCTTCCTGTGACAGTGGTG | 95 | 26695 | 26714 | 27 |
|  | 927 | 946 |  |  | 32242 | 32261 |  |
|  | 1611 | 1630 |  |  | 43335 | 43354 |  |
|  | 1953 | 1972 |  |  | 48879 | 48898 |  |
|  | 2295 | 2314 |  |  | 54425 | 54444 |  |
|  | 3321 | 3340 |  |  | 72042 | 72061 |  |
| 494285 | 586 | 605 | GTTCTTCCTGTGACAGTGGT | 95 | 26696 | 26715 | 28 |
|  | 928 | 947 |  |  | 32243 | 32262 |  |
|  | 1612 | 1631 |  |  | 43336 | 43355 |  |
|  | 1954 | 1973 |  |  | 48880 | 48899 |  |
|  | 2296 | 2315 |  |  | 54426 | 54445 |  |
|  | 3322 | 3341 |  |  | 72043 | 72062 |  |
| 494286 | 587 | 606 | GGTTCTTCCTGTGACAGTGG | 95 | 26697 | 26716 | 29 |
|  | 929 | 948 |  |  | 32244 | 32263 |  |
|  | 1613 | 1632 |  |  | 43337 | 43356 |  |
|  | 1955 | 1974 |  |  | 48881 | 48900 |  |
|  | 2297 | 2316 |  |  | 54427 | 54446 |  |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494287 | 588 | 607 | AGGTTCTTCCTGTGACAGTG | 95 | 26698 | 26717 | 30 |
|  | 930 | 949 |  |  | 32245 | 32264 |  |
|  | 1614 | 1633 |  |  | 43338 | 43357 |  |
|  | 1956 | 1975 |  |  | 48882 | 48901 |  |
|  | 2298 | 2317 |  |  | 54428 | 54447 |  |
| 494288 | 589 | 608 | CAGGTTCTTCCTGTGACAGT | 91 | 26699 | 26718 | 31 |
|  | 931 | 950 |  |  | 32246 | 32265 |  |
|  | 1615 | 1634 |  |  | 43339 | 43358 |  |
|  | 1957 | 1976 |  |  | 48883 | 48902 |  |
|  | 2299 | 2318 |  |  | 54429 | 54448 |  |
|  | 2983 | 3002 |  |  | 66500 | 66519 |  |
| 494290 | 592 | 611 | TGGCAGGTTCTTCCTGTGAC | 90 | 26702 | 26721 | 32 |
|  | 934 | 953 |  |  | 32249 | 32268 |  |
|  | 1618 | 1637 |  |  | 43342 | 43361 |  |
|  | 1960 | 1979 |  |  | 48886 | 48905 |  |
|  | 2302 | 2321 |  |  | 54432 | 54451 |  |
|  | 2986 | 3005 |  |  | 66503 | 66522 |  |
| 494291 | 593 | 612 | TTGGCAGGTTCTTCCTGTGA | 89 | 26703 | 26722 | 33 |
|  | 935 | 954 |  |  | 32250 | 32269 |  |
|  | 1619 | 1638 |  |  | 43343 | 43362 |  |
|  | 1961 | 1980 |  |  | 48887 | 48906 |  |
|  | 2303 | 2322 |  |  | 54433 | 54452 |  |
|  | 2987 | 3006 |  |  | 66504 | 66523 |  |
| 494292 | 594 | 613 | CTTGGCAGGTTCTTCCTGTG | 94 | 26704 | 26723 | 35 |
|  | 936 | 955 |  |  | 32251 | 32270 |  |
|  | 1620 | 1639 |  |  | 43344 | 43363 |  |
|  | 1962 | 1981 |  |  | 48888 | 48907 |  |
|  | 2304 | 2323 |  |  | 54434 | 54453 |  |
|  | 2988 | 3007 |  |  | 66505 | 66524 |  |
| 494294 | 596 | 615 | AGCTTGGCAGGTTCTTCCTG | 90 | 26706 | 26725 | 36 |
|  | 938 | 957 |  |  | 32253 | 32272 |  |
|  | 1622 | 1641 |  |  | 43346 | 43365 |  |
|  | 1964 | 1983 |  |  | 48890 | 48909 |  |
|  | 2306 | 2325 |  |  | 54436 | 54455 |  |
|  | 2990 | 3009 |  |  | 66507 | 66526 |  |
| 494299 | 626 | 645 | ACTATGCGAGTGTGGTGTCA | 91 | 26736 | 26755 | 37 |
|  | 968 | 987 |  |  | 32283 | 32302 |  |
|  | 1310 | 1329 |  |  | 37830 | 37849 |  |
|  | 1652 | 1671 |  |  | 43376 | 43395 |  |
|  | 1994 | 2013 |  |  | 48920 | 48939 |  |
|  | 2336 | 2355 |  |  | 54466 | 54485 |  |
|  | 2678 | 2697 |  |  | 60021 | 60040 |  |
|  | 3020 | 3039 |  |  | 66537 | 66556 |  |
| 494300 | 627 | 646 | GACTATGCGAGTGTGGTGTC | 93 | 26737 | 26756 | 38 |
|  | 969 | 988 |  |  | 32284 | 32303 |  |
|  | 1311 | 1330 |  |  | 37831 | 37850 |  |
|  | 1653 | 1672 |  |  | 43377 | 43396 |  |
|  | 1995 | 2014 |  |  | 48921 | 48940 |  |
|  | 2337 | 2356 |  |  | 54467 | 54486 |  |
|  | 2679 | 2698 |  |  | 60022 | 60041 |  |
|  | 3021 | 3040 |  |  | 66538 | 66557 |  |
| 494301 | 628 | 647 | CGACTATGCGAGTGTGGTGT | 93 | 26738 | 26757 | 39 |
|  | 970 | 989 |  |  | 32285 | 32304 |  |
|  | 1312 | 1331 |  |  | 37832 | 37851 |  |
|  | 1654 | 1673 |  |  | 43378 | 43397 |  |
|  | 1996 | 2015 |  |  | 48922 | 48941 |  |
|  | 2338 | 2357 |  |  | 54468 | 54487 |  |
|  | 2680 | 2699 |  |  | 60023 | 60042 |  |
|  | 3022 | 3041 |  |  | 66539 | 66558 |  |
| 494302 | 629 | 648 | CCGACTATGCGAGTGTGGTG | 94 | 26739 | 26758 | 40 |
|  | 971 | 990 |  |  | 32286 | 32305 |  |
|  | 1313 | 1332 |  |  | 37833 | 37852 |  |
|  | 1655 | 1674 |  |  | 43379 | 43398 |  |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1997 | 2016 | | | 48923 | 48942 | |
| | 2339 | 2358 | | | 54469 | 54488 | |
| | 2681 | 2700 | | | 60024 | 60043 | |
| | 3023 | 3042 | | | 66540 | 66559 | |
| 494303 | 630 | 649 | TCCGACTATGCGAGTGTGGT | 93 | 26740 | 26759 | 41 |
| | 972 | 991 | | | 32287 | 32306 | |
| | 1314 | 1333 | | | 37834 | 37853 | |
| | 1656 | 1675 | | | 43380 | 43399 | |
| | 1998 | 2017 | | | 48924 | 48943 | |
| | 2340 | 2359 | | | 54470 | 54489 | |
| | 2682 | 2701 | | | 60025 | 60044 | |
| | 3024 | 3043 | | | 66541 | 66560 | |
| 494304 | 631 | 650 | GTCCGACTATGCGAGTGTGG | 94 | 26741 | 26760 | 42 |
| | 973 | 992 | | | 32288 | 32307 | |
| | 1315 | 1334 | | | 37835 | 37854 | |
| | 1657 | 1676 | | | 43381 | 43400 | |
| | 1999 | 2018 | | | 48925 | 48944 | |
| | 2341 | 2360 | | | 54471 | 54490 | |
| | 2683 | 2702 | | | 60026 | 60045 | |
| | 3025 | 3044 | | | 66542 | 66561 | |
| 494305 | 632 | 651 | GGTCCGACTATGCGAGTGTG | 93 | 26742 | 26761 | 43 |
| | 974 | 993 | | | 32289 | 32308 | |
| | 1316 | 1335 | | | 37836 | 37855 | |
| | 1658 | 1677 | | | 43382 | 43401 | |
| | 2000 | 2019 | | | 48926 | 48945 | |
| | 2342 | 2361 | | | 54472 | 54491 | |
| | 2684 | 2703 | | | 60027 | 60046 | |
| | 3026 | 3045 | | | 66543 | 66562 | |
| 494306 | 633 | 652 | GGGTCCGACTATGCGAGTGT | 92 | 26743 | 26762 | 44 |
| | 975 | 994 | | | 32290 | 32309 | |
| | 1317 | 1336 | | | 37837 | 37856 | |
| | 1659 | 1678 | | | 43383 | 43402 | |
| | 2001 | 2020 | | | 48927 | 48946 | |
| | 2343 | 2362 | | | 54473 | 54492 | |
| | 2685 | 2704 | | | 60028 | 60047 | |
| | 3027 | 3046 | | | 66544 | 66563 | |
| 494307 | 1190 | 1209 | CTGCTCAGTCGGTGCTTGTT | 91 | n/a | n/a | 45 |
| | 2558 | 2577 | | | | | |
| 494310 | 1193 | 1212 | CCTCTGCTCAGTCGGTGCTT | 90 | n/a | n/a | 46 |
| | 2561 | 2580 | | | | | |
| 494311 | 1194 | 1213 | GCCTCTGCTCAGTCGGTGCT | 88 | 37714 | 37733 | 47 |
| | 2562 | 2581 | | | 59905 | 59924 | |
| 494334 | 1267 | 1286 | CTTCCAGTGACAGTGGTGGA | 90 | 37787 | 37806 | 48 |
| | 2635 | 2654 | | | 59978 | 59997 | |
| 494336 | 1269 | 1288 | TTCTTCCAGTGACAGTGGTG | 90 | 37789 | 37808 | 49 |
| | 2637 | 2656 | | | 59980 | 59999 | |
| 494337 | 1270 | 1289 | GTTCTTCCAGTGACAGTGGT | 95 | 37790 | 37809 | 50 |
| | 2638 | 2657 | | | 59981 | 60000 | |
| 494338 | 1271 | 1290 | GGTTCTTCCAGTGACAGTGG | 91 | 37791 | 37810 | 133 |
| | 2639 | 2658 | | | 59982 | 60001 | |
| 494521 | 6393 | 6412 | GACCTTAAAAGCTTATACAC | 82 | 140049 | 140068 | 51 |
| 494525 | 6397 | 6416 | GTCAGACCTTAAAAGCTTAT | 84 | 140053 | 140072 | 52 |
| 494530 | 6402 | 6421 | TGTCAGTCAGACCTTAAAAG | 82 | 140058 | 140077 | 53 |
| 494535 | 6407 | 6426 | GAATTTGTCAGTCAGACCTT | 85 | 140063 | 140082 | 54 |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494536 | 6408 | 6427 | AGAATTTGTCAGTCAGACCT | 83 | 140064 | 140083 | 55 |
| 494544 | 6417 | 6436 | CCTTAATACAGAATTTGTCA | 82 | 140073 | 140092 | 56 |

TABLE 5

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 81985 | 82004 | 62 |
| 494387 | 3978 | 3997 | TTCCTGTAACAGTGGTGGAG | 82 | 81986 | 82005 | 63 |
| 494388 | 3979 | 3998 | CTTCCTGTAACAGTGGTGGA | 86 | 81987 | 82006 | 64 |
| 494389 | 3980 | 3999 | CCTTCCTGTAACAGTGGTGG | 92 | 81988 | 82007 | 65 |
| 494390 | 3981 | 4000 | TCCTTCCTGTAACAGTGGTG | 92 | 81989 | 82008 | 66 |
| 494391 | 3982 | 4001 | GTCCTTCCTGTAACAGTGGT | 84 | 81990 | 82009 | 67 |
| 494392 | 3983 | 4002 | TGTCCTTCCTGTAACAGTGG | 81 | 81991 | 82010 | 68 |

TABLE 6

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 21210 | 21229 | 11 |
| 498369 | 3203 | 3222 | TGGAGCCAGAATAACATTCG | 91 | 70667 | 70686 | 69 |
| 498379 | 3213 | 3232 | CCTCTAGGCTTGGAGCCAGA | 85 | 70677 | 70696 | 70 |
| 498408 | 3323 | 3342 | AGTTCTTCCTGTGACAGTGG | 86 | 72044 | 72063 | 71 |
| 498433 | 3367 | 3386 | GTCCGACTATGCTGGTGTGG | 87 | 72088 | 72107 | 72 |
| 498434 | 3368 | 3387 | GGTCCGACTATGCTGGTGTG | 86 | 72089 | 72108 | 73 |
| 498435 | 3369 | 3388 | GGGTCCGACTATGCTGGTGT | 83 | 72090 | 72109 | 74 |

TABLE 7

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 498229 | 2871 | 2890 | CCTCTAGGCTTGGAATCGGG | 90 | 65117 | 65136 | 75 |
| 498238 | 2883 | 2902 | GTTCAGAAGGAGCCTCTAGG | 93 | 65129 | 65148 | 76 |
| 498239 | 2884 | 2903 | TGTTCAGAAGGAGCCTCTAG | 94 | 65130 | 65149 | 77 |
| 498240 | 2887 4573 | 2906 4592 | GCTTGTTCAGAAGGAGCCTC | 98 | n/a | n/a | 78 |
| 498241 | 2888 4574 | 2907 4593 | TGCTTGTTCAGAAGGAGCCT | 94 | n/a | n/a | 79 |
| 498242 | 2889 4575 | 2908 4594 | GTGCTTGTTCAGAAGGAGCC | 96 | n/a | n/a | 80 |
| 498243 | 2890 4576 | 2909 4595 | GGTGCTTGTTCAGAAGGAGC | 97 | n/a | n/a | 81 |
| 498244 | 2891 4577 | 2910 4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |
| 498252 | 2899 | 2918 | TGCTCAGTTGGTGCTTGTTC | 90 | n/a | n/a | 84 |

TABLE 8

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498517 | 3548 | 3567 | GCTTGGATCTGGGACCACCG | 89 | 76233 | 76252 | 85 |

TABLE 9

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 94 | 21210 | 21229 | 11 |
| 498833 | 4900 | 4919 | GCCTCCATGCTTGGAACTGG | 94 | 114205 | 114224 | 86 |
| 498859 | 4926 | 4945 | GCTCAGTTGGTGCTGCTTCA | 92 | n/a | n/a | 87 |
| 498868 | 4978 | 4997 | CCTCGATAACTCTGGCCATT | 94 | 115488 | 115507 | 88 |
| 498875 | 5003 | 5022 | TCCTGTGACAGTGGTGGAGA | 94 | 115513 | 115532 | 89 |

TABLE 10

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 92 | 21210 | 21229 | 11 |
| 499020 | 6257 | 6276 | GTAGGTTGATGCTTCACTCT | 91 | 139913 | 139932 | 90 |
| 499041 | 6318 | 6337 | CGTTTGATTGCTGTCTATTA | 90 | 139974 | 139993 | 91 |

TABLE 11

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498523 | 3554 | 3573 | CTCTGTGCTTGGATCTGGGA | 94 | 76239 | 76258 | 92 |
| 498524 | 3555 | 3574 | CCTCTGTGCTTGGATCTGGG | 96 | 76240 | 76259 | 93 |
| 498525 | 3556 | 3575 | GCCTCTGTGCTTGGATCTGG | 94 | 76241 | 76260 | 94 |
| 498529 | 3560 | 3579 | AGAAGCCTCTGTGCTTGGAT | 89 | 76245 | 76264 | 95 |
| 498535 | 3566 | 3585 | TTCAGAAGAAGCCTCTGTGC | 89 | 76251 | 76270 | 96 |
| 498550 | 3582 | 3601 | GCTCCGTTGGTGCTTCTTCA | 90 | n/a | n/a | 97 |
| 498553 | 3585 | 3604 | TTTGCTCCGTTGGTGCTTCT | 87 | n/a | n/a | 98 |
| 498555 | 3587<br>3905 | 3606<br>3924 | GCTTTGCTCCGTTGGTGCTT | 90 | n/a | n/a | 99 |
| 498556 | 3588<br>3906 | 3607<br>3925 | GGCTTTGCTCCGTTGGTGCT | 89 | 77509<br>81914 | 77528<br>81933 | 100 |
| 498557 | 3589<br>3907 | 3608<br>3926 | GGGCTTTGCTCCGTTGGTGC | 89 | 77510<br>81915 | 77529<br>81934 | 101 |
| 498579 | 3662 | 3681 | CCTTCCTGTGACAGTGGTAG | 87 | 77583 | 77602 | 102 |
| 498580 | 3663 | 3682 | TCCTTCCTGTGACAGTGGTA | 92 | 77584 | 77603 | 103 |
| 498581 | 3665<br>5009 | 3684<br>5028 | TGTCCTTCCTGTGACAGTGG | 94 | 77586<br>115519 | 77605<br>115538 | 104 |

TABLE 12

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 100 | 21210 | 21229 | 11 |
| 494230 | 477<br>819<br>1161<br>1503<br>1845<br>2187<br>2529 | 496<br>838<br>1180<br>1522<br>1864<br>2206<br>2548 | CCTCTAGGCTTGGAACCGGG | 95 | 25380<br>30927<br>36471<br>42020<br>47564<br>53110<br>58662 | 25399<br>30946<br>36490<br>42039<br>47583<br>53129<br>58681 | 105 |
| 494243 | 494<br>836<br>1178<br>1520<br>1862<br>2204<br>2546 | 513<br>855<br>1197<br>1539<br>1881<br>2223<br>2565 | TGCTTGTTCGGAAGGAGCCT | 93 | n/a | n/a | 106 |
| 494244 | 495<br>837<br>1179<br>1521<br>1863<br>2205<br>2547 | 514<br>856<br>1198<br>1540<br>1882<br>2224<br>2566 | GTGCTTGTTCGGAAGGAGCC | 95 | n/a | n/a | 107 |

TABLE 13

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 96 | 21210 | 21229 | 11 |
| 494466 | 4208 | 4227 | GCTTGGAACTGGGACCACCG | 95 | 85138 | 85157 | 108 |
| 494470 | 4212 | 4231 | CTGTGCTTGGAACTGGGACC | 94 | 85142 | 85161 | 109 |
| 494472 | 4214 | 4233 | CTCTGTGCTTGGAACTGGGA | 92 | 85144 | 85163 | 110 |

Example 3

Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 μM, 0.125 μM, 0.25 μM, 0.500 μM, or 1.000 μM concentrations of antisense oligonucleotide. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 14

| ISIS No | 0.0625 μM | 0.125 μM | 0.250 μM | 0.500 μM | 1.000 μM | $IC_{50}$ (μM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 15

| ISIS No | 0.0625 μM | 0.125 μM | 0.250 μM | 0.500 μM | 1.000 μM | $IC_{50}$ (μM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 16

| ISIS No | 0.0625 μM | 0.125 μM | 0.250 μM | 0.500 μM | 1.000 μM | $IC_{50}$ (μM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 17

| ISIS No | 0.0625 μM | 0.125 μM | 0.250 μM | 0.500 μM | 1.000 μM | $IC_{50}$ (μM) |
|---|---|---|---|---|---|---|
| 144367 | 0 | 29 | 45 | 73 | 92 | 0.27 |
| 494311 | 28 | 53 | 65 | 85 | 95 | 0.13 |
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 18

| ISIS No | 0.0625 µM | 0.125 µM | 0.250 µM | 0.500 µM | 1.000 µM | IC$_{50}$ (µM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 19

| ISIS No | 0.0625 µM | 0.125 µM | 0.250 µM | 0.500 µM | 1.000 µM | IC$_{50}$ (µM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 20

| ISIS No | 0.0625 µM | 0.125 µM | 0.250 µM | 0.500 µM | 1.000 µM | IC$_{50}$ (µM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |
| 498580 | 36 | 57 | 81 | 91 | 96 | 0.10 |
| 498581 | 34 | 64 | 75 | 93 | 97 | 0.05 |

TABLE 21

| ISIS No | 0.0625 µM | 0.125 µM | 0.250 µM | 0.500 µM | 1.000 µM | IC$_{50}$ (µM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |

TABLE 21-continued

| ISIS No | 0.0625 µM | 0.125 µM | 0.250 µM | 0.500 µM | 1.000 µM | IC$_{50}$ (µM) |
|---|---|---|---|---|---|---|
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 22

| ISIS No | 0.0625 µM | 0.125 µM | 0.250 µM | 0.500 µM | 1.000 µM | IC$_{50}$ (µM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the Tables above, ISIS 494157 (SEQ ID NO: 12), ISIS 494158 (SEQ ID NO: 13), ISIS 494159 (SEQ ID NO: 14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO: 60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO:

85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGATAACTC-CGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 4

Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 µM, 0.148 µM, 0.444 µM, 1.333 µM, or 4.000 µM concentrations of antisense oligonucleotide, as specified in Tables below. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the Tables below, ISIS 494157 (SEQ ID NO: 12), ISIS 494158 (SEQ ID NO: 13), ISIS 494159 (SEQ ID NO: 14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 23

| ISIS No | 0.049 µM | 0.148 µM | 0.444 µM | 1.333 µM | 4.000 µM | $IC_{50}$ (µM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |
| 494283 | 18 | 45 | 80 | 93 | 91 | 0.18 |
| 494284 | 9 | 53 | 80 | 95 | 94 | 0.18 |

TABLE 24

| ISIS No | 0.049 µM | 0.148 µM | 0.444 µM | 1.333 µM | 4.000 µM | $IC_{50}$ (µM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 25

| ISIS No | 0.049 µM | 0.148 µM | 0.444 µM | 1.333 µM | 4.000 µM | $IC_{50}$ (µM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 26

| ISIS No | 0.049 µM | 0.148 µM | 0.444 µM | 1.333 µM | 4.000 µM | $IC_{50}$ (µM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |

TABLE 26-continued

| ISIS No | 0.049 μM | 0.148 μM | 0.444 μM | 1.333 μM | 4.000 μM | IC$_{50}$ (μM) |
|---|---|---|---|---|---|---|
| 498408 | 1 | 38 | 63 | 79 | 80 | 0.32 |
| 498433 | 23 | 43 | 70 | 77 | 79 | 0.21 |

TABLE 27

| ISIS No | 0.049 μM | 0.148 μM | 0.444 μM | 1.333 μM | 4.000 μM | IC$_{50}$ (μM) |
|---|---|---|---|---|---|---|
| 144367 | 0 | 40 | 76 | 90 | 93 | 0.26 |
| 498434 | 32 | 44 | 64 | 78 | 84 | 0.20 |
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 5

Antisense Inhibition of Human Apo(a) in Transgenic Mouse Primary Hepatocytes

Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises of ten 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 28

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
|  | 583 | 599 | CCTGTGACAGTGGTGGA |  | 26693 | 26709 |  |
|  | 925 | 941 | CCTGTGACAGTGGTGGA |  | 32240 | 32256 |  |
|  | 1609 | 1625 | CCTGTGACAGTGGTGGA |  | 43333 | 43349 |  |
|  | 1951 | 1967 | CCTGTGACAGTGGTGGA |  | 48877 | 48893 |  |
|  | 2293 | 2309 | CCTGTGACAGTGGTGGA |  | 54423 | 54439 |  |
|  | 3319 | 3335 | CCTGTGACAGTGGTGGA |  | 72040 | 72056 |  |
|  | 4663 | 4679 | CCTGTGACAGTGGTGGA |  | 94404 | 94420 |  |
|  | 5005 | 5021 | CCTGTGACAGTGGTGGA |  | 115515 | 115531 |  |
| 510543 | 242 | 258 | TCCTGTGACAGTGGTGG | 75 | 21203 | 21219 | 112 |
|  | 584 | 600 | TCCTGTGACAGTGGTGG |  | 26694 | 26710 |  |
|  | 926 | 942 | TCCTGTGACAGTGGTGG |  | 32241 | 32257 |  |
|  | 1610 | 1626 | TCCTGTGACAGTGGTGG |  | 43334 | 43350 |  |
|  | 1952 | 1968 | TCCTGTGACAGTGGTGG |  | 48878 | 48894 |  |
|  | 2294 | 2310 | TCCTGTGACAGTGGTGG |  | 54424 | 54440 |  |
|  | 3320 | 3336 | TCCTGTGACAGTGGTGG |  | 72041 | 72057 |  |
|  | 4664 | 4680 | TCCTGTGACAGTGGTGG |  | 94405 | 94421 |  |
|  | 5006 | 5022 | TCCTGTGACAGTGGTGG |  | 115516 | 115532 |  |

TABLE 28-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 510544 | 243 | 259 | TTCCTGTGACAGTGGTG | 73 | 21204 | 21220 | 113 |
|  | 585 | 601 | TTCCTGTGACAGTGGTG |  | 26695 | 26711 |  |
|  | 927 | 943 | TTCCTGTGACAGTGGTG |  | 32242 | 32258 |  |
|  | 1611 | 1627 | TTCCTGTGACAGTGGTG |  | 43335 | 43351 |  |
|  | 1953 | 1969 | TTCCTGTGACAGTGGTG |  | 48879 | 48895 |  |
|  | 2295 | 2311 | TTCCTGTGACAGTGGTG |  | 54425 | 54441 |  |
|  | 3321 | 3337 | TTCCTGTGACAGTGGTG |  | 72042 | 72058 |  |
|  | 4665 | 4681 | TTCCTGTGACAGTGGTG |  | 94406 | 94422 |  |
|  | 5007 | 5023 | TTCCTGTGACAGTGGTG |  | 115517 | 115533 |  |
| 510545 | 244 | 260 | CTTCCTGTGACAGTGGT | 65 | 21205 | 21221 | 114 |
|  | 586 | 602 | CTTCCTGTGACAGTGGT |  | 26696 | 26712 |  |
|  | 928 | 944 | CTTCCTGTGACAGTGGT |  | 32243 | 32259 |  |
|  | 1612 | 1628 | CTTCCTGTGACAGTGGT |  | 43336 | 43352 |  |
|  | 1954 | 1970 | CTTCCTGTGACAGTGGT |  | 48880 | 48896 |  |
|  | 2296 | 2312 | CTTCCTGTGACAGTGGT |  | 54426 | 54442 |  |
|  | 3322 | 3338 | CTTCCTGTGACAGTGGT |  | 72043 | 72059 |  |
|  | 3664 | 3680 | CTTCCTGTGACAGTGGT |  | 77585 | 77601 |  |
|  | 4666 | 4682 | CTTCCTGTGACAGTGGT |  | 94407 | 94423 |  |
|  | 5008 | 5024 | CTTCCTGTGACAGTGGT |  | 115518 | 115534 |  |
| 510546 | 245 | 261 | CCTTCCTGTGACAGTGG | 74 | 21206 | 21222 | 115 |
|  | 3665 | 3681 | CCTTCCTGTGACAGTGG |  | 77586 | 77602 |  |
|  | 4667 | 4683 | CCTTCCTGTGACAGTGG |  | 94408 | 94424 |  |
|  | 5009 | 5025 | CCTTCCTGTGACAGTGG |  | 115519 | 115535 |  |
| 510547 | 246 | 262 | TCCTTCCTGTGACAGTG | 77 | 21207 | 21223 | 116 |
|  | 3666 | 3682 | TCCTTCCTGTGACAGTG |  | 77587 | 77603 |  |
|  | 4668 | 4684 | TCCTTCCTGTGACAGTG |  | 94409 | 94425 |  |
|  | 5010 | 5026 | TCCTTCCTGTGACAGTG |  | 115520 | 115536 |  |
| 510548 | 247 | 263 | GTCCTTCCTGTGACAGT | 73 | 21208 | 21224 | 117 |
|  | 3667 | 3683 | GTCCTTCCTGTGACAGT |  | 77588 | 77604 |  |
|  | 4669 | 4685 | GTCCTTCCTGTGACAGT |  | 94410 | 94426 |  |
|  | 5011 | 5027 | GTCCTTCCTGTGACAGT |  | 115521 | 115537 |  |
| 510549 | 248 | 264 | GGTCCTTCCTGTGACAG | 67 | 21209 | 21225 | 118 |
|  | 4670 | 4686 | GGTCCTTCCTGTGACAG |  | 94411 | 94427 |  |
| 510595 | 632 | 648 | CCGACTATGCGAGTGTG | 76 | 26742 | 26758 | 119 |
|  | 974 | 990 | CCGACTATGCGAGTGTG |  | 32289 | 32305 |  |
|  | 1316 | 1332 | CCGACTATGCGAGTGTG |  | 37836 | 37852 |  |
|  | 1658 | 1674 | CCGACTATGCGAGTGTG |  | 43382 | 43398 |  |
|  | 2000 | 2016 | CCGACTATGCGAGTGTG |  | 48926 | 48942 |  |
|  | 2342 | 2358 | CCGACTATGCGAGTGTG |  | 54472 | 54488 |  |
|  | 2684 | 2700 | CCGACTATGCGAGTGTG |  | 60027 | 60043 |  |
|  | 3026 | 3042 | CCGACTATGCGAGTGTG |  | 66543 | 66559 |  |
| 510597 | 634 | 650 | GTCCGACTATGCGAGTG | 70 | 26744 | 26760 | 120 |
|  | 976 | 992 | GTCCGACTATGCGAGTG |  | 32291 | 32307 |  |
|  | 1318 | 1334 | GTCCGACTATGCGAGTG |  | 37838 | 37854 |  |
|  | 1660 | 1676 | GTCCGACTATGCGAGTG |  | 43384 | 43400 |  |
|  | 2002 | 2018 | GTCCGACTATGCGAGTG |  | 48928 | 48944 |  |
|  | 2344 | 2360 | GTCCGACTATGCGAGTG |  | 54474 | 54490 |  |
|  | 2686 | 2702 | GTCCGACTATGCGAGTG |  | 60029 | 60045 |  |
|  | 3028 | 3044 | GTCCGACTATGCGAGTG |  | 66545 | 66561 |  |
| 510598 | 635 | 651 | GGTCCGACTATGCGAGT | 70 | 26745 | 26761 | 121 |
|  | 977 | 993 | GGTCCGACTATGCGAGT |  | 32292 | 32308 |  |
|  | 1319 | 1335 | GGTCCGACTATGCGAGT |  | 37839 | 37855 |  |
|  | 1661 | 1677 | GGTCCGACTATGCGAGT |  | 43385 | 43401 |  |
|  | 2003 | 2019 | GGTCCGACTATGCGAGT |  | 48929 | 48945 |  |
|  | 2345 | 2361 | GGTCCGACTATGCGAGT |  | 54475 | 54491 |  |
|  | 2687 | 2703 | GGTCCGACTATGCGAGT |  | 60030 | 60046 |  |
|  | 3029 | 3045 | GGTCCGACTATGCGAGT |  | 66546 | 66562 |  |

TABLE 29

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 83 | 21210 | 21229 | 11 |
| 510783 | 6400 | 6416 | GTCAGACCTTAAAAGCT | 75 | 140056 | 140072 | 122 |
| 512944 | 3561 | 3577 | AAGCCTCTGTGCTTGGA | 81 | 76246 | 76262 | 123 |
| 512947 | 3560 | 3576 | AGCCTCTGTGCTTGGAT | 85 | 76245 | 76261 | 124 |
| 512958 | 3559 | 3575 | GCCTCTGTGCTTGGATC | 82 | 76244 | 76260 | 125 |
| 512959 | 3585 | 3601 | GCTCCGTTGGTGCTTCT | 77 | n/a | n/a | 126 |

TABLE 30

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 76 | 21210 | 21229 | 11 |
| 510701 | 4217 | 4233 | CTCTGTGCTTGGAACTG | 78 | 85147 | 85163 | 127 |
| 510702 | 219 | 235 | TGCCTCGATAACTCTGT | 79 | 21180 | 21196 | 128 |
|  | 561 | 577 |  |  | 26671 | 26687 |  |
|  | 903 | 919 |  |  | 32218 | 32234 |  |
|  | 1245 | 1261 |  |  | 37765 | 37781 |  |
|  | 1587 | 1603 |  |  | 43311 | 43327 |  |
|  | 1929 | 1945 |  |  | 48855 | 48871 |  |
|  | 2271 | 2287 |  |  | 54401 | 54417 |  |
|  | 2613 | 2629 |  |  | 59956 | 59972 |  |
|  | 4299 | 4315 |  |  | 86472 | 86488 |  |
| 510704 | 563 | 579 | TGTGCCTCGATAACTCT | 80 | 26673 | 26689 | 129 |
|  | 905 | 921 |  |  | 32220 | 32236 |  |
|  | 1247 | 1263 |  |  | 37767 | 37783 |  |
|  | 1589 | 1605 |  |  | 43313 | 43329 |  |
|  | 1931 | 1947 |  |  | 48857 | 48873 |  |
|  | 2273 | 2289 |  |  | 54403 | 54419 |  |
|  | 2615 | 2631 |  |  | 59958 | 59974 |  |
|  | 4301 | 4317 |  |  | 86474 | 86490 |  |
|  | 4985 | 5001 |  |  | 115495 | 115511 |  |
| 510757 | 4929 | 4945 | GCTCAGTTGGTGCTGCT | 74 | n/a | n/a | 130 |

Example 6

Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 µM, 0.313 µM, 0.625 µM, 1.250 µM, 2.500 µM, or 5.000 µM concentrations of antisense oligonucleotide, as specified in the Tables below. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each study represented in a separate table. The half maximal inhibitory concentration ($IC_{50}$) of each oligonucleotide is also presented in the Tables.

TABLE 31

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 32

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 33

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 34

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |
| 510704 | 54 | 61 | 77 | 84 | 89 | 80 | 0.12 |
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the Tables above, ISIS 510542 (SEQ ID NO: 111), ISIS 510545 (SEQ ID NO: 114), ISIS 510546 (SEQ ID NO: 115), ISIS 510547 (SEQ ID NO: 116), ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 7

Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS 494311, ISIS 494337, ISIS 494372, ISIS 498238, ISIS 498523, ISIS 498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in Table 35, expressed as percent inhibition of apo(a) mRNA compared to the PBS control.

TABLE 35

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in Table 36, expressed as percent inhibition of apo(a) mRNA compared to the PBS control.

TABLE 36

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 37, expressed as percent inhibition of apo(a) mRNA compared to the PBS control.

TABLE 37

Dose-dependent inhibition of human apo(a) mRNA in transgenic mice

| ISIS No | Dose (mg/kg/wk) | % inhibition | $ED_{50}$ |
|---|---|---|---|
| 144367 | 100 | 71 | 31 |
|  | 30 | 42 |  |
|  | 10 | 0 |  |
|  | 3 | 5 |  |
| 494159 | 100 | 91 | 5 |
|  | 30 | 67 |  |
|  | 10 | 48 |  |
|  | 3 | 39 |  |
| 494161 | 100 | 82 | 6 |
|  | 30 | 49 |  |
|  | 10 | 61 |  |
|  | 3 | 30 |  |
| 494162 | 100 | 90 | 5 |
|  | 30 | 67 |  |
|  | 10 | 58 |  |
|  | 3 | 25 |  |
| 494163 | 100 | 83 | 5 |
|  | 30 | 66 |  |
|  | 10 | 58 |  |
|  | 3 | 21 |  |
| 494243 | 100 | 80 | 32 |
|  | 30 | 26 |  |
|  | 10 | 0 |  |
|  | 3 | 6 |  |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO: 17), and ISIS 94163 (SEQ ID NO: 18) were more efficacious than the benchmark ISIS 144367 (SEQ ID NO: 11).Reduction of human apo(a) protein levels Blood was collected from the treatment groups, and human apo(a) protein levels were quantitated by an Apo(a) ELISA kit (Mercodia 10-1106-01, Uppsala, Sweden). The results are presented in Table 38, expressed as percent reduction of apo(a) protein levels compared to the PBS control.

TABLE 38

Dose-dependent inhibition of human apo(a) protein in transgenic mice

| ISIS No | Dose (mg/kg/wk) | % inhibition | $ED_{50}$ |
|---|---|---|---|
| 144367 | 100 | 73 | 71 |
|  | 30 | 0 |  |
|  | 10 | 6 |  |
|  | 3 | 69 |  |
| 494159 | 100 | 88 | 2 |
|  | 30 | 88 |  |
|  | 10 | 85 |  |
|  | 3 | 36 |  |
| 494161 | 100 | 90 | 2 |
|  | 30 | 85 |  |
|  | 10 | 73 |  |
|  | 3 | 44 |  |
| 494162 | 100 | 89 | 3 |
|  | 30 | 78 |  |
|  | 10 | 76 |  |
|  | 3 | 24 |  |
| 494163 | 100 | 90 | 3 |
|  | 30 | 86 |  |
|  | 10 | 60 |  |
|  | 3 | 37 |  |
| 494243 | 100 | 61 | 174 |
|  | 30 | 0 |  |
|  | 10 | 0 |  |
|  | 3 | 0 |  |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 39, expressed as percent inhibition of apo(a) mRNA compared to the PBS control.

TABLE 39

Dose-dependent inhibition of human apo(a) mRNA in transgenic mice

| ISIS No | Dose (mg/kg/wk) | % inhibition | $ED_{50}$ |
|---|---|---|---|
| 144367 | 50 | 75 | 22 |
|  | 15 | 60 |  |
|  | 5 | 0 |  |
|  | 1.5 | 0 |  |
| 494244 | 50 | 73 | 18 |
|  | 15 | 41 |  |
|  | 5 | 34 |  |
|  | 1.5 | 0 |  |
| 494283 | 50 | 74 | 16 |
|  | 15 | 52 |  |
|  | 5 | 24 |  |
|  | 1.5 | 0 |  |
| 494284 | 50 | 73 | 16 |
|  | 15 | 58 |  |
|  | 5 | 17 |  |
|  | 1.5 | 2 |  |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 40, expressed as percent reduction of apo(a) protein levels compared to the PBS control.

TABLE 40

Dose-dependent inhibition of human apo(a) plasma protein in transgenic mice

| ISIS No | Dose (mg/kg/wk) | % inhibition | $ED_{50}$ |
|---|---|---|---|
| 144367 | 50 | 64 | 16 |
|  | 15 | 14 |  |
|  | 5 | 0 |  |
|  | 1.5 | 0 |  |
| 494244 | 50 | 67 | 2 |
|  | 15 | 60 |  |
|  | 5 | 58 |  |
|  | 1.5 | 0 |  |
| 494283 | 50 | 64 | 4 |
|  | 15 | 65 |  |
|  | 5 | 64 |  |
|  | 1.5 | 69 |  |
| 494284 | 50 | 66 | 4 |
|  | 15 | 63 |  |
|  | 5 | 51 |  |
|  | 1.5 | 54 |  |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 41, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 41

Dose-dependent inhibition of human Apo(a) mRNA in transgenic mice

| ISIS No | Dose (mg/kg/wk) | % inhibition | $ED_{50}$ |
|---|---|---|---|
| 494285 | 50 | 98 | 1 |
|  | 15 | 97 |  |
|  | 5 | 79 |  |
| 494286 | 50 | 97 | 1 |
|  | 15 | 91 |  |
|  | 5 | 80 |  |
| 494301 | 50 | 98 | 3 |
|  | 15 | 96 |  |
|  | 5 | 59 |  |
| 494302 | 50 | 98 | 2 |
|  | 15 | 88 |  |
|  | 5 | 72 |  |

TABLE 41-continued

Dose-dependent inhibition of human Apo(a) mRNA in transgenic mice

| ISIS No | Dose (mg/kg/wk) | % inhibition | ED$_{50}$ |
|---|---|---|---|
| 494311 | 50 | 99 | 1 |
|  | 15 | 96 |  |
|  | 5 | 87 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 42, expressed as percent reduction of apo(a) protein levels compared to the PBS control. The data demonstrates significant reduction of apo(a) plasma protein levels by ISIS 494285, ISIS 494286, ISIS 494301, ISIS 494302 and ISIS 494311.

TABLE 42

Dose-dependent inhibition of human apo(a) protein in transgenic mice

| ISIS No | Dose (mg/kg/wk) | % inhibition | ED$_{50}$ |
|---|---|---|---|
| 494285 | 50 | 88 | 2 |
|  | 15 | 88 |  |
|  | 5 | 72 |  |
| 494286 | 50 | 90 | 2 |
|  | 15 | 85 |  |
|  | 5 | 75 |  |
| 494301 | 50 | 89 | 5 |
|  | 15 | 86 |  |
|  | 5 | 38 |  |
| 494302 | 50 | 90 | 3 |
|  | 15 | 82 |  |
|  | 5 | 61 |  |
| 494311 | 50 | 90 | 3 |
|  | 15 | 82 |  |
|  | 5 | 69 |  |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 43, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 43

Dose-dependent inhibition of human Apo(a) mRNA in transgenic mice

| ISIS No | Dose (mg/kg/wk) | % inhibition | ED$_{50}$ |
|---|---|---|---|
| 494372 | 50 | 88 | 18 |
|  | 15 | 49 |  |
|  | 5 | 0 |  |
| 498524 | 50 | 83 | 8 |
|  | 15 | 74 |  |
|  | 5 | 34 |  |
| 498581 | 50 | 98 | 7 |
|  | 15 | 58 |  |
|  | 5 | 48 |  |
| 498721 | 50 | 97 | 14 |
|  | 15 | 68 |  |
|  | 5 | 0 |  |
| 498833 | 50 | 61 | 155 |
|  | 15 | 0 |  |
|  | 5 | 17 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 44, expressed as percent reduction of apo(a) protein levels compared to the PBS control. The data demonstrates significant reduction of apo(a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 44

Dose-dependent inhibition of human apo(a) protein in transgenic mice

| ISIS No | Dose (mg/kg/wk) | % inhibition | ED$_{50}$ |
|---|---|---|---|
| 494372 | 50 | 68 | 32 |
|  | 15 | 25 |  |
|  | 5 | 12 |  |
| 498524 | 50 | 38 | 118 |
|  | 15 | 0 |  |
|  | 5 | 0 |  |
| 498581 | 50 | 79 | 9 |
|  | 15 | 52 |  |
|  | 5 | 49 |  |
| 498721 | 50 | 81 | 10 |
|  | 15 | 63 |  |
|  | 5 | 29 |  |
| 498833 | 50 | 15 | 738 |
|  | 15 | 0 |  |
|  | 5 | 67 |  |

Example 8

Tolerability of Antisense Oligonucleotides Targeting Human Apo(a) in Rodent Models Gapmer antisense oligonucleotides targeting human apo(a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 mice: Study 1

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 45. ISIS oligonucleotides that caused changes in the levels of any of the liver or kidney function markers outside the expected range for antisense oligonucleotides were excluded in further studies.

TABLE 45

Plasma chemistry markers of CD1 mice

|  | ALT (IU/L) | AST (IU/L) | Albumin (g/dL) | BUN (mg/dL) | Creatinine (mg/dL) | Bilirubin (mg/dL) |
|---|---|---|---|---|---|---|
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in Table 46. ISIS oligonucleotides that caused any changes in organ weights outside the expected range for antisense oligonucleotides were excluded from further studies.

TABLE 46

Organ weights of CD1 mice (g)

|  | Kidney | Liver | Spleen |
|---|---|---|---|
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |
| ISIS 494337 | 0.56 | 2.3 | 0.17 |
| ISIS 494372 | 0.60 | 2.5 | 0.27 |
| ISIS 510548 | 0.55 | 3.7 | 0.20 |

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, NY). The results are presented in Table 47. ISIS oligonucleotides that caused changes in the levels of any of the liver or kidney function markers outside the expected range for antisense oligonucleotides were excluded in further studies.

TABLE 47

Plasma chemistry markers of Sprague Dawley rats

|  | ALT (IU/L) | AST (IU/L) | Bilirubin (mg/dL) | Albumin (g/dL) | BUN (mg/dL) | Creatinine (mg/dL) |
|---|---|---|---|---|---|---|
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function To evaluate the effect of ISIS oligonucleotides on kidney function, urine levels of total protein and creatinine were measured using an automated clinical chemistry analyzer (Hitachi Olympus AU400e, Melville, N.Y.). Results are presented in Table 48, expressed in mg/dL.

TABLE 48

Kidney function markers (mg/dL) in Sprague-Dawley rats

|  | Creatinine | Total protein |
| --- | --- | --- |
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in Table 49. ISIS oligonucleotides that caused any changes in organ weights outside the expected range for antisense oligonucleotides were excluded from further studies.

TABLE 49

Organ weights of Sprague Dawley rats (g)

|  | Kidney | liver | Spleen |
| --- | --- | --- | --- |
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 9

Pharmacokinetics of Antisense Oligonucleotide in CD1 Mice

CD1 mice were treated with ISIS oligonucleotides and the oligonucleotide concentrations in the liver and kidney were evaluated.
Treatment Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.
Measurement of Oligonucleotide Concentration The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 50, expressed as µg/g liver or kidney tissue. The data indicates that ISIS 494372 was at an acceptable concentration in the liver and kidneys.

TABLE 50

Oligonucleotide concentration (µg/g tissue) of ISIS oligonucleotides in CD1 mice

| ISIS No | Liver | Kidney |
| --- | --- | --- |
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 10

Pharmacokinetics of Antisense Oligonucleotide in Sprague Dawley Rats

Male Sprague Dawley rats were treated with ISIS oligonucleotides and the oligonucleotide concentrations in the liver and kidney were evaluated.
Treatment Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.
Measurement of Oligonucleotide Concentration The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 51, expressed as µg/g liver or kidney tissue. The data indicates that ISIS 494372 was at an acceptable concentration in the liver and kidneys.

TABLE 51

Oligonucleotide concentration (µg/g tissue) of ISIS oligonucleotides in Sprague Dawley rats

| ISIS No | Liver | Kidney |
| --- | --- | --- |
| 494283 | 220 | 434 |
| 494284 | 178 | 573 |
| 494286 | 234 | 448 |
| 494301 | 279 | 540 |

TABLE 51-continued

Oligonucleotide concentration (μg/g tissue) of ISIS oligonucleotides in Sprague Dawley rats

| ISIS No | Liver | Kidney |
|---|---|---|
| 494302 | 205 | 387 |
| 494372 | 288 | 663 |

Example 11

Effect of Isis Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in Table 52. Each antisense oligonucleotide targets more than one region in SEQ ID NO: 132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 52

Antisense oligonucleotides complementary to SEQ ID NO: 132

| ISIS No | Start Site | Mismatches |
|---|---|---|
| 494283 | 278 | 2 |
|  | 620 | 2 |
|  | 923 | 2 |
|  | 1265 | 2 |
|  | 1607 | 1 |
|  | 1949 | 1 |
|  | 2267 | 1 |
|  | 2609 | 1 |
|  | 2951 | 1 |
|  | 3293 | 1 |
| 494284 | 279 | 1 |
|  | 621 | 1 |
|  | 924 | 1 |
|  | 1266 | 1 |
|  | 1608 | 1 |
|  | 1950 | 1 |
|  | 2268 | 1 |
|  | 2610 | 1 |
|  | 2952 | 1 |
|  | 3294 | 1 |
| 494286 | 281 | 1 |
|  | 623 | 1 |
|  | 926 | 1 |
|  | 1268 | 1 |
|  | 1610 | 2 |
|  | 1952 | 2 |
|  | 2270 | 2 |
|  | 2612 | 2 |
|  | 2954 | 2 |
|  | 3296 | 2 |
| 494301 | 322 | 2 |
|  | 664 | 2 |
|  | 967 | 2 |
|  | 1309 | 1 |
|  | 1651 | 2 |
| 494302 | 323 | 2 |
|  | 968 | 2 |
|  | 1310 | 1 |
|  | 1652 | 2 |
| 494372 | 1186 | 2 |
|  | 1870 | 1 |
|  | 2188 | 1 |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized. Scheduled euthanasia of the animals was conducted on days 86 and 87 by exsanguination under deep anesthesia. The protocols described in the Example were approved by the Institutional Animal Care and Use Committee (IACUC).

Target Reduction

RNA Analysis

On day 86, RNA was extracted from liver tissue for real-time PCR analysis of apo(a) using human primer probe set ABI Hs00916691_m1 (Applied Biosystems, Carlsbad Calif.). Results are presented as percent inhibition of apo(a) mRNA, relative to PBS control. As shown in Table 53, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 53

Percent Inhibition of apo(a) mRNA in the cynomolgus monkey liver relative to the PBS control

| ISIS No | % inhibition |
|---|---|
| 494283 | 91 |
| 494284 | 99 |
| 494286 | 96 |
| 494301 | 88 |
| 494302 | 89 |
| 494372 | 93 |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in Table 54, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 54

Apo(a) plasma protein levels (% inhibition over baseline values) in the cynomolgus monkey

|  | Day 16 | Day 30 | Day 44 | Day 56 | Day 72 | Day 86 |
|---|---|---|---|---|---|---|
| PBS | 0 | 0 | 10 | 0 | 0 | 0 |
| ISIS 494283 | 78 | 79 | 81 | 66 | 66 | 70 |
| ISIS 494284 | 92 | 95 | 95 | 93 | 93 | 94 |
| ISIS 494286 | 92 | 95 | 96 | 94 | 94 | 94 |
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies

Body and Organ Weight Measurements

To evaluate the effect of ISIS oligonucleotides on the overall health of the animals, body and organ weights were measured at day 86. Body weights were measured and are presented in Table 55. Organ weights were measured and the data is presented in Table 56. The results indicate that treatment with ISIS 494372 was well tolerated in terms of the body and organ weights of the monkeys.

TABLE 55

Body weights (g) in the cynomolgus monkey

|  | Day 14 | Day 35 | Day 49 | Day 56 | Day 70 | Day 84 |
|---|---|---|---|---|---|---|
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 56

Organ weights (% body weight) in the cynomolgus monkey

|  | Spleen | Kidneys | Liver | Heart | Lungs |
|---|---|---|---|---|---|
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in Table 57, expressed in IU/L. Bilirubin, a liver function marker, was similarly measured and is presented in Table 57, expressed in mg/dL. The results indicate that treatment with ISIS 494372 was well tolerated in terms of the liver function in monkeys.

TABLE 57

Liver function markers in cynomolgus monkey plasma

|  | ALT (IU/L) | AST (IU/L) | Bilirubin (mg/dL) |
|---|---|---|---|
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-Reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 58

C-reactive protein levels (mg/L) in cynomolgus monkey plasma

|  | CRP |
|---|---|
| PBS | 1.4 |
| ISIS 494283 | 14.7 |
| ISIS 494284 | 7.7 |
| ISIS 494286 | 4.4 |
| ISIS 494301 | 3.5 |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 59

Complement C3 levels (mg/dL) in cynomolgus monkey plasma

|  | Pre-dose | Post-dose |
|---|---|---|
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing $K_2$-EDTA. Samples were analyzed for red blood cell (RBC) count, white blood cells (WBC) count, as well as for platelet count, using an ADVIA120 hematology analyzer (Bayer, USA). The data is presented in Table 60.

The data indicate that treatment with ISIS 494372 was well tolerated in terms of the hematologic parameters of the monkeys.

TABLE 60

Blood cell counts in cynomolgus monkeys

|  | WBC ($\times 10^3/\mu L$) | RBC ($\times 10^6/\mu L$) | Platelet ($\times 10^3/\mu L$) |
|---|---|---|---|
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 12

Characterization of the Pharmacological Activity of Isis 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 61

Dosing groups in cynomolgus monkeys

|  |  |  | Number of animals for necropsy | | |
|---|---|---|---|---|---|
| Group | Test Article | Dose | Interim | Terminal | Recovery |
| 1 | PBS | — | 4 | 6 | 4 |
| 2 | ISIS 494372 | 4 | — | 6 | — |
| 3 |  | 8 | — | 6 | — |
| 4 |  | 12 | 4 | 6 | 4 |
| 5 |  | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns. After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_m1, Applied Biosystems, Carlsbad Calif.) targeting position 1512 of the rhesus monkey apo(a) mRNA transcript GENBANK Accession No XM_001098061.2 (SEQ ID NO: XXX) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in Table 62, treatment with ISIS 494372 resulted in a dose-dependent reduction of apo(a) mRNA in comparison to the PBS control. At day 30, hepatic apo(a) mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, P<0.05).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 62

Percent inhibition levels of liver apo(a) mRNA in the dosing phase in cynomolgus monkeys treated with ISIS 494372

| Day | Dose (mg/kg/wk) | % inhibition |
|---|---|---|
| 30 | 12 | 73 |
|  | 40 | 99 |
| 93 | 4 | 44 |
|  | 8 | 43 |
|  | 12 | 53 |
|  | 40 | 93 |

Protein Analysis

Approximately 20 µl of plasma was analyzed using a commercially available apo(a) ELISA kit (Mercodia 10-1106-01, Uppsala, Sweden). The assay protocol was performed as described by the manufacturer. The results are presented in Tables 63 and 64 as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 63

Apo(a) plasma protein levels as a percent of Day 1 levels in the dosing phase in cynomolgus monkeys treated with ISIS 494372

| Day | Dose (mg/kg/wk) | % |
|---|---|---|
| 30 | 4 | 93 |
|  | 8 | 70 |
|  | 12 | 49 |
|  | 40 | 15* |
| 93 | 4 | 73 |
|  | 8 | 56 |
|  | 12 | 32* |
|  | 40 | 11* |

TABLE 64

Apo(a) plasma protein levels as a percent of Day 1 levels in the recovery phase in cynomolgus monkeys treated with ISIS 494372

| Day | Dose (mg/kg/wk) | % |
|---|---|---|
| 121 | 12 | 38* |
|  | 40 | 22* |
| 182 | 12 | 84 |
|  | 40 | 93 |

Example 13

Measurement of Viscosity of Isis Antisense Oligonucleotides Targeting Human Apo(a)

The viscosity of select antisense oligonucleotides from the studies described above was measured with the aim of screening out antisense oligonucleotides which have a viscosity more than 40 cP. Oligonucleotides having a viscosity greater than 40 cP would have less than optimal viscosity.

ISIS oligonucleotides (32-35 mg) were weighed into a glass vial, 120 µL of water was added and the antisense oligonucleotide was dissolved into solution by heating the vial at 50° C. Part (75 µL) of the pre-heated sample was pipetted to a micro-viscometer (Cambridge). The temperature of the micro-viscometer was set to 25° C. and the viscosity of the sample was measured. Another part (20 µL) of the pre-heated sample was pipetted into 10 mL of water for UV reading at 260 nM at 85° C. (Cary UV instrument). The results are presented in Table 65 and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 65

Viscosity and concentration of ISIS antisense oligonucleotides targeting human Apo(a)

| ISIS No | Motif | Viscosity (cP) | Concentration (mg/mL) |
|---|---|---|---|
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A modified oligonucleotide, wherein the modified oligonucleotide is 14 to 25 linked nucleosides in length and has a nucleobase sequence comprising a portion of at least 14 contiguous nucleobases complementary to an equal length portion of nucleobases 3900 to 3923 of SEQ ID NO: 1, and wherein the nucleobase sequence of the modified oligonucleotide is at least 95% complementary to SEQ ID NO: 1.

2. The modified oligonucleotide of claim 1, wherein the modified oligonucleotide consists of 18 to 24, 19 to 22, 15 to 25, 16 or 20 linked nucleosides.

3. The modified oligonucleotide of claim 1, wherein the modified oligonucleotide has a nucleobase sequence comprising a portion of at least 16, at least 17, at least 18, at least 19, or at least 20 contiguous nucleobases complementary to an equal length portion of SEQ ID NO: 1.

4. The modified oligonucleotide of claim 1, wherein the nucleobase sequence of the modified oligonucleotide is at least 96%, 97%, 98% or 99% complementary to SEQ ID NO: 1, or is 100% complementary to SEQ ID NO: 1.

5. The modified oligonucleotide of claim 1, wherein the modified oligonucleotide has a nucleobase sequence comprising at least 14, at least 15, at least 16, at least 17, at least 18, at least 19, or 20 contiguous nucleobases of the nucleobase sequence of SEQ ID NO: 58.

6. The modified oligonucleotide of claim 1, wherein at least one internucleoside linkage is a modified internucleoside linkage.

7. The modified oligonucleotide of claim 6, wherein the at least one internucleoside linkage is a phosphorothioate internucleoside linkage.

8. The modified oligonucleotide of claim 1, wherein the modified oligonucleotide comprises at least one modified sugar.

9. The modified oligonucleotide of claim 8, wherein at least one modified sugar is a bicyclic sugar.

10. The modified oligonucleotide of claim 8, wherein at least one modified sugar comprises a 2'—O-methoxyethyl, a constrained ethyl, a 3'-fluoro-HNA or a 4'—(CH$_2$)$_n$—O-2' bridge, wherein n is 1 or 2.

11. The modified oligonucleotide of claim 1, wherein at least one nucleoside comprises a modified nucleobase.

12. The modified oligonucleotide of claim 11, wherein the modified nucleobase is a 5-methylcytosine.

13. The modified oligonucleotide of claim 1, wherein the modified oligonucleotide comprises:
    a gap segment consisting of linked deoxynucleosides;
    a 5' wing segment consisting of linked nucleosides;
    a 3' wing segment consisting of linked nucleosides;
    wherein the gap segment is positioned between the 5' wing segment and the 3' wing segment and wherein each nucleoside of each wing segment comprises a modified sugar.

14. The modified oligonucleotide of claim 13, wherein the modified oligonucleotide consists of 20 linked nucleosides.

15. The modified oligonucleotide of claim 1, wherein the modified oligonucleotide consists of 20 contiguous linked nucleosides of SEQ ID NO: 58 and the modified oligonucleotide further comprises:
    a gap segment consisting of ten linked deoxynucleosides;
    a 5' wing segment consisting of five linked nucleosides;
    a 3' wing segment consisting of five linked nucleosides;
    wherein the gap segment is positioned between the 5' wing segment and the 3' wing segment, wherein each nucleoside of each wing segment comprises a 2'-O-methoxyethyl sugar, wherein at least one internucleoside linkage is a modified internucleoside linkage and wherein each cytosine residue is a 5-methylcytosine.

16. The modified oligonucleotide of claim 15, wherein the at least one internucleoside linkage is a phosphorothioate internucleoside linkage.

17. The modified oligonucleotide of claim 1, wherein the modified oligonucleotide has a viscosity of less than 40 cP.

18. A modified oligonucleotide, wherein the modified oligonucleotide is 20 linked nucleosides in length and consists of the sequence of SEQ ID NO: 58, wherein the modified oligonucleotide further comprises:
    a gap segment consisting of ten linked deoxynucleosides;
    a 5' wing segment consisting of five linked nucleosides; and
    a 3' wing segment consisting of five linked nucleosides;
    wherein the gap segment is positioned between the 5' wing segment and the 3' wing segment; wherein each nucleoside of each wing segment comprises a 2'—O-methoxyethyl sugar; wherein at least one internucleoside linkage is a phosphorothioate internucleoside linkage; and wherein each cytosine is a 5-methylcytosine.

19. The modified oligonucleotide of claim 18, wherein the modified oligonucleotide is a pharmaceutically acceptable salt.

20. The modified oligonucleotide of claim 19, wherein the pharmaceutically acceptable salt is a sodium salt.

21. The modified oligonucleotide of claim 19, wherein the pharmaceutically acceptable salt is a potassium salt.

22. A composition comprising the modified oligonucleotide of claim 19 and a pharmaceutically acceptable carrier or diluent.

23. A kit for reducing apo(a) and/or Lp(a) levels, wherein the kit comprises: (a) a modified oligonucleotide consisting of 14 to 25 linked nucleosides and comprising a nucleobase sequence comprising a portion of at least 14 contiguous nucleobases complementary to an equal length portion of nucleobases 3900 to 3923 of SEQ ID NO: 1, wherein the nucleobase sequence of the modified oligonucleotide is at least 95% complementary to SEQ ID NO: 1; and (b) instructions for use.

* * * * *

SEQUENCE LISTING

<160> NUMBER OF SEQ ID NOS: 134

<210> SEQ ID NO 1
<211> LENGTH: 6489
<212> TYPE: DNA
<213> ORGANISM: Homo sapiens

<400> SEQUENCE: 1

```
aggtaccttt ggggctggct ttctcaagga agcccagctc cctgtgattg agaatgaagt        60
gtgcaatcgc tatgactggg attgggacac actttctggg cactgctggc cagtcccaaa       120
atggaacata aggaagtggt tcttctactt cttttatttc tgaaatcagc agcacctgag       180
caaagccatg tggtccagga ttgctaccat ggtgatggac agagttatcg aggcacgtac       240
tccaccactg tcacaggaag gacctgccaa gcttggtcat ctatgacacc acatcaacat       300
aataggacca cagaaaacta cccaaatgct ggcttgatca tgaactactg caggaatcca       360
gatgctgtgg cagctcctta ttgttatacg agggatcccg gtgtcaggtg ggagtactgc       420
aacctgacgc aatgctcaga cgcagaaggg actgccgtcg cgcctccgac tgttaccccg       480
gttccaagcc tagaggctcc ttccgaacaa gcaccgactg agcaaaggcc tggggtgcag       540
gagtgctacc atggtaatgg acagagttat cgaggcacat actccaccac tgtcacagga       600
agaacctgcc aagcttggtc atctatgaca ccacactcgc atagtcggac cccagaatac       660
tacccaaatg ctggcttgat catgaactac tgcaggaatc cagatgctgt ggcagctcct       720
tattgttata cgagggatcc cggtgtcagg tgggagtact gcaacctgac gcaatgctca       780
gacgcagaag ggactgccgt cgcgcctccg actgttaccc cggttccaag cctagaggct       840
ccttccgaac aagcaccgac tgagcaaagg cctggggtgc aggagtgcta ccatggtaat       900
ggacagagtt atcgaggcac atactccacc actgtcacag gaagaacctg ccaagcttgg       960
tcatctatga caccacactc gcatagtcgg accccagaat actacccaaa tgctggcttg      1020
atcatgaact actgcaggaa tccagatgct gtggcagctc cttattgtta tacgagggat      1080
cccggtgtca ggtgggagta ctgcaacctg acgcaatgct cagacgcaga agggactgcc      1140
gtcgcgcctc cgactgttac cccggttcca agcctagagg ctccttccga acaagcaccg      1200
actgagcaga ggcctggggt gcaggagtgc taccacggta atggacagag ttatcgaggc      1260
acatactcca ccactgtcac tggaagaacc tgccaagctt ggtcatctat gacaccacac      1320
tcgcatagtc ggaccccaga atactaccca aatgctggct tgatcatgaa ctactgcagg      1380
aatccagatg ctgtggcagc tccttattgt tatacgaggg atcccggtgt caggtgggag      1440
tactgcaacc tgacgcaatg ctcagacgca gaagggactg ccgtcgcgcc tccgactgtt      1500
accccggttc aagcctaga ggctccttcc gaacaagcac cgactgagca aaggcctggg      1560
gtgcaggagt gctaccatgg taatggacag agttatcgag gcacatactc caccactgtc      1620
acaggaagaa cctgccaagc ttggtcatct atgacaccac actcgcatag tcggacccca      1680
gaatactacc caaatgctgg cttgatcatg aactactgca ggaatccaga tgctgtggca      1740
gctccttatt gttatacgag ggatcccggt gtcaggtggg agtactgcaa cctgacgcaa      1800
tgctcagacg cagaagggac tgccgtcgcg cctccgactg ttaccccggt tccaagccta      1860
gaggctcctt ccgaacaagc accgactgag caaaggcctg gggtgcagga gtgctaccat      1920
ggtaatggac agagttatcg aggcacatac tccaccactg tcacaggaag aacctgccaa      1980
gcttggtcat ctatgacacc acactcgcat agtcggaccc cagaatacta cccaaatgct      2040
ggcttgatca tgaactactg caggaatcca gatgctgtgg cagctcctta ttgttatacg      2100
```

```
agggatcccg gtgtcaggtg ggagtactgc aacctgacgc aatgctcaga cgcagaaggg    2160
actgccgtcg cgcctccgac tgttaccccg gttccaagcc tagaggctcc ttccgaacaa    2220
gcaccgactg agcaaaggcc tggggtgcag gagtgctacc atggtaatgg acagagttat    2280
cgaggcacat actccaccac tgtcacagga agaacctgcc aagcttggtc atctatgaca    2340
ccacactcgc atagtcggac cccagaatac tacccaaatg ctggcttgat catgaactac    2400
tgcaggaatc cagatgctgt ggcagctcct tattgttata cgagggatcc cggtgtcagg    2460
tgggagtact gcaacctgac gcaatgctca gacgcagaag ggactgccgt cgcgcctccg    2520
actgttaccc cggttccaag cctagaggct ccttccgaac aagcaccgac tgagcagagg    2580
cctggggtgc aggagtgcta ccacggtaat ggacagagtt atcgaggcac atactccacc    2640
actgtcactg aagaacctgc caagcttggt catctatgac accacactc gcatagtcgg    2700
accccagaat actacccaaa tgctggcttg atcatgaact actgcaggaa tccagatcct    2760
gtggcagccc ttattgttta tacgagggat cccagtgtca ggtgggagta ctgcaacctg    2820
acacaatgct cagacgcaga agggactgcc gtcgcgcctc caactattac cccgattcca    2880
agcctagagg ctccttctga acaagcacca actgagcaaa ggcctggggt gcaggagtgc    2940
taccacggaa atggacagag ttatcaaggc acatacttca ttactgtcac aggaagaacc    3000
tgccaagctt ggtcatctat gacaccacac tcgcatagtc ggaccccagc atactaccca    3060
aatgctggct tgatcaagaa ctactgccga aatccagatc ctgtggcagc cccttggtgt    3120
tatacaacag atcccagtgt caggtgggag tactgcaacc tgacacgatg ctcagatgca    3180
gaatggactg ccttcgtccc tccgaatgtt attctggctc aagcctaga ggcttttttt    3240
gaacaagcac tgactgagga aaccccgggg tacaggact gctactacca ttatggacag    3300
agttaccgag gcacatactc caccactgtc acaggaagaa cttgccaagc ttggtcatct    3360
atgacaccac accagcatag tcggacccca gaaaactacc caaatgctgg cctgaccagg    3420
aactactgca ggaatccaga tgctgagatt cgcccttggt gttacaccat ggatcccagt    3480
gtcaggtggg agtactgcaa cctgacacaa tgcctggtga cagaatcaag tgtccttgca    3540
actctcacgg tggtcccaga tccaagcaca gaggcttctt ctgaagaagc accaacggag    3600
caaagccccg gggtccagga ttgctaccat ggtgatggac agagttatcg aggctcattc    3660
tctaccactg tcacaggaag gacatgtcag tcttggtcct ctatgacacc acactggcat    3720
cagaggacaa cagaatatta tccaaatggt ggcctgacca ggaactactg caggaatcca    3780
gatgctgaga ttagtccttg tgttatacc atggatccca atgtcagatg ggagtactgc    3840
aacctgacac aatgtccagt gacagaatca agtgtccttg cgacgtccac ggctgtttct    3900
gaacaagcac caacggagca aagccccaca gtccaggact gctaccatgg tgatggacag    3960
agttatcgag gctcattctc caccactgtt acaggaagga catgtcagtc ttggtcctct    4020
atgacaccac actggcatca gaaaccaca gaatactacc caaatggtgg cctgaccagg    4080
aactactgca ggaatccaga tgctgagatt cgcccttggt gttataccat ggatcccagt    4140
gtcagatggg agtactgcaa cctgacgcaa tgtccagtga tggaatcaac tctcctcaca    4200
actcccacgg tggtcccagt tccaagcaca gagcttcctt ctgaagaagc accaactgaa    4260
aacagcactg ggtccagga ctgctaccga ggtgatggac agagttatcg aggcacactc    4320
tccaccacta tcacaggaag aacatgtcag tcttggtcgt ctatgacacc acattggcat    4380
cggaggatcc cattatacta tccaaatgct ggcctgacca ggaactactg caggaatcca    4440
```

```
gatgctgaga ttcgcccttg gtgttacacc atggatccca gtgtcaggtg ggagtactgc    4500
aacctgacac gatgtccagt gacagaatcg agtgtcctca caactcccac agtggccccg    4560
gttccaagca cagaggctcc ttctgaacaa gcaccacctg agaaaagccc tgtggtccag    4620
gattgctacc atggtgatgg acggagttat cgaggcatat cctccaccac tgtcacagga    4680
aggacctgtc aatcttggtc atctatgata ccacactggc atcagaggac cccagaaaac    4740
tacccaaatg ctggcctgac cgagaactac tgcaggaatc cagattctgg gaaacaaccc    4800
tggtgttaca caaccgatcc gtgtgtgagg tgggagtact gcaatctgac acaatgctca    4860
gaaacagaat caggtgtcct agagactccc actgttgttc cagttccaag catggaggct    4920
cattctgaag cagcaccaac tgagcaaacc cctgtggtcc ggcagtgcta ccatggtaat    4980
ggccagagtt atcgaggcac attctccacc actgtcacag gaaggacatg tcaatcttgg    5040
tcatccatga caccacaccg gcatcagagg accccagaaa actacccaaa tgatggcctg    5100
acaatgaact actgcaggaa tccagatgcc gatacaggcc cttggtgttt taccatggac    5160
cccagcatca ggtgggagta ctgcaacctg acgcgatgct cagacacaga agggactgtg    5220
gtcgctcctc cgactgtcat ccaggttcca agcctagggc tccttctga caagactgt     5280 atgtttggga atgggaaagg ataccggggc aagaaggcaa ccactgttac tgggacgcca    5340
tgccaggaat gggctgccca ggagccccat agacacagca cgttcattcc agggacaaat    5400
aaatgggcag gtctggaaaa aaattactgc cgtaaccctg atggtgacat caatggtccc    5460
tggtgctaca caatgaatcc aagaaaactt tttgactact gtgatatccc tctctgtgca    5520
tcctcttcat ttgattgtgg gaagcctcaa gtggagccga agaaatgtcc tggaagcatt    5580
gtaggggggt gtgtggccca cccacattcc tggccctggc aagtcagtct cagaacaagg    5640 tttgaaagc acttctgtgg aggcacctta atatccccag agtgggtgct gactgctgct     5700
cactgcttga agaagtcctc aaggccttca tcctacaagg tcatcctggg tgcacaccaa    5760
gaagtgaacc tcgaatctca tgttcaggaa atagaagtgt ctaggctgtt cttggagccc    5820
acacaagcag atattgcctt gctaaagcta agcaggcctg ccgtcatcac tgacaaagta    5880
atgccagctt gtctgccatc cccagactac atggtcaccg ccaggactga atgttacatc    5940
actggctggg gagaaaccca aggtaccttt gggactggcc ttctcaagga agcccagctc    6000
cttgttattg agaatgaagt gtgcaatcac tataagtata tttgtgctga gcatttggcc    6060
agaggcactg acagttgcca gggtgacagt ggagggcctc tggtttgctt cgagaaggac    6120
aaatacattt tacaaggagt cacttcttgg ggtcttggct gtgcacgccc caataagcct    6180
ggtgtctatg ctcgtgtttc aaggtttgtt acttggattg agggaatgat gagaaataat    6240
taattggacg ggagacagag tgaagcatca acctacttag aagctgaaac gtgggtaagg    6300
atttagcatg ctggaaataa tagacagcaa tcaaacgaag acactgttcc cagctaccag    6360
ctatgccaaa ccttggcatt tttggtattt tgtgtataa gcttttaagg tctgactgac     6420
aaattctgta ttaaggtgtc atagctatga catttgttaa aaataaactc tgcacttatt    6480
ttgatttga                                                           6489
```

<210> SEQ ID NO 2
<211> LENGTH: 150001
<212> TYPE: DNA
<213> ORGANISM: Homo sapiens

<400> SEQUENCE: 2

```
atctttcagc ctctatatta ttttattgtg attttaatt tccttgaatt ggattttgcc      60
```

```
attgtgctaa atcttgatga tcttcatttg tatccgtagt ctgaattata tttctgtcat     120
ttgagttagc tcagtcttgt taagaaccct tgttggaaaa ctggtgcagt tgtttggagg     180
acatatgacc ttctggccat ttgatttatt ggagttctta cgttggttct ttctcatgtc     240
tctgtgtggg tgtttcttta actgcagtgt agattgagta cagccaatag acttcttctt     300
tggaggtttt cacagggcca aggccttgta cagggtcttt atttgtagct gacttcttgt     360
ctttggtttc atagtggggc atgttagcaa atagttttg ctgttgaagt tttggggtgt      420
gatccatttt ttattttaat gattgtgtat ttcctttata cctaaaacaa gcagaaaacc    480
agtaaaggtc tttgagtctc tgaattcata actccagcat tcatattgct tcctcaggta    540 agtgggttt tcacccagcc cttaagggtg ttagattatt ttttatgtga aattagccag     600
attgtatttc taaacatgat gtaaaacaat aatgacaaaa gttataataa actagccttc    660
ttaccaaatc cacatgtcta atgtgtgtgg gagggtgtta ggcagggac ctgcagctaa     720 gggagaggca gacaggcccc atggccccaa atctaggata gtatttggta ttggttgatg    780
ggtgagagaa agagagggaa catctgtgca ggatgtggta tcagcacctg gactacatct    840
tagggattcc ttcttcattt ttcagtatgc cctgacaata attatatcta tcagacttac    900 cccttgacc actggaacac taagactgtt ttgggatctc tgcctgactt tctcagaggt     960
gctggtgagg acattatgag tctggaacct agaaaagcgt tctgactctg ctgactttct   1020
cagaggtgct ggtgaggaca ttatgagtct ggagccctag aaaagcgttc tgactctgcc   1080
actagccaga cagacctgga ctaggcacgt taactctttg tatgacttga ctccaacccc   1140
tcatttgtaa aaccagcatt ttcaagtggt gttttccaca tcagccttt gcataagctg    1200 tcatttgaag aaaggttttt gtttgtttgt ttttgttta acaaaaaggt taaaaaccac    1260
tggtctagat aattgcaaag tttgctttcc ttttttctgtg cttttttctac tattttaaa  1320 atgtcatcct ccttggtttc ttgatccccc tttctgcact cctgagtctg gaacactga   1380 ggccaactaa aaggaaactt ggcaaaagag gaacaccttt gggtgtgcca ggctgctccc   1440
agtgttttgc acttataaaa atttaaatgc tgcaaacctc taagacttag atattattgt   1500
tcctatttta caagtgagga acctgaggct cagagaaggt gcaggatggc acagggagac   1560
ctgaattgga accctggttc ccacttactg gctgtcggga cttagaaaag tcatgaactc   1620
tcattgattg ttttcttata tgaaatgggg gctgcagggt tgtcggggga gaaacaataa   1680
gaatgtgcat caagtgtcga gcacgtgcta cgcactccat catggcagct cctactaata   1740
tacagaatag agttgtatct aacatgactc tttcttgcaa gtgacagaaa tccaactta    1800 agatggatta agcaaaaaag gggaattctt gttgagctga aaagtcttta ggctcacatg   1860
atggccccag ggcccaggcc ctgtccagcc atgcagtagg catcatcctt gggcacaaag   1920
gtgagattct tgtggtggca gatgctgtgg cagctcttgc tttgccagga aagactgagg   1980
aaggccactg tccccattaa gtgaacaata gttggccagg tctgagaggt tgaacttggg   2040
tcacaggcct gtccctgaac ccatcactga ttggctccaa cctgcatcag ctattacatg   2100
ctagaggtgg aggcaggacc ccactcatac ccagaagggc aaagggtgga tccctcaaca   2160
ggattatggg atgtaggtg atagactgct gggcagccaa aaagcaaaca gatcctctcc    2220
aatacctcaa ctgatgaaag caccaagcta aaatcataag gatctgggtg tgaattctgg   2280
ctctaccatc ttccatgtga cattgggcag ttatttaatc tcttttagcc ttggcttct    2340 tacctgtact aacatataag gtgattgtga tgagcatcat catcgtcaac atcatcatca   2400
```

```
ccatccacat tgccaccacc actcccatta tcatcttcat caacatcatc accaccgcca    2460
ccatcaccat tatcattacc accaccgcta tcactattat catcaccctc aacatcatca    2520
ccatcatcac tatcatcacc accaccatca tcgttactac cactaccacc accatcatca    2580
ccacagccac caccaccatc accatcatta ctactcagca ccaccatcat cattccacca    2640
ccatcaccat cattccacca tcaccattat cattaccacc accactgtca ctattatcat    2700
caccctcaac atcatcacca ccaccatcat cattactacc accaccacca ccatcaccat    2760
catcatcatt ctaccaccat caccattatc atcaccatca ccatcaccac cgctatcatc    2820
atgataatca ttatcattac caccaccatt agcattatca ttaccaccac catcactatc    2880
actatcacca tcaccacgac cactaccacc atcaccaaca ccatcattac tacccaccac    2940
caccatcatc atcattccac caccatcaca attattacca ccaccaccat caccaccacc    3000
accaccatca ctatcatcat cagtagacat catataacca gtttgtagct ggcccagagc    3060
ctacttgctg tttcttctgc cccacaacca tccacacatt tctaaccacc atcccccact    3120
aggcttctgc ctcgcctggt ctcacctgca ggtccactga gaaaatgatt ctcagaacac    3180
taactagacc atgaggtgcc acaaaacata actcaggcct gttcatcaat tttctacatg    3240
tcaataatga catcaggtca attggcgttc tcagcctctg agagggaggt caaagttttc    3300
ctgctctccc cttcatgttt ccaggtgttc cctgacttgg atcaaatgca gagtttggag    3360
gtgttgaggc caaggggatt ttccaggtca gtcgtcatcc acaatcaatg gactgatcct    3420
gccgctggac ttaccctgct gccctctccc caaggcccca tcagggaggg cttcaatcct    3480
cttgtcacct gtggcctacc tgccctcaga gatgacatct ctatgtcggc cactggatgg    3540
cagcacctac tcgcagacca catcaacttt cctggcaact gcggtaggt tttcaccatt     3600 atcaggatgt ttgccttgct caaatagcag attctagaga acgtgctcc ctcacacaac     3660 tatgtagtcc aggtgatgca ccctctgccc gatgcttggt agtcagaaac ttccatcatg    3720
cagctctgcc cagattgagc tgagctggcc tctggagtga ggtgctggga caaacatctt    3780
ccatgctgct catgtcaact ccagatgcag tcaggtttct gaaccaaagt caatgatcta    3840
agtgcagtca aaggctctgg gggaagaaag agagagtgcc tcatctcttg cctgtgccat    3900
gctcgcaaag caaggatttt tgcaaaattc taatgaaagc tgggcttgca aaattagaaa    3960
actggattat ttgtgagaac actgaaacat ccctgggtgt gtccatctgg aaaaacagca    4020
tttcctctgg caattttgca accgttctat ttgaatttgg caaagaaaat aaagcagttt    4080
ttcacaaaag aataaacaca accaggagaa tcttcactct cccaaattgt caaagaagta    4140
taaattagaa aatgaatcag gacaatttca acctgttaga ttagctaata tttaaaaatt    4200
gaacactcat acaagtgtgg tgaagtgatt gttttctagt gacattttac actgtcataa    4260
ccttctagaa aataaattgg cagtgttatt gggagacaga aatatgtcta tataatttat    4320
gggaacttag gctcagaaaa tattaaggaa taagaatgaa ctttatgaac aaagatgtgg    4380
agggttggaa gcaagagggg ggccaacgcg cacggggagg aagcatttgg gcagtgactc    4440
cgcagaccca ggctcaggtt gaactagaca acctccttac acctcagttt ccttaactgt    4500
agagcaggag tgatggaact gcctgtttca taggactgtt gtgaggatga agtgagatac    4560
accacattat aagcttgtgc ctggaaagga taatgcttag taaatgatga ctattctttt    4620
ttattgcaat aaaatgtaca cagcgtaaga gttactattt taaccatttt tgcagggtac    4680
caccaagtgg catttagtac attcacagtg gtgtgcaacc atcatcatat ttccagaata    4740
ttttcctcat ccccaaagga aacctcatgc tcattaatca gtagctctcc tttaaaatat    4800
```

```
tagttatgaa gatcatagca ctatacaaaa ctcattatgt aatgttgagt gaaaaaatca   4860
gggtgtgaaa ttttgtgata tgatgtaatt agtgaaagaa gcatacaaaa agtctgaaaa   4920
tataaaaaca atagcaattg catttctcag actctacatt taaacattat tctttatggt   4980
tttaaaagca aagaaaaagg taagaaaaca acaaccaacc gcaaagcacc atgacaaagc   5040
tcagattgtt aaatccaggt ttttggaaca tagactctta tatgacgttt acactctcca   5100
gggttcagag agtctggcag cattgggagc tgccttgtgt tctacagcct cacggacaga   5160
caggaggtcc atcaccactg ctctgttctt ctggagtttc cttgtgaaca tgttgtggac   5220
gtagttacca tttctttcat cttttttaaac acaggtacct ttggggctgg ctttctcaag   5280
gaagcccagc tccctgtgat tgagaatgaa gtgtgcaatc gctatgagtt tctgaatgga   5340
agagtcaaat ccactgagct ctgtgctggg catttggctg gaggcattga cagttgcaag   5400
gtaagaaaag atcaagagac caaagttagt cttgtgctct cctgtctcag tctcagtccc   5460
ttagacttga gtcccaaagt agcgaattca agtaggattt aatcaatgga agacccagt    5520 ctaagtgttg ctcagaaact ccctagatct gtcccaaatg tatattcaga tcatccaagg   5580
ggacttcttg gggcttgagt tccagatcag cagcaaggga gccataagtg ccataactac   5640
ctcagaccac tcaccctcct ggggtgtccc ggtggccagg gactaaagtg gtgattttc    5700 tggtagggaa ggaggtagag ggtacaggac agagactaac tgcacacaat atctgagact   5760
ggagctcaga tattgctgat gatcagagtt ggcgtgtctc cccaattgat ttacaactgg   5820
ggcttggata ctgttttaaa cgggaggagc ctcctaacca tcttgacaca accactgacg   5880
tgactacact agagatagac tctttccact taattctacc actcttgctt tacttcatga   5940
gaacgaaaat gtaagattgc accatgaatt catttgcgga aagattgata ctatgctttt   6000
attttatttt attttatttt attttatttt attttatttt attgagactc tcaccccggt   6060
tgaagtgcac tgacgtgatt ttggctcact gcaacttcca cctcctgggt tcaagtgaat   6120
actccagcct cccagtagc tgggattaca ggtgcccacc accacgcctg gctaattttt    6180
gtatttttag tagagatggg gtttcaccac attggcctgg ctggtctcaa actcctgacc   6240
ttgtgatcca cctgtcttgg cctcccaaag tgctgggatt acagagttga gccaccgcac   6300
tcgaccctat gttttatttt taaaaatatt tatttattta tttaagccac aactactaga   6360
ataggaagga ttgatatttt attaatttta tttggtattt attatttttt tttctttcct   6420
gagacattct tgctctgtca cccaggctgg agtgcagtgg cacattcttg gctcactgca   6480
acctccatct cctgtgttca agcaattcta gtgcctcagc ctacttagta gctgggatga   6540
ctggcatgtg cctccacacc cagctaattt ttgtattttt tgtagagaca gggttttggc   6600
atgttgccca ggcttgtctc aaactcctgg cctcaggtga tccatctgcc gtggcctccc   6660
aaaatgctgg gattataggc atgagccacc accccctcct ggaaggattg atatcttata   6720
acataattta taattacaga aaacatgtga gttcactagg aataaataaa ttttgaagat   6780
aataaaagat tttcacttat gttgtcattt cggcacagtt tggtatagga tgtggagatg   6840
ttaacattta tacctagctt gctcgtaaac taagacctga aagggttgtg tctatcagct   6900
gcacccctgg gtagcgacac aacctcggga aggcctcagc cccctcctcg tacagcactg   6960
cctgttggaa agcttgaggg aggctatgga tgtgcagcac ttggcagagg gtctggtcat   7020
ggaagttacc agcaaatatg agctactttt atgattttat tttatccaaa agaaagagaa   7080
tgaaagaaga ggggaggaaa caagactaat caggaaagat gaaggtctag gggtgaggga   7140
```

```
aggagtaagg agacataaag gcaatgtgga gcagctgagg ggggaaatgg ctttcaccac    7200
ttcccagcat ctattgacat tgcactctca aatattttat aagactctat attcaaggta    7260
atgtttgaac cctgctgagc cagtggcatg ggtctctgag agaatcatta acttaatttg    7320
actatctggt ttgtgggtgc gtttactctc atgtaagtca acaatgtcct gggattggga    7380
cacactttct gggcactgct ggccagtccc aaaatggaac ataaggaagt ggttcttcta    7440
cttcttttat ttctgaaatc aggtaagaca tagtttttt aaattataag aattattttt    7500
tctcccacaa tgtagtaaaa atacatatgc catggcttta tgtgcaattc atttaatttt    7560
tgattcatga aattcccagt tcaaaatctt gtatatgatt gaaaattct taaaaaaata    7620 agtttaattt ccccgtgaag actgtcacgg tgctggaatg aatgggcaga aaaataatg    7680 gttgattttt ctaatctaaa agagtgtgcc tacatgatgg ccagtctggc tgaaaaataa    7740
atagccattg tagctaacta tgcaaaggat ggctaagctc ttcgcttggt tctcagtttc    7800
attaatttat atcatctctg ttcaggtgcc atgctcccct cactagcaag ttgaaacaat    7860
gaaataactc tttgaatatg tttggttcct tgacctgttc atggagtggg actcagcatt    7920
tctctctttg ttatggcctg agtaaggctt ccatcggta tacatttgct tcttatccct    7980
ggagaaatta tacacatcca tttgccagat gatatacgca tataatgatt caacaaatac    8040
tcagggtatt tgttgagtgg gttaggtccc cacatttta tacatacata cacacataca    8100
caccgtgtgt gattgtgaat gtaagtgtgt gtccttaca aatactagct tatttagctc    8160
atggtatagg tagggtagca tagtcatccc cattttataa acaaagaaat ctagacttag    8220
gaaaatcatg ttatttgtct cgtgaccaaa ttcccaaatc aaggaaataa agaaacctgg    8280
atttaagcca gatttccaag aaaaaatcta gggctcttct cacttttca tctttgttcc    8340 aacatttgaa aaaataaatc taaacacatt ccaatgtaac tgaagagcag gttaattgtt    8400
tgccacttgc agaatccaat taagaagaga gaagtctggt ataagaaag tgatttgctt    8460 ccaaagctag cttaggggaa gaaatgcagc agtcctgccg tactacttca ctttaggagc    8520
agaaagtggc acttttaaaa ggcaacagag gaggcgagca aggattcagg ggtccatgct    8580
agcttgggca ccttatccac caggtagttg agcagttgcc tgctggtgcc tttgtgagca    8640
gggtgttgtc ccttgaggca aatctctgga gggtgagagt tttgtagtgg gcatgctttg    8700
gtttataaat cacctgtgaa ctcaggagtt ccatcttgaa gcacatacat agttagatga    8760
acttgccctg cagggagagt ctgatgaaag ggaggtagat gcttgcaatt taatctataa    8820
attaccagat aaaattttac aagttgactt taaagtcaaa cacatttgaa tttagtggaa    8880
gccattcaag aaaatatcaa agaaaataca gagcaggaga agattaagca aagagttttt    8940
tggggaaatt ggtgtctatg tctgtgtgtg taggagtgc aggggatatg aatattctat    9000
ttcagcccat ggaaactagg atgtagatca ctgtgaactt attcagcagg ctacacccaa    9060
aggctagaac aaacttctct gccacaggat taacatatgt tttaatcgac ctgggggca    9120 cattctctga taagctcttt tggaaagcca ggctttctgt ggacgtgtta tctttccaat    9180
gtgtgctgga atgcccgggg agaggaaaaa gtttctttta cagccatgct cagtgagaag    9240
cggagaaaca tcttctattc acaaattgct aagtctttta cacatgcaaa tatgcataca    9300
cattcacaca ccacagtgag gaagaaattc tcacaccatt aataaaatac atttacttca    9360
gtagcaatat acatctacat tttgcctata atataaagt attttccta ttaaagatt     9420 tgtttaatgt ttcttcacca acaaataaac cctattaaat ccccattgcc atatgagccc    9480
tggaggtgaa tcagagaaac aaaaggattg tggaaaaatc atcaggttaa aaaagaaaa    9540
```

-continued

```
attgattctg ttttgggata tttcctagca acatgagctg gggaggggat ctcagcagtg    9600
atgctctatg aagcataata aaatgacaca gttacaggta acttagttaa aggggggaaat   9660 aaatggaagt ttcctctttt tgaatatcaa ttgtagcctg ctctgctaca tttcaaaaac   9720
actcttcaaa atgtttaact gaactcactg taggaagcac cttattaatt tattgtgtgt   9780
tttgaagtca cactgtgagc tatagaattt acccaagcac aactcttcct ggaaaagaga   9840
gttcaaatga gaaacagtgc ggggtgaaga catggatatg gcctaaaat atctatttct    9900 caatgatatt ttgatatatc tatcaagtgc ttttttagtgg attaggttca gaatgcatca   9960
gccaatgcct gttcaataat ccagttttcc agcatagagc atattaaatt gaggaaggac   10020
aaagtcacag aggtggggag caggtggact gtggccaagg actttgcatg aaacagtgag   10080
cgtgcatcct cctccttgcc ctgccctcat ggtctgtgta ctctcaggag gtcaggacag   10140
gcctttctga gaatgagaat ctgttcatct gcctttctac tggatacttg tcatcggcat   10200
acaaacacat gttctctgca gtgtgtcatc tttcagaacc tcccctgacc ctgtattccc    10260
tagaagtctc gctgctttca gagccaggct tctctcctgc tgccacccc actgctcttc    10320 tagtcactct ttaacccact ccatctgcat gtggccccca ccacacccct caaagtggtc   10380
aaggttgtcc tgttgcttaa ttccatggaa gcttggctat cttcatttta ttagcctctt   10440
ttggcctctc accctgtgaa atcactaca ttttgtgcca gagatggagc tggcatctcc     10500
aggcttggaa gagggctgct gaagctcagc caggtgtcct aaggagcctc aggacagggg   10560
atgctcagta gccttgcaat gggaacacag ctgagcccca cttggccacc ctttgccaca   10620
accaggcaga aagcagcttt tgaacagatt tgttgcctca gatttgatct caaagaaaaa    10680
tcgtgggcag tattggtccc aggttctgct tttttacaat ttcctctgaa atctggatgc   10740
ctatcaacac cttggaaaaa ctgaattctc cccaactaat agtggtgtgt cactgtagta   10800
agcctagtac aaaaatggcc ttctttgtgg aggagcttca tatcctccat ttttttttg    10860 cttaattttt gcccaagatg agaacataat ttagttcact ttttatttat tcccaacatc    10920
atccatgcac caacattttt gtaactaaag gagggaccat tcagaagatg cttatcaact   10980
gtcaaagtga cagtgttaca accaatgcac atattgtaag aaatcaaaca atggcctcca   11040
aggttcattt ctacacaggg attagcagat caacatcaat cttggcaaca cagttgccac   11100
tgatggtgtc ttattttttt tatcatgaca tggcaatcaa gagcaaacat gatttattct   11160
tatttaagat tttatggtta gactaggcag atagctagat atgagcagga ggtggaagcc   11220
cctgagagaa tggaggtctg gagaatctga accccagag attacccaag tcctgcatgc    11280
tagacatgag tggaggaggg ggaataccta ggtagaaaag aatgccccctt aagatgccca   11340 gcagtcgctc actgtgcagt taacttttca gaatgctgct agatacatgc tgataggag    11400 ggaagagggc aaaggagaaa ttcctaagag atacacggtt gcagttagta tacatctgag   11460
tgctatacaa ccttctttgg gtggtggcaa gaagcaatgc agccattacg tagaattcat   11520
atcaaacacc tgtatcacag gtgttaaaga aacaagaaac attgtacttc ttgtattctt    11580
aataatgatt tgcaatattg tctttagtat cactgcaaac ctctataaat atgattttta    11640
aaaagtattt ctttaggttg gaattacttc tacgcattga cttatcttcc tgggtttcat    11700
tagccgtacc cgttgtactt tcttccttac cactgtttat ctcaaactct tgagattaaa   11760
gtatgggctc aggagggagc gaggagcttc aggactctca cggacctcca gcacagtgta   11820
gctgccttat ggaaaagtgg ccacactgtt ttctgcactg gtccctgccc ctactattcc    11880
```

```
tcactgggca gagcacagcc accctggccc tgcctgaaca ttttagtcag tgttggctct    11940
gtgcttctct ggggaggaaa tccaagagac aacccacagc ccctctgcca tttcagctgc    12000
agcagtacca ccgttaatgc ccttgggctt gagaaagaag ggacctggcc acttccctga    12060
cacctccagc acacagcagg gaaagaattc cagtttctct ttcttgtgag ctttcacctg    12120
ctactcttca ccaggcaagg ctcctggctt gggcccacag tgcaggcacc tcgaactcag    12180
ttgaacattt ccactggctg cactctgtgt ttttgtgggg tgaagctccc agaggtgact    12240
gaaagtcctt ctgccactaa cactgcagtc atactgccct tgctgtactt ggactaggga    12300
aggaaaaaag atcctgagtg ctttactcac accccagtgt gccccagcca ccctatggaa    12360
aagaggccag tgtgtcatcc ctgcaagcac cctgaggccc ctgcccctgc tgcccccaag    12420
ctgtagagcc agaatataaa gctggcagaa aaatgtaaaa aggctagact ggcttagcct    12480
cccagcctac atctttctcc tgtgctggat ccttcctgct cttgaacatc ggactccaag    12540
ttcttcagct gtgggacttg gactgtcttc cttgctcctc agattgcagg tggcctatta    12600
tgggaccttg taatcttgtg agttaatacc acttaataag ctccccttg tgtgagtata    12660 tctatatcta tagatagata taggtatact cactatatat acacatatat acatatactc    12720
tctctctctc tctctcatat atatatatat ataatctcct attagttctg tccctctaga    12780
gaaccccgac taatacagat tttcatacca gaagtggttc ttgaggaaca gaatattaag    12840
gatggaattc tttcattggt tttgggactt ctggtgttgg ctgattaata tgattagacc    12900
aaaaaatgct aaggactcta cttctaatag tatggagaac actgatagta cttggcctga    12960
attgtttaga gagtttatgca aaataaatgc atttgacact actgattcat cacttatgag    13020
aggcaaggag tttagtgact ctatacataa tacctttgac tatatgtgga gaaccaagga    13080
acataatgaa gttggttgat tgctcctaag ttctctggag aaagagatga aagaaaatga    13140
tgatctcagg ggatctgtct cccaccttca gaagcagata ctgagccaca aatctgctaa    13200
gattgccctg aatgagagtt ttaactcctg tagagaaaga gttgaaattg tgaaaaaaca    13260
gagacaagct gttatcatgc gagtagctga tctgcaacaa gaggtgcatg cacagccttg    13320
ccaggtgttt actgttaaag tgagggcatt gactggaaaa aaatgggacc ctggaacttg    13380
gagtggggat gtgtgggaga accctgatga agctgaggac actgagtttg tgaactctga    13440
tgaaactttt ttgccagaag aaacagtttc cccatcccca gtagtggtaa catcccctcc    13500
ctgacccgtg ctgccattag ccttttccacc tttgtctgag gatgtaaacc ctgcactgct    13560
tgaggcaaca gtgatggcct tccctgaggc agctgccagg caagataatg ttgattctcc    13620
tcaagaggca cccctaatgc ccctgaatgc ttctagacct ataactaggc taaattcctt    13680
gcgggcccca gaggtgaggt tcagagtgtg acccatgagg aggtgcatta tactctaaaa    13740
gaactgctta agctttctaa tttatattgg cagaaatctg gagaacaggc atgggaatgg    13800
atattaaggg taagggataa tggtggaagg gacatagagt tggatcaagc tgaatttatt    13860
ggtttggccc tactaagtag ggattctgca tttaatgttg cagctcgggg acttagaaaa    13920
ggttctgata gggccgggag cagtggctca cgcctgtaat cccagcacct gggaggcgg    13980 gggcgggcag atcacgagat caggagattg agacaattct ggctaaaatg gtgaaacccc    14040
atctctgcta aaaatacaaa aattagctgg gcatggtgat gcgtaactgt aatctcatct    14100
acttgggagg ctgaggcaag agaactgctt gaacctgtga ggcagagatt gcagtgagcc    14160
aagatcgccc cactgcattc cagcctggta acagagcaag actccatttc caaaaaaaaa    14220 aaaaaaaag ttataatagt ttatttgctt ggttagctga aatatggatt aaaagatggt    14280
```

```
ccaatgttag tgagctggaa atgccttggt ttaatgtaga ggaagtgatc caaaggctta    14340
gggagattag gatggtggag tggattagtc actttagacc tactcatccc agctgggagg    14400
gtccagaaga tacacccttg gccgaagctt tgtgaaatag atttgtgaga gcagcacctg    14460 tattttgaa gagcccgtaa ttgctcttct ctgtatgtca gatctaacag taggaaccac     14520
agtcactcaa ctacaaaatt taaatacaat gggaataatt ggatcctgag gtggcagggg    14580
ccaagtgttg gcactgaacc atcaaaggca aggtgggcat aactaccata atagacagca    14640
gaggcaaagc agccatcaga atagtctgac tcatgtagag ctctggcatt ggctaattaa    14700
tcatggtgtt cctagaagtg aaattgatgg gaaacctact gtattcctac ttgatttata    14760
taaacaaaaa actgccaggt agaatggact aaagactaat ctgaattata aaacagaga    14820 atcatgggcc ctcaatcaat ttccagactc gaacctgtta cagttccaga acccactgaa    14880
tgaaggggag gctggatccc cttgaggaag acaccacta ggctactgac aacttatgct     14940
gttactcttt ctcccatcct tccctaagga gacctctggc cttttaccag ggtaactgtg    15000
tgtactggag aaagggaagt aatgagacat ttcagaaagt actggacact ggctctgagc    15060
tgacgttgat tccagggtac ccaaaacgtt attgtggttc cccagttaaa gtagggctt     15120 atggaggtta ggtaattaat ggagttttag ctcatttctg acttacagtg gttccagtgg    15180
gtccctggac ttatcctctg gtcatttttcc cagtgccaaa atgcataatt tgtatagaca   15240
tacttattag ctggcagaaa tgccacattg gctccctgac tggtaggatg agggctatta    15300
tggtgggaaa ggccaaacag aagccattag agctgtctct acctagaaaa ataaaaaaat    15360
caaaaacaat atcccatccc tggagggact gaagtgatta gtgtcaccat caaggacttg    15420
aaagacgcag gggtggtgat tcccaccaca tccctgttca actctcccat ttgacctgtg    15480
cagaggacag atggatcttg gaaaatgatg gtggattatt ttaagcttaa ccaagtggtg    15540
actccaattg cagctgctct accagttgtg gttttgttgc ttgagcaaat taacacatct    15600
cctggtgcct ggtatgcagc cattggcttg gcaagtggct ttttctccat tcctgtccat    15660
aagacccacc agaagcaatt tgccttcagc tgacaaggcc agcattatac ctttaccacc    15720
ctacctcagg ggtgtatcaa ctctccagct ttgtgtcata atcttatttg gagagaccct    15780
gctcgctttt cacttccacg agatataaca ctggtccatt acattcatga cattatgatg    15840
attggataca gtgagcaaga agtagcaaac acactgaact tattggtgag acatttgtat    15900
gccagaggat gggaaataaa tccagctaaa atttagggac tttctacctc ggtaaaattt    15960
ctagggttcc agtggcatga gacctatgga gatattcctt ctaaggtgaa gcataacttg    16020
ctgcgtttgg cccctcttac aaccaagaaa gaggcacaat gcctggtggg cctatttgga    16080
ttttggaggc aacacattcc tcgtttgggt gtgttactct ggcccattta tcgagtgacc    16140
tgaaaggctg ccagatttaa gtgcagtcta gaacaaaaga aggctctgaa acaggtccag    16200
gctgctgtga aagctgctct gccatttggg ccacatgacc ccgcagatcc aatggtgctt    16260
gaggtgtcag tggcagatag ggatgctgtt tggagccttt ggcaggcccc cataggtgaa    16320
tcacagtgga gacctctagg attttggagc aaggccctgc cacttctgca gataactact    16380 ctcctttga gagacagcta ttggtctgtt attgggcttt ggtggtaact gaacgtttga     16440
ctgtgggtca taaagtcacc atgctacctg aacctgccta tcatgaactg gttgcttctc    16500
gacccatcta gccatgaagt gggtcagcac agcggcattt catcatcaaa ttgaagtggt    16560
gtgtatgtga tcgggcttga gcaggtcctg aaggcacaag taagttacat aaggaagtgg    16620
```

```
ctcaaatgcc catgttctcc actcatgcca ccctgccttc cctcccccag cctgcaccaa    16680
tggcctcatg gggagttccc tatgatcagt tgacagagga agggaagact aaggactggt    16740
tcatagatgg ttctgcacga tatgcaggca ccacccgaaa gtggacagct gcagcactat    16800
atccactttc taaatgcatg tgtacacttg tgctaagaaa atatctttat tttatttcct    16860
ttatttttcc tttatcatgt gaccttagat ttatggactt cacatcagca tttaagcatt    16920
taagtgttgt tcatatcagc atttaaatat tgttaacctt atgtaataac ttttggtttg    16980
gggattggtg cgtttctggt tgtatgagga tagttgtatt atattaggca taattatgac    17040
cttattattg tctttatttg aagattatgt atgatttcag gatgtgtgta tgggttcaag    17100
ttgacaagga gttggacttg tgatggttaa tactgtcaac ttgattggat tgaaagatgc    17160
aaagtattaa tctcggttat gtctgtgagg gtgtggcaaa aggagattaa catttgagtc    17220
agtgggctgg gaaggcagac ccacccttaa tctgggtaca caccatctaa tcaagttcca    17280
gtgtggccag attgtaaagc agggagaaaa atgtgaaaag actagactga attagcttcc    17340
cagcctacat ctttctcctg tgccaaatgc ttcctgctct tgaacatcgg actccaagtt    17400
cttcagcgtt gggagttgga ctggctttct tgctcctcag cttgcagagg gcctgttgtg    17460
gaaccttgtg atccgctgag ttaatactac ttaataagat ccctttata tacatataat    17520 atattatatt atatataata tatataaat atattatata taatatatat aatatattat    17580
atattatata taatatatat tatatattat atataatata tattatatat aatatatatt    17640
atatattata tattatatat aatatatatt atatataata tatataaaat atatatatat    17700
cctattagtt ctgtccctct agagaaccct gactaataca atttatgtca ttaatctcat    17760
ttattgattt gtatacattg aaccaacctt atatcccagg aataaaacct acttgattgt    17820
ggtggattag cttttttgatg tactcttgga ttcaattgct ggtatttttat tgagaatttt    17880 tgcatctgtg ttcatcaagg atattggctt gaagttttct tttttttgttg ttccatatca    17940 gaatgatgac gacctcatag aatgagttag tctgtcctct tttatctttt ggaattgttt    18000
caggaggctt gatatcagct cttctttata tgactggtat actttggcta ggaatctctc    18060
tggtccaggg gttttttctgg tgtaggtttt taattactga ttcaacttca gaactcatta    18120
ctcattattg agttctaaaa ctcactttca tgtactcttc aaaagactgt cttcttctgt    18180
tgttgagcgg ggtgttctct caaggtcgtt taggtgaagg tggttgctgg tgttcttctg    18240
tatccttact gcttgtctttt ctctttttttt attgactact gaggattaat ggtgatgtgt    18300
ccaactttaa ctctagatta gtctatttct cttttagatt gtaactctgt tttatatatt    18360
ttgaagctct gttgttaggc atgtgtattt ggattgttag gtcttcttga tgatgacctt    18420
tatcattatg taatgtttct tcttatctct ggaagtattc gttgttctga agtctatttg    18480
tgctgatatg aatacagcct tcacagctct attttcacta gtatttgtat atctttttct    18540 cagctttttaa attgagatgt tcagaccatt tgcattaaag tagttgttaa taggattaaa    18600
tttaaatcta ccattaagtt ggttatttct ctttgtccca tttaaacttt gttcctttt    18660 tcatatttt ctgccttcat ttatattgag tttatctcca cgacttactt attaaattaa    18720
tttttaatgg ttttagtatt ttccacaatg tttataatat atactttgat tttttcacat    18780
tccaccttca aatgacagaa ttatactgga tatatagaaa tcttacatca ttgcacttct    18840
ccttcctccc tctcaaaatg ttgtgctatt gctctttgta atagaggctt acttctatta    18900
tgttatagct ctcataatac attgacacta ttttacccct gaataatcag ttgttttta    18960 aagtgattat gactacaaat attttgaata atttcttat tttaccatttt ctggtgctcc    19020
```

```
ttatctttta cagtagatcc caatttccat ctggagtcac attctttctg tgaaaaacaa    19080
cctttagcat ttcttatagc acgggactgc tgttgctgtt gtctttcagc ttttctttgt    19140
ctgaagaagt ctttatttttg ccttcagttt ttaaaagtga ttttgctgag tatagatact    19200
gggttgagag tttcattcct tgtatcattt aacaatgat gttccattat attccgtttt    19260
gaatagtttc tgactagaaa tctgatcttt gtttctttgt attcaatagt tccttttttct    19320
ctgactgcct ttaagatatt ctcatctttg tttttcaaca gtttgactat aatttgttta    19380
ttattaactt tttgtatta ttctgcttga ggtttcctga gctccttgga tttgcagatt    19440
gttgattttt attgttttg taaaattcat agccattatc tattctactg ttttgttttt    19500
tttttcactt ctctctctct gtattcttct ttttggactg taagtattca aatgttagat    19560
cattcatatt gcttcataaa ccttatatgc ttccttctgct tttttttttt tgtcaggaac    19620
tctttttttg tatctgtgtt ggtttggata agttctagta gactatgttc aagtttatgg    19680
attattttgt tagttgtgtc taattgactc ctcagtgcat tcagagaatt cttcatctct    19740
gatattataa atctcttcct agcattttca tgttactctt ttctatagtt tccatctctt    19800
tgctgaaatt ctccccctat ccatggatat tgtccacctt taccacaaga ttctttaaca    19860
tattaacata ggtatcatac aaacccaaac tgatagtttc cagatggtgt cttttctgag    19920
tctgtctgtc ttgattgctt tattatttaa cagtgactta tcttccctct tcagcttttg    19980
gtgtgtcttg taattgttta atcaaacact gggtatcata aatggaggaa cagtagagat    20040
tgcagtaaat attatttatg ctttgaaatg ggcacccatc ttctgttgaa aatatgttttt    20100
gtggtcaatt gagtcaacct agtaactggt tgaactgaat ttggcatttg tgcttgttgc    20160
ttttatctta aatgcaccac aggtttaaat tcctccagtg atgggttgct gctatctttt    20220
gcttagagtg gggcctgggg tgtggaagaa ttttctcagt gttcctatct attattagat    20280
tttagcagtc actgcatgcc tgcactacag aggggatatc ttcatacaca taatctaacc    20340
ccattgaaac tgctgtttct tcttaatgaa tgctcaatct ttggtggaaa taaacaaatg    20400
ctgtatctcc tggagccact tcagtcttag tcaggttctg cagggctttg aagggaatgc    20460
attctcagta ttcttgtgcc ttatttggat ggaacttgaa cctgtggtgg gtttggagag    20520
aaagagtagc agacgtctgc tatgttgcaa tgcaggatgc tgggcacaag aaaatttcca    20580
gtctctcctc caaggaaata agatttgatc atctacctat ccctgagaag tgaagggctt    20640
tgcctgcggt gctagatgca aaccattttt tctccccccca ttgcccagaa acttaaggct    20700
ttggcttttc tgagcagtgg tctagggaat tgtgcaaggt tttcatattt gaccctgaca    20760
gcccatcacc acctacagct tgcagtgcca aatgtatctc cctctgatct ctcctgtcct    20820
gtggtcctca tgaacattaa gaagagattt ctaaaaaaga gcttgcacat gagcatagtt    20880
tctggtgaga agaattctga tatgttaact tcctctaaac ttttaaataa aatatttcta    20940
agaattaaat aaagttctag aatgatatga atctattcct ttggtttttt gcacgtctgt    21000
ctgcctgcta atcaagagaa gagaatggtc gtaattctca gagacttttt cctgtttgtg    21060
tcataaatga cttcacattt ttttctgttc taagaactat tcagcttgat ttcttctgtt    21120
ttaatttttag cagcacctga gcaaagccat gtggtccagg attgctacca tggtgatgga    21180
cagagttatc gaggcacgta ctccaccact gtcacaggaa ggacctgcca agcttggtca    21240
tctatgacac cacatcaaca taataggacc acagaaaact acccaaatgc gtatgtcatt    21300
aatcttacag taagcaaaac aaggtccaag taaaatttgt cttagaaaag gtgtgcgtca    21360
```

| | | | | | |
|---|---|---|---|---|---|
| agctaacttc | ttatgattaa | attttctca | cacatagaat | gcatggcaaa | atgtctgaga | 21420 |
| aacattactt | tgagcaaaga | gtatgataga | agagaaatgt | taagctggct | ctctttcctg | 21480 |
| agagtttgat | aaaatcagga | gaatatctgg | cggtggtgag | gccacaataa | tggaaaatca | 21540 |
| gaatgtttag | acagagtcag | cttcaacaac | actcactaaa | ggtcaatgtg | atctttaccc | 21600 |
| cttgaaattc | tataattcta | atctccaatt | cctgaagtga | aggttgtgtt | ggcctttct | 21660 |
| gtcttggctc | acaagtaaat | gatatgtgca | tatctatgga | aaggcgaatc | tatctttttc | 21720 |
| tatatctatg | tctattccaa | cgggtagaaa | caccctgggt | cctgagcacc | agtggtctga | 21780 |
| aggaatacgg | gttgccagga | agagagaagc | aaaggcagga | aggcagatga | aagtaagaaa | 21840 |
| tgagacagat | gctaaacaat | aaaaagtgcg | ggaagataga | cagaagctgg | ggtctgacca | 21900 |
| caccatggcc | agtctttcac | acataagtga | ctaccaaaga | caagaaaaaa | tgatttccgc | 21960 |
| ttgttggaca | atagatggta | gaggaccaag | ggaattgcga | gagagagaac | aatgagatca | 22020 |
| actcaacaga | tgcactggtt | ttcttcctgg | agacccttcc | tgcactgaag | ggcaggagat | 22080 |
| ggagcccaaa | aaaaactgta | gccatcttgc | tgaacagagg | agggacattg | gagtttggga | 22140 |
| ttattcaggt | ggctaggatt | ttctaggcct | gctaacaatg | agaacagatt | tgtggaggaa | 22200 |
| aggagttcta | gaaatatgca | tagaaatctc | ctcgagtcat | tggctaaaca | tgaagctgca | 22260 |
| tgtacacaga | aaatagatcc | acaagaaagt | agggcaaaga | acatctacgg | aagagcagca | 22320 |
| actcaatgg | aacagtgagc | tcaataaaca | tgacagagct | caaatagcac | taaggatat | 22380 |
| tggagtttgg | accacacaga | ggagagagac | ttcactgaac | atcttgggca | ttcagtagag | 22440 |
| acccaggaaa | agccatactt | taggagtaga | attagtatat | tcttagaata | aaggcagctc | 22500 |
| cacacaaaca | atagcaaaac | tgaaaaggaa | gtctccaagc | atcagaatga | tgtccaagtc | 22560 |
| aatgaactgc | ctctgagagg | aaaactcaac | catcttaga | ggtaaacatc | aaagtcaagt | 22620 |
| ggctcagcta | tgcagtatcc | acagtgtgag | gcctaaatat | aaaacttgac | tacacataga | 22680 |
| aaccttttag | tgtgacccac | aagcaggagg | aaaatcagcc | aatacaaaca | gacccagaag | 22740 |
| agacagaaat | gattagaatg | gcataaaaat | ttgacatatc | actatataat | aattgagttc | 22800 |
| taggatttaa | gaaaacatga | atatagaatg | caacagacac | cttatccaga | gacagtaaga | 22860 |
| gtataaagag | ccaaatcgaa | gaactactaa | gagatatgtc | ttaaatgaaa | aaattactag | 22920 |
| atggcctccc | catctagtta | gacatttcag | aagaaaatac | caaatgaaaa | ataattgcat | 22980 |
| agaacctaca | gaaccagata | cacacataca | aaacacacgc | atgcatacac | acacactcaa | 23040 |
| acatgtataa | gcttacaaac | acacacacac | atccacaaat | gctgaaaaat | gaaatcaacc | 23100 |
| gagccacaca | gacataaagg | aaaacataaa | aagatttcct | acatgtggga | agcaagtcac | 23160 |
| agaaagggg | aaggagattg | gaacagaaat | atatactgaa | agcaaggatg | gctgaaaatt | 23220 |
| ttccaaatat | aaagaagatt | aaaaaatcac | ggactcaaga | agctcaatgg | atcagaaaaa | 23280 |
| taatttctaa | aatgacaatt | ataggatgcc | actgggtaca | tagcagttca | actgtcagag | 23340 |
| ggcaaagaca | taatacacag | aaaaatctcg | taaggaacgg | gaaaaacaaa | aagctgtgtc | 23400 |
| ttgctagagg | aacagtgata | caagtgacta | atgtgttccc | atcagaaaca | ctgcaacctg | 23460 |
| gacacaaaag | aataacatta | aagtaataaa | cgtaagaaag | aagagctcaa | ctgagaaggc | 23520 |
| tacatccagc | aataaaatgc | cttgaagttc | atccatgttg | gaggaatgca | cattgtgcac | 23580 |
| tccctaaac | aaagaaaccg | gaaactgtaa | gactttggaa | tcagcaggct | tatgtaacaa | 23640 |
| aagaggtgac | cctaaggaat | taaggagaag | aagaatagaa | caagagggga | actttctgca | 23700 |
| gcctatataa | tgaagaacct | agcaattggc | aaatgtagat | gaaaatgcta | catgtttct | 23760 |

```
tgatcaaacg tttatatctt tttaaatgag agttgacgag ttgaagcaaa atgataccaa    23820
tatatttaac tttaccatat gtagaagtaa aaatttgaac atgtagcata aatcatgtag    23880
ggattaattg gaagtgtacc actgtaagtt tcttacctca tgcacgatag tatgtaatac    23940
taataaaagg ttaatgtgtg ggttcaaagg gatattgcaa atcctagagc aatcacaaag    24000
tttttaactc tgaggtttgt tgtataataa caatatttta tgtattcaaa agagggaagc    24060
caaggaagaa aaaaaagtct ttaaagagct ctggctctta gtacatccag ttgctcattg    24120
aatgagcttc ctggaatgga gggtctggga ctgagactag gccacatgtg tagagccact    24180
agagacacaa tgttggatcc ccatggccca taatacattt cccatttttct caggcagcca    24240 caggtcatga atgtgaggat actgagaggt tggagcaacg ttcttgggag gcataaggaa    24300
gagcgaatgc ttcaagatcc ccgcagccca aactcctcag ctgctttgcc tcctaattca    24360
ttgttttttg ctcctccata gctgtccgac ctcttcagat ctcttagtct tcctgccatc    24420
ttcctttatg ccatgggacc cactgttctt tcaactcatc ccccagttct ggagtggctg    24480
tggacagcag aggatagact gagagcagga gagaaggtcc tgcccaggaa cccattctag    24540
agatactgca ttctgcctgg gagcaagttt tccaggcag cttttgagaag tcttgcagaa    24600 acaaacctac ttgaccgaca tgatatggga atgacagaca gtaatactat ttgcacaatg    24660
cttttccatg ggaaaggtag agccttttca ctaggttttg agtacatgga gtgtgagagt    24720
tgacctggaa aggttatcct ccttgatgcc atgttttctc tgaagaacta catgttcgtt    24780
gcaactccca cattagaata tgaagtccta ccgagagaga tacggagact agacagatac    24840
agatgcattt gcatgtgaat acacaatccc acaatacaga cgtcaaaacc cataccagtt    24900
attccagaga gatggattgg gcagaaggca gaaggagaat actctgatcg tttttcggcc    24960
acgtgtgtgt gttatctcag tgtttctaag aagcgtttgc tactttagat tttttattta    25020
aaaaaaatag taataatcta ttaagtatga gagatgtgca gagaggatta gtgatcgaga    25080 gccattttttg ctggtggcaa tcatatggta cttttaatgg gaatattaga aaggcaccgg    25140
taatgacctt gttgcagcac aaaggagaga gtgtggggtg cccctgcatg ttgtcccacc    25200
tcttgtgacg tgtatcgttt tggaatttcc agtggcttga tcatgaacta ctgcaggaat    25260
ccagatgctg tggcagctcc ttattgttat acgagggatc ccggtgtcag gtgggagtac    25320
tgcaacctga cgcaatgctc agacgcagaa gggactgccg tcgcgcctcc gactgttacc    25380
ccggttccaa gcctagaggc tccttccgaa caaggtaagg agtctgtggc cagacatcta    25440
cacgcttcga tgctgggatg aaaagccatg gaaattccca ctgatgcagc cgccttcaat    25500
ggtaaacgga tgctcgagtg ttgcctgagt tctaccatgt aggaggaagc ctccgtgcac    25560
tctctggggg agccagcgga gtgatttctg gtgcaacgtg gttgggcttt gtctttagga    25620
tgggcacaaa ccctccaggg ggatcgactt caaaattcac cttgttgtaa aacgggctac    25680
ctcagtgtcc cagccaaaat ttttattgta acatgctgtc aggtgtgtca ctcttttcaa    25740
gccagtaagc ttttccgggg atttcttcaa gtagccagca ttcagagcaa tcttcagcat    25800
tgcagattct gagaaatgtg gctctggagc ctgtcaccct cgagaaacct aagagggctg    25860
cattgattcc atgtggccct gggtctatgg agcagtacat gagctcccag tgctctaagg    25920
ctcttcagcc ctaggctttg aagggagtga tttctcagta ttcttaaacc tctttctgat    25980
gacacttgta cctgtgaggg gtctagagag aaagagtagt agactcctac tttactacaa    26040
ttcaggatgc agggcatgag aggattccct ctctcctcca agggaagaag cttttggcgt    26100
```

```
gcacacatcc ctgagaagca aagtgtcttt gtcttcagtc agatacatag gaccgttttc    26160
tgccccatgg cccggaagcc aaaggccttg gctttcatga tcaacggtct agggaaacat    26220
gcaaaatttc catgtctgtc ccaaactctg cccccgacag ccaattacca cctgcagccc    26280
gcattgccaa atgcggtgcc gtttgcatga agattcagta gagtttccta gaaaggtgct    26340
acctcgtgag ctcactttcc aatgaggaat ctgatctgtt gtgtttctct aaggtgtcag    26400
gtgaaatatt tccaagaact tactacagtt ctagaatggg aggaatctgt tgctttggtg    26460
tttgtttgtt ggtcggtttt ctcacatcca tctgcctatg gataaggaaa agagaacggt    26520
cgtaattctc atagactcct ttctggttgt gtcacaaatg gcttcacatg tttctctatg    26580
ctcagagata ctcagcttga tttcccgtgt tttcatttca gcaccgactg agcaaaggcc    26640
tggggtgcag gagtgctacc atggtaatgg acagagttat cgaggcacat actccaccac    26700
tgtcacagga agaacctgcc aagcttggtc atctatgaca ccacactcgc atagtcggac    26760
cccagaatac tacccaaatg cgtatgtctt tgttctttac cataagagaa gaaagggcca    26820
agtgaagttt ctgttacaag agatgtgtct caagctgagt tctccgaact caacttgtga    26880
cagatgcaga tggcgtagca aaatgtctca ggatgattgc cttggagcta agggtctgag    26940
agaagggaaa tgttaagctc cctctccttc ctcctagttc tattgagcag aagggaaatc    27000
tggaggtgag gagatcacat tatgaagaaa gtcagaatga caaaggacca gacacttaga    27060
ttacccttcc acaacaccaa ctaaacgtca atggagactt tccagttgga attccgttat    27120
tctggcttcc acttcctgaa gggaaggttg cgtttgcctt ttctctctgg gttcaagagg    27180
aaagaatagg tgcttattta tggacaggtg aattgatctg tttctatatc tacgtatatt    27240
ccgattgtca gaaaaacact cgttcctaag taccagtggc ctgaagggat acaggttccc    27300
agcaagagaa gatccaagga aggaaggcag atgagagtca gcacagagag ggatgctgaa    27360
aagtaaaagg gatgggtgga tggagagaag cccgggtctg accacccaat ggccaatatt    27420
ttggccacaa gcgactacca gagacatgga aaaatggttt ctacatgtgg gacaacagat    27480
ggtagaggac ctagagaatt gagagagggg caatgatggg ctccactccg cagatgcctt    27540
ggctttcttc ctggatacc ttcctgcact gaatagcaag gagatggagc ccaagcagac    27600
tgtagccatc ttgctgaatg gaggagaggg attggagttt gggatgactg tggtagctga    27660
aatttttcta ggtctgctag aaataagaac tggtttgtgt ggaggaaaag agctctacaa    27720
atacgcatag aagtctcctc cagtcgttgg cctgacatga cgctgcctgt gcacaggaaa    27780
tggttccacg agaaagtgtg gcaaagaaca tttactgaga aacagcaagt acaagagcac    27840
aggaagctca ataaagaaga gagagatcac atagcactct gggatactgg agttcttccc    27900
agctagacca gagagtcctc acggagcaca ttgccaattc agtggagacc ccagaacagc    27960
cgtaatttaa aggtacactt agtatattac tagaataaag tcagctgcag acaacccctt    28020
gcacagctgg aaagcaagtg tccaagcatc aaatcggttt ccaatcaatg aagtgcctgt    28080
gagaggaaat ctcaactctc tttagaagta acaacaaag tcgattgcct cagctatgcg    28140
gtatccgcag agtgagtcct aaatttaaaa tctgactaca tgtagaaaag cgtttcgtgt    28200
gacccatgac caggaaataa atcgggtaat acaaacaggc tcaggaatga gagaaatgat    28260
tagaattgcg tgaaaatttg acatatcagt atgataactg atttcaaata tttaaaaaaa    28320
caacatgcaa gaaagcagat atcatatcaa gagaaattaa cagtacagaa tagccaaatt    28380
aaattaaaga ggtagtataa aaaaagtatg tcttaattga aaaaaattac tgtatggccg    28440
gctgatcaat ttagacgttt cagaggaaaa cattacccaa cacacaattc tagagaacct    28500
```

```
acagaatgag ctacacacac acacacacac acacacacac acactgaaaa cacacccata   28560
ctcacacaca cgcagaaact cacaagttct aacacacaca gacacgcgca cccctgaaga   28620
aacagtgaaa tataaaatta agcgagcctc acagacatgt aggaaaatat gaaaagattt   28680
cctgcatgtg ggaagcaagt cacagtaaag agcaaggggc tttataatag aaacaaatac   28740
cagaatcaag gatggctgat aacttttcaa ttacgaagaa cattaaaaaa aatcacagaa   28800
tcgtgaaact caagggatca tagggaatt tcggaaaaa aaacccaacc tgtatgatgt     28860
acttttgtac atcacagttc gaaggtaaca aggcaaagat gtaataagaa gaaacctgtc   28920 acgaaaact ggaggaaaaa gagctgtgtc ttcctacaag tacactgata caaattgcca    28980
atgtgttcac ctcagaaaca ctggaagcca gataccaggg aatattgtta aaatgataat   29040
caggaacaaa aagagatcaa ccgggaatgc tgaatccagc aataaaatgc cttgaaggtc   29100
atccatgtcg gataaatgca tattgtgcac tgccccaaag aaagaaaccg gaaactgtaa   29160
gaattggaaa tcagcaggct tatgtaacaa gagaggtgac ccgaaggaat taggtagaag   29220
aagaattgaa caagaaagga acttctgca gcccacgtaa tgaagaatcc agcaattggc    29280
aaatgtagat agatgtaaat gcaaaatatt ttcttgatca aatttctata tctttgtaaa   29340
tgagagttga ctacttgaaa caaaatgata gcaagatatt taacttcagc atatgtagag   29400
gtaagaattt gaaatggtag cataaatcac gaagggatta attcgaagtg taccgttgta   29460
agtttcttta cctcatgcac gatggtgtgt catattaata aaagggtact gtgcgggttc   29520
gaagggatat tgcaaatcct agagcaatca caaaggtttg aactctgagg ttttggtat    29580 aataagaata gtccatgcat tcaaaagagg gaagccaagg aagaactaga agtctttcaa   29640
gagctcaggc tcttatacat ccagttgctc attgaaccag cttcctggaa tggagggtct   29700
ggggttgaga ctaggccaca agtctagagt ctctagagag acagtgttgg aaccccatgg   29760
cccataatac atttcccatt ttctcaggca gccagaggtc atgaatgtga ggatactggg   29820
aggttggagc aacgttcttg ggaggcataa ggaagagcga atgcttcaag atccccgcag   29880
cccaaactac tcgcctgctt tgcccccctaa tgcatttttc tctgctgctc cgtagctgtc   29940
cgacctcttc agatctctta gtccaccctg ccgtcttcct ttatgccatg ggtcccactg   30000
ttctttcaac tcatcccct ttccctcagt cccggagtag ctgcggccag cagagggtag    30060
actgagagca ggagagaagg acctgcctag gaaccccttc tagagatact gcatcctgcc   30120
tgggagcaag ttttccaggg cagctttgag aagtcttgga gaaacaaacc tactaaacct   30180
gacagacagt aatactattt gcacaatgct tttctgtggg aaaggtagag ccttttcact   30240
acgtattgag tacatagagt gtgagggttg acctggaacg gctatcctcc tggatgacgt   30300
gtgttttctg aagaactaca tgttcgttgc aactcccaca ttagaatatg aagtcctacc   30360
gagagagata cggagactag acagatacag atgcatttgc atgtgaatac acaatcccac   30420
aatacagacg tcaaacccca taccagttat tccagagaga tggattgggc agaaggcaga   30480
aggagaatac tctgatcgtt tttcggccac gtgtgtgtgt tatctcagtg tttctaagaa   30540
gcgtttgcta ctttagattt tttatttaaa aaaatagtaa taatctatta agtatgagag   30600
atgtgcagag aggattagtg atcgagagcc attttttgctg gtggcaatca tatggtactt   30660
ttaatgggaa tattagaaag gcaccggtaa tgaccttgtt gcagcacaaa ggagagagtg   30720
tggggtgccc ctgcatgttg tcccacctct tgtgacgtgt atcgtttttgg aatttccagt  30780 ggcttgatca tgaactactg caggaatcca gatgctgtgg cagctcctta ttgttatacg   30840
```

```
agggatcccg gtgtcaggtg ggagtactgc aacctgacgc aatgctcaga cgcagaaggg    30900
actgccgtcg cgcctccgac tgttaccccg gttccaagcc tagaggctcc ttccgaacaa    30960
ggtaaggagt ctgtggccag acatctacac gcttcgatgc tgggatgaaa agccatggaa    31020
attcccactg atgcagccgc cttcaatggt aaacggatgc tcgagtgttg cctgagttct    31080
accatgtagg aggaagcctc cgtgcactct ctggggagc cagcggagtg atttctggtg    31140
caacgtggtt gggctttgtc tttaggatgg gcacaaaccc tccagggga tcgacttcaa    31200 aattcacctt gttgtaaaac gggctacctc agtgtcccag ccaaaatttt tattgtaaca    31260
tgctgtcagg tgtgtcactc tttccaagcc agtaagcttt tccggggatt tcttcaagta    31320
gccagcattc agagcaatct tcagcattgc agattctgag aaatgtggct ctggagcctg    31380
tcaccctcga gaaacctaag agggctgcat tgattccatg tggccctggg tctatggagc    31440
agtacatgag ctcccagtgc tctaaggctc ttcagcccta ggctttgaag ggagtgattt    31500
ctcagtattc ttaaacctct ttctgatgac acttgtacct gtgaggggtc tagagagaaa    31560
gagtagtaga ctcctacttt actacaattc aggatgcagg gcatgagagg attccctctc    31620
tcctccaagg gaagaagctt ttggcgtgca cacatccctg agaagcaaag tgtctttgtc    31680
ttcagtcaga tacataggac cgttttctgc cccatggccc ggaagccaaa ggccttggct    31740
ttcatgatca acggtctagg gaaacatgca aaatttccat gtctgtccca aactctgccc    31800
ccgacagcca attccacct gcagcccgca ttgccaaatg cggtgccgtt tgcatgaaga    31860
ttcagtagag tttcctagaa aggtgctacc tcgtgagctc actttccaat gaggaatctg    31920
atctgttgtg tttctctaag gtgtcaggtg aaatatttcc aagaacttac tacagttcta    31980
gaatgggagg aatctgttgc tttggtgttt gtttgttggt cggttttctc acatccatct    32040
gcctatggat aaggaaaaga gaacggtcgt aattctcata gactcctttc tggttgtgtc    32100
acaaatggct tcacatgttt ctctatgctc agagatactc agcttgattt cccgtgtttt    32160
catttcagca ccgactgagc aaaggcctgg ggtgcaggag tgctaccatg gtaatggaca    32220
gagttatcga ggcacatact ccaccactgt cacaggaaga acctgccaag cttggtcatc    32280
tatgacacca cactcgcata gtcggacccc agaatactac ccaaatgcgt atgtctttgt    32340
tctttaccat aagagaagaa agggccaagt gaagtttctg ttacaagaga tgtgtctcaa    32400
gctgagttct ccgaactcaa cttgtgacag atgcagatgg cgtagcaaaa tgtctcagga    32460
tgattgcctt ggagctaagg gtctgagaga agggaaatgt taagctccct ctccttcctc    32520
ctagttctat tgagcagaag ggaaatctgg aggtgaggag atcacattat gaagaaagtc    32580
agaatgacaa aggaccagac acttagatta cccttccaca acaccaacta aacgtcaatg    32640
gagactttcc agttggaatt ccgttattct ggcttccact tcctgaaggg aaggttgcgt    32700
ttgccttttc tctctgggtt caagaggaaa gaataggtgc ttatttatgg acaggtgaat    32760
tgatctgttt ctatatctac gtatattccg attgtcagaa aaacactcgt tcctaagtac    32820
cagtggcctg aagggataca ggttcccagc aagagaagat ccaggaagg aaggcagatg    32880 agagtcagca cagagaggga tgctgaaaag taaagggat gggtggatgg agagaagccc    32940
gggtctgacc acccaatggc caatattttg gccacaagcg actaccagag acatggaaaa    33000
atggtttcta catgtgggac aacagatggt agaggaccta gagaattgag agaggggcaa    33060
tgatgggctc cactccgcag atgccttggc tttcttcctg atacccttc ctgcactgaa    33120 tagcaaggag atggagccca agcagactgt agccatcttg ctgaatggag gagagggatt    33180
ggagtttggg atgactgtgg tagctgaaat ttttctaggt ctgctagaaa taagaactgg    33240
```

```
tttgtggagg aaaagagctc tacaaatacg catagaagtc tcctccagtc gttggcctga    33300
catgacgctg cctgtgcaca ggaaatggtt ccacgagaaa gtgtggcaaa gaacatttac    33360
tgagaaacag caagtacaag agcacaggaa gctcaataaa gaagagagag atcacatagc    33420
actctgggat actggagttc ttcccagcta gaccagagag tcctcacgga gcacattgcc    33480
aattcagtgg agaccccaga acagccgtaa tttaaaggta cacttagtat attactagaa    33540
taaagtcagc tgcagacaac cccttgcaca gctggaaagc aagtgtccaa gcatcaaatc    33600
ggtttccaat caatgaagtg cctgtgagag gaaatctcaa ctctctttag aagtaaacaa    33660
caaagtcgat tgcctcagct atgcggtatc cgcagagtga gtcctaaatt taaaatctga    33720
ctacatgtag aaaagcgttt cgtgtgaccc atgaccagga aataaatcgg gtaatacaaa    33780
caggctcagg aatgagagaa atgattagaa ttgcgtgaaa atttgacata tcagtatgat    33840
aactgatttc aaatatttaa aaaaacaaca tgcaagaaag cagatatcat atcaagagaa    33900
attaacagta cagaatagcc aaattaaatt aaagagctag tataaaaaaa gtatgtctta    33960
attgaaaaaa attactgtat ggccggctga tcaatttaga cgtttcagag gaaaacatta    34020
cccaacacac aattctagag aacctacaga atgagctaca cacacacaca cacacacaca    34080
cacaaactga aaacacaccc atactcacac acacgcagaa actcacaagt tctaacacac    34140
acagacacgc gcacccctga agaaacagtg aaatataaaa ttaagcgagc ctcacagaca    34200
tgtaggaaaa tatgaaaaga tttcctgcat gtgggaagca agtcacagta aagagcaagg    34260
gagtttggaa tagaaacaaa taccggaatc aaggatggct gataacttttt caattacgaa    34320 gaacattaaa aaaaatcaca gaatcgtgaa actcaaggga tcacataggg aatttcggaa    34380
aaaaaaccca acctgtatga tgtacttttg tacatcacag ttcgaaggta acaaggcaaa    34440
gatataataa gaagaaacct gtcacgagaa actggaggaa aaagagctgt gtcttcctac    34500
aagtacactg atacaaattg ccaatgtgtt caccctcagaa acactggaag ccagatacca    34560
gggaatattg ttaaaatgat aatcaggaac aaaaagagat caaccgggaa tgctgaatcc    34620
agcaataaaa tgccttgaag atcatccatg tcggataaat gcatattgtg cactgcccca    34680
aagaaagaaa ccggaaactg taagaattgg aaatcagcag gcttatgtaa caagagaggt    34740
gacccgaagg aattaggtag aagaagaatt gaacaagaaa ggaactttct gcagcccacg    34800
taatgaagaa tccagcaatt ggcaaatgta gatagatgta aatgcaaaat attttcttga    34860
tcaaatttct atatctttgt aaatgagagt tgactacttg aaacaaaatg atagcaagat    34920
atttaacttc agcatatgta gaggtaagaa tttgaaatgg tagcataaat cacgaaggga    34980
ttaattcgaa gtgtaccgtt gtaagtttct ttacctcatg cacgatggtg tgtcatatta    35040 ataaagggt actgtgcggg ttcgaaggga tattgcaaat cctagagcaa tcacaaaggt    35100
ttgaactctg aggttttttgg tataataaga atagtccatg cattcaaaag agggaagcca    35160
aggaagaact agaagtctttt caagagctca ggctcttata catccagttg ctcattgaac    35220
cagcttcctg gaatggaggg tctggggttg agactaggcc acaagtctag agtctctaga    35280
gagacagtgt tggaaccccca tggcccataa tacatttccc attttctcag gcagccagag    35340
gtcatgaatg tgaggatact gggaggttgg agcaacgttc ttgggaggca taggaagag    35400 cgaatgcttc aagatccccg cagcccaaac tactcgcctg ctttgccccc taatgcattt    35460
ttctctgctg ctccgtagct gtccgacctc ttcagatctc ttagtccacc ctgccgtctt    35520
cctttatgcc atgggtccca ctgttctttc aactcatccc cctttccctc agtcccggag    35580
```

```
tagctgcggc cagcagaggg tagactgaga gcaggagaga aggacctgcc taggaaccccc   35640 ttctagagat actgcatcct gcctgggagc aagttttcca gggcagcttt gagaagtctt   35700
ggagaaacaa acctactaaa cctgacagac agtaatacta tttgcacaat gcttttctgt   35760
gggaaaggta gagccttttc actacgtatt gagtacatag agtgtgaggg ttgacctgga   35820
acggctatcc tcctggatga cgtgtgtttt ctgaagaact acatgttcgt tgcaactccc   35880
acattagaat atgaagtcct accgagagag atacggagac tagacagata cagatgcatt   35940
tgcatgtgaa tacacaatcc cacaatacag acgtcaaaac ccataccagt tattccagag   36000
agatggattg gtaggaggc agaaggagaa tactctgatc gttttttcggc cacgtgtgtg   36060 tgttatctca gtgtttctaa gaagcgtttg ctactttaga ttttttattt aaaaaaaata   36120
gtaataatct attaagtatg agagatgtgc agagaggatt agtgatcgag agccattttt   36180
gctggtggca atcatatggt acttttaatg ggaatattag aaaggcaccg gtaatgacct   36240
tgttgcagca caaggagag agtgtggggt gccctgcat gttgtcccac ctcttgtgac   36300
gtgtatcgtt ttggaatttc cagtggcttg atcatgaact actgcaggaa tccagatgct   36360
gtggcagctc cttattgtta tacgagggat cccggtgtca gtgggagta ctgcaacctg   36420 acgcaatgct cagacgcaga agggactgcc gtcgcgcctc cgactgttac cccggttcca   36480
agcctagagg ctccttccga acaaggtaag gagtctgtgg ccagacatct acacgcttcg   36540
atgctgggat gaaaagccat ggaaattccc actgatgcag ccgccttcaa tggtaaacgg   36600
atgctcgagt gttgccggag ttctgccatg ttgggggaag cctccgtgta ctctctgggg   36660 gagccagcg agtgatttct ggtgcaactt gggtgggctt tgtctttaga atgggcacaa   36720
accttccagg gtgatgggct tcacaactca cctccttcta aaatgggcta tctcagtgtc   36780
ttagccaaaa ttttttattgt aacgtgctgt caggtgtgtg attctttctg tcgcagtaag   36840
cttttctggg gatttcttca agtagccagc agtcagtgca atcttcagca ttgcagattt   36900
caaaaaatgt ggctctggag cctgtcatcc tcgagaaacc taacagggct gcattaattc   36960
catatggtcc tgggtctatg agcagtata tgagctccca atgctctaag gctcttcagt   37020
cctaggcttt gaagggagtg atttctcagt gttcttaaac ctcttctga tggcacttgt   37080 acctgtgagg ggtctagaga gaaaggttag tagacttctc ctttactgca attcaggatg   37140
cagggcatga gaagattccc tccctcctcc aagggaagaa ggttttggcg tgcacacatc   37200
cttgagaagc aaagtgtctt tgccttcagt cagatatata ggatcgtttt ctgccccatg   37260
gcctggaagc cagaggcctt ggctttcatg atcaacgatc tagggaaaca tgcaaaattt   37320
ccatgtcttt cccctcctct gccctcgaca gccaattacc acctgcatcc tgcattgcca   37380
aatgcagtgc cctttgtatg aacattcagt agagtttcat agaaaggtgc tacttcgtga   37440
gcgcactttg cagtgagaag gagtctgttc tgttctgttt ttctaaggat ttcaggtgaa   37500
atatttccta gaacttacta cagttctaga ttggtaggaa tctgtaggtt tgctgtatgt   37560
tttttggttg gttttctccc atccatctgc ctacaggtaa gggaaagata acgttcgtaa   37620
ttctcataga ctccttcctg gttgtgtcat aaatggcttc acatatttcg ttattctcag   37680
agatactcag tttatttctt gtgttttcat ttcagcaccg actgagcaga ggcctggggt   37740
gcaggagtgc taccacggta atggacagag ttatcgaggc acatactcca ccactgtcac   37800
tggaagaacc tgccaagctt ggtcatctat gacaccacac tcgcatagtc ggaccccaga   37860
atactaccca aatgcgtatg tctttgttct ttaccataag agaagaaagg gccaagtgaa   37920
gtttctgtta caagagatgt gtctcaagct gagttctccg aactcaactt gtgacagatg   37980
```

```
cagatggcgt agcaaaatgt ctcaggatga ttgccttgga gctaagggtc tgagagaagg    38040
gaaatgttaa gctccctctc cttcctccta gttctattga gcagaaggga aatctggagg    38100
tgaggagatc acattatgaa gaaagtcaga atgacaaagg accagacact tagattaccc    38160
ttccacaaca ccaactaaac gtcaatggag actttccagt tggaattccg ttattctggc    38220
ttccacttcc tgaagggaag gttgcgtttg ccttttctct ctgggttcaa gaggaaagaa    38280
taggtgctta tttatggaca ggtgaattga tctgtttcta tatctacgta tattccgatt    38340
gtcagaaaaa cactcgttcc taagtaccag tggcctgaag ggatacaggt tcccagcaag    38400
agaagatcca aggaaggaag gcagatgaga gccagcacag agagggatgc tgaaaagtaa    38460
aagggatggg tggatggaga gaagcccggg tctgaccacc caatggccaa tattttggcc    38520
acaagcgact accagagaca tggaaaaatg gtttctacat gtgggacaac agatggtaga    38580
ggacctagag aattgagaga ggggcaatga tgggctccac tccgcagatg ccttggcttt    38640
cttcctggat accttcctg cactgaatag caaggagatg gagcccaagc agactgtagc    38700
catcttgctg aatggaggag agggattgga gtttgggatg actgtggtag ctgaaatttt    38760
tctaggtctg ctagaaataa gaactggttt gtggaggaaa agagctctac aaatacgcat    38820
agaagtctcc tccagtcgtt ggcctgacat gacgctgcct gtgcacagga aatggttcca    38880
cgagaaagtg tggcaaagaa catttactga gaaacagcaa gtacaagagc acaggaagct    38940
caataaagaa gagagagatc acatagcact ctgggatact ggagttcttc ccagctagac    39000
cagagagtcc tcacggagca cattgccaat tcagtggaga ccccagaaca gccgtaattt    39060
aaaggtacac ttagtatatt actagaataa agtcagctgc agacaacccc ttgcacagct    39120
ggaaagcaag tgtccaagca tcaaatcggt ttccaatcaa tgaagtgcct gtgggaggaa    39180
atctcaactc tctttagaag taaacaacaa agtcgattgc ctcagctatg cggtatccgc    39240
agagtgagtc ctaaatttaa aatctgacta catgtagaaa agcgtttcgt gtgacccatg    39300
accaggaaat aaatcgggta atacaaacag gctcaggaat gagagaaatg attagaattg    39360
cgtgaaaatt tgacatatca gtatgataac tgatttcaaa tatttaaaaa acaacatgc    39420 aagaaagcag atatcatatc aagagaaatt aacagtacag aatagccaaa ttaaattaaa    39480
gagctagtat aaaaaaagta tgtcttaatt gaaaaaaatt actgtatggc cggctgatca    39540
aattagacgt ttcagaggaa acattaccc aacacacaat tctagagaac ctacagaatg    39600
agctacacac acacacacac acacacacac acactgaa aacacaccca tactcacaca    39660
cacgcagaaa ctcacaagtt ctaacacaca cagacacgcg cacccctgaa gaaacagtga    39720
aatataaaat taagcgagcc tcacagacat gtaggaaaat atgaaaagat ttcctgcatg    39780
tgggaagcaa gtcacagtaa agagcaaggg agtttggaat agaaacaaat accggaatca    39840
aggatggctg ataactttc aattacgaag aacattaaaa aaaatcacag aatcgtgaaa    39900
ctcaagggat catatagggga atttcggaaa aaaacccaa cctgtatgat gtacttttgt    39960
acatcacagt tcgaaggtaa caaggcaaag atataataag aagaaacctg tcacgagaaa    40020
ctggaggaaa aagagctgtg tcttcctaca agtacactga tacaaattgc caatgtgttc    40080
acctcagaaa cactggaagc cagataccag ggaatattgt taaatgata atcaggaaca    40140 aaaagagatc aaccgggaat gctgaatcca gcaataaaat gccttgaaga tcatccatgt    40200
cggataaatg catattgtgc actgccccaa agaaagaaac cggaaactgt cagaattgga    40260
aatcagcagg cttatgtaac aagagaggtg acccgaagga attaggtaga agaagaattg    40320
```

```
aacaagaaag gaactttctg cagcccacgt aatgaagaat ccagcaattg gcaaatgtag   40380
atagatgtaa atgcaaaata ttttcttgat caaatttcta tatctttgta aatgagagtt   40440
gactacttga aacaaaatga tagcaagata tttaacttca gcatatgtag aggtaagaat   40500
ttgaaatggt agcataaatc acgaagggat taattcgaag tgtaccgttg taagtttctt   40560
tacctcatgc acgatggtgt gtcatattaa taaaagggta ctgtgcgggt tcgaagggat   40620
attgcaaatc ctagagcaat cacaaaggtt tgaactctga ggttttggt ataataagaa    40680 tagtccatgc attcaaaaga gggaagccaa ggaagaacta gaagtctttc aagagctcag   40740
gctcttatac atccagttgc tcattgaacc agcttcctgg aatggagggt ctggggttga   40800
gactaggcca caagtctaga gtctctagag agacagtgtt ggaaccccat ggcccataat   40860
acatttccca ttttctcagg cagccagagg tcatgaatgt gaggatactg ggaggttgga   40920
gcaacgttct tgggaggcat aaggaagagc gaatgcttca agatcccgc agcccaaact    40980 actcgcctgc tttgcccct aatgcatttt tctctgctgc tccgtagctg tccgacctct    41040
tcagatctct tagtccaccc tgccgtcttc ctttatgcca tgggtcccat tgttctttca   41100
actcatcccc ctttccctca gtcccggagt agctgcggcc agcagagggt agactgagag   41160
caggagagaa ggacctgcct aggaacccct tctagagata ctgcatcctg cctgggagca   41220
agttttccag ggcagctttg agaagtcttg gagaaacaaa cctactaaac ctgacagaca   41280
gtaatactat ttgcacaatg cttttctgtg ggaaggtag agccttttca ctacgtattg     41340
agtacataga gtgtgagggt tgacctggaa cggctatcct cctggatgac gtgcgttttc   41400
tgaagaacta catgttcgtt gcaactccca cattagaata tgaagtccta ccgagagaga   41460
tacggagact agacagatac agatgcattt gcatgtgaat acacaatccc acaatacaga   41520
cgtcaaaacc cataccagtt attccagaga gatggattgg gcagaaggca gaaggagaat   41580
actctgatcg ttttcggcc acgtgtgtgt gttatctcag tgtttctaag aagcgtttgc     41640
tactttagat ttttattta aaaaaatag taataatcta ttaagtatga gagatgtgca     41700
gagaggatta gtgatcgaga gccatttttg ctggtggcaa tcatatggta cttttaatgg   41760
gaatattaga aaggcaccgg taatgacctt gttgcagcac aaaggagaga gtgtggggtg   41820
cccctgcatg ttgtcccacc tcttgtgacg tgtatcgttt tggaatttcc agtggcttga   41880
tcatgaacta ctgcaggaat ccagatgctg tggcagctcc ttattgttat acgagggatc   41940
ccggtgtcag gtgggagtac tgcaacctga cgcaatgctc agacgcagaa gggactgccg   42000
tcgcgcctcc gactgttacc ccggttccaa gcctagaggc tccttccgaa caaggtaagg   42060
agtctgtggc cagacatcta cacgcttcga tgctgggatg aaaagccatg gaaattccca   42120
ctgatgcagc cgccttcaat ggtaaacgga tgctcgagtg ttgcctgagt tctaccatgt   42180
aggaggaagc ctccgtgcac tctctggggg agccagcgga gtgatttctg gtgcaacgtg   42240
gttgggcttt gtctttagga tgggcacaaa ccctccaggg ggatcgactt caaaattcac   42300
cttgttgtaa aacgggctac ctcagtgtcc cagccaaaat ttttattgta acatgctgtc   42360
aggtgtgtca ctctttccaa gccagtaagc ttttccgggg atttcttcaa gtagccagca   42420
ttcagagcaa tcttcagcat tgcagattct gagaaatgtg gctctggagc ctgtcaccct   42480
cgagaaacct aagagggctg cattgattcc atgtggccct gggtctatgg agcagtacat   42540
gagctcccag tgctctaagg ctcttcagcc ctaggctttg aagggagtga tttctcagta   42600
ttcttaaacc tctttctgat gacacttgta ccctgtgaggg gtctagagag aaagagtagt   42660
agactcctac tttactacaa ttcaggatgc agggcatgag aggattccct ctctcctcca   42720
```

```
agggaagaag cttttggcgt gcacacatcc ctgagaagca aagtgtctttt gtcttcagtc   42780 agatacatag gaccgttttc tgccccatgg cccggaagcc aaaggccttg gctttcatga   42840
tcaacggtct agggaaacat gcaaaatttc catgtctgtc ccaaactctg cccccgacag   42900
ccaattacca cctgcagccc gcattgccaa atgcggtgcc gtttgcatga agattcagta   42960
gagtttccta gaaaggtgct acctcgtgag ctcactttcc aatgaggaat ctgatctgtt   43020
gtgtttctct aaggtgtcag gtgaaatatt tccaagaact tactacagtt ctagaatggg   43080
aggaatctgt tgctttggtg tttgtttgtt ggtcggtttt ctcacatcca tctgcctatg   43140
gataaggaaa agagaacggt cgtaattctc atagactcct ttctggttgt gtcacaaatg   43200
gcttcacatg tttctctatg ctcagagata tcagcttga tttcccgtgt tttcatttca   43260
gcaccgactg agcaaaggcc tggggtgcag gagtgctacc atggtaatgg acagagttat   43320
cgaggcacat actccaccac tgtcacagga agaacctgcc aagcttggtc atctatgaca   43380
ccacactcgc atagtcggac cccagaatac tacccaaatg cgtatgtctt tgttcttac   43440 cataagagaa gaaagggcca agtgaagttt ctgttacaag agatgtgtct caagctgagt   43500
tctccgaact caacttgtga cagatgcaga tggcgtagca aaatgtctca ggatgattgc   43560
cttggagcta agggtctgag agaagggaaa tgttaagctc cctctccttc ctcctagttc   43620
tattgagcag aagggaaatc tggaggtgag gagatcacat tatgaagaaa gtcagaatga   43680
caaaggacca gacacttaga ttaccttcc acaacaccaa ctaaacgtca atggagactt   43740
tccagttgga attccgttat tctggcttcc acttcctgaa gggaaggttg cgtttgcctt   43800
ttctctctgg gttcaagagg aaagaatagg tgcttattta tggacaggtg aattgatctg   43860
tttctatatc tacgtatatt ccgattgtca gaaaaacact cgttcctaag taccagtggc   43920
ctgaagggat acaggttccc agcaagagaa gatccaagga aggaaggcag atgagagtca   43980
gcacagagag ggatgctgaa aagtaaaagg gatgggtgga tggagagaag cccgggtctg   44040
accacccaat ggccaatatt ttggccacaa gcgactacca gagacatgga aaaatggttt   44100
ctacatgtgg gacaacagat ggtagaggac ctagagaatt gagagagggg caatgatggg   44160
ctccactccg cagatgcctt ggcttttcttc ctggatoccc ttcctgcact gaatagcaag   44220
gagatggagc ccaagcagac tgtagccatc ttgctgaatg gaggagaggg attggagttt   44280
gggatgactg tggtagctga aattttttcta ggtctgctag aaataagaac tggtttgtgg   44340
aggaaaagag ctctacaaat acgcatagaa gtctcctcca gtcgttggcc tgacatgacg   44400
ctgcctgtgc acaggaaatg gttccacgag aaagtgtggc aaagaacatt tactgagaaa   44460
cagcaagtac aagagcacag gaagctcaat aaagaagaga gagatcacat agcactctgg   44520
gatactggag ttcttcccag ctagaccaga gagtcctcac ggagcacatt gccaattcag   44580
tggagacccc agaacagccg taatttaaag gtacacttag tatattacta gaataaagtc   44640
agctgcagac aacccttgc acagctgaa agcaagtgtc caagcatcaa atcggtttcc   44700
aatcaatgaa gtgcctgtga gaggaaatct caactctctt tagaagtaaa caacaaagtc   44760
gattgcctca gctatgcggt atccgcagag tgagtcctaa atttaaaatc tgactacatg   44820
tagaaaagcg tttcgtgtga cccatgacca ggaaataaat cgggtaatac aaacaggctc   44880
aggaatgaga gaaatgatta gaattgcgtg aaaatttgaa atatcagtat gataactgat   44940
ttcaaatatt taaaaaaaca acatgcaaga aagcagatat catatcaaga gaaattaaca   45000
gtacagaata gccaaattaa attaaagagc tagtataaaa aaagtatgtc ttaattgaaa   45060
```

```
aaaattactg tatggccggc tgatcaattt agacgtttca gaggaaaaca ttacccaaca    45120
cacaattcta gagaacctac agaatgagct acacacacac acacacacac acacacaaac    45180
tgaaaacaca cccatactca cacacacgca gaaactcaca agttctaaca cacacagaca    45240
cgcgcacccc tgaagaaaca gtgaaatata aaattaagcg agcctcacag acatgtagga    45300
aaatatgaaa agatttcctg catgtgggaa gcaagtcaca gtaaagagca agggagtttg    45360
gaatagaaac aaataccaga atcaaggatg gctgataact tttcaattac gaagaacatt    45420
aaaaaaaatc acagaatcgt gaaactcaag ggatcacata gggaatttcg gaaaaaaaac    45480
ccaacctgta tgatgtactt ttgtacatca cagttcgaag gtaacaaggc aaagatataa    45540
taagaagaaa cctgtcacga gaaactggag gaaaagagc tgtgtcttcc tacaagtaca    45600
ctgatacaaa ttgccaatgt gttcacctca gaaacactgg aagccagata ccagggaata    45660
ttgttaaaat gataatcagg aacaaaaaga gatcaaccgg gaatgctgaa tccagcaata    45720
aaatgccttg aagatcatcc atgtcggata aatgcatatt gtgcactgcc ccaaagaaag    45780
aaaccggaaa ctgtaagaat tggaaatcag caggcttatg taacaagaga ggtgacccga    45840
aggaattagg tagaagaaga attgaacaag aaaggaactt tctgcagccc acgtaatgaa    45900
gaatccagca attggcaaat gtagatagat gtaaatgcaa aatattttct tgatcaaatt    45960
tctatatctt tgtaaatgag agttgactac ttgaaacaaa atgatagcaa gatatttaac    46020
ttcagcatat gtagaggtaa gaatttgaaa tggtagcata aatcacgaag ggattaattc    46080
gaagtgtacc gttgtaagtt tctttacctc atgcacgatg gtgtgtcata ttaataaaag    46140
ggtactgtgc gggttcgaag ggatattgca aatcctagag caatcacaaa ggtttgaact    46200
ctgaggtttt tggtataata agaatagtcc atgcattcaa aagagggaag ccaaggaaga    46260
actagaagtc tttcaagagc tcaggctctt atacatccag ttgctcattg aaccagcttc    46320
ctggaatgga gggtctgggg ttgagactag gccacaagtc tagagtctct agagagacag    46380
tgttggaacc ccatggccca taatacattt cccattttct caggcagcca gaggtcatga    46440
atgtgaggat actgggaggt tggagcaacg ttcttgggag gcataaggaa gagcgaatgc    46500
ttcaagatcc ccgcagccca aactactcgc ctgctttgcc ccctaatgca tttttctctg    46560
ctgctccgta gctgtccgac ctcttcagat ctcttagtcc accctgccgt cttcctttat    46620
gccatgggtc ccactgttct ttcaactcat cccccttttcc ctcagtcccg gagtagctgc    46680
ggccagcaga gggtagactg agagcaggag agaaggacct gcctaggaac cccttctaga    46740
gatactgcat cctgcctggg agcaagtttt ccagggcagc tttgagaagt cttggagaaa    46800
caaacctact aaacctgaca gacagtaata ctatttgcac aatgcttttc tgtgggaaag    46860
gtagagcctt tcactacgt attgagtaca tagagtgtga gggttgacct ggaacggcta    46920
tcctcctgga tgacgtgtgt tttctgaaga actacatgtt cgttgcaact cccacattag    46980
aatatgaagt cctaccgaga gagatacgga gactagacag atacagatgc atttgcatgt    47040
gaatacacaa tcccacaata cagacgtcaa aacccatacc agttattcca gagagatgga    47100
ttgggcagaa ggcagaagga gaatactctg atcgttttc ggccacgtgt gtgtgttatc    47160
tcagtgtttc taagaagcgt ttgctacttt agatttttta tttaaaaaaa atagtaataa    47220
tctattaagt atgagagatg tgcagagagg attagtgatc gagagccatt tttgctggtg    47280
gcaatcatat ggtactttta atgggaatat tagaaaggca ccggtaatga ccttgttgca    47340
gcacaaagga gagagtgtgg ggtgcccctg catgttgtcc cacctcttgt gacgtgtatc    47400
gttttggaat ttccagtggc ttgatcatga actactgcag gaatccagat gctgtggcag    47460
```

```
ctccttattg ttatacgagg gatcccggtg tcaggtggga gtactgcaac ctgacgcaat    47520
gctcagacgc agaagggact gccgtcgcgc ctccgactgt taccccggtt ccaagcctag    47580
aggctccttc cgaacaaggt aaggagtctg tggccagaca tctacacgct tcgatgctgg    47640
gatgaaaagc catggaaatt cccactgatg cagccgcctt caatggtaaa cggatgctcg    47700
agtgttgcct gagttctacc atgtaggagg aagcctccgt gcactctctg ggggagccag    47760
cggagtgatt tctggtgcaa cgtggttggg ctttgtcttt aggatgggca caaaccctcc    47820 aggggatcg acttcaaaat tcaccttgtt gtaaaacggg ctacctcagt gtcccagcca    47880
aaatttttat tgtaacatgc tgtcaggtgt gtcactcttt ccaagccagt aagcttttcc    47940
ggggatttct tcaagtagcc agcattcaga gcaatcttca gcattgcaga ttctgagaaa    48000
tgtggctctg gagcctgtca ccctcgagaa acctaagagg gctgcattga ttccatgtgg    48060
ccctgggtct atggagcagt acatgagctc ccagtgctct aaggctcttc agccctaggc    48120
tttgaaggga gtgatttctc agtattctta aacctctttc tgatgacact tgtacctgtg    48180
aggggtctag agagaaagag tagtagactc ctactttact acaattcagg atgcagggca    48240
tgagaggatt ccctctctcc tccaagggaa gaagcttttg gcgtgcacac atccctgaga    48300
agcaaagtgt ctttgtcttc agtcagatac ataggaccgt tttctgcccc atggcccgga    48360
agccaaaggc cttggctttc atgatcaacg gtctagggaa acatgcaaaa tttccatgtc    48420
tgtcccaaac tcttcccccg acagccaatt accacctgca gcccgcattg ccaaatgcgg    48480
tgccgtttgc atgaagattc agtagagttt cctagaaagg tgctacctcg tgagctcact    48540
ttccaatgag gaatctgatc tgttgtgttt ctctaaggtg tcaggtgaaa tatttccaag    48600
aacttactac agttctagaa tgggaggaat ctgttgcttt ggtgtttgtt tgttggtcgg    48660
ttttctcaca tccatctgcc tatggataag gaaaagagaa cggtcgtaat tctcatagac    48720 tccttctgg ttgtgtcaca aatggcttca catgtttctc tatgctcaga gatactcagc    48780
ttgatttccc gtgttttcat ttcagcaccg actgagcaaa ggcctggggt gcaggagtgc    48840
taccatggta atggacagag ttatcgaggc acatactcca ccactgtcac aggaagaacc    48900
tgccaagctt ggtcatctat gacaccacac tcgcatagtc ggaccccaga atactaccca    48960
aatgcgtatg tctttgttct ttaccataag agaagaaagg gccaagtgaa gtttctgtta    49020
caagagatgt gtctcaagct gagttctccg aactcaactt gtgacagatg cagatggcgt    49080
agcaaaatgt ctcaggatga ttgccttgga gctaagggtc tgagagaagg gaaatgttaa    49140
gctccctctc cttcctccta gttctattga gcagaaggga aatctggagg tgagaagatc    49200
acattatgaa gaaagtcaga atgacaaagg accagacact tagattaccc ttccacaaca    49260
ccaactaaac gtcaatggag actttccagt tggaattccg ttattctggc ttccacttcc    49320
tgaagggaag gttgcgtttg cctttctctct ctgggttcaa gaggaaagaa taggtgctta    49380
tttatggaca ggtgaattga tctgtttcta tatctacgta tattccgatt gtcagaaaaa    49440
cactcgttcc taagtaccag tggcctgaag ggatacaggt tcccagcaag agaagatcca    49500
aggaaggaag gcagatgaga gtcagcacag agagggatgc tgaaaagtaa aagggatggg    49560
tggatggaga gaagcccggg tctgaccacc caatggccaa tattttggcc acaagcgact    49620
accagagaca tggaaaaatg gtttctacat gtgggacaac agatggtaga ggacctagag    49680
aattgagaga ggggcaatga tgggctccac tccgcagatg ccttggcttt cttcctggat    49740
acccttcctg cactgaatag caaggagatg gagcccaagc agactgtagc catcttgctg    49800
```

-continued

```
aatggaggag agggattgga gtttgggatg actgtggtag ctgaaatttt tctaggtctg    49860
ctagaaataa gaactggttt gtgtggagga aaagagctct acaaatacgc atagaagtct    49920
cctccagtcg ttggcctgac atgacgctgc ctgtgcacag gaaatggttc cacgagaaag    49980
tgtggcaaag aacatttact gagaaacagc aagtacaaga gcacaggaag ctcaataaag    50040
aagagagaga tcacatagca ctctgggata ctggagttct tcccagctag accagagagt    50100
cctcacggag cacattgcca attcagtgga daccccagaa cagccgtaat ttaaaggtac    50160
acttagtata ttactagaat aaagtcagct gcagacaacc ccttgcacag ctggaaagca    50220
agtgtccaag catcaaatcg gtttccaatc aatgaagtgc ctgtgagagg aaatctcaac    50280
tctctttaga agtaaacaac aaagtcgatt gcctcagcta tgcggtatcc gcagagtgag    50340
tcctaaattt aaaatctgac tacatgtaga aaagcgtttc gtgtgaccca tgaccaggaa    50400
ataaatcggg taatacaaac aggctcagga atgagagaaa tgattagaat tgcgtgaaaa    50460
tttgacatat cagtatgata actgatttca aatatttaaa aaaacaacat gcaagaaagc    50520
agatatcata tcaagagaaa ttaacagtac agaatagcca aattaaatta aagaggtagt    50580
ataaaaaaag tatgtcttaa ttgaaaaaaa ttactgtatg gccggctgat caatttagac    50640
gtttcagagg aaaacattac ccaacacaca attctagaga acctcagaa tgagctacac     50700 acacacacac acacacacac acaaactgaa aacacaccca tactcacaca cacgcagaaa    50760
ctcacaagtt ctaacacaca cagacacgcg caccctgaa gaaacagtga aatataaaat     50820
taagcgagcc tcacagacat gtaggaaaat atgaaaagat ttcctgcatg tgggaagcaa    50880
gtcacagtaa agagcaaggg agtttggaat agaaacaaat accggaatca aggatggctg    50940 ataactttc aattacgaag aacattaaaa aaaatcacag aatcgtgaaa ctcaagggat     51000
cacatgggga atttcggaaa aaaaacccaa cctgtatgat gtacttttgt acatcacagt    51060
tcgaaggtaa caaggcaaag atataataag aagaaacctg tcacgagaaa ctggaggaaa    51120
aagagctgtg tcttcctaca agtacactga tacaaattgc caatgtgttc acctcagaaa    51180
cactggaagc cagataccag ggaatattgt taaaatgata atcaggaaca aaagagatc      51240 aaccgggaat gctgaatcca gcaataaaat gccttgaagg tcatccatgt cggataaatg    51300
catattgtgc actgccccaa agaaagaaac cggaaactgt aagaattgga aatcagcagg    51360
cttatgtaac aagagaggtg acccgaagga attaggtaga agaagaattg aacaagaaag    51420
gaactttctg cagcccacgt aatgaagaat ccagcaattg gcaaatgtag atagatgtaa    51480
atgcaaaata ttttcttgat caaatttcta tatctttgta aatgagagtt gactacttga    51540
aacaaaatga tagcaagata tttaacttca gcatatgtag aggtaagaat ttgaaatggt    51600
agcataaatc acgaagggat taattcgaag tgtaccgttg taagtttctt tacctcatgc    51660
acgatggtgt gtcatattaa taaagggta ctgtgcgggt tcgaagggat attgcaaatc     51720
ctagagcaat cacaaaggtt tgaactctga ggttttggt ataataagaa tagtccatgc     51780
attcaaaaga gggaagccaa ggaagaacta gaagtctttc aagagctcag gctcttatac    51840
atccagttgc tcattgaacc agcttcctgg aatggagggt ctggggttga gactaggcca    51900
caagtctaga gtctctagag agacagtgtt ggaaccccat ggcccataat acatttccca    51960
ttttctcagg cagccagagg tcatgaatgt gaggatactg ggaggttgga gcaacgttct    52020
tgggaggcat aaggaagagc gaatgcttca agatccccgc agcccaaact actcgcctgc    52080 tttgcccccct aatgcatttt tctctgctgc tccgtagctg tccgacctct tcagatctct    52140
tagtccaccc tgccgtcttc ctttatgcca tgggtcccac tgttctttca actcatcccc    52200
```

```
ctttccctca gtcccggagt agctgcggcc agcagagggt agactgagag caggagagaa    52260
ggacctgcct aggaacccct tctagagata ctgcatcctg cctgggagca agttttccag    52320
ggcagctttg agaagtcttg gagaaacaaa cctactaaac ctgacagaca gtaatactat    52380
ttgcacaatg cttttctgtg ggaaaggtag agccttttca ctacgtattg agtacataga    52440
gtgtgagggt tgacctggaa cggctatcct cctggatgac gtgcgttttc tgaagaacta    52500
catgttcgtt gcaactccca cattagaata tgaagtccta ccgagagaga tacggagact    52560
agacagatac agatgcattt gcatgtgaat acacaatccc acaatacaga cgtcaaaacc    52620
cataccagtt attccagaga gatggattgg gcagaaggca gaaggagaat actctgatcg    52680
tttttcggcc acgtgtgtgt gttatctcag tgtttctaag aagcgtttgc tactttagat    52740
tttttattta aaaaaaatag taataatcta ttaagtatga gagatgtgca gagaggatta    52800
gtgatcgaga gccattttg ctggtggcaa tcatatggta cttttaatgg gaatattaga     52860
aaggcaccgg taatgacctt gttgcagcac aaaggagaga gtgtgggtg ccctgcatg      52920
ttgtcccacc tcttgtgacg tgtatcgttt tggaatttcc agtggcttga tcatgaacta    52980
ctgcaggaat ccagatgctg tggcagctcc ttattgttat acgagggatc ccggtgtcag    53040
gtgggagtac tgcaacctga cgcaatgctc agacgcagaa gggactgccg tcgcgcctcc    53100
gactgttacc ccggttccaa gcctagaggc tccttccgaa caaggtaagg agtctgtggc    53160
cagacatcta cacgcttcga tgctgggatg aaaagccatg gaaattccca ctgatgcagc    53220
cgccttcaat ggtaaacgga tgctcgagtg ttgcctgagt tctaccatgt aggaggaagc    53280
ctccgtgcac tctctggggg agccagcgga gtgatttctg gtgcaacgtg gttgggcttt    53340
gtctttagga tgggcacaaa ccctccaggg ggatcgactt caaaattcac cttgttgtaa    53400
aacgggctac ctcagtgtcc cagccaaaat ttttattgta acatgctgtc aggtgtgtca    53460
ctctttccaa gccagtaagc ttttccgggg atttcttcaa gtagccagca ttcagagcaa    53520
tcttcagcat tgcagattct gagaaatgtg gctctggagc ctgtcaccct cgagaaacct    53580
aagagggctg cattgattcc atgtggcct gggtctatgg agcagtacat gagctcccag      53640
tgctctaagg ctcttcagcc ctaggctttg aagggagtga tttctcagta ttcttaaacc    53700
tctttctgat gacacttgta cctgtgaggg gtctagagag aaagagtagt agactcctac    53760
tttactacaa ttcaggatgc agggcatgag aggattccct ctctcctcca agggaagaag    53820
cttttggcgt gcacacatcc ctgagaagca aagtgtcttt gtcttcagtc agatacatag    53880
gaccgttttc tgccccatgg cccggaagcc aaaggccttg gctttcatga tcaacggtct    53940
agggaaacat gcaaaatttc catgtctgtc ccaaactctg cccccgacag ccaattacca    54000
cctgcagccc gcattgccaa atgcggtgcc gtttgcatga agattcagta gagttttccta   54060
gaaaggtgct acctcgtgag ctcactttcc aatgaggaat ctgatctgtt gtgtttctct    54120
aaggtgtcag gtgaaatatt ccaagaact tactacagtt ctagaatggg aggaatctgt     54180
tgctttggtg tttgtttgtt ggtcggtttt ctcacatcca tctgcctatg gataaggaaa    54240
agaaacggt cgtaattctc atagactcct ttctggttgt gtcacaaatg gcttcacatg     54300
tttctctatg ctcagagata ctcagcttga tttcccgtgt tttcatttca gcaccgactg    54360
agcaaaggcc tggggtgcag gagtgctacc atggtaatgg acagagttat cgaggcacat    54420
actccaccac tgtcacagga agaacctgcc aagcttggtc atctatgaca ccacactcgc    54480
atagtcggac cccagaatac tacccaaatg cgtatgtctt tgttctttac cataagagaa    54540
```

```
gaaagggcca agtgaagttt ctgttacaag agatgtgtct caagctgagt tctccgaact    54600
caacttgtga cagatgcaga tggcgtagca aaatgtctca ggatgattgc cttggagcta    54660
agggtctgag agaagggaaa tgttaagctc cctctccttc ctcctagttc tattgagcag    54720
aagggaaatc tggaggtgag gagatcacat tatgaagaaa gtcagaatga caaaggacca    54780
gacacttaga ttacccttcc acaacaccaa ctaaacgtca atggagactt ccagttgga    54840 attccgttat tctggcttcc acttcctgaa gggaaggttg cgtttgcctt ttctctctgg    54900
gttcaagagg aaagaatagg tgcttattta tggacaggtg aattgatctg tttctatatc    54960
tacgtatatt ccgattgtca gaaaaacact cgttcctaag taccagtggc ctgaagggat    55020
acaggttccc agcaagagaa gatccaagga aggaaggcag atgagagtca gcacagagag    55080
ggatgctgaa aagtaaaagg gatgggtgga tggagagaag cccgggtctg accacccaat    55140
ggccaatatt ttggccacaa gcgactacca gagacatgga aaaatggttt ctacatgtgg    55200
gacaacagat ggtagaggac ctagagaatt gagagagggg caatgatggg ctccactccg    55260
cagatgcctt ggctttcttc ctggataccc ttcctgcact gaatagcaag gagatggagc    55320
ccaagcagac tgtagccatc ttgctgaatg gaggagaggg attggagttt gggatgactg    55380
tggtagctga aattttcta ggtctgctag aaataagaac tggtttgtgt ggaggaaaag    55440
agctctacaa atacgcatag aagtctcctc cagtcgttgg cctgacatga cgctgcctgt    55500
gcacaggaaa tggttccacg agaaagtgtg gcaaagaaca tttactgaga aacagcaagt    55560
acaagagcac aggaagctca ataaagaaga gagagatcac atagcactct gggatactgg    55620
agttcttccc agctagacca gagagtcctc acggagcaca ttgccaattc agtggagacc    55680
ccagaacagc cgtaatttaa aggtacactt agaatattac tagaataaag tcagctgcag    55740 acaaccccctt gcacagctgg aaagcaagtg tccaagcatc aaatcggttt ccaatcaatg    55800
aagtgcctgt gagaggaaat ctcaactctc tttagaagta acaacaaag tcgattgcct    55860 cagctatgcg gtatccgcag agtgagtcct aaatttaaaa tctgactaca tgtagaaaag    55920
cgtttcgtgt gacccatgac caggaaataa atcgggtaat acaaacaggc tcaggaatga    55980
gagaaatgat tagaattgcg tgaaaatttg acatatcagt atgataactg atttcaaata    56040
tttaaaaaaa caacatgcaa gaaagcagat atcatatcaa gagaaattaa cagtacagaa    56100
tagccaaatt aaattaaaga gctagtataa aaaagtatg tcttaattga aaaaaattac    56160
tgtatggccg gctgatcaaa ttagacgttt cagaggaaaa cattacccaa cacacaattt    56220
tagagaacct acagaatgag ctacacacac acacacacac acacacacac acacaaactg    56280
aaaacacacc catactcaca cacacgcaga aactcacaag ttctaacaca cacagacacg    56340
cgcacccctg aagaaacagt gaaatataaa attaagcgag cctcacagac atgtaggaaa    56400
atatgaaaag atttcctgca tgtgggaagc aagtcacagt aaagagcaag ggagtttata    56460
atagaaacaa ataccagaat caaggatggc tgataaacttt tcaattacga agaacattaa    56520
aaaaaatcac agaatcgtga aactcaaggg atcatatagg gaatttcgga aaaaaaaccc    56580
aacctgtatg atgtactttt gtacatcaca gttcgaaggt aacaaggcaa agatgtaata    56640
agaagaaacc tgtcacgaga aactggagga aaaagagctg tgtcttccta caagtacact    56700
gatacaaatt gccaatgtgt tcacctcaga aacactggaa gccagatacc agggaatatt    56760
gttaaaatga taatcaggaa caaaagaga tcaaccggga atgctgaatc cagcaataaa    56820
atgccttgaa ggtcatccat gtcggataaa tgcatattgt gcactgcccc aaagaaagaa    56880
accggaaact gtaagaattg gaaatcagca ggcttatgta acaagagagg tgacccgaag    56940
```

```
gaattaggta gaagaagaat tgaacaagaa aggaactttc tgcagcccac gtaatgaaga    57000
atccagcaat tggcaaatgt agatagatgt aaatgcaaaa tatttcttg atcaaatttc    57060 tatatctttg taaatgagag ttgactactt gaaacaaaat gatagcaaga tatttaactt    57120
cagcatatgt agaggtaaga atttgaaatg gtagcataaa tcacgaaggg attaattcga    57180
agtgtaccgt tgtaagtttc tttacctcat gcacgatggt gtgtcatatt aataaaaggg    57240
tactgtgcgg gttcgaaggg atattgcaaa tcctagagca atcacaaagg tttgaactct    57300 gaggttttg gtataataag aatagtccat gcattcaaaa gagggaagcc aaggaagaac    57360
tagaagtctt tcaagagctc aggctcttat acatccagtt gctcattgaa ccagcttcct    57420
ggaatggagg gtctggggtt gagactaggc cacaagtcta gagtctctag agagacagtg    57480
ttggaacccc atggcccata atacatttcc cattttctca ggcagccaga ggtcatgaat    57540
gtgaggatac tgggaggttg gagcaacgtt cttgggaggc ataaggaaga gcgaatgctt    57600
caagatcccc gcagcccaaa ctactcgcct gctttgcccc ctaatgcatt tttctctgct    57660
gctccgtagc tgtccgacct cttcagatct cttagtccac cctgccgtct tcctttatgc    57720
catgggtccc actgttcttt caactcatcc ccctttccct cagtcccgga gtagctgcgg    57780
ccagcagagg gtagactgag agcaggagag aaggacctgc ctaggaaccc cttctagaga    57840
tactgcatcc tgcctgggag caagttttcc agggcagctt tgagaagtct tggagaaaca    57900
aacctactaa acctgacaga cagtaatact atttgcacaa tgcttttctg tgggaaggt    57960 agagccttt cactacgtat tgagtacata gagtgtgagg gttgacctgg aacggctatc    58020
ctcctggatg acgtgcgttt tctgaagaac tacatgttcg ttgcaactcc cacattagaa    58080
tatgaagtcc taccgagaga gatacggaga ctagacagat acagatgcat ttgcatgtga    58140
atacacaatc ccacaataca gacgtcaaaa cccataccag ttattccaga gagatggatt    58200
gggcagaagg cagaaggaga atactctgat cgttttttcgg ccacgtgtgt gtgttatctc    58260
agtgtttcta agaagcgttt gctactttag attttttatt taaaaaaaat agtaataatc    58320
tattaagtat gagagatgtg cagagacgat tagtgatcga gagccatttt tgctggtggc    58380
aatcatatgg tacttttaat gggaatatta gaaaggcacc ggtaatgacc ttgttgcagc    58440
acaaaggaga gagtgtgggg tgccctgca tgttgtccca cctcttgtga cgtgtatcgt    58500 tttgaatt ccagtggctt gatcatgaac tactgcagga atccagatgc tgtggcagct    58560
ccttattgtt atacgaggga tcccggtgtc aggtgggagt actgcaacct gacgcaatgc    58620
tcagacgcag aagggactgc cgtcgcgcct ccgactgtta ccccggttcc aagcctagag    58680
gctccttccg aacaaggtaa ggagtctgtg gccagacatc tacacgcttc gatgctggga    58740
tgaaaagcca tggaaattcc cactgatgca gccgccttca atggtaaacg gatgctcgag    58800
tgttgcctga gttctaccat gtaggaggaa gcctccgtgc actctctggg ggagccagcg    58860
gagtgatttc tggtgcaacg tggttgggct ttgtctttag gatgggcaca aaccctccag    58920
ggggatcgac ttcaaaattc accttgttgt aaaacgggct acctcagtgt cccagccaaa    58980 attttattg taacatgctg tcaggtgtgt cactctttcc aagccagtaa gcttttccgg    59040
ggatttcttc aagtagccag cattcagagc aatcttcagc attgcagatt ctgagaaatg    59100
tggctctgga gcctgtcatc ctcgagaaac ctaacagggc tgcattaatt ccatatggtc    59160
ctgggtctat ggagcagtat atgagctccc aatgctctaa ggctcttcag tcctaggctt    59220
tgaagggagt gatttctcag tgttcttaaa cctctttctg atggcacttg tacctgtgag    59280
```

```
gggtctagag agaaaggtta gtagacttct cctttactgc aattcaggat gcagggcatg   59340
agaagattcc ctccctcctc caagggaaga aggttttggc gtgcacacat ccttgagaag   59400
caaagtgtct ttgccttcag tcagatatat aggatcgttt tctgcccat ggcctggaag    59460 ccagaggcct tggctttcat gatcaacgat ctagggaaac atgcaaaatt tccatgtctt   59520
tcccctcctc tgccctcgac agccaattac cacctgcatc ctgcattgcc aaatgcagtg   59580
ccctttgtat gaacattcag tagagtttca tagaaaggtg ctacttcgtg agcgcacttt   59640
gcagtgagaa ggagtctgtt ctgttctgtt tttctaagga tttcaggtga aatatttcct   59700
agaacttact acagttctag attggtagga atctgtaggt ttgctgtatg ttttttggtt   59760
ggttttctcc catccatctg cctacaggta agggaaagat aacgttcata attctcatag   59820
actcctttct ggttgtgtca taaatggctt cacatatttc gttattctca gagatactca   59880
gtttatttct tgtgttttca tttcagcacc gactgagcag aggcctgggg tgcaggagtg   59940
ctaccacggt aatggacaga gttatcgagg cacatactcc accactgtca ctggaagaac   60000
ctgccaagct tggtcatcta tgacaccaca ctcgcatagt cggaccccag aatactaccc   60060
aaatgcgtat gtctttgttc tttaccataa gagaataaag gccaactga agtttctgtg    60120 acaagagaca tgcttcaagc tgagttctcc gaactcaact tgtgtcagat tcagatggtg   60180
tagcaaaatg tctcaggatg atttccttgg agctaagggt ctgagagaag agaaatgtta   60240
agctgcctca ccttcctcct agttttgtgg agcagaaggg aaatgaggag gcgaggagat   60300
caccttatga agaaagtcag aatgacgaac caccaaacac ttagattacc cttgcccaac   60360
acccactaag cgtcaatgaa gactttccag ttggaattcc gttattctga cttccaattc   60420
ctgaagggaa gattgtgttt gccttttctg tctgggctca tgaggaaagt ttatgtgctt   60480
acttatggac aggtgaattg atctgtttct atttctacct gtattccaat agggagaaaa   60540
tctcttggtc ctaagtacca gtggcctgaa aggatagagg ttcccagcaa gagaagatcc   60600
aaggaaggaa ggcagatgag agtcagcaca gagagggatg ctgaaaagta aaagggatgg   60660
gtagatggat agaagccctg gtctgaccac cccatggcca atcatttggc cataatcaac   60720
aaccaaagac atggaaaaat ggtttctaca tgtgggacaa cagatggtag aggacctaga   60780
gaattgagag agggccaatg atgagctcaa ctccatagat gccttggctt tcttcctgga   60840
tacccttcct gcactgaata gcaaggagat ggagctcaag cagcctgtag ccatctagct   60900
gagcagagga gagggattgg agtttgggat gactctggta ttttctaggt ccgctacaaa   60960
taagaactgg tttgtggagg aaaggagctc tacaaatacg catagaagtc tcctccagta   61020
gttggcctca catgacactg catgtgcaca gaaaatggtt ctacagaaag tgtggcaaag   61080
aacatttact gagaaacagc aactacaaga gaacagcaag ctcaattaag aagatagaga   61140
tcacatagca ctctgtgtta ttggagttct taccagctag atgagagagt gctcacggaa   61200
cacattgcca attcagtgga gaccccagaa cagccataat ttcaaagtac aattagtata   61260
ttactagaat aaaggcagct gcagacaacc ccttgcacag ctgaaaagca agtgtccaag   61320
catcaaatgg gtttccaatc aatgaagtgc ctgtgagagg aaatctcaac tctcttcaga   61380
agtaaacaac aaagtcaatt gcctcagcta tgcggtatcc ccagagtgag tcctaaatta   61440
aaaatttgac tacgtgtaga aaagaatttc gtgtgatcca tgaccagaaa ataaatcagg   61500
caatacaaac aggctcagaa atgacatcga taattagaat tgcatgaaaa tttgacatat   61560
cagtatgata actgatttca gatatttaaa aaaagtgcaa caaagcaggt atcatatcaa   61620
gacaaattaa tagtatagaa tagccaaatc aaattaaaga actattatac aaaaagtatg   61680
```

```
tcttaaatga agaaattact gtatgtccgc ctgaaaaatt tagatgtttc agaagaaaaa    61740
attaaccaaa aacaattctg cagaacctac agaatgagcc acacacacac acattcaaaa    61800
cacacccata cacacacaca tgcaaaaact cacaagttct aacacacaca caaacacaca    61860
cacacatgca catccctaaa gaaatagga aatataaaat taaccgaccc tcagagacat    61920
gcaggaaaat ataagaagat ttcctgcatg tgggaagcaa gtcacagtaa agagcaaggg    61980
agtttggagt agatacaaat accggaatca cggatggctg ataacttttc aattatgaag    62040
aacgttagaa aaatcacaga ttcatgaaac taaagggatc aaataggaaa tttcgagaaa    62100
aaaaactaca tgatgcactt ctctacatca cagttcaaag gtaacaaggc aaggatataa    62160
gaagaagaaa catctcacga gaaactggag aaaaagagc tgtgtcttcc tagagtacag    62220
tgatacaaat tgctaatgcg ttcacctcag aaacactgga agccagatac cagggaatat    62280
tattaaaatg ataatgagga acaagaagag atcaaccgag aatgctgaat ccagcaataa    62340
aatgccttga agatcatcca tgttggataa atgcatattg tgcactgccc aaaacaaaga    62400
aactggaaag tgtaagactt tggaatcagc aggcttatgt agcaacagag gtgacccgaa    62460
agaattaggt ataagaagaa tagaagaatt gcatgaaaat ttgacatatg actaagataa    62520
ctatttcaaa tatttaaaaa aagatgaata tgtaataaaa cagataaaat atcaaaagaa    62580
agtaacagta ttgactagcc aaatcaaatt aaagacttag tgtaaaaagc tatgtcttaa    62640
aagaaaaaat tactggatgg ctgcctgatc aatttagaca tttctgaata ggaaactaac    62700
caaaaatcaa ttctcagaa ccaactacac acatatatac acatacaaca cacccataca    62760
cacccacgca aaaactcaca agttcacaca cacacacaca cacacacaac cctcaagaaa    62820
tagtgaaata gaaaaccaac cgaacctcac agacatgttg caaaatagga aaagatttcc    62880
tgcatatggg aagcaagtca cagaaaagag aacgggagat tggaaacaga aacaaatacc    62940
ggaatcaagg atggccgaaa acttttcatt gatcaagaat attaacaaaa tcgcaaaaac    63000
acgaaattca atgcatcaaa taggcgtttc gaaaaaaga aaaaatctgg tatgatgcac    63060
ttttgtactt cacattttca cggtaagaag acaaagatat aataacaaga aacttcttat    63120
gagaaactgg ggaaaaacaa gctgtttctt gctagaagaa cagtgataca aattgctaat    63180
gcattctcgt caaaaacact ggaagccaga taccgggaat gttattaatg tggtaaacag    63240
gaacaagaag agatcaacca agaatgctaa atccagcaat aaaatgcctt gaagatcatc    63300
catgctgcat aaatgtatgt tgtgcactgc cccaaacaaa gaaaccggaa actgtaagaa    63360
tttggaatca gcaggctgat gtaacaagag aggtgaccca aaggaattag gtagaagaag    63420
aatagtacaa gaagggaact ttctgcagcc catgtaatga agaacccagc aattggcaaa    63480
tgtagatgta aatgcaaaat attttcttga ccaaatttct atatatttt aaatgagcgt    63540
tgactactgg aaacaaaatg atagcaatat atttaatttt agcatatgta gaggtaagaa    63600
tttgaacaag tagcgtaaat catgtaggga ataattagaa gtgtaccatt gtaagttct    63660
tacctcatgc acaatggtat gtaatattaa taaaatgtta ctgtgtgggt tcaaggagat    63720
attgcaaatc ctagagcaat cacaaagttt tgaactctga ggtatattgt ataataagaa    63780
tattccatgt attcaaaaga gagaagccaa ggaagaaaga aatttgtcac gagtttgggc    63840
tcttagtaca tcctgtagct cattgaacca gcttcctgga atggagggtc tgggattgac    63900
actaggccac atgtatagag tctctagaga gacagtgttt catccccatg gcccgtaata    63960
catttcccat tttctcaggc agccacaggt catgaatgtg aggatagaga gaggttggag    64020
```

```
caacgttctt gggaggcata aggaagagca aatgcttcaa gatccccgca gcccaaactc    64080
ctacctgctt tgccccctaa tgcagtgttc ctccgtagct gtccgacctc ttcagatctc    64140
ttagtctacc ctgccatctt cctttatgcc atgggtccca ctgttctttc aactcatccc    64200
cctttccctc agtgcagagt agctgcggcc agcagagggt agactgagag caggagagaa    64260
ggtcctgccc aggaacccat tctagagatg ctgcattctg cctgggagca gttttccag    64320 ggcagctttg agaagtcttg cagaaacaaa cctatttgac ccacatgata tgggaatgac    64380
agaaagtaat acaatttgca cagtgctttt ccatgggaaa agtagagcct tttcgcgagg    64440
ttttgagtac atagagagtg aaggttgacc tggaaaggtt atcctcctgg atcccatgtt    64500
ttttctgaag aactacctgt tagttgcaac ttgcacatta gaatatgaag tcctaccgag    64560
agagatacgg agaactagat aaatacagat acttttgtat gtgaataaac gattccacaa    64620
tacacacatc aaaatccata ccagttattc cagagagatg gattgggcag aaggcagaag    64680
gagaatactc tgatcgtttt ttgcccacgt gtatgtatta tctcagtgtt tctaagaagc    64740
gtttgctact ttagattttt ttttataata ataatcttt aagtatgaga aatgtgcaga    64800
caggattagt gattgagagc catttgtgct tgtggcaatc atatggtact tttatgggaa    64860
tattagaaag gcactggtaa tgaccttgtt gcagcacaaa ggagagggtg tggggtgccc    64920
ctgcatattg tcccacctct tgtgacgtgt atcgttttgg aatttccagt ggcttgatca    64980
tgaactactg caggaatcca gatcctgtgg cagccccta tgttatacg agggatccca    65040 gtgtcaggtg ggagtactgc aacctgacac aatgctcaga cgcagaaggg actgccgtcg    65100
cgcctccaac tattacccg attccaagcc tagaggctcc ttctgaacaa ggtaaggagc    65160
ctgtggccag aaacctacac gtttcgatgc tgggatgaaa agccatggaa attcccactg    65220
atgcagcagc ctccaatggt aaacggatgc tcgagtgttg actgagttct gtcatgtagg    65280
aggaagcctc cgtgcactct ctgggggagc cagcggattg atttctggta caacgttggg    65340
tgggctgtgt ctttagaatt ggcacaaacc ctccagggtg atcgacttca caactcacct    65400
cgttgaaaaa tgggctatct cagtgtctta gccaaaattt ttattgtaac atgctgtcag    65460
atgtgtgact ctttccaagc cagtaagctt ttcctgggac ttcttcaatt agccagcatt    65520
cagtgcaatc ttcagcattg cagattcaga gaaatgtggc tctggagcct gtcacccttg    65580
agaaacaggg ctaacagggt tgcattaatt ccaaatcacc ctggttctat ggagcagtac    65640
atgaactccc aatgatctat gtttcaggac ttcctcagtc ataggtgggc tctgcagccc    65700
taggttttta agtgagtgac tgccccgtgt tctggtggca gttgtacctg tgagcggtct    65760
ggatagaaag agtcggagac ttctgtatta ttgcaactca ggatgtgggt catgagagga    65820
tttcatctct cctgcagggg agtaagctgt tcgcctccac ccatccctga taactgaagt    65880
gtctttgtct gcagtcctag acgaaggact gttgtctctc ccatggccca gaagctgaag    65940
accttgcctt ttgttatgaa acgttcattg tttttcatgtc tgtccgtttc tctgccccta    66000
acacccaatc accatgtatg gcctgtaccc ccaaatgcat cgtgctttgc tgtttgctgc    66060
cccatagtcc tcatgaacat tcagtagaaa ttcccataaa tgtgcttgca cgtgagcaca    66120
gtttccattg agaagccctc tcatttgtcc ttttttcta agcttttatg tgaaatattt    66180
ctaagaactt actacagttc taaagtgtta ggaatttgtt tctttggtgt ttttgtttgt    66240
tggttggttg ttgcttttct caagtccatc tgcctacaaa taaagaaaca agaatgttac    66300
ttgtcatatt ctcctgaggt cataattctc agagactttt ttctggtttg tgccataagt    66360
ggcttcacat gtttgtctct tcttggaaac actcagtttg atttcttttc ttttcatttc    66420
```

```
agcaccaact gagcaaaggc ctggggtgca ggagtgctac cacgaaaatg gacagagtta   66480
tcaaggcaca tacttcatta ctgtcacagg aagaacctgc caagcttggt catctatgac   66540
accacactcg catagtcgga ccccagcata ctacccaaat gcgtatgtct attttcttta   66600
ccataagtga aggaagggtc agtggaaatt tctgttagta gagtcatgct tcaagctgag   66660
tgttcaggac tcaagttgtc tcagatgaac agtgcatagc aaaatgtctc aggaacattg   66720
tctttgagca aagagtctaa gagaagacaa atgttaatct ggctctcctt cctcctagtt   66780
taatggagca gaaaggtatc tggaggcaag gatatcacat taagaaacaa gtcaagatga   66840
caaatgatga aactcttaga gtacccttcc acaacaccca ctaaggttca atgcagcctt   66900
ttctccttgg aattctatta aactaaactc caattcctga agtgaaggtt ctgttggggt   66960
tttctgtttt ggcttacaag gaaagtatat atgtatatct atggagaggc aaatctatct   67020
ctttctatat ctacgtctat tccaatatgt agaaacacag tcggttctga ccaccagtgg   67080
tctgaaggga tactggttgt tagagaataa aaatggcagg aaggcagatg agagtcagca   67140
aagagagaga tcctgtaaag taaaagggtg gatagatgga cagaagccca ggtctgacca   67200
gcccatggcc aggctttagg ccataagtga caccaaagac atggaaaaat ggtttctaca   67260
tgttggacaa cagacagtag tggaccaaaa gaatagtgac aggggaaca atgagatcaa   67320 ctccatagat accttggctt tcttcctgga ggcccttctt gcactgaaga gcaaggtgat   67380
ggagcccaga tggactgtag ccatcttcct gaatgcagga gagagattgg aatttgggac   67440
tactgtggta gctaggattt tataggcctg ctgagaatga gaatggattt gtggatgaaa   67500
ggagctccag gggcacgcat agtagtctcc tcgaatcttt ggctaaacat gacgttgcat   67560
gtgcccagaa aaaggttcca caagaaagta gagaaaagaa tatatcctga ggaatagcaa   67620
ctgcgattga acagtgagct caataaagag gacagagccc tcatagcatt ctgggatact   67680
ggagttctga ccagctggag gagagacctc actgaacctc ttgggaatac agtagagact   67740
ccagaaaagt catactttag gagtagaatt agtaaatttc tagaaaaaaa ggcagctcta   67800
gacaaaccct ggcaaaactg aaaagcaagt ctccaagcat taaaatcatt tccaagtcaa   67860
ttaactgcct gggagaggaa aaccctcttt agaggtaaac aacaaagtca agtggctcag   67920
ctatgtggtg ttcacagtgt gagttctaaa tttaaaactt gactacacat agagaagctt   67980
ttagtatgaa ccatgaccag gtgaaaaatc agtcaataca aatagaccta gaaatgcacag  68040 aaatgattag aatggcaaaa aatttgacat atcaatatgt caactgagtt ttaggtttta   68100
agaaaacatg aatacggaat gaagcagata ccatatcaag agacagtaac agtatagaag   68160
agccaaatta aattaaagaa ctagtataag aaggtatgtc ttaaatgaaa aaattactgg   68220
atgtattccc aatggagtga gatgtttcag aagtaaaaac taactgaaaa acaattttat   68280
accacctaca gaaccagcta cacatacaca aatgacacac acatatacac acatactcac   68340
acatgcacag gcttagaaac atgcacgcac acacacacac acacacacac acacctccac   68400
aaatactaaa aaatgaaatc cactgatcct cacagacagg cgggaaaata taaaaagatt   68460
tcctgcatgt gggtaggaag tcacagaagg agaggaagga gagattgcta caggaacaaa   68520
tactggaagc aaggatagct aaaaactttt caaataagaa gaatattaaa aaccacagat   68580
tcaagaagct gaatgaatca gacagggaat ttccaaaaaa aaaaaaaaaa aaactgtatg   68640
attcactttt gtacatcacc gttcaacagt cagaaggcaa agatataata acaagaaaca   68700
tctcatgaga aactggagga aaaagagctg tgtcttgcta gaagaacagt gatacaaatt   68760
```

```
gctaatgcat tctcatcaga aacactggaa cccagttaac aggggatatc attaaaatga  68820
taaactagaa aaaaaagaga tcaaatgaga atgctacatc cagcaataaa atgccttgaa  68880
gatcatccat gttggataaa tgcatattgt gcactgcccc aaataaataa accaaaaact  68940
aataatttgg aatcagcagg cttgtgtaac aagagatgtt gcccaaagaa aattagctag  69000
aagaagaata gttcaagagg agaactttct gcagcccacg taatgaagaa cccagcaaat  69060
ggcaaatgta gatgtaaatg caaaatattt tcttgatcaa atttctatat ctttttaaat  69120
gagagttgac tacttgaagc aaaatgatag caatatattt aactttagca tatgtagagg  69180
taaaaatttg aacatataga ctaaatcatg tggggaataa ttggaagtgt accattgtaa  69240
gtttcttacc ttatccacga tggtatgtaa tattaatgaa aggttgaatt tgtgggtcca  69300
aagggatatt gtaaatccta aagcaatcat aaaattttga attctgaggg atattatata  69360
ataagaattt tccatgtatc caaagagggg aagccaagga agaaaaagaa gtctttcaag  69420
tactcaagct ctgagcacat ccagttgctc attgaaccag cttcctggaa tggagggtct  69480
gggcttgaga ctaggtcaca tgtgtagagt ctctagagag acagtgttgg atccccatgg  69540
cccataatac atttcccgtt ttcccaggca gccacaggtc acgaatggga ggattctgag  69600
aggttggagc aatgttctta ggaggcataa ggaggagtga atgctctgag atttccccag  69660
cctgaggtcc tccatagctg cccgacctct tcagacctca tagtctgccc agctgtctcc  69720
ctttatgcca tgagtgccac tgttctttca actcatcccc cattccctca gtcccggaat  69780
tgctgtggcc agcagaggat ggactgagag caggagagga agtcctgacc aggaacccat  69840
cctagagata ctgcatcctg cctgaaagct aggtttccag ggcagctttg agaagtcttg  69900
cagaaagaaa cccacttgac ccacctgata cggtatcgac agacaggaat acttttgtg   69960 caatggtttt acatgctgaa catagagcct tttggctaca ttttgagtac attgaatgag  70020
actgctggcc tgggaaggat atcatgctgg atgccatttt tttctctgga gaactatgtg  70080
ttagttccaa ctcgcacatt actatatgaa gtcctacaca gagagatacg gagagctaga  70140
cagatagaga tacttttgta tgtgcataac caattccaca atacacacgt caaaatccat  70200
accagttatt ccagagagat ggattgggca gaaggcagaa ggaggatatt ctgatcccct  70260
tttggccaca tgtatgtata atctcagtgt ttctaggaag tgtgtgctgc attagatttt  70320 ttttcttttaa aaaagtgat aatatattaa gtatgagaaa tgtgcagaga ggattagaga  70380
ttgagagcca tttgtcattg tggcaattgt atggtatctc ttttgggaat atttcaaagg  70440
caccagtaat gaccttgttg tagcaaaata tacagtgttc ctgcatatgt acccattttt  70500
tgtgatgtgt attcttttgg aatttccagt ggcttgatca agaactactg ccgaaatcca  70560
gatcctgtgg cagccccttg gtgttataca acagatccca gtgtcaggtg ggagtactgc  70620
aacctgacac gatgctcaga tgcagaatgg actgccttcg tccctccgaa tgttattctg  70680
gctccaagcc tagaggcttt ttttgaacaa ggtaagaagt tgtgccagac atttacctgc  70740
ttggatgctg ggatgaaaag ccatggatac ccccactgac gcacaaccct tcagtgctac  70800
actggttctc gtgtgttggt tctgggtctg ccatgtggga ggaagcctta gcgcactctc  70860
tgggggagcc agaggtgtga ttttggtgc aacctgtgcg agctgtgtct ttaggatggg  70920
cggaaaccat tctgggtgct cgacttcacc actcccctca ttgtaaaagg ggctatctca  70980
ttgtcctaga caaaattctt attgtaatat gctgtcagat gtgtgtgtct ttccaagcca  71040
gtaaactttt ccagggattt cttcaagtag acagcattca gtgcaatctt cagcattgca  71100
gattccgaga aatgtggctc tagatcctgt tatccttgag aaacctaact gggttgcatt  71160
```

```
aattccatat ctccctgggt ctgtggagta gtacatgagc tcccgaagct ctatctctca   71220 ggtcttttc  agtccgaggc aggttgtgca gttcttagct ttgaagggag tgattttttc   71280
gtgtgctttt gcctctttct gatggaactt gtacctgcgg ggggtctgga gaaaaagagt   71340
agtagacttt tgctttattg caatgcatta tgctgggcac gagaggattc cctatcttat   71400
tgtaggtgat aagcttttgg cctccactca tccctgagaa gtgaagtgtt gttgcctaca   71460
gttttagctg caggactgtt gtctgcccca tcaccaggag tttaatgctt tcttttttga   71520
gcaatcatct agggacacat gcaaggtttt tatatgtcct tgcctcctcc ccaaaaaacc   71580
attttaatgc ttggagactt gcttttcagc tttgccaaat gcatcaccct ttcttctatg   71640
ctgttccatg tcgtcatgaa cactctgtag agattcctag aaatgagctt ccatgttagt   71700
ggagtttccg atgagaagca atctgatatt tcttttccac taagttttac atgaaatatt   71760
tctaagaact tactacagtt ctagaatggt aggcatctct tactttcgtg tttgtttgtg   71820
tgttttctca tgtccatttg cctattaata aagaatagag aatggttgta aatctcagtg   71880 actcttttt  ggtttatgtc ataaatggct tcctgtattt ttctgttcta ggaaataata   71940
agcttgatgt cttctgtttt aatttcagca ctgactgagg aaaccccgg  ggtacaggac   72000 tgctactacc attatggaca gagttaccga ggcacatact ccaccactgt cacaggaaga   72060
acttgccaag cttggtcatc tatgacacca caccagcata gtcggacccc agaaaactac   72120
ccaaatgcgt acgtctttgt tctttaccat aagcgaagga agggccaatg aagtttctg   72180 ttagaagagt catgcttcaa ggtgactgct caggactcaa cttggctcag atgcagagga   72240
acatttcctg tgagcaaaag ttcttagaga agactttgtt ttttgagac agagtcttgc   72300 tttgttgccc aggctggagt gcagtggcat gatctcggct cactgcaagc tccgcctccc   72360
gggttcacac cattctcctg cttcagcctc tctagcagct gggactacag gcacccacca   72420
ccacacccgg ctaattttt  gtattttag tagagacagg gtttcactgt tctagccagg   72480
atggtcttgg tctcctgacc tcgtgatccg cctgcctcag cctcccaaag tgctgggatt   72540
acaggcgtga gccaccgtgc ctggctgaga agacattttt taagctggct ctccttcctc   72600
ctagttttat ggaagcagaa ggatatatgg agttgagaag atcttattaa taaacagcc   72660 gggatgacaa atgaccaaag agttagagta tccttctaca acatcggctg agggttaata   72720 caacctttc accttggaat tctatcattc taagctctag tccctgaagt gaatgttgtg   72780 ttggccttt  gcatcttggg tcacagggaa ttgatacttg cacatctatg gagaggcaaa   72840 tcttttcta tctacttctt tttcaatggg tacaaacaca cttggtcctg agcaccagtg   72900
gtctgaagag atacggtctg cccagaggag aagaacaaag gcaggaaagc agatgagagt   72960
cagcaaaggg gcgatgctga aaagtaaaag gggcgggtag atggacagaa gccatgatct   73020
ggccattcta tggccagtct ttcggccata agtgactacc aaagacacgg caaaacggtt   73080
tccacatgtt gaacaacaga tgctagagga ccaagagtat tgcaagaggg agaaaatgag   73140
atcaacccat caatgccttg gctttcttca aggagaccct tcctgcactg aagagcaagg   73200
agatggagcc caagctgact gtagccatgt tgctgaacag aggagagtga ttggactttg   73260
ggattactca ggtagttagg attttctagc catgctaaga gtaagaatgg acttgtggag   73320
gataggagct ccaggcatag aagtctcctc aagtgttagt ctaaacataa agcagcactt   73380
gcatagaaga ttttccacaa gaaaatatgg caaaaaaca  ccatatattg aggaacaaca   73440
actacaaggg aacagtgagc ttaataaagg tgacagagct cacatagtgc tctggaatat   73500
```

```
tggagttttg accagctaga gagaagagac ctcattgaaa atcttgggca ttcagtagag    73560
acctcagaaa agtcagactt tatgagtaga ctttgtatat tcctagaata aaggcagctc    73620
cagaaaaaac ctagcaaagc tgaaaagcaa atctccaagc attaaaatgg tgtcctagtc    73680
aattaactgc cttctagaag aaaactcaac actctttaca ggtgaacaac aaagttaagt    73740
tgctgagcta tgcaatatcc acagtgtgag tcctaaattt ataactttac tacacataaa    73800
aaagcattta gtgtgaacca taaccaggaa aataatcagt caataaaaat agaaccagga    73860
atgatagaaa tgatttaaat ggcatgagaa tttgacatat tagtatcata actgcattgc    73920
tggatttaag aaaacataaa catggaacgt aacagatatc atatcaaggg aaagtaaaag    73980
gataaaagag tcaaatcaaa ttaaaggact attaaaaggt atatcttaaa tgaaaaattc    74040
actggatggt ctcccaatca ggttagttgt ttccagggaa aaaattaact gaaaaataat    74100
tcaatagaat ctacagaaat agctgcacat atatacacac aatggcacac gtgcacacac    74160
ccacacccac acaggtgtga atcctagagc cacacgagca ttgaaacata gagaagtaaa    74220
aattgttcat tgaggaatat gtagcaatgc tcaatgtgtt ttaccctaat aagagctttt    74280
gtgatgtatg attgaaaaac tgacacaact gaagagagaa atagataagc ccacactctg    74340
agttagagat ttccttgatt ctctcactat ggttataaat ctttcccaaa cacaacaggc    74400
tagaacaaat atgcagaaaa ttagacatag tatctttgtt ctcaataaaa acgtcgacct    74460
atttaacatt ataccgaact accgagtaca cattaaagtg tgcatggagc attcactgag    74520
gtgtactcta cacatgacct tccagcaagt ctccatagat ttaaaagaat taaagtcata    74580
cagagtgtgt cactttattc tcccagaata aagtgagata tgaataatga gaagtttgcc    74640
agcttctcaa atatttggga gtcatacggt gcatttcaaa atactctttg ggacaaagaa    74700
aacatcacta aggaatttag aaaagttttg aactgagtaa gaatataaca caatttatcc    74760
aaacttagga gatgcagtga atgtctttag gcttttacat aattttagat gctcttaggg    74820
aaaaacagaa gcatgtaata atcaagattt caaactgcaa ttctcaaagt gtagtctaga    74880
gaaacctgag gacctttgag taccttcaga gacagtccat gaggttaaag gactttgcta    74940
cgtgaaaagt aagatgctat tggcccttt tactttcatt ttccaacaag agaagagggg     75000
agttttccag cagttacata atatgtaatg gcatcatgtc tctgatggct aagaaaatgg    75060
gcaattgttg actttgtgtg ttaaaaaaat tctcagtgtt ggtttcttat actataaata    75120
ttcatcttgt gttttgaaaa agaaaagctc tttggaatcc cctatgaaca aagactttga    75180
cagttgttga tctaagacca cagcttaaat atctacacaa gaaaaaaaaa aaaagcaaat    75240
aagagccaag gaaagcagat ggaaggaagt agtccaaacc agtgacattc agtgaacaag    75300
aaaagagacc aacaagggag taaactcttg aaacagaaag ttgattcttt gaaaagatcc    75360
atatgattga acacagtctg gctaaacaaa tgacagacca atgagggtgc acaaccatca    75420
ccatctggag taacagagga gaggtgccat tactatagca tcttccagtt ctgaaagctg    75480
aaaagaagat tttgagaaca attgtatgtg aataaattca ggaatgttaa tcatgtgggc    75540
caattcctga ggaagacaac aaatcagcaa accagatgct gaatagttag tgtagtcctg    75600
tagagagaca tacagagagg ctgacagaga atatttgta tgtgcataaa acaatctaca     75660
agacacactt caaaatcaat ctcagttaat ctggaggaac atatttcaca gaaggtggaa    75720
ggagggtatt ctgatcctct tgtacattgt acaacattgt acaatgtaca gagtataatt    75780
gtacaagtac aattgaagtt gtacaagtac aagtgcaact tgcacaatgt acagagtaaa    75840
cattgatgtt tactctcaat tttcttatgg agcacagatg actttggatg tgttacaata    75900
```

```
tgaatgataa tttgtctttg agatgttcgc agttgtttag aagttgagga ccatttgtgc    75960
atattatggg acctttagtg aaaatatttc aaagtctctt tttacacttt gttacagcaa    76020
aatgtagagg gcgctaagtg cccttgaatc ttctcccatc tctggtgacc tgtgttgttt    76080
tgaaatttgc agtggcctga ccaggaacta ctgcaggaat ccagatgctg agattcgccc    76140
ttggtgttac accatggatc ccagtgtcag gtgggagtac tgcaacctga cacaatgcct    76200
ggtgacagaa tcaagtgtcc ttgcaactct cacggtggtc ccagatccaa gcacagaggc    76260
ttcttctgaa gaaggtagga agtctatggc cagacaacca caccctagga cgttgggatg    76320
aaaagagttg caaatcttta gtgatataga agccttccat gctcacacaa ttccaagtag    76380
aatgtggact cagggtcagc cactgggaag gaacactcag cgccttctct gggagaacca    76440
gagctgtgat gtttggtacc ctgtgaaagg gtggtatcta taggaagggt gcagaccctc    76500
tagggcactg gacttaccac tcccctggtt attcaaagga tcattttagt gtcttagcca    76560
gaagaatatt ctaacatttt gccaaatttg tgaagattta ccaagctcat gataagcctt    76620
tcatggtatt tcttcaagta gtcagtgttc attgcatctt tggctttgcg gtttcggagg    76680
aatgcggttt ttgagtctgt catccttgag aaacctaata tgacttttct tagttccata    76740
tacttctggg tccaggtagc agtacatagc caacaaatgc tccatcgttc tggcctatct    76800
ccatcttaag ccagtcctgc acaactaggc tttgatggga gggatctctc agtgttcttg    76860
cccctccttc tcatggaaca tatatctgtg ttggtctctg agaagaagag tagtggatat    76920
ctactttgtt gcaatgcaga atcctgggcc aaagatacca gccatccctc caagggaata    76980
aaattttggc cagtagccct ctctgagaga caatttgtct ttgcctacga gtcctagatg    77040
caggaccgct tcctgcccca tcttcaagaa gctgaaggct ttggctttgg aggatcagca    77100
gtctagggaa atgtgtgacg gtttcatgtc tgtccccact gacagtcaat caccacctac    77160
aacctgcaca gcctgatgca tagcagtcta gttcctgcc ttattctcag gaacacccag    77220
aagatgtcta tattaaagag catgcacatg agtgcaattt tgactgatag gcactctgat    77280 cttcctttg gtgcctgtgt tttaaaggaa atctttctaa gaactcgtta aagttctaga    77340
atgctatgaa tctttgggtt ttattattgg tatgtccatc tgcctgctag tacagaacag    77400
agcatggtag tctttctcag agacaatgat cctgtttcag tcacagattt cttctgatgc    77460
ttctgtgttc tagaaattac tcagcttgat ttctcctctt tgaatttcag caccaacgga    77520
gcaaagcccc ggggtccagg attgctacca tggtgatgga cagagttatc gaggctcatt    77580
ctctaccact gtcacaggaa ggacatgtca gtcttggtcc tctatgacac cacactggca    77640
tcagaggaca acagaatatt atccaaatgg gtacaacctt gagttttctt caaagacaga    77700
cagcagcccc cttacatttc tcttggaagg gccatgcttc caactaactt cttatgacaa    77760
atttatctca gatctggaat gttgggtaga atgtctcagg cttctttctt caggcacagt    77820
gtctgaaagg agagaaatgt caggccagct ctcttttctc atagttgaca gaagcaggag    77880
gatatttgaa ggtggtgagt tctcatgaat agaaagctca ggacacatgg ccacgtgctt    77940
agaaatagca ccattccaca atgcccacta aagaccaatg caatagttca accagggatt    78000
tctgtcattc taatctccaa gtcctgaagt gaaggttgta ttagccatgt tcatcttggg    78060
caacaaataa aggatatcta tgttgacatc cagatcttcc aatcactttc tcctctaacc    78120
tgtacctggg ttctgagaac aaggtatctg aagagctatg tgttgccagc acatgagggg    78180
caaaagtagg aaggcagctg agagtcagga agtataaaga ttctgaagag ttacacatgc    78240
```

```
aggaagatgg acagaaaccc agttcagacc acgtcagcgt ttctgccatg aaggactatc    78300
aaatacatag gaaaagtgtt ttcataggtt ggacaacaga catgacaggc ctgagaaaat    78360
tcagaaaggg aatcaaagga gatcaacctt atcatgtccc tggcatcctt ccttgagacc    78420
cttgaagggc aagcagatgg agcccagctg accacagcag tcttgcttaa ctgaggagag    78480
agactggagt ttgtgatgcc tcaggcatct gacgtattct aggctggcta agaatgagag    78540
gggatttgtg gaggaaagga gctccaagaa tacacaccga agtcttctca aggctttggc    78600
taaatacaaa gctgcgtatg cacaaggaga gtttttcacaa agaaagaaca ataaagaaaa    78660
gctactgggg aaagaacaac tgcaagggaa cagtgagctc aatggagatg ctagagctca    78720
catagcactg ggggatattt gagttctgac cactcagagg agagacacct cactgaacat    78780
cttgggcatt cagtagaggt caaagaaagc cataatttgg gagtaggatc ttcggattcc    78840
tagaaataag gtgactccag aaacactcca gcaacccttc ttccaagcca gtctaaaagg    78900
atccaaatga tttccaagta aattaactgc cttccagaaa aaagtaaaact caaccctcct    78960 tagaggtaag gaacgaatac aagtttctca gttatatgac atccccagag tgcaacttgc    79020
atttaaaaat ttactagaca caaaagaagt tttcactgtg atccataact gggagaaaaa    79080
tcactcaaca caaataggcc cagaaataat agaaattatg gcattggcaa gaacatttaa    79140
aatgcacctc tgagaactgt gtttcaggaa aatgtcagca aaagctgacc atgagagaaa    79200
tgaatgcata atatcagaaa agaaaagaat tgaagagcca aatggaaatt taaaaactga    79260
gaaaagttat atctgtaatg aggaattcac tggatggcct tataaccagt ttagatatta    79320
tggtaggaaa aggtgaacga gaaatgattt caattaaagc tagacaaacc acaagacaga    79380
cagacagaca caaatacaca tacacacaat gactgaacca attaatcaac agagcctcaa    79440
ggacatctag gaaaacatcc acacatttaa tatatgtgtt aggcaagtca cagaaagaga    79500
ggaaaaagat aatgtgacag aagttatact tgaagccatg acggctgaca aatttccaaa    79560
catacagaaa atgagaaatt catagtcatg aagctcaatg actcaggtat agattttaa     79620 agagcaaaac tctgatttac tggggtacat catagttaaa ttgtctgatt tcaaagctaa    79680
gaagaaaaaa aggggggttcc tatgaacaaa catttttgaca gttgatctaa gaccacagct    79740
taaatatcta ggcaaggaaa agcaaataag acacaaggaa aggggatgga tggaaatagt    79800
ccaaaccaat gacattcagt gaacaagaaa atagaccaac aaaggagtaa atccatgaaa    79860
cagaaagttg gttctttgaa aagattcatg tgattgacca cagtctggct gaacagatga    79920
cagaccaagg agggagtaca accatcacca tttgaagtaa caggggagag gagccattgc    79980
tataccatac tccaggtctg aaagctgaca agaagatatc aagaaaaact gtatgtgaat    80040
aaattcatga atgtagatca tgtggatcaa ttccttaggt aaacaacaaa tcagcaaacc    80100
agatactgaa tagattgggt actcctatag aaagacatac agatagccag acagagaaac    80160
atttgtacgt gcataaaaca atctacaaga ctcacttcaa aatctctcag ttaatccaaa    80220
gtaacatatt tggcagaagg tggaaggagg gtattctgat cctttcttgt acacattgat    80280
gttttctctc ggttttctta tggagtatag acgagtttgg atgtgttaca ataagaatga    80340
taatctgtct ttgaaatgtt cacagttgtt tagaagttga ggacgatttg tgattgttac    80400 aggacccttta gtgagaatat ttcaaagtca cttttttacca ctttgttaca acaaaatgta    80460
gaggatgtct ggtgcccttg tatcttctcc catctctggt gaactgtatt gttttgtaat    80520
ttgcagtggc ctgaccagga actactgcag gaatccagat gctgagatta gtccttggtg    80580
ttataccatg gatcccaatg tcagatggga gtactgcaac ctgacacaat gtccagtgac    80640
```

```
agaatcaagt gtccttgcga cgtccacggc tgtttctgaa caaggtaaga agtctctggc    80700
cagacaacca cacccttgga cgttgggata aaaagagttg caaaatctta gtgatacaga    80760
agccttccat gctgcacggg aatctgaatg tggactcagg gtcagccaat gggaaggaag    80820
cctcagcgcc ttctctgggg gaaccagggc tgagattttt ggcaccccgt gacagggtgg    80880
tgtctttagg aagcgtgcag accttctagg gcactggatt taccactccc ctggttattc    80940
aatagattat ttcagtgtcc tagtgaaaat ggatattcta acatcctgcc aaatttgtga    81000
tgatttacca agctcatcat gagccttttcc tggtatttct tcaagtagac agtactcatt    81060
gcaaacttca gctttacagt ttcagaggaa tgtggttttt gagtctgtca tccttgagaa    81120
acctgatatg actttactta gttccatatc ctcctgggtc taggtaacag tacatagcca    81180
gcaaatgctc tatctccctg tctaccttaa tcttaggcag gtgctgcaca cctaggcttt    81240
gatggaaggg atttcttagt gttcttgccc ctccttctca tggaacacgt atctgtgttg    81300
ctgtttgtga agaagagtag tggatgtcta ctttgttgca atgcaggatc ctgggcccaa    81360
gatttcccgc cgtccctcca agggaataaa attttggcca gtacccctct ctgagagaca    81420
atgtgtcttt gcctggaagt cctagatgga ggaccacttc ctgccccatc ttccagaaac    81480
ttaaggcttt ggctttggag gatcagtgct ctggagaaat gtgtgacggt ttcatgtctg    81540
cccccactga caaccaccac ctacagcctg caccgcctga tgcatggcac tctggtctcc    81600
tgccttgttc tcaggaacac ccaaaagaga tctttgccaa agaacaggca catgagtgca    81660
attttgactg ataggcactc tgatctgtcc tttggtgccc aggttttaaa gaaaatcttt    81720
ctaaaaactc attgaagttc cagaatgcta tgaatctttg agctttgtta ttggcatgtc    81780
catctgccta ctaatgtaga acagagcatg gtcgtcattt tcagagatga tgtcctgttt    81840
ctatcatgga tttttttttct catgcttctg tgttctggaa attactcagt ttgttttctc    81900
ctctttgaat ttcagcacca acggagcaaa gccccacagt ccaggactgc taccatggtg    81960
atggacagag ttatcgaggc tcattctcca ccactgttac aggaaggaca tgtcagtctt    82020
ggtcctctat gacaccacac tggcatcaga gaaccacaga atactaccca aatgggtatg    82080
tctttgagtt ttctcccaag agaaacagcc acccacttaa atttctcctg gaagagccat    82140
gcttccagct aacttcttat gacccaattt ctctcagacc cagaatgttg gacagaatgt    82200
ctcaggcttc ttgctttggg cacagggtct gagaggagag aaatgtcagg ccagctctct    82260
tttctcatag ttgatagaag taggaggata cttggaggtg gtgaggtctc atgaatagaa    82320
agctcagaag aacatatgac catgtgctta gaaatagcac cattccacaa tgcccactaa    82380
agaccagtga aatagttcaa ccagggaatt ctgtcattct aatctccaag ccctggagtg    82440
aaggttgtgt ttgccatgtt tgtcttgggt aacaagtgaa ggatatctat attgacttcg    82500
agatcttccg atcactttct cctctaacct gtataaacac attgggttct gagaacaagg    82560
tgtctgaaaa gctatgtgtt gccagcccat gaggggcaaa aggaggaagg cagctgagag    82620
tcaggaagta tagagatgct gaagagttac acattcagga agatggacag aaacccatgt    82680
ctggctatgc cagcctttct gccatgaagg actatcaaat acatgagaaa acagttttca    82740
caggttggac aacagatatg gtaggcttga gagaactgag aaagggaatc aaaggagatc    82800
aacttcatca ttaacctgtc ttccttcctg gacacagtgt tggattgaag gacaagcaga    82860
tggagcccag ctgaccacag cagtcttgct taactgagga gagagactgg agtctgcgat    82920
gcctcaggca gctgatgtgt tctaggctgg ctaagaatga gaagggattt gtggaagaaa    82980
```

```
ggagctccag gaatacacac agaagtctcc tcaaggcttt ggctaaatac aaagctgcgt   83040
atgcacaggg agagttttca taaagaaaga acaacaaaga aaagctactt gggaaagaac   83100
aactgcaggg gaacagtaag ctcaatggag atgccagagc tcacatagca ctgggggata   83160
tttgaattct gaccactcag aggagaaaca cctcactaca ttttgggcat tcagtagaga   83220
ccaaagaaag ctgtattttg ggattgggat catcttattc ctagaatcaa ggtgactcca   83280
gaaaaactcc aacaacccctt cttccaagcc agtctaaaag gatccaaatg atctccaagt   83340
aaattaactg cattccacaa gaaaaaaaaa actcaacccc ccttagaggc aagggacaaa   83400
tacaagttgc tcagttatat ggcattccta ttgcgttact tctatttaaa aatttaatag   83460
agacacaaga agctttcact gtgatacata actgggagaa aaaatcactc aacacaaaca   83520
ggcccagaaa ttatagaatt gatgacattg gtgagaacat ttaaaatgca cctctgagaa   83580
ctgtgtttca ggaaaatgtc agcaaaagct gaccatgaga gaaacaaaag cagaatagca   83640
agagaaaaga aaagaaccgg agagccaaat gaaaattaaa gaactgagaa aaggtacatc   83700
tctaatgaag aactcactgg atggccttat catcacttta gacattacgg taggaaaggt   83760
gacctagaaa ataattcaat aggagctaca caaatcacag gacagacaga cagaccaaca   83820
gacagaaaca cacacacaca cacacacaca cacacacaca cacacacaca cacacaaaga   83880
ctgaacctat taatcaacag agcctcaagg gcatctagga aaaatccaca catttaatat   83940
atgtgttagg caagtcacag aaggagaaga aaaagatatc atgacagaca ttatacttga   84000
agcgatgatg gctcgcaaca cgccaaatat acagaaaaca agaaactcat agtcaagaag   84060
ctaaatgact caggtataga attttaaaga gcaaaactct atgatttact gggatatatc   84120
atagttaagt tgcctcaatt caaagctaaa agaaaaaaaa gggggttcct atgaacaaca   84180
gctttgacag ctgttgatct aagaccacag cttaaatatc taggcaagga aaagcaaata   84240
aggcacaagg aaagaggatg gaaggaaata gtccaaacca atgacattca gtggaaaaga   84300
aaatagacca acaaaggagt aaatccatga aacagaaagt taggttcttt gaaaagtcta   84360
tatgattggc caaagtctgg ctaaacagat gacagaccaa ggagggagca tatccatcac   84420
catcatgagt aacaggagag agatgccatt gctatagcat cctccaggtg tgaaagctga   84480
gaagtagata ttgagatcaa ctgtatgtaa ataaattcat gaatgtagat catgtggatg   84540
gattgcttag gtaaataaca aatcagcaaa tcaaacactg aatagatcat gcagttttat   84600
agagacttac agacagcctg acagataaac atttgtatgt acgtgaaaca atctccaaga   84660
cacacttcaa aatccctctc ggttaatcca aaggaatgta tttggcagaa ggtagaagga   84720
gggtattctg atcctttctg gtacacattg atgttttctc tcagtttttct tataaagcat   84780 agattacttt gaatgtgtta caataagaat cataagctgt cttttgaaatg ttgacagttg   84840 tttagaagtt gaggaccatt tgtgagtgtt atgggacttt agtgagaata tttcaaattt   84900
gcttgtttac actttgttac aagaaaacat agagggtgcc aggtggtgct gtatcttctc   84960
caatctctgg tgacctgtat tgttttggaa tttgcagtgg cctgaccagg aactactgca   85020
ggaatccaga tgctgagatt cgcccttggt gttataccat ggatcccagt gtcagatggg   85080
agtactgcaa cctgacgcaa tgtccagtga tggaatcaac tctcctcaca actcccacgg   85140
tggtcccagt tccaagcaca gagcttcctt ctgaagaagg taagaagcct gcagtcagac   85200
aaccataccc tcggacattg ggataaaaag atttgcaaaa tctttgtgat gcagaaaact   85260
tccatgctgc acaggaagtc gaaggtgaag tcatggacag ccaatgggaa ggaagcttca   85320
gtgccttctc tgggggggacc agagctggga tgttgagtgc cttgtgaggg atggtgtctt   85380
```

```
taaaagggc acagaccctc taggacactg gatttatcac ttccctgtta tcaaacgaat    85440
catattagtg tcctagccaa gatggatatt ctaacatcct gccaaacttg tgaagatata    85500
ccaagctcct aagcctgtcc agcccttct tcaagtaggc agtgtttatt gcagtcttca    85560
gctttaccat tttgaaggaa tgccatttt gaggctgttg ttcttgagaa acctaacatg    85620
tcttcattag atccgtattg tcctgagact ttgaagcagt acatagccac caaattgttt    85680
atctccccag cctaccttca tcttgggcat gccttccaca cctaggattt gagggaaggg    85740
atttctcagt gttctcatcc ctgcttctca tggaacattt atctccgttg tttttttgaga    85800 agaagagtag tggatgtcag ctttcttgta atgagggatc ctgggcccaa gattccctgt    85860
ctcccctcct aggctataaa attttggcct gtactccttc tccctgagag gcaatgtgtc    85920
tttacctaca agtcctagat gcaagatcct tttctgcccc acaccccaga atctgaaggc    85980
ttttgctttg gaggagcagt ggtctagtgt gcaagggttt catgtatacc ccccactaac    86040
agccaatcac cacctatagc ctgaacagct tgatgcatgg caccctggtc tcctgccttg    86100
ttctcatgaa cacccagaag aggtgtaagc aaaagaccat tcacatgagt gtaattttga    86160
agtataggca ctctgatctg ttttttgttt gtttctttgt ttgtttgttt tccagggttg    86220
aattaaaata tttatgacta cttattaaat ttctagaatc ctataagtct atttgtattt    86280
ttattctaca tttcaatttg catgctaata tagaagagtg taaattgtta atcctcagat    86340
tattccactt tgtgtgtcat aatttttttc acatttccct tttctaggca atactgagct    86400
tgattttctc ttttaatttc agcaccaact gaaaacagca ctggggtcca ggactgctac    86460
cgaggtgatg gacagagtta tcgaggcaca ctctccacca ctatcacagg aagaacatgt    86520
cagtcttggt cgtctatgac accacattgg catcggagga tcccattata ctatccaaat    86580
gcgtatgtct atcatgttag ccataaaagg aacaatagtc aactaaaatt tctcttagct    86640
ggcccatgct acaagctcac ttcctaggtc caaatttctc atagactcag agtttgtagc    86700
aaaatgtctc aggaaactta cttttgagca aaggtctga atgaagagaa gttttaggat    86760
tgctatcttt cataacaatt tgatggaagc agcaggatat atggaggtgg tgaagtctca    86820
ttaatgtaaa gctaaggaga tcaaatgacc aaatgctgag acaaagtatc attccacaat    86880
gcccactaaa ggtccatgca gtcttttcaac catgcaattc tatcattcta tcctccattc    86940
cctgaagtga aatttgtgtt tgccattttt gacacgaatc agaagtaaca aattcaggct    87000
gggtgcagtg gctcaggcct gtgatcccaa cactttggga ggacaagacg ggcagatcac    87060
cagaggtcag gagttcaaga ccagcctggc taacatggca aaacccatc tctacgaaaa    87120 attaaaaaat tagccggtca tggtggtggg tacctgtaat cccaactact gggaggctg    87180 aggcaggaga aacacttgag cctgggattc agagtttgct gtgagccgag aacatgccac    87240
tgcactccag cctgggtgac agagcaagac tcaatctcaa aaaaaaaaa aagaagaag    87300 aagaagaaaa gaagaagagg aagaagaaga agaagaagaa gaagaagaag aagaagagga    87360
agaggaagag gaggaggagg aggaggagga agaagaagaa gaagaagaag aagaagaaga    87420
agaagaagaa gaagaagaag aagaagaaga agaagaaaat agaaatgagt gcatatattt    87480
atatatgagt actagcctgt atgaacacac tgggttctaa gcaccagttt tctgaaggga    87540
tatgggttgt caggcagagt aaaagcagga atgcagatga gagtcaggaa gtaaacagat    87600
gtggtgatta aatgggcag gtacatggac aaaaaatgc atgtctgaca aaactggcc    87660 tcttgccata agtgagtatg aataatatgg aaaaactgtt tgcacatgtt gaacagcaga    87720
```

```
cagtacaacc tgagatagtt tagaaaggga acaaataag atcaaccccca taattaccct    87780 tcctagactt aagggcaaag agttttaacc aaagcattcc acagcagtct tgctaaactg    87840
gggagagaga ctggagtttt gtttactaat aaaaccgaga ttttctaggt taggtaataa    87900
tgagaaagta tttgtggaga aaaggagctc caggaataca cacagaagtc tcttcaagtc    87960
tctggctgaa cagaaagctg tgtatgcaca gaaagagttt ccagagagaa aggagaacaa    88020
agaacagcta ctggggaaag aacaactgct ggggaacagt gagctcaatg aagatgccag    88080
agctcacata gcactgggag gtatttgagc tctgaccagc ctgaggagag acacttcatt    88140
gaacatcttg ggcattcagc aaagaccccca aaaaaccata cttcaggagt agaattaatg    88200
cattcctaga ataaagtcta ctccagaaac accctagaaa agcttagaaa ccaagtctaa    88260
aaagatccaa atgatctcca gtaaaattaa ttgcctgtca gaagaaaaca acctcttcag    88320
aggtaaacaa caaaattaaa ttgctcaatt atatagtatg cacaatgtgt ggcatacatt    88380
taaaaatttg ctaaacatac aaaaagcatt tagtgtgacc cataaccagg agaaaaatca    88440
gtcaatacaa atagacccaa aaatgataaa aataacagaa ttggcaagga gatttaaaat    88500
gtatgtatca taattgtgtt caaggattta aagaaagcgt ggacaagaaa taaataaatg    88560
gataatatca acagaaagaa aaattgtaaa aggaccaaat ggagagtcaa gaactgaaaa    88620
aaaagacatc tctttaatga gaaaatcact acatggcctt ataatcatat tagatagtac    88680
agatgataaa gctaactaga aaatattagg gtggtgcaaa ccatagcacg cttatacaaa    88740
gcctgagaag ataaacagag cctcaaggac atctatgaaa atatcaaaat atttaatatt    88800
tgtttaaagc aagtcacaga ggaagggaaa gagatattgg aacagaaaaa atacttgaag    88860
cagtgatggc tgatgacttt ctaaatatgg aaaaaatgat aaactcacat agtcaagaag    88920
ctcaatggat cagatatagg attttaaaaa gtaaagctgt atgatttatt tggacacatc    88980
ataattaaat tgtccataat caaagataga aagtaaaatc ttatttgaag cccaagggaa    89040
aaaacatacc tttacataga gtaacagtga cacaaatgac tgatgccttc tcatcagaaa    89100
caacacaaat cagaaacaat agaataacac ctttagagtg gtaagaagaa aaaaagatca    89160
aatcagaaac aacaaaataa cacgtttaga gtggtaagga ggaaaacaag atcaaatcag    89220
aaacaatgga ataacacctt tagagtgtaa gaaagaaaaa aagatcaaat caggaacaac    89280
agaataacgc cttcagagtg gtaagaagga aacaagata aaatcagaaa caatgaaata    89340
acacctttag agtagtaaga agaagaaaag atcaggtcag aaaaaatgga ataatatgct    89400
aagaagaaaa aaaagatca agtcagaaac aatggaataa cacctttaga gtgaaaagaa    89460
ggaaaaaaac ccagcaagct taaacgctat gcacagcaaa caattccact gaaaatgaat    89520
gttacgtaag tacatattct gtcctcctaa aaacaaagaa caaataaaag aatgtttcat    89580
cagcaggatt atgtaataaa agatgtgaaa gaatgctatg taagtagaag aaaaataata    89640
ccatatggga attggcatca aaaccacaaa atactatcaa aacaaaaaaa ctttattgat    89700
aaatttaaca caatatgcaa aagaactata ccatgtatac tacataacat tggtgagaag    89760
aaaattagaa gatctaaata aagacacatc atgcttatag attaaaaaat ccaatgtcac    89820
ttttcacaaa actgatcttt agtttcaacc cacacccaag cagaattcct gcagtctttt    89880
cttgaaaacc taacagaatg tatatgctag aatcaccaag acaatcttta aaaagaataa    89940
aaaacttgga ataaaatcac aagtttgtgg gatagatgca tatggtaata tggaaattct    90000
cataaagaca cagtaatcaa gacatgtggt attggctggg acgcttggct gtaatcctaa    90060
cactttggga ggccaagatg agaggattgc ctgagatgag gagttgcaga caagcctggg    90120
```

```
caacatagca agaccctcat ctctacaaat atttaaaaaa attagccagg tttggtgcca   90180
tgtgcctgta gtcccagcta ttcaggaagc tgaggtggga ggatcactgg agcccatgag   90240
gtggaggctg aaatgagcca tgattgtgct actgaacttt agcctgggag acagattaaa   90300
accttccctc tctctctcaa acaaacaaac aaaaaataca tagtattggg caaaacatat   90360
gcaaacaaaa acagaaaagg gtcagcataa atttacatat atggtcaatt tattttcaat   90420
acaggtagca aagcaattta atgaggaaat ttttttccaa aattggtctg aaacaactgg   90480
atagccatag aaaaaaacta taacaaatgt gacgcttgaa tcctactgta tgactcaaat   90540
taaattaatt tgagatagct cttagacctc aatgtaacag ctaattctga ggctgaaata   90600
taagactgct atgaaaaagt atagtatctt ataaccttgg agaaggaaaa attttttgag   90660
ggaagaacca gaaacactaa actgtaaaag aaaacaaatg ataatgtgga cattcattga   90720
ataaaaactt atgctcacca aatatgactg ttaagaaaat aaataagtaa gtaacacact   90780
ggaagaaaaa cactctcatc catatatctg acaaatggcc tgtatccaga gtatagaaac   90840
atttctccca ctcactaatc agaggacaaa caacctaatc aaaatgggca acaggcttga   90900
atagtcattt cttaggagaa gatgcacaca gagccaacaa tcacctgaaa aagtgcacaa   90960
catcttagcc atcaaaaatc aagagttata accctcataa gatgacactg aacatccagt   91020
gtacatggat atcattaaga agacacaata ataagtggtg tcaccgattt ggagctagaa   91080
tgtgccactc tctcatatgc tggtggaagt tcaaaatcat acaacaaatt aaaaaatcag   91140
tctgatgctt tcttataaag ttcgataaat atgcatctat cctacaaacc tgtaattcta   91200
ttcttgaata tttaccccc aaaatgaaaa cataagtcca caaaaatcta tataaatatt   91260
catagcagct ttatgtttta taaactcaaa ataaaaacta tttcaatgtt ttcatcaaaa   91320
gaaaatgaaa actatttaaa tggtttcatc aaaagaaaat gaaaaagaa tttccagtat   91380
atttatacaa aggaatacta ttcatcaaca aggaacaagt tactgatagt ctcagaagca   91440
tgaacaaacc tcaaaaatat attaaggaaa gaagccagac gtcaaagtgt atagtctgta   91500
tgagtccatt catgtgagtt tatagaaaac acaatttatg gtgaaagaaa ccaatagcat   91560
ttgacactgg ccgtgggaag agggtagcag agattgattg agcagccaca caagggagtt   91620
tctggggtgg tgaaaatgtt ctgcattgtg agggcagtgt gggctacaca agtatatgta   91680
tttatcaaat ctcatccagc tacatttaag atctgtgcat ctcactctat gtgaaaatat   91740
actcaactga aaacagagc aggtatctgt ttcaggtgct acatcacttg atacgtccag   91800
ttgtgttaaa aaccactgcc taacatcctc aaatggggga tctgggcttg agactaggtc   91860
acatgtgtag agtctctaca gagaccgtgt tggattccca tgctccataa tacgttccaa   91920
gttttctcag acagccacag gtcatgaatg tgaggattct gagaggttgg agcaacgttc   91980
ttgggaggca taatggggaa ggcattctcc aagattcctc cagcctgggg tcttcacctg   92040
ctgtgcctct tactgcattg tttctgact catccatagc cacttgaccc cttcagatcc   92100
catagtctac ctagccgtct cccttatgc cttgggtccc gctgttcttt caactcatca   92160
cccattcctt cagtcccaga gtggctgcag ccagcagagg atggactgag agcaggagag   92220
gaggtcgtgc ccatgaaccc atcctagaga agcagcatcc tgcctgggag ctagttttcc   92280
agggaagctt ttataagtcc tgtagaccca aacccacttg ctctaccaga tacagtattt   92340
atagtaatac tattttcatg attatttat attgcaaatg tagagcattt atgctacact   92400
atgagtaaat agagtaaggg ggctggcatg ggaattatat aatcttggat gccacttctt   92460
```

| | |
|---|---|
| ccttggggaa atgtatttga gttccaactt acatattact atatagtctt atagagagag | 92520 |
| agacaaagag ctagacagac agagatatct ttgtatgtgc attaaaaaat ctaagataca | 92580 |
| tatttcaaaa tctgtgtcat ttattctgga ggaaagtatt tggcagaagg tgaaaggaag | 92640 |
| atattctgat cctttcttgt acagacatgt attatctcag ttttcataga gagcatatac | 92700 |
| tacttttgat gttttaaaac aaaaattata atctgtgatg tgtccacagt tgtttaaaag | 92760 |
| ttgaagctga agaccatttg tgcttgtggc aatattattg tggtataatg ggaatatttc | 92820 |
| aaaggcactt gttaacactt tgttacagca aaatgtagag ggcgctaagt gcccttgaat | 92880 |
| attctcccat ctctggtgac ctgtgttgtt ttgaaatttg cagtggcctg accaggaact | 92940 |
| actgcaggaa tccagatgct gagattcgcc cttggtgtta ccatggat cccagtgtca | 93000 |
| ggtgggagta ctgcaacctg acacgatgtc cagtgacaga atcgagtgtc ctcacaactc | 93060 |
| ccacagtggc cccggttcca agcacagagg ctccttctga acaaggtaag aaatttgtgg | 93120 |
| ttagacatct atatactggg atgaaaaacc atggaaaatc ttactgatgc agaagccttc | 93180 |
| agtggtacac tggagggttg gttgagggtc tgcaatgtgg aggaaagcct cagcgccctc | 93240 |
| tctgggggat ccagaactgt gattttggc acgctgtgag gaggcagtgt ctttaggaag | 93300 |
| ggcacggtgt ctttaggaag ggcacagacc cgccagggca ctggacttac cactcccctg | 93360 |
| gttattaaat gggtcatttc agtgtcctag ccaaaatgga tattctaaca gcctgccaaa | 93420 |
| tatgtgaaga tttccaagcc aataagcctt tccagtgatt taaagtagac tttttcatt | 93480 |
| gcaatctaca gtttgcagtt tcttaagaac atggcctttg agtatgatat cctagagaaa | 93540 |
| cctaaggaga ctgcattatt tttctattgt cctggggctg catagcagga ggtaaccaac | 93600 |
| gaatgctgtc tctccctggc ctatctcagt cttcacagg ctctgttcac ctcagctttg | 93660 |
| aagttagaaa tttctaggtg ttcttgcctc ttccttctcat gaaacctgca ttggcagtga | 93720 |
| gtctacagaa gaagaggaag agaattctgc tttgttacaa ttcaggactc tgggcactag | 93780 |
| aagattccct atctctcctc caagggaata agttgtttgt ctctaaccct ccttgagaaa | 93840 |
| caatgagtct ttgcctgcac tcctaaatgt aggatgattt cctgcccaaa ttttcaaaag | 93900 |
| attaagcctt ttgccttggt atgagcaatg gtctagggaa atgcgcaagg gtcttgtgtc | 93960 |
| ggcccctgac tgaccaccag tcacctccta cagcctgcac caaggaatgc attgcattct | 94020 |
| ggtcttctgc cctgtggttc tcatgaaaac cagcagagat tcatatgatg gagctgcaca | 94080 |
| tgaatgtaat ttccaatgtc cagcattctc ctctgttctt tatctttaga tttaaaaata | 94140 |
| atgtttctat gaacttatta aaattctaga atactatgaa tctactgggt cttttcacat | 94200 |
| ccttttgcta ctagtagaaa aaagaatagt aataattttc agaggctact gtccagtatg | 94260 |
| tgacataaat tgtctcccat gtttctctgc tcatgcaatt actgagtatg atttatttta | 94320 |
| ttttaatttc agcaccacct gagaaaagcc ctgtggtcca ggattgctac catggtgatg | 94380 |
| gacggagtta tcgaggcata tcctccacca ctgtcacagg aaggacctgt caatcttggt | 94440 |
| catctatgat accacactgg catcagagga ccccagaaaa ctacccaaat gcgtatgtat | 94500 |
| ttgattaaaa ccataagagg agcaacagcc aactcaaata ttggttagaa gacccatgct | 94560 |
| ttaagctcac ttcctaggga caaatttctc ttagactcac attttggcaa aatgtctcag | 94620 |
| gacctttgct tttgagcaaa gagtctaaga gaagagaaat tttaggcctg ctattttttcc | 94680 |
| taatagtttt atggaaggag tagaatatac ggaagtggcg aagtcatatt aatgtaaagc | 94740 |
| tcagaagata aatgaccaaa gcttaaacac agcaccattc cacaatgccc actaaaaatc | 94800 |
| aatgtcatct ttcactcgtg caattctgtc attctaaatt tcaattcccg aaggtttgtt | 94860 |

```
tgccattttt gtcatgggta ataagtaaaa aaaaaaaaat taagatgtgt atatatatat    94920
atatatatat atatatacac acacacacac acacacaaac atctgaatat ttatatatat    94980
gtctgaatat ttatatactt gtgtataaaa cttatattta aatttttgca taaatttata    95040
tatttttaat atttcattaa aaattatatt gtttcactat gtatgtctga gtattttat     95100 atattttaat ataacatttt aaatatttat ataaaatat tcaggtatgt aactgaatat     95160
tcatttacac acacaaatat atgtgtgcat gtgtgtatat atatatatac ccatatatat    95220
atatatatat atatatacat atatatatat atatatatat gtatatatat atatatatat    95280
atatatacac acacacacac acacacatac atacaggtat aaacacactg ggcctgaagc    95340
accagtggtc tgaaaggaca tgtgttgcca ggacttgaag agcaaaagca ggaaggcgga    95400
tgagagtcag gaggtacaca aacgctgaaa agtaaaatgg acaagtacat ggacaaaaag    95460
caggtataag cataacagcc ttttggaagt aaatgactat aaaatatatg aaaatactgt    95520
tttcacaagt tgcacaacag atagtagtgt attgagataa tttagaacag aaaacaaatg    95580
tgatcaaccc cataagtgtg ctgtatttca tcatggattg aaggaaaaag agatggagcc    95640
caagaagacc acagcagtct tgatgaactg agagacacca gagtttggga ttacaaaggc    95700
agctgggatt ttctacactt ggtaataatg agaaagaatt tgtggagata aagagctaca    95760
gtcatgtacc tagaagtcac ctcagtgtaa tataaatctg catatgcaca gggagtgatt    95820
ccacaatgaa agtaggacaa agaacagcta ctggggaaag aataactaca agggaacaat    95880
gagttcaatg gagatggcag agctcacaaa gcactggggg atatttgagt tcttaccagc    95940
tagaaaagag acctcattgc aaatcttggg cattcagtag agaccccaga aaagccactc    96000
tttggaaaca gagttgatgt attttaagag caaaatctac tccacaaaaa tcctagcaaa    96060
attgaaaagc aagtcagaaa gaccaaaatc ctctcaacat aaattagttg cccatcagaa    96120
gaaagcttaa cctcttcata ggtaaacaat aaaatcaaat tgctcagtta tctggcatcc    96180
acaatatgtg acataaattt aaaaatttac tagacataca agaagcattt agtgtgatcc    96240
ataaccagga gaaaaatcat tcaatacaaa tagacccaga aatgacagaa atgatagaat    96300
tagcaaaaac atttaaaata tacatatgat catttgatct tgtgatcaga tatcacaaga    96360
gaagaaagag atacttgaac agaaaaaatg cctgaagcaa tgatggctga aaactttcca    96420
aatatgaaga aaaaaaagct cacagattca agaaaactaa tcaatcagaa atatgatttt    96480
gaaaagtaaa aatgtatgat ttactttggc aaatcttctt ggttaaattg tctaaaatca    96540
aagaaagcta ggaaaatttt ataagccaga ggaaaaaaga ttgtttatat aaaggaacag    96600
ttacacaaat gactgatgcc ttctcatcag aaacaatgaa agtcagaaac aataaagtaa    96660
catctttaaa gtaatagaag aaaaacccaa gaggtgaggg atcgtggcag acaggaggca    96720
ggactagatt gcagctctgg acagagcagc atgcagaggc tcatattgtg aatttttagcc   96780 ccatattgac tgcaagaaca gaccagcaat cctgagagga cccacagacc gtgtgaagga    96840
agcagactgc tcctgcagga taagggagac accccaaata ctgtgagttc cccaactgca    96900
gaagtggaaa agggaggcct tactccctca aacacacccc acaactggag aagctgaaag    96960
tctgtttgca ggagaagttc ccaacttac ctgggcctca gtaaatttag agagctgagc     97020
caagcaaaat ataggggtag aggaagcagc agagaagacc tcagagcttg ctggatcccc    97080
aagcagctca ttcctgcctg gcaccacaga gatccatcag aagtgtggcc aaaggaacag    97140
agggtaaaac tccacatgga ggactgctct acctgaactt tctaacaatt tgaacagggg    97200
```

| | | | | |
|---|---|---|---|---|
| gagaagcctc | ctggccagaa | cttggggag | ggcatgaatc | tggtttgcag acttcacagg 97260 |
| tggggaagg | actaaagccc | ttttctttca | cagctgggag | gtggaaagcc tcaggcaagt 97320 |
| tttcaagcct | gactttcccc | ccacctggaa | acagacttgg | agctgttgcg gggttgggg 97380 |
| catggtggga | gtaagaccag | cccttcagtt | tgcatgggtg | ctgggtgagg cctgtgactg 97440 |
| acagcttccc | tccacttccc | cgacaactca | gatgactcag | cagaggcagc cataatcctc 97500 |
| ctaggtacac | aactccagtg | acctgggaac | ttcaccccca | caccatacag aagcttcagt 97560 |
| aagacgtgcc | caaggaaagt | ctgagctcag | acacgcctag | tcccaccccc aactgatggt 97620 |
| ccttccctac | ccaccctggt | agcagaagac | aaagagcata | taatctttgg agttctaggg 97680 |
| cccacccacc | tctagtccct | ctccacacta | gtatagctga | tgcaggaggc caaccagcac 97740 |
| aaaaatagag | cattaaacca | ccaaagctag | gaacccctat | ggagtccatt gcaccctcct 97800 |
| ccacctccac | cagaacaggc | actggtatcc | acagctgaga | gacccataga tggttcacat 97860 |
| cacaggactc | tgtacagaca | gtccccagta | ccagcccaga | gctgggtaga cttgctaggt 97920 |
| ggcaagaccc | agaagacagg | caataatcac | tgcagttcag | ctcacaggaa gccacatcca 97980 |
| taggaaaaga | gggagagtac | tacatcaagg | gaacacccca | tgggataaaa acatctgaac 98040 |
| aacagccttc | agccctacct | tccctctgac | acagtctacc | caaatgagaa ggaaccagaa 98100 |
| aaccaaccct | ggtaatatga | caaaacaagg | ctcatcacac | tcccagttca ccagcaatgg 98160 |
| atccaaacca | agaagaaatc | cctgatttac | ctgaaagaga | attcaggagg ttagttatta 98220 |
| agctaatcag | ggagggacca | gagaaaggca | agcccaatg | caaggaaatc caaaaaaaaa 98280 |
| aaggtataag | aagtaaaagg | tgaaatattc | aacaaaatag | atagcttaat aaaaaaacaa 98340 |
| taaaaaattc | agtagacttt | ggacacacct | ttggaaatgt | gacatgctct ggaaagtctc 98400 |
| agcaatagaa | ctgaacaagt | agaaaaaata | aattcagagc | tcaaagacaa ggacttcaaa 98460 |
| ttaacccaat | ccaacaaaga | caaagaataa | aggataagaa | aatatgaaca aagccttcaa 98520 |
| gatgtctggg | attatgttaa | atgaccaaat | ataagaataa | tcgtggctcc tgaggaaaaa 98580 |
| gacaatacta | aaagcttgga | aaacatattt | gggggaataa | ctggggaaaa cttacctggc 98640 |
| cttgctggac | acctagacat | gcaaatacaa | gaaaacacaaa | gaacatgtaa atacaagcag 98700 |
| cacaaagaac | acctgggaaa | ttcatcacaa | aaagatctta | gcctaggcac attctcatca 98760 |
| ggttatgcaa | agttaagacg | aaggcaagaa | tcttaagagc | tgtgagacag aagcaccagg 98820 |
| taatgtataa | aggaaaccct | atcagattaa | cagccagttt | ttcagcagga actgtacaag 98880 |
| ctataaagga | ttggagccct | atcatagcct | cctcaaacaa | aacaattatc agtcaagaat 98940 |
| tttgtatcca | gcgaaagtaa | gcatcatata | tgaaggaaag | atacagtcgt ttttggacaa 99000 |
| acaaatgcta | agagaattca | ccattaccaa | gtcaccacta | gaagaactgc taaaaggagc 99060 |
| tctaaatctt | gaaacaaatc | ctagaaacac | atgaaaacag | aatctcttta aagcataaat 99120 |
| cacacaggac | ctataaaaca | aaagtacaag | ttaaaaaaca | aaaacaaaaa acaaaaccaa 99180 |
| agtacggagg | caataaagaa | tatgatgaat | gcagtggcac | ctcacatttc aatgctaaaa 99240 |
| ttgaatctaa | atggcctaaa | tgctccactt | aaaggataca | aaaagagttg gtggctggca 99300 |
| agatggctga | ataggaacag | ctccagtctg | ccgctcccg | tgagatcaac acataggtg 99360 |
| ggtcatttct | gcatttccaa | ccaaggtacc | cggctcatct | cattgggact ggttagacag 99420 |
| tgggtgcagc | ccacagaggg | tgacctgaag | cagggtgggg | tgtcacctca cctgggaagt 99480 |
| ggaagggtc | agggaactcc | ctcccctagc | caaaggaagc | cgtgaggac tgtgccgtga 99540 |
| agaccagtgc | attctggcac | aaatactatg | cttttcccac | ggtctttgca acctgaagac 99600 |

```
caggagattc ccttgggtgc ctacaccacc agggccctgg atttcaagcc caaaactggg  99660
ctggcatttg ggcagacact aagctagctg caggagtttt ttttcatacc ccagtggtcc  99720
ctggaatgcc agcaagacag aaccattcac ccccgtgaag aaagggctga agccagggag  99780
ctaagtggtc tttctcagtg gatcccaccc ccatggagcc cagcaagcta agctccactg  99840
gcttgaaatt cttgctgcca gcacagcagt ctgaagttga cctgggacgc tcaagcttgg  99900
tgggaggagg ggtatccaca aatactgggg cttgagtagg aggttttccc ctcacagtgt  99960
aagcaaaacc gctaggaagt ttgaactggg cagggtgcac tgcagcttgg caaagccatt 100020
gtagcaagag tgcctctcta gattcctcct ctctgggcag ggcatctctg aaagaaaggc 100080
agcagcccca gtcagaagct tatagataaa actcccatct ccctgggaca gagcaactgg 100140
aggaaggggt ggctgtgagt gcagctccag cagacttagt ttcctgcctg ccagctctga 100200
aaagagcacc agatccccca acacagcact agagctctga taagggacag actgcctcct 100260
caagtgggtc ctggtttcag aagataataa gaaactcctc tgagctaaag gagcatgttc 100320
taacacaatg caaggaagct aagaaccttg aaaaggtca gaggaattgc taactacagt 100380
aagcagttta gagaagaaca taaatgacct tagggagctg aaaaacacag cacgagaact 100440
tcatgacaca tacacaagta tcaatagcaa aatcgatcaa gtggaagaaa ggatatcaga 100500
gattgaaaat caacttaatg aagtaaagcg tgaaaacaag attaaggaat aaagaatgaa 100560
aaggaatgaa caaatcctcc aagtatggga ctatgtgaaa agattgaacc tacgtttgat 100620
tggtgtacct gaaagtgatg ggagaatgga accaagttgg aaaacactct tcaggatatt 100680
atccaggaga acttccccaa cctagcaaga caggccaaca ttcaaattaa ggaaatacag 100740
agaataccac attcaaattc aggaaataca gagaacacca caaagatact cctcaagaag 100800
agcaacctga agacacataa tcgtcagatt caccaaggtt gaaatgaagg aaaaaaatgt 100860
tgagggcagc cagagagaaa gtttgggtta cccacaaagg gaaccccatc agactaacag 100920
tggatcttcc tgcagaaact ctacaagcca gaagagagtg ggaggccaat attcaacatt 100980
cttttttact attattatac tttaagttct agggtacatg tgcacaaggt gcaggtttgt 101040
tacatatgta tacatgtgcc atgttggtgt gctgcaccca ttaactcttc atttacatta 101100
ggtatatctc ctaatactat ccctccccac tccccccatc ccatgacagg cccggtgtg 101160
tgatgttccc cactctgtgt ccatgtactc tcattgttca attcccacct atgagtgaga 101220
acattcggtg tttggatttc tgtccttgtg atagtttgct gagaatgatg gtttccagct 101280
tcatccacat ccctacaaag gacatgaagt catccttctt tatggctgca tagtattcca 101340
tggtgtatat gtgccacatt ttcttaatcc agtctaccat tgatggacgt ttgtgttggt 101400
tccaagtctt tgctattgtg aatagtgccg caataaacat atgtgtgcat gtgtctttat 101460
agcagcatga tttataatcc tttagatata tatccagtaa ttgtatggct gtgtcaaatg 101520
gtatttctag ttctaaatcc ttgaggaatc accgcactgt cttccacaat ggttgaacta 101580
gtttacagtc ccaccaccag tgtaaaaatg ttcctatttc tccacatcct ctctagcatc 101640
tgttgtttcc tgacttttta atgatcacca ttctaactgg tatgagatgg tatctcattg 101700
tggttttgat ttgcatttct ctgatggcca gtgatggtga gcactttttc atgtgtctct 101760
tgactgcata aaagttttct tttgagaatt gtctgttaat atcctttgcc aacttttttga 101820
tggggttgtt tgatttttt tcttgtaaat ttgtttatgt tctttgtaga ttctggatat 101880
tagccctttg tcagatgggt agattgtaaa aattttctcc cattctgtag cttgcctgtt 101940
```

```
cattctgagg gtagtttctt ttgctgtgca gaagctcttt agtttaatta gatcccattg    102000
gtcaattttg gcttttgttg ctattgcttt tggtgattta gtcatgaagt ccttgcccat    102060
gcctatgtcc tgaatggtat tgcttaggtt ttcttctagg gtttatatgg ttttaggtct    102120
aacatttaag tctttaatcc atcttgaatt aattttata taaggtgtaa ggaagggatc    102180
cagtttcagc tttctacata tggctaggca gttttcccag caccatgtat taaataggga    102240
aacctttccc tatttcttgt ttttgtcagg tttgtcatag atcagatggt tgtagatgtg    102300
tggtattatt tctgagggct ctgttctgtt ccattggtct atatctctgt tttggtacca    102360
gtaccatgct gttttggtta ctgtagcctt gtaatgtagt ttgaagtcag gcagagtgat    102420
gcctccagct ttgcttttt ggcttaggat tgtcttggca atgcatgctc ttttttgttc     102480
catatgaact ttaaagtagt tttttccaat tctgtgaaga aagtcattgg tagcttgatg    102540
gggatggcat tgaatctata aattaccttg ggcagtatgg ccattttcac aatattgatt    102600
cttcctatcc atgagcatgg aatgttcttc catttgtttg tgtcctcttt tatttcatta    102660
agcagtggtt tgtagttctc cttgaagagg tccttcccat cccttgtaag ttggattcct    102720
aggtatttta ttctctttga agcaattgtg aatgggagtt catccatgtc cctacaaagg    102780
acatgaagtc atgtatggga atgcttgtga tttttgcaca ttgattttgt atcttgagac    102840
tttgctgaag ttgcttatca gcttaaggag attttggtct gagaagatgg ggttttctaa    102900
atatacaatc atgtcatctg caaacaggga caattaact tcctcttttc ctaactgaat     102960 acccttatt tccttctcct gcctaattgc cctggccaga acttccaaca ctatgttgaa      103020
taggagtggt gagagagggc atccctgtct tgtgccagtt tcaaaggga atgcttccag      103080 tttttgccca ttcagtatga tattggctat gggtttgtca taaatagctc ttattatttt    103140
gagatatgtc ccatcaatac atagtttatt gagagttcag catggagagc tgttgaattt    103200
tgtcaaaggc cttttctgca tctattgaga taatcatgtg gtttttgtct ttggttctgt    103260
ttatatgatg gattacattt attgatttgc atatgttgaa ccagccttgc atcccaggga    103320
taaagccaac ttgatcatgg tggataagct ttttgatgtg ctgctggatt cggtttgcca    103380
gtattttatt gaggattttt gcatcaatgt tcatcatgga tgttggtcta aaattctcat    103440
ttttgttgtg tctctgccag gatttggtat caggatgatg ctggcctcat aaaatgagtt    103500
agggaggatt ccctcttttt ctatgattgg aatagtttca gaagaattgg taccagctcc    103560
tctttgtatc tgtggtagaa ttcggctatg aatctctcct ggacttttt tggttggtag    103620 gctcttaatt attgcctcaa tttcagagcc tgttattggt ctattcaagg attcaatttc    103680
tttctggttt agtcttggta gggtgtatgt gtccaggaat ttttccattt cttctagatt    103740
ttctagttta tttgcacaga ggtgtttata atattctctg atggtagttt gtatttctgt    103800
gggattggta gtgatatccc ctttatcatt ttttattgca tctatttgat tcttctctct    103860
ttcttctttt attagtcttg ctagtggtct atcaatttg ttgatctttt caaaaaacca     103920
gctcctggat tcattgatgt tttgaaggtt ttttgtgtc tctatctcct tcagttctgc     103980
tctggtctta gttatttctt gccttctgct agcttttta tgtgtttgct cttgcttctc    104040
tagttctttt aatggtgatg ttagggtgtc aatttagat cttcctgct ttctcttgtg     104100 ggcatttagt gctgtaaatc tccccctaca cactgcttta aatgtgtccc agagattctg    104160
gtatgttgtg tctttgttgt cattggtttc aaagaatatc tttatttctg ccttcatttc    104220
gttacatacc cagtagtcac tcaggtgcag gttgttcagt ttccatatag ttgagcagtt    104280
tttaatgagt ttcttaatcc tgagtcctag tttgattgca ctgtggtctg agagacagtt    104340
```

```
tgttataatt tctgttcttt tacatttgct gaggaatgcc tcacttccaa ctatctggtc    104400
aatttcagaa taagtgcgat gtggtgctga gaagaatgta tattctgttg atttggggtg    104460
gagagttctg tagatgtcta ttaggtctgc ttggtgcaga gctgagttca attcctggat    104520
atccatgtta actttctgtc tcattgatct gtctaatgtt gacagtgggg tgttaaagtc    104580
tcccattatt attgtgtggg agtctaagtc tctttgtagg tctctaagga cttgctttat    104640
gaatctaggt gctcctgtat tgggtgcata tatatttagg atagttagct cttcttgtta    104700
aattggtccc tttaccatta tgtaatggcc ttctttgtct cttttgatct tgttagtttt    104760
aaagtctgtt ttatcagaga ctaggattgc aacccctgct ttttttgttg ttttccattt    104820
gcttggtaga tcttcctcca tcccttkatt ttgagcctat gtgtgtctct gcacgtgaga    104880
tgtgtcttca gaatacagca cactgatgga tcttgactct ttatccaatt ttccagtctg    104940
tgtctttTaa ttggagcatt tagcccattt acatttaagg ttaatatttt tatgtgtgaa    105000
tttgatcctg tcatcatgat gttcgctggt tattttgctc attagttgat gcagtttctt    105060
cctagcatcg atggttttta caatttggca tgtttgtgca gtggctgata ccgattgttt    105120
cttTccatgt ttagtgcttc cttcaggagc tcttgtaagg caggcctggt ggtgacaaaa    105180
tctctcagca tttgcttgtc tgtaaaggat tttatttctc cttcacttat gaagcttagt    105240
ttggctggat atgatattct cagttgaaaa ttcttttctt taagaatgtt gaatattggc    105300
tgccactctc ttctggcttg tagagtttct gctgagagat ctgctgttag tctgatgggc    105360
ttcccttTgt gggtaacccg acctttctgg tgaatctgac aattatgtgt cttggagtta    105420
ctcttctcga ggagtatttt tgtggcattc tctgtatttc ctgaatttga atgttggcct    105480
gcctttgtag gttggggaag ttctcctgga taatatcctg aagagtgttt tccaacttgg    105540
ttccattctc ctcgtcactt tcaggtacac caagcagatg tagatttggt cttttcacat    105600
agtcccatat ttattggagg cttTgttcat ttcttttTac tccttttttt ctctaaactt    105660
ctcttctcgc ttcatttcat tcatttgatc tttaatcact gatacccttt cttccacttg    105720
attgaatcaa ctactgaaac ttgttcatgt gtcacgtagt tctcgtgcca tggttttcag    105780
ctccattaga tcatttaagg tcttctctat gctgtttatt ttagtctgcc attcatctaa    105840
acttTttcaa ggttTttagc ttcttTgcaa tgggttcgaa catccttctt tagctcggag    105900
aaatttgtta ttacagatcg tctgaagcct tcttctctca actcatcaaa gtcattctct    105960
gtccagcttt gttctgttgc tcgtgaggag ctgcgttcct tcggaggaga agaggcaccc    106020
tgatttttag aattttcagc tgttctgctc tggtttctcc ccatctttgt ggtttatcta    106080
cctttggttc ttgatgatgg tgatgtacag atggggtttt ggtgtggatg tctTttctgt    106140
ttgttagttt tccttctaac agtcaggacc ctcagctgca ggtctgttgg agtttgctgg    106200
aggtccactc cagtccctgt ttgcctgggt attaccagtg gaggctgcag aacagcaaat    106260
attacagaac agcaaatgtt gctgcctgat tcttcctctg gaagcttcat ctcagagggg    106320
cacccagctg tatgaggtgt cagttggccc ctactgggag gtgtccccca gttaggctac    106380 tcggggtca cggacccact tgaggaggca gtctgtccat tctcagatct caaactctct    106440
gctgggagaa ccactactct cttcaaagct gtcagacagg gatgtttaag tctgcagaag    106500
tttctgctgc cttttgttca gctatgccct gcccccagag gtggagtcta cagaggcagg    106560
caggtctcct tgagctgtgg tgggctccac ccagtttgag cttcctggtc gctttgttta    106620
cctactcaag tctcagcaat ggcagacgcc cctcccccag ctttgctgcc gccttgcagt    106680
```

```
tcggtctcag actactgtgc tagcagttca atctcagact gctgtactag cagtgagcaa    106740
ggctctgtgg gcatgggacc ctctgagcca tgtgcaggat ataatctcct ggtgtgccgt    106800
ttgctaagac cattggaaaa gtgcaatatt agggtgggag tgtcccgatt ttccgggtac    106860
atctgtcatg gcttcccttg gctaggaaag ggaattccct gacccttac acttcccggg     106920 tgaggcaata tcccgccttg cttcggctca ctctccgtgg gctgcaccca ctgtctgaca    106980
agccccggtg agatgaaccc agtacctcag ctggaaatgc agaaaccacc catcttctgc    107040
tttgctcatg ctgggaactg tggactggag ctgttcctat tcggccatct tgaaacctcc    107100
cctctctcac gatcacaagg tcccacaata ggccgtctgc aggctgagga gcaagaaaag    107160
ccagtctgaa ttccaaaact gaagaaattg gagtctgatg ttcaagggca ggaaacatcc    107220
agtgccaaag aaagatgtag aatattcaac attcttaaag aaaataattt tcaacctaga    107280
atttcatatc cagccaaact aagctttata acaaggaga agtaaaatcc tttacaaaca      107340
agcaaatgct gaggaatttt gtcaacacca ggcctgcctt acaagaggtc ctgaagaaaa    107400
cactaaatat ggaaaggaaa aaccagtaac agctactgca aaaacatacc aaattgtaaa    107460
caccatcaac actataaaga aactgcatca actaatgggc aaaatagcca gctagcatca    107520
taatgacagg atcaaattca cacataacaa tattaacctt aaatgtaaat gggctaaatg    107580
ccccaattaa aagacacaga ctgggaaatt gaataaagag tcaagaccca ttggtttgct    107640
gtgttcagaa gacccatctc agggtgaaaa gacatacatg ggctcaaaat aaagaaatga    107700
aggaatattt accaagcaaa tggaaagaaa aaaaagcag cggttgcaat cttagtctttt    107760 gatgaaacag actttaaacc atcaaagatc aaaagagaca aaggagggca ttacctaatg    107820
gtaaaagtat caatgcaaca agaagatctg actgtcctac ttatatatgc acccaataca    107880
ggagcaccca gattaataaa gcaagttctt agagacctac aaagagactt agacttccac    107940
acaaaaatag tgggagactt taacacccca cagccaatat tagatcgacg tgacagaaaa    108000
ttaacaagga tattcaggac gtgaattcag ctctggacca agctgaccta atagacatct    108060
acagaactcg acaccacaaa tcaacagaat atacattctt ctcagcacca cattgcactt    108120
attctaaaat tgaccacata attggaagta aaacacttct cagcaaatgc cgtagaatgg    108180
aaatcataac aaacagtctc tcagaccaaa gtgcaatcaa actagaactc aggattaata    108240
aactcactca aaaccacaca actatatgga aactgaacaa cctgctcctg aattactact    108300
gggtaaataa caaaattaag gcagaagtag ataagttctt agaaaccaaa gagaacaaag    108360
acacaatgtg ccagaatctc tggtacacag ctaaagccat gtttagaggg aaatttatag    108420
cactaaatgc ccacaggaga aagcgggaaa gatctaaaat caacacccta acatcacaat    108480
tcaaagaacc agagaagcaa gagcaaacaa atacaaaagc tagcagaaga caagaaataa    108540
ctaagatcag agcagaactg aaggggataa agacacgaaa acccttaaa aaattaataa      108600 atccaagagc tggttttttg aaaagattaa caaaatacat agaagcctag ccagactaat    108660
aaagaagaaa atagagaaga atcaaataga cacaataaag aataataaag gggatatcac    108720
caatgatgcc acagaaatac aaactaccat cagagaatac tttaaacacc tctatgcaaa    108780
taaaatagaa aatctaaaag aaatggataa attcctggac acatacaccc tcccaagact    108840
aaaccaggaa gaagtcaaat ccctgaatag accaataaca gttctgaaa tcgaggcagt      108900 aattaatagc ttaccaacca aaaaagccc agaccagagg gattaacagt caaatcctaa      108960
cagaggtaca aagaagagct agtactattc cttctgaaac tattccacac aatagaaaaa    109020
gagggactcc tgcctaactc atttatgag gccagcatca ttctgatacc aaaacctggc      109080
```

```
agagacacaa caagaaaaga aaatttcagg ccaacatccc tgatgaacat caatgtgaaa 109140
atcctcaata aaatactggc aaactgaatc cagcagcaca tcaaaaagct tatccaccat 109200
gatcaagttg gcttcatccc tgggatgcaa ggctggttca acatattcaa atcaataaac 109260
ataatccatc acataaacag aaccaatgac aaaaaccgta tgattatcgc aatagacgca 109320
gaaaaggcct ttgataaaat tcaatacccca atcatgctaa aaactcttaa taaactaggt 109380
attgatggag catgtctcaa aataataaga gctacttatg acaaatgcat agccaatatc 109440
atactgaatg agcagaagct ggaagcattc cctttgaaaa ccagcacaag acaaggatgc 109500
cctctctcac cactcctatt caacatagta ttggaaattc tgtccagggc aatcaggcaa 109560
gagaaagaaa taaggtatt caagtgggaa gagagggagt caaattattt ctctttgcag 109620
atgacatgat tgtatattta gaaaactcta tcatctcagc ccaaaatctc cttaagctga 109680
taagcaactt cagcaaagtc tcaggataca aaatcaatgt gcaaaaatca caagcattcc 109740
tatacaccaa taagagacac agagccaaat cctgagtgaa ttcccattca caattgctac 109800
aaagagaata aaatatacct aggaatccaa cttacaaggg atgtgaagga cctcttcaag 109860
gagaactaca aaccactgct caaggaaata agataggaca caaacaaatg gaaaacatt 109920 ccatgctaat ggattggaag aatcaatatt gtgaaaattg ccatactgcc caaagtgatt 109980
tatagattca atgttatccc catcaagcta ccattgattt cttcacataa ttagaaaaaa 110040
ctactttcaa tttcatatgg aatagaaaaa gggcctgtat atccaagaca acctaagcaa 110100
aaagaacaaa gctggaggca tcatgctatc tgacttcaaa atatactaca aggctacagt 110160
aacaaaaaca gcatggtatg gtactggtac caaaacagat atatagacca atagaacaga 110220
acagaggcct cagaaataac accacacatc tacaactatt ggatctttga caaactggac 110280
aaaaataagc aatggggaaa ggattcccta tttaataaat ggtgttggga aaactggcta 110340
gccatatgca gaaaactgaa actggatccc ttccttacac cttatacaca aattaactca 110400
agatagatta aagaattaaa tgtaagacct aaaaccataa aaaccctaga agacactttg 110460
ggaggccgag gtggatggat cacgaggtca ggagatcgag accatcttgg ctaacacagt 110520
gaaagcccat ctctactaaa aatacaaaaa attagctggg tgtggtcgtg ggcacctgta 110580
gtcccagcta cttgggaggc tgaggcagga gaatggcatg agctgaggag gttgagcttg 110640
cagcaagcca agattgtgcc actgcactcc agcctgggca acagagtgag actccatcaa 110700
aaaaacaaaa acaaaaacaa aaaatcaaac cctagaagaa aacataggca ataccattca 110760
ggacataggc atgggagaag acttcatgac taaaacagca aaaccaatgg caacaaaagc 110820
caaaatttac aaatcagatc taattaaaat aaagagcttc tgcacagcaa aaaactctca 110880
tcagagtgaa aaagcaacct atggagaaaa attctgtggt ctagccatct gacaaagggc 110940
taatgtttag aatgtacaag caacttaaac aaatgtacaa gaaaaaaaaa acaaccccat 111000
caaaaagtgg gcaaaggata tgaacagaca cttctgacag gaagacctt atgtggctga 111060 caaacatgaa aaaagctcat catcactgtt aattagagaa atgcaaatcg aaaccacaat 111120
gagataccat ctcatgcccg ttagaatggc gatcattaaa aagtcaggaa acaacagatg 111180
ctgaagagga tgtgtggaga aagaggaaca catttacact gttggtggga gtgtaaatta 111240
gttcaaccat tgtggaagac agtgcggtga ttcctcaagg atctagaacc agaagtacca 111300
tttgacccag caatcccatt actgggtata tacccaaagg attataaatc attctacaat 111360
aaagacacat gcacacgtat gtttattgta gcactattca caatagcaaa gacttggaac 111420
```

```
caactgaaat gcccatcaat gatagactgg ataaagaaaa tgtggcacat atacactgtg   111480
gaatactatg cagccataaa acaggatgag ttcatgtctt ttgcagggac atggatgaag   111540
ctggaaacca tcattctcag caaactaaca caagaacaga aaaccaaaca ccatatgttc   111600
tcactcataa gtgtgagttg aacaatgaga acacatggac acaggaaggg gaacatcaca   111660
cacaggggcc tgttggggag ttgaggctag gggagggatt ggattaggag aaatacctaa   111720
tgtagatgat gggttgctgg gtgcagcaaa ccaccatgac acgtgtatac ctatgtaaca   111780
aacccacaca ttctacacat gtatctcaga acttaaagta taataataat aagatacaga   111840
actgcagaat gaataagaac tcaccaacca tctgctgcct tcaggagact catttaagac   111900
ataaggactc acataaactt aaagtaaatg ggtggaaata ataataagtg gtgtcactga   111960
tgtggaggta gattataaaa ctcttatcat atgctggtgg aagatcaaaa tgataaaacg   112020
aattaaaaaa tcagtcagat ggtttcttaa aaagttccat caatatgcct ctatcttaca   112080
aacctgcaat tctattcctg aatctttatc ccaaggaaat gaaaaagtaa gtccacaaag   112140
agttctatat gaatatttat aggagcttta tttattataa ttcaaactgt aaaaataatt   112200
tcaatgttca tcaataacaa aatgaaaaaa taatttgcaa cctactggta cacttgaata   112260
ctattcagca ctgagtatct taaatagcat ggatggagct caaaaatata ctcaggaaag   112320
aagccatgta tattctgtat gagttcattt acatgagatc atttacattt cctccaaaag   112380
aggaaaaact aatttctgtt gaaagaaacc aatgtatttg cctctggcag tggtaagggg   112440
gtagcacaga ttaattgggt agggactcaa gagagtttct ggggtcacag aaatgttccg   112500
tgtggtgatg ggagtttggg ctccacaggt ataggtgttg atccaaaatc atcaaaaaaa   112560
caacattgca gatctgtgca tctcactctg tgggaaagta tatctcaact gtaaaagggg   112620
cagaaattgc ttttaaacgc tcagccttt agcacatcca gttgcttgga gaaccagctt   112680
actcaaatgg gggtctaggc tggagactag gtcacaggca tagagtctct aaactttccc   112740
atggcacata atacgtttca ggttttctca gagagctgca ggttagtaat ctgaggattc   112800
tgacaagttg ggtcaacgtt cctaggaggc atgaatggga gtgcattctc taagatccct   112860
ccaccccagg gtccttgctt tctgtgcctc ttactccatt gttttctgac tcctctgtag   112920
ccactcgacc tcttcagatc ccattgtcta cccagccatc gcccttatg acttgggtcc    112980 cactgttctt tcatctcatc ctccattccc tcagtttcgg agtggctgcc gctagcagag   113040
gatggactga gagcaggaga ggtggtcctg cccaggaacc catcctagag aaatggcatc   113100
ctgtctggga gctagttttt tagggcaggt tttataagtc ttgtaaagcc agacacactt   113160
gatctacctg gtatgttatt tacagtaata ctattttcat aattgctttt cactctaaaa   113220
gtagagcctt ttagctacac tgtgagtaaa taaaggggct ggcctgggaa tggtatcatg   113280
ttggatgttg tttcttccct gaagtaatat atatcagtta caatttacat gttactgcag   113340
agtcctagag agagacacag agaatgagac agataccaat acatttttat gtgcattaaa   113400
aaaatctaag gccaggcgca gtggctcaca cctgtaatcc cagcactttg ggaggccgag   113460
gtgggtggat cacgaggtca ggagattgag accatcctgg ctaacacggt gaaaccctgt   113520
ctctactaaa aatacaaaaa attagccagg cgtggtggcg ggcgcctgta gtcccagcta   113580
ctcaggagac tgaggcagga aatggcttg aacccaggag gcagaccttg cagtgagccg   113640
agattgcgcc actgcactcc agtctgggcg acagagcgag actccgtcac aaaaaaaaaa   113700
aaaaatctaa aatgcactct tcaaaatcta tgtcatttat tctggaggaa tgcagttggc   113760
agaaggagga agatattccg aattttttctt gtatacattt atgtatgatc tcagttttttt   113820
```

```
tatggatcat agaccaattt tgatatttta aaataaaaat tataatctat cttggaaatt  113880
tacatggttc tttagaactt gaggaccgtt tttgcttttc ggaatattat tgtacctaaa  113940
atgggaatat tacaacgtca cttttaaca ctttgttata acaaagttta gacagcgctg  114000 ggtgccctg aattttttcc cgcctcttgt gacctgtgtt gttttggaat ttgcagtggc  114060
ctgaccgaga actactgcag gaatccagat tctgggaaac aaccctggtg ttacacaacc  114120
gatccgtgtg tgaggtggga gtactgcaat ctgacacaat gctcagaaac agaatcaggt  114180
gtcctagaga ctcccactgt tgttccagtt ccaagcatgg aggctcattc tgaagcaggt  114240
aagaagtctg tggccagata tctacacatt tgaacattgg gatgaaaaga gatggaaaat  114300
ctgactgatg cagaagcctt ccatgctaca cagaaacttg agggtatggc aggtggaaag  114360
aagcctcagc actctctctg gtggagcaat ttttggcgca acgtgcgtgg gcggtgactt  114420
caggaatggt gcaaacccac ctgggcactt gacttaccac tcactttgtt atgaaagggg  114480
ttatctcggt gttccagaca aaattccaat tctaacatca ggccaaattt gtgccaaatt  114540
tcacactagt gagtgtttcc aggcatttat taaaatggac agtgttcatt gcaatcttca  114600
gcattgcagt tgctgaggta tgtggccgct gagtttgtca tcctggggaa acctaatatg  114660
atgatattta ttccatctaa tcctggggct atttggcagt aaataccaca gaatacacta  114720
tttctctggc ttatttcagt cttaggtagg ctctgcacac ctatgcttgg aaggcaggaa  114780
tttcttggtg ttcttgtgcc ttcttctcat ggaacgtgca tctttggtgt gtgttgagag  114840
gaagggtagt agacttctgc tttgttgcaa tgcaggatgc tggaacaaga ggattccctg  114900
tctctactgt aagggaataa gattttagcc tccatccttc tctaagaagc aatgtgtctt  114960
tgcctccaag tactagatgc aggaccatga actgccccgt ccaccagaag cttaaggctt  115020
tggcttttca ggagcaatca tctagggaac tgtgcagggt tttcatgtct gtcccctact  115080
gacagccaat caccatacag cctgcataac ctaatccatc atcgtctggt ttcctgcctc  115140
attgttttca tgaacaacca gtagagagcc atacgaaaga gcttgcacat gagtctttgt  115200
tccaattgta agagcactga taggtccttt tcccaccagg ttttgaatat aaaatttcta  115260
agaacttatt aaaatattag aatgttatta atctattgtt tttgcttcag catgtccttc  115320
tgcttgtgag tatactaaag agaacagtca taattctgaa actactgtcc tgtttgtgtc  115380
ataaattgct tcacatgttt ctgcatacta gtagttactc agcttgattt tgtctatttt  115440
cagcaccaac tgagcaaacc cctgtggtcc ggcagtgcta ccatggtaat ggccagagtt  115500
atcgaggcac attctccacc actgtcacag gaaggacatg tcaatcttgg tcatccatga  115560
caccacaccg gcatcagagg accccagaaa actacccaaa tgagtatgtc tttgatgtta  115620
cttgtaagag gagcaacagc caacttaagt tcctcctaga agagccttgc ttcaagctaa  115680
cttgttagga caaatttccc ttagacccag aaggtgtgtc aaaatgtcca gacaactttg  115740
cttttgatca aagagtctga gagaataggt attttaggct tgctatcttt tctaatagtc  115800
tgatggaagc agaaggctac atggagctga tgaggtcttt ttaatataaa gctcaagaga  115860
tcaaatgatc aaatacttag agtgccattc tacaaggctc ataaaagatc aatgcactct  115920
ttcacccatg caattctatc attctaacct cccttctctg aaatgaaggc tttttgccat  115980
ttttgtcatg ggtcacaagt aaataattca catgtatatg agtatatata taaccaggtg  116040 tgttattca gactagtatg tatatatata catatatatg ttcatataag ttagtattca  116100
tatatatgtt catatatata tgttcataca gactagtatt catatatata tacatatata  116160
```

```
tatacacaca catatatata tatatatata tgttctaggg aaacatgcaa ggtttttatg    116220
tctgtccctg actgatgacc aaatacccta tagcctgcac agctgcaagc tgtatagcca    116280
tacaatttgc aggacacaca cacatacaca cacacacaca cacacacaca cactaacata    116340
taatataata taatataata taatataata taatataata taatataatt aatatatata    116400
aacctgtgtg aacacactgg gttctaagct ccagttttct gaagggatat gggttgccag    116460
gagaggaaga gcaaaagcaa gaatgtagat gagaattagg aagtaaacag atatggagat    116520
taaaatgggc aggtacatgg acaaaaaacc aggtctgaca aaaactggct ttctgccata    116580
aatgactata aaagatatta aaaaacactt tccacatgtt ggacaagaga cagtacagga    116640
ctgagataat ttagaaaagg aaatgaatga gcgcaactcc gtaactatta tgactttctt    116700
cctggagaac cttcctggac tgaagggcaa ggaattggag ccaaagccaa ccacagcagt    116760
cttgctgaac tgaggaaaga gactggagtt tgggatagct aagaaaatgt gtattttcta    116820
tgctaggtaa taatgagaaa gaatttgtgg tgaaaaggag ctgaaggaat atgcatggaa    116880
gtctaatata aactgcatat gcacaggag aaattctaca aagtgggaca gagaaccact     116940
actggggaaa ggacaaattc agggaaacag tgagctcaat ggtgacgcca gagctcacgt    117000
agcactgggg gataccgggg ttctgatcag cccgaggaga gacacctcat tgaacatctc    117060
gggcattcag tagagacccc agaaaagtca tactttagga gtaggattta tgccttctta    117120
gaataaagac taccccagaa acaccctagt aaagcttaaa aaccaagtct aaaaggaccc    117180
aaatgatctc caagtaaatt aactgcctga cagaagaaaa ctcaaccatc actggaggta    117240
aataacatga ttacagtgct ctgtaatgtt gcattcacaa ggagtgacat catttaaaaa    117300
tttatgaggc aggaaaaagc aattagtgtg atccataact aggagaaaaa ccagtcaata    117360
caaatagacc aagaaatagt agaaacgatg gaattgacaa agaaattaaa actgtatata    117420
tgataattgt gttcaaagat ttaaagaaaa catgaacatg agggaaacaa atgcagaata    117480
taaaaaaaag caaatgcgta aaacaaccaa atggaaatta agaactaca aaaaagtata     117540 accttaataa aatactcact ggatggcctt aatattagtt tatacattac agaagaaaaa    117600
gtgaaccaga agataactca atgaaagcca tacaatctgt aagacacaca cacgcaca      117660 cgcgcgcgcg cgcacacaca cacacacaca gagagagaga gagagagaaa gagagagaga    117720
gaaaggctga aaaaaataaa tagaaaccta aggtatcag tgaaaatagc aaaagattta     117780
atatatgggt aaagcaagtc acagaaggac gggaaggaga tattgggaca gaaaaaaata    117840
ctcaaagcaa tgatggctga agactttaca cgtatgaaga aaatgataaa ctcacagtca    117900
agaagctcaa tgaatcagaa atagtatttt taaaagcaaa actctatgat ttacttgggt    117960
acattataga taaatcgtcc aacatcaaag ataacaagga taatcttata agccagagga    118020
aaacaatatc atttacatag agggacagta atgaaagtga ccgatgcctt ctccttggaa    118080
acaatggcat aacatcttta aagtgataaa gagaaataaa aacagatcaa cctaggacga    118140
catgtccagc caaacaaac aaataaacaa aaaaacccctt taaaataaac gtgatgtaaa    118200
tacgtattct gccacctcca gaggaaacaa gcaaaaaaac aaaagaatgt ttccaaggca    118260
ggcttctgta ttaaaagatt ttaaggaaag ttattcaggt agaagaaaaa taataccaga    118320
tgggaacttt aatccatact aagtaatgaa gagccctgga aatggcaaat ggcaatgtca    118380
atataaaata ctcttattta tctaattttt aaatgtattt aaaggacaat ttgtgatatt    118440
aattaaaata ataggaatat attgttgttt caacgtatgt agtagtaaaa ttcataaaaa    118500
cagtagcaca aataatgcag atgataactg gaagtatact gttaatgagt tttttgcatt    118560
```

```
atccatgaag ttatataata ttaatagatg gttgaatgtg atagtttaag gtgggatatt   118620
ataaatccta ggacaaccaa aaaaatttaa actgagagga atggatagta agaggaatag   118680
tccttttatg caaaagaagg aagaaaaaga ggaataaaga atataaaaga tatggtgtaa   118740
acagaaaata catagcatta ttgtagacac aaactgaact accttatgag tatattaaat   118800
ataaaaggat taagcattac aaataaaagg cagagattgt aaattgaata aaaaccacag   118860
ctaagtgtgt tctttttaga ataaatactc tttaagtgta aagatctact ttaaacacca   118920
aaatatgaaa aaggatatat accatgaaaa cctgaatcat aaataagctg gagtggtgat   118980
taatggatgc aggcactcct aaagactaat aagtgaatgt ggtcaaattg aagaaacaaa   119040
agtatatacg tgctcaatgt gcaaaaactt tttctgtata catgctatga tcctttggaa   119100
aattaaagtt ttaaagcaat atcactgaca atagtatcaa aaccaaaaaa tatttagtga   119160
taaatttcac acactatgct caaggactat acaccttgca ctagaaaaca atgttgagga   119220
aagaattaaa agatctaaat atacaccatg cttatagatt aaaagactcc atatcagttc   119280
tcgtgaaatt gatctttgga tgaaacccac acccaagcac tattgcaaca gtcctttttt   119340
ggaaaaaaaa attggaggac ttatatacct taatataaag acttataaaa gtacaggaat   119400
caagacatgt ggtattggcc tggccccttg gctcatgcct gttaccccaa cattttggga   119460
ggctgagtct ggaggatggc ttgagcccag atgttcaaga ccagccttag caacagagtg   119520
agaccctctc tctacaaaaa ataaacaatt agatcgatgt gatgacttgc acatgtagtt   119580
tcagctactc ggaatgctga ggtgagagga ttgcttgact caggaggtct agccatgagt   119640
gagcattgat catgcctctg cattccagcc tggatgatgg aatgagacac tgtctcaaaa   119700
aaaaaaaaaa aaaaggatat gtgttattgg ccaaaaaagt atgcaaacct aaaaagggat   119760
ggcccaccac cagacccaca tacatatatg gtaaatggat tttccgtata gatggcaaag   119820
caattcaatg gagacaaaaa tgttttacaa aatcattctg aaccatttgg atatccatga   119880
tacaaaacaa aagcagaact tgacttttgc ttttcatctc aaattatttt gatatctctt   119940
ccacctaagt gtcagagcta aaactgaacc tgaaatatga aagttccatg aaaaaatata   120000
aaatcttcac aaccttggag aaggcaaact tttttgaggc aggagtctgt aaacactcac   120060
tataaaataa aacaaattat aatgtgggct ttcatgaaaa ctcatgctta ccaaaagtca   120120
ttgttaagaa aataaatagg caagtaacac atgagaagaa aaatgctctc tgtccatata   120180
tctgacaaat ggcttgtgtc cagaatatag gaacatttct cccactcact aaacagagga   120240
caaacaacta atgggcaaca gattgaatag gcatttcttg gggatagata gatgtacaca   120300
tagccaataa gcacctgaaa aaatgtccag tatctcagcc atgaaaaata aagagttata   120360
atcatcatga gatgtcacca aacacccaat ggacatggat attattaaga agacaccaca   120420
gtaactgatg tcactgatgt agagcaagga tgtgaaactc tctcatatgc tggtgaaagt   120480
gcaaaatgat acaaccactt ttgaaatcag tctgatagtt tctccaaaag ttcaataaat   120540
gcacttttac cctacaaacc tgcaatcctg tttgtgaata tttaccccac agaaatggaa   120600
acataagtcc acgaagacat ctccaagaat attcatagca gctttatttt ttataacccc   120660
aaactgtaga caatttcaat gtcaatcaat aagaaaatga ataataatt tgtgaactag   120720 tcatacaatg gcatactgtt cagcaataaa agggagcatg ttttgatac tctcaaatag   120780 tatggaagat gctcaaaaat attacattaa agaaagatgc cagataacaa aaatgaacat   120840
tatgtatgag tctattgatg taaggttcca gaaaggtaaa actaatttct ggtgaaagaa   120900
```

```
accaatatca tttgcctctg gccatgggaa gagagtagca gagattgatt gagcagtaaa 120960
acgaagtttt tttctggggt gatgtaaatg tcctgtattg tgattgaagt gtgagttaca 121020
caagtgtaca tgttcatcag aagtcatcaa actacatcta agatctgtgc atttgactat 121080
acatgaaaat atacctcagt tgaaaataga tcaataacct ccctcatata ctatacttgc 121140
taacacagcc agctgcttgg agaaccagct tgctggaatg gagaatctgg gcttgagact 121200
gggtcacatg tatagagtct ctacagagac aatgttgcat tcccacggta cataatacat 121260
ttcaaggttt ctcagacagc cacatgtcat gaatgtgagg attctgagag gttggagcaa 121320
cattcctggg aggaacgaag gggagcacat tctccaagat cccccaccac cggggtcctc 121380
accggctgtg cttttttttt tttttttctt gacagagtct cgctctgtcg ccaggcagga 121440
gtgtaatggc ccaatctcgg ctgattgcag cctccaactc cagggttcaa gagattctcc 121500
tgcctcagct tcatgagtag ctgggactac agatgtgcgc cactgcgccc agctaatttt 121560 tgtatttta gtagacgg ggttttgcca tgttggccaa gatggtctcg ctctgttgac 121620
ctcgtgatcc acccgccttg gcttcccaaa gtgctgggat tacaggcgtg agccaaagca 121680
cccagcctgt gcctctcact tactcaattg ttttctgaa ccctccatag ctggtggacc 121740
ttttcagatc ccatagtcta gccagccctc tcactttatg ccttgggtcc cactgttcct 121800
tcatctcatc cccttctgt cagtcccgca gtggctgtgg ccagtagagg atggactgag 121860
agtaggagag gaggttctgc ccaggaaccc atcctagaga aacagcatcc tgcctgggac 121920
ctagtcttcc aggtcagctt ttataagtct tttagactca aactcacttg acccacctga 121980
agtggtattg acaataatgc tattttcatg gttgttttc actgtaaatg cagagccttt 122040
tagctacacg actagtacag agagtaaggg aggctggcct gggaatgata tcatcttgga 122100
tggcatttcc tccttggaga aatatatgtt agttccaact cacatgttac tatacagtcc 122160
tgtagaaaga gatacagaga gttagacagg tatagacgca tttgtatatg cataacaatc 122220
tataagacac acatcaaaat ccgtataccg gttcctctag gggtatgtgc ttggcagaag 122280
gtagaaggag ggtattctgg ttcctttctt ttgcacattt atgtatgatc tcagttttta 122340
tatggagcat tgatagggtt tggctatgtc cccacccaaa atctcatctt gacttgtaat 122400
ctctataatc ctgataatcc ccatgtgtca agggcaggac caggtggagg taactggatc 122460
atgggggcag tttctcccag gctgttctca tgacagtgag agagtctcct gagatctgat 122520
ggttttgtaa gtgtctggca tttcccctac ttgcacttac tctgtcctgc cgcctgtgaa 122580
gaaggtgcct gtttctccct tgccttctgc catgactgta aatttccaga ggcctcccca 122640
gcaatgtgga actgtgagtc aattaaaact cttttctttg taacttaccc agtctgtctc 122700
gggtatttcc tcatagcaat gtgagaacgg gctaatacaa gcatatacta cttttgatat 122760
tttaaaataa aaattatcat ctatctttga aaggcatgca caaatgggaa gttgaggaac 122820
atttgtgttg tggcaattgt atgataccctt taatgggaat atttcaaaga cacttgttaa 122880
gactttgtta gaacaaaatg tagagggtgc tggatgtccc tgaatattct tccgcctcct 122940
gtaacttgta ttgctttgga atttccagtg gcctgacaat gaactactgc aggaatccag 123000
atgccgatac aggcccttgg tgttttacca tggaccccag catcaggtgg gagtactgca 123060
acctgacgcg atgctcagac acagaaggga ctgtggtcgc tcctccgact gtcatccagg 123120
ttccaagcct agggcctcct tctgaacaag gtaagaagtc tgtgtcttac cttgtctagc 123180
acatacctct ctatgtgctt ggacaacggg atgaaaagac atgaaaaacc acactgatgc 123240
agaagccttt agtgctacac gggagctcga gtgttggttg aggttctgcc atgaccaagg 123300
```

```
aagtctcagt gccgtccctg ggaaagccag agctgtgatt tttggcacaa cttgtgggag   123360
tagtgacttt aggactggcg caaaacctcc agggtgctca acttaaccac tcaccttatt   123420
ctaaaatggg ttatttcagt gtcccagtca aattcctatt ctaacatgct gtcaactgtg   123480
tgattatttc caagccaata agcatttcca gtaatttctt aaaatagtgt tcattgcagt   123540
cttcagcgtt gtggctcctg agggatgtgg cccctgattc tgtcgtccta gagaagcctg   123600
acatgactgc attgattctg tatcgtcctg ggtctatgtg gctgcctggc tgtctgtaat   123660
catctgtttt attttttattt ttttctacag actgtatgtt tgggaatggg aaaggatacc   123720
ggggcaagaa ggcaaccact gttactggga cgccatgcca ggaatgggct gcccaggagc   123780
cccatagaca cagcacgttc attccaggga caaataaatg ggcaggtctg gaaaaaaatg   123840
taagccactt tgatttggac tcttttttccc tttgctgaca aatcttttca aacagaagag   123900
gggcagagga aaatactgga aagacttcag gaggctaagc gtaattagcc ttagcatgga   123960
aagtgcaagc agcacaggcc agcaaagccc cacgcgtgtg ggggttctca ggcctcttct   124020
cttttgacat ttctttactg tttccattgt tgggtgctgt ttctcgtttc tagtgcttgt   124080
cctctaagcc aggggtcccc actccagtac tggtactggt actggtactg gaactggtaa   124140
ttatctgtgg cctgttagga actgggctgc acagcaggag gtgagcttcg ggggagcaaa   124200
caaagcttca tctgtatttt ctgctgcttc ccatcactct catagctgcc tgagctctgc   124260
cagctgtcag atcagaggca gcattagatt atcatagcac aaaccctatt gtgaactgca   124320
catgtgagga atctagattg catgctcctt atgagaatct aatgcctgat gatctgtcat   124380
gcttccatca cccccagatg ggaccaccta cttgcaggaa aattagctca gggctcccac   124440
tgattttacc ttatggtgag atgcacattt atttcattat atattacaat gtaataataa   124500
ttgaaataaa gtgcacgata aatggaaggt acttgagtca tcctttaacc atcgcccct   124560 cacccccaggt gcacagaaaa attgcctttt atgaaactgg tctctggtgc caaaaaagtt   124620
ggggaaccac actgctctgg gttctagtag tcagagatgc cctctatgag gcttaagtca   124680
gatttttcta gaaagattt ggatgggcca tcaggtcacc atgagacttc ccttagcctc   124740
atgcattctc tgtgatggtt tactttgggg cctatgaata gggaagactg agatatagga   124800
aaaaccaaag tgtctgtgtt cccccactct cacacccatg taacataaca cttctcacac   124860
cagatatggg gggatttctc ctcacacccc aagcgagtct ccagcagata ccagctgggt   124920
gtcctacaat gtaactcggt cctgacactc tatctggaga cagtgtcaga tcccacaagt   124980
taaggctcag tcctacaaga ctgccccact gcagatgcca atcccaagtt gcaggctgtg   125040
acctgtactt ctgcccagct ggataaagat ctgttttttct atatgaccct ccatgggttt   125100
gattactttg ctagagtggc tcacagaact cagggaaaca cgttactttt atttacccat   125160
ttattataaa agatattaaa aaggatcctg gtgaacagcc aggtggaaga gatgcacagg   125220
gcaaggcacg tgggaagggg ctcagagcct ctatgccctc tccagtgcac cagtcccag   125280 taccctaagt gttcagcaac ccagaagctc tccaagtgca gtcttgttgg gtttttatgg   125340
aggcttcatt acagaggcac agttgattac atcattggcc atcggtgatc ggctcacctt   125400
cggcccctct tccctccctg gaggttggag ggtgggggctg aacagttcca accctcaagt   125460
cacatggttg gttcccttgg caaccagccc ctggggctat ccaggaaccc accaagagtt   125520
gcttcattgc agctcccttc acccaggaaa ctccaaggga tttaggagct ctgtgttaag   125580
aactgggggg cagagaccca atatacattt cttattctat cacaatatca caggaagcta   125640
```

```
aggatgatac tgcctttgtg tgtcttggct gtggatggtg cataatgcat ggaagtaagc   125700
atttctgaat caacagcaaa caggctttat caggtagaag accccctcagc gccccaggga  125760 caaagctcat caatgatgtc ccactgtcct ctgaggctct agctctaaga cctccagtgg   125820
gtcaagctcc tggagaagtg gcacattctc caaagaccct tcagggtcac cacaccctgg   125880
ttaagggtgt ggcctcataa ctccttttga ctatgactga tggcttacag catagaaaga   125940
aataactttg tcaaaaaata taataatgat agaaaggaag aaggaacgct cccttttgtc    126000
ttctaagaat agatgtgaaa tgtgtgtgcc ttagaatatc ttctccctct cctgctccac   126060
gtgagctgga gcttacatgc ctgcttgttt tcagtactgc cgtaaccctg atggtgacat   126120
caatggtccc tggtgctaca caatgaatcc aagaaaactt tttgactact gtgatatccc   126180
tctctgtggt aagttgcctt ctgttttggt aaggaaactg cttccttaat atggatttgg   126240
aaaaaaaaaa gcaaaaaaaa cagaaaatgg cttttgagct gagtgcttct ggggaggaga   126300
tggctgccct ctccaccaga gcctgctttt catcatggcc accttgaacc tgccctacta   126360
ttggccccat ttgttaggaa acacccgcc cctcccacca cacacacata aataaaataa     126420
atgtcaaatt cccaaagggc aaacttagag gtgatctaat cagcccggga tagtcccacc   126480
gaacccttct ttgtctagcg tgggatgcat gaaaaacaaa tttagagtca ttatgatgaa    126540
aaactgtcct cttctgcagc tgagaagaaa aaaaaaatac gagcagcagg aaacagctaa    126600
gcatgtaatg cacattgtaa acctcagatg gccatcctag gaaatcaatg aagggtagtg    126660
cagctcttta gccccagatg gcctttctcg taagattact actcatgagt cccattagcg    126720
acattgctta gagactgctt gttaggttcc ttcctcattg ctctgagact cttattggga    126780
gtatgaggct tggatcaggg gaaggggaat tgacattaga tcttaaatga ttggggtaac    126840
aaatccatgg gggaaaaaaa gccacttgta cttgttccct attttcttcc tgctgaccaa    126900
tcaacttgtc tgtccgagtt acagaacacc accctggact tttcttttgt gtaatttggt    126960
tgcttgtggt tgggtctgcc atgtgaaggg accttgagct gggggaagaa ggttggcctc    127020
caagtccact gaagaccagc atcctgagat tgcctgggga ggtggtacag ggcagtgatg    127080
aagatcatgg gagccacact gcccatcgtc acatttgggc cactcctggg gagagcaaga   127140
gggaagaagg agaggttagg gtgataggaa agattctact tggccaatat tattataatg    127200
tggcattgtg gtctctggat ttagtgtgag ttgatagctg acttttttct cgagtggggtg  127260 cttttgttct attttgtcgg tgctattgca gaagcatctt ggtggttcct ctacctcaaa    127320
gtctcttgat ggggtcagtt ccagttctcc gcttctggcc ccatctagta cacgccactg    127380
cctctcactg cctgggctct ctatccttga caggctgcct tgaatttaag cccagtctga    127440
cttacctgcc tcaaacaccc acagtagtgc ctgggactca tgcacctttg actcccatgg    127500
aagggaagtg cagtagcttc ccaggtgcaa ttctgctgtc ctcacccaca ttgaggatgt     127560
atgagaatca ggttcttaga gattggagaa agaaggaaga atgggaacaa gatttcttcc    127620
aatggactgt gaggttcccc accttacttt gatgtaagac aagtgaggtt aaccccaagc    127680
ctggtgagga gggttcccat cagacacttg gaaatcctga ggactgtttc ctgcagaagg    127740
atgtggttgg tgggatattc aggtttgact catgattgag aaagttagag cctctggttg    127800
gagaaagagt ttaataacta tttcatttcc accaacacat tcagtacgaa taataaataa    127860
gtaaaaataa atagaaacat tcagttttat tttgaatagt aggagtaggg tataattttct   127920 gtagttactc ttttagtaca atgatgcatg tttactgtat gtaaggcata ctagcagaaa    127980
ttgagctcag cactagaaaa gatgattgca ttccatgcca tgcttctttt ttacaaaga     128040
```

```
cttctataga tagattctca aaacaaccca cagcaaatga aaagttattt ggaaaactca  128100
ggttccagat tcactggagt gtagaatctc tggttggttg gggaggaatt tcctcttgca  128160
gttgttatta ataattatat gaataattat taactatatt aatatttata gttttgaaga  128220
ccttgaaggg ctggagacaa cagagaagca tttttgaaca ccctctgtag cccctgcact  128280
gttgtaggca ttgatgggtg gtaccaaaga tgggacactt tccctacctc cagagacctt  128340
gtgggcttgc tgcagagaga aggcagggag gaggaaaaga agaatagagg cacatgtgtg  128400
taaattaccc ccacagcagt cagttagtca tgggaggctc cccagaagaa ctgtcctgaa  128460
gctggctgag agaaggcaac atttcaacat aggacagtta tccttgctac ataaaatcac  128520
atacacacat gcacatatgt ccacacacag agactcacat gcaaaagaat cctttgtgcc  128580
tttcagtaaa ctttcatgg tttagaaaga acttatattt ccttgaaagg agagtgtcct   128640
ttgttgttta ctaccacttt ttaaacttag aaagaaaaat ctaaagagtg tttatgattt  128700
taccatttaa tttcaccttt gagatgtgaa aaactagtgc ttggaattcg tcctgaatta  128760
aacgacacaa ttgctaactt ggactcaaat gcgacttctt ttcccacctt gtgccacagc  128820
atcctcttca tttgattgtg ggaagcctca agtggagccg aagaaatgtc ctggaagcat  128880
tgtagggggg tgtgtggccc acccacattc ctggccctgg caagtcagtc tcagaacaag  128940
gtaagaacag gcccagaaac catctatact gtccttccat gtaagcccca caaacccttt  129000
ctacatttac acagaaccca cacagctgat gcatcaatac ctgcctctct gttttctgaa  129060
ggaggaaaaa atatagaaaa attaaaaaaa gttatattat tataggttct ctacttgaa   129120 aatagccaaa atacaaatct ttttcttgat ctgggcagtt ccatcaaaat ctgtaggcac  129180
agtgatttgc accaagttcc aatacttttg gaaaatattg aagatgctct gagggtttct  129240
atggatatcc attgtctcac tgtcagatga aaagaaaggg aagttttag aaatgtgaca   129300 ctttgcagtg agggaggaca agagcaaact tacctacagt ctatcacagg cacagatttt  129360
tttttacact tttgtgaatc attgaattca atgccgaggc tattcatcta ttcacaaaca  129420
catgaacaaa ttatggggtg tgatccccat aaatgaagag taatcagtcc gaacccacag  129480
aacctggaca ttttgggtat cgtttcagtg gaacatgcaa ttcgtaagtt cagttttgctt 129540 gggtgtctct taggaagaac acataggaca cagacccatc tgcctgcatg ttttgcttcc  129600
tcatctcctt tctacaccag gcacctgtg ctcaattgct gttctcctct aaagagactt    129660
ccttctgtaa gtttgtgaaa tgccatcgac aaacctgatc gcatcgcatt tcactctgct  129720
gttgagttga tttttcttta ctttatcgtt tgtaacttct tgctctacag gctttcacc   129780 ttccacatat ttcagattca ttcttttccta aactgtgtgg tggtctatgt cctcactgac 129840
tatcaacata ctgccatcat gcacttccta tctctattcc tcttcgttgc aatctggctc  129900
caagtggctc acaccattat tctgatctat caactgccta cacagtccta gaaagtaagt  129960
gagtcaagaa acatccccca aaagtaaaact tttcaggtaa gatcagaaga ccctcatgag  130020
tcactgctgc tcaggatcgt atctggctcc ttgaagagtg accttgcata gatcttgtca  130080
taaaaaatga aagagacctt gggaaggtct tgggctggtc acttttgtca gagtccaggg  130140 ctgtgggtg aaagccacag ctatagagct tcattctgga gtcacttagc tttgctctcc    130200
tggggacagg ctgtgcctat tcttgcctca ggcatcaaaa aaagtggcac agatgggccc  130260
ttctgaaaaa tctcactact ggagcacagc tcgaagtttc tactatcctg acgttgggcg  130320
gtagtccttt gctttgggaa tatgaacatg atcaaaactg agtgaacttg tcttcctggc  130380
```

```
tttctgtaca atgaagtaga acaaaccatc caatttgacc aaagccttgg catgttttct    130440
ttctaggttt ggaaagcact tctgtggagg caccttaata tccccagagt gggtgctgac    130500
tgctgctcac tgcttgaaga agtacgttta agggaaaact gacatggggt cttatcttca    130560
agacttttt cctccctctc ttcctccatc ccttctttct tcccaccctc cccttccttc    130620
ctccccacct ctcttccttt tctggaagga acactaggaa ccagggaatg catgcagaat    130680
cctgaggcag aatttccagg gcaattggat gagagaggag ggaagtgttt ctagaggaa     130740
tctgcagagg gaagacccag tgcaagtgat tttttggacc tgtataaacc gcaggacaga    130800
gctgttcact accagaggca tcaatctgta ttgcattgct ctagagcaat atctgaggct    130860
gaataattta taaagaaaag agtttaattg gcacatgttt ctgcaggctt tacaggaagc    130920
aggatgctgt catctcctct gcttctgtgt gggcctaagg aagattacaa tcatggtgga    130980
gggcaaagtg ggagcaggca tgtcacatgg ccagagcagg agcaagagac agagagagat    131040
ggggtggggg tgctgcacaa taccaaatga ccagactttg caagaactaa gagtgagagc    131100
tcactgatca ccatgaagat gtggcccaag ccattcaaga gggatgcacc tctatgatcc    131160
aaacccctt cacaggccat agctccatca ctggggacta cagttgaaca cgagatttag    131220
gtggggacaa atatacaaac tatatcacag tctctgatga aacagattga aacagacct     131280
taactgtcag tttccagcaa attgtgaatt ttgtttcttg ccactcataa gtcactgatt    131340
ctgggtggcc gagggtgtca gagggacagc gccaagttca tggcacagag gatacctgaa    131400
ggggctggac catattttc tcttgacatc ctcatctttt ctaggtcctc aaggccttca    131460
tcctacaagg tcatcctggg tgcacaccaa gaagtgaacc tcgaatctca tgttcaggaa    131520
atagaagtgt ctaggctgtt cttggagccc acacaagcag atattgcctt gctaaagcta    131580
agcaggtact cgctcacctg tggtcttcac cccacgctgg tgaagatatt tgctttatgt    131640
ctgggtttta tgggccatgg ccactgcatg gcagtgggga ggaactgtct atcacatgaa    131700
aggctcaagg gctttgggga cagcatcaat cttcaacccc agccctgcca catgttagtt    131760
gtgctcttta aaaggcaga aggattcgtt tcctcacgtg gaaaagaga taccctgtta     131820
cccgtaaaac ttacttaatg ttcaccagtt catccacatt catgatcagg gaaaggttgt    131880
tattccaggc taactattct cctttcataa taatatgctg gagagaatca aatgagattg    131940
catttcaaag cgcttgaaaa accaccatat cgagccatgc ttagtgtggg cgcctctaat    132000
cactgctatt caggaggctg acgaggaaga attgcttgag cccaggactt caaggctgta    132060
ggcagctatg attgtgccac tgcactccag gctgggtgac agatcaagac cctgtctcaa    132120
caaaagaaaa gaaaacaaaa caaatgaaca gaaatattcc acaatgtcaa aaaaaaaaa    132180
aacccacaca acatacaatt tacaaatgca aataataata ttattgttgt cttctttgat    132240
tttctctttc ctggtgaaat tttgttttat taagcctgac aaagtgatac ctttgcttac    132300
atcacttaaa gttagtctat ttggacctag gtgacagtac aatcagctaa gaaacagtat    132360
ttgtaggaga ggcaggtttg ggacaggtga caaggcatgt gggggtgctcg ctgtgctggt    132420
ggctctggaa ggcagggtgt caatgcagac agggatgagc atggcctggt tgggaaggca    132480
tggggcaggc aggagcctga gctgctctcc tgggcctggt cacaagccca tggcagcttc    132540
tctgggtctg tgaactgagg ggtgatgtcc tggaatcctc tgacactcta ggaaggagag    132600
aagggccttt ctggctcagc ctttataaac agtagctgat ctccctcttg ctccccaggg    132660
tcctccccac catcccagca aatgtgcaaa tacaagatct ctgctcctca tggtcctcag    132720
agagctgggg tgttctgatg gcttgaacaa gtcacttagg aaatgtgggg ttttggaggc    132780
```

```
attctctgat aggctgatac gttttgagtt tagagttccc accgcacatc cccacacccc 132840
tagagtctag ggcatttagt gctccatgag ggaacctgta gagtgaggac atctgcatca 132900
caggctgggc cttctagtgt ccagaagcag aaagtgtgtc tgcttcaaag ttggtgctaa 132960
tgatgatttt tggtcagaat acggcatttc tcatttccat tcctttatcc ccttgaactt 133020
actaaagtag aatcaggtct aaaaaccaga gttctaatct ttaagagtcc ctgggattct 133080
aaggtatatg aatgtccttg gaaaacaata ccatttagtt catgcaaggt gcttatttcc 133140
catcctcttt catttgatgt ctagcatttt actgcattct taccaccacg gtttagtaac 133200
attcacgagg aggaagtgga ggatccagat ggagcaactt gctctgggca cacaaggcat 133260
ttgcaatttt ataccctctt gatgatgtct cagccagaca ttctgcccag tcatcaatgc 133320
cctcttcaat taatatgaaa ggacacactt ggcatgagat tccaatcgtg cacagaatat 133380
acatgagaag tgtgcctttg tcatccctac tttcaaaggc taaggccacc ctcagtttct 133440
tgcatgcaac tgatgccttt caaatgaaac cttacatctg tgtagtccat aggcaaccac 133500
aggcaaatgt gagggtgaaa cgctgtgttc tacattgttc tgtgtcagtg aagcaaggca 133560
gtgccagctc agagggctct ggggcttcaa ggcaggatg cctggttgta ggtactgcca 133620
cttccagctg ggcagtgaaa cataactgct aatactttcc ttacaggcct gccgtcatca 133680
ctgacaaagt aatgccagct tgtctgccat ccccagacta catggtcacc gccaggactg 133740
aatgttacat cactggctgg ggagaaaccc aaggtgagat caattccatt gcccacgtaa 133800
caaattgttt ttgaccttca gtgcatgtta caaaatgagc attttggaga tagttgtaca 133860
aattcctacc catgaatgtg gtctacccac tcctgacttt gcctggacac ctgtctatgt 133920
ctccataatc agtcttcaag ggacttgggc aaggggagcg gtgccatttc cttgagtctc 133980
tctcttttt gttttcagaa tcttttaatt tttttttgtaa tgattgtatg tttcccttac 134040
aacaaaaaca aacaccagta gaggtctttg agtctcttaa tcataatttc agcattcata 134100
ttgcttcccc aggtaagtgg ggttttgacc cagccctcaa gttaagggtg ttagattatt 134160
tttcatgtga aattagacag actgcgtttc taaacatggt gcaaaacagt aacgacaaaa 134220
gttgtaatta aactattctt cttcccaaat acccacatgt ctaatgtgtg tgtgagggtg 134280
ttaggcaggg gacctgaagc tgggggagag gcagacagtt cccatggccc caagtctagg 134340
atggcatttg gtattggttg atgggtgaga gcaagagagg gaatatttt gtgcatgatg 134400
tggtatcagc acctgtacta cattttatgg attccttctt ctctttgcgg tatgccctga 134460
caataattat atccgtcagc cttaccccct tggcagtagg aaaactgaaa ctgtcttaaa 134520
gtctcagctc tactttctca gaggtgcagg caagggcact gggagtctgg ggccctggaa 134580
aactgttctg actctgccac ttgccagata gacctgaact agacacgtta cctctttgta 134640
ccacttggct ctaatccctt atctgtaaaa ccagcatttt caaatggtgc tttgcacatc 134700
agccttttgc ataagctttg atttgataaa atgttttttg tgtttttaaa aagattaaaa 134760
accacaggtt tagataattt caaagtaggc ttccctttt ctgtcatttt cctattattt 134820
ttaaaacctc acctccttga ctccttgttc cctttttctg cactgctgag tctgggagca 134880
ctgaggccag gtaaaaggaa acttggcaaa tgaggggcac ctatgggtgt gggaggctgc 134940
tcctggtgtt tgcatatttt aaaatttaaa tgctacaaac cactgtgagt taggtattat 135000
tgttcctatt ttaccattga ggaagctggg gctcagagaa ggtggagggt ggtacagaca 135060
aacctgaatt ggaaccctgg ctcctgccta tgggctgtca ggacttagaa aagtcgtgag 135120
```

```
ctctcgctga ttgtttcctc agctgatgtg ggctgcaggg ctgttatggg ggaaataata   135180
agaaagtgca tcaagtgctg agcacatcct aagcactcca tcatggcagc tcctactact   135240
aataaagaat agaattatat ctaacatgat tctttcttgc aagtgacaga aaatccaact   135300
caaattggat taagcaaaac aagggaaatt cttagtgagc tgcaaagttt tcaggctcac   135360
atgatggccc caaatcccag gtcctcccaa tcatggagta ggcactattt gggggcacaa   135420
aggtgacatt cccatggctg cagatgctgt ggtgctgtgg ctgtaccggg aaagaataag   135480
aaaggccact ctcccaatta tgtgaacaat agtctgccca ctctgagaag tcaaacttgg   135540
gtcacagtcc tgcccctgaa cccatcactg actggctctg acctgcacca attgttccat   135600
gttggaggtg aaggcaagac cccactaata cccataaggg gcaaaagtta gatagatcct   135660
tcaagaggat tatgggaggt agggcaaaaa gctgctgggc agccagaaag caaacagagc   135720
ctctatgata cctcaactga tgaaagcatg aagctaaaat cataaggatc tgggtgtgag   135780
ttctggctct cccatcttcc atgtgacatt gggcagttat ttaatctctt ttagcctccg   135840 cttttctcatc ttacatatga gataattgtg aggattaaga ttacacataa tcatcatcat   135900
caccgtccac cactaccacc atcatcccca tcaacatcat cgccaccact atcatcattc   135960
ttactggcac taccatcacc atcaccacca ttccaccacc atcaccaata tcatcactgt   136020
caacatcatt accaccatca ccatcaccac caccatcatc attactacca ctaccactac   136080
taccaccatc accatcacca ccattccacc accatcacca atatcatcac tctcaacatc   136140
atcaccatca ccatcaccac caccatcatc atcattacta ccactaccac tactaccacc   136200
atcaccatca ccactgtccc actactatca gcatgacatc accatcacca ccaccatcat   136260
cattaccacc gctactacca acatcaccat caccacaatt ctactgccat caccattaac   136320
attaccacca ccatcatcac tatcaccatc accaccatca tcaccactgc cattatcact   136380
gccaccatca tcactatcct ctatatttcc tcatctgtat tatcattact accaccatca   136440
ctatcaccac catcgtcacc atcataatca ccatcaacac catctccaat accaccatca   136500
ctgtaaccat catcaccacc accatgatca ctatcaccat catcacaatg atcactgtaa   136560
ccatcattac tacccaccac catcaccact actccaccac catcaccatt atcattacca   136620
tcaccattat caccaccatc atcatcacca gcaccaccat catcaccagc accaccatca   136680
ccatcaccat cattaacacc atcactatca ccattggttt aatcatcacc accatcatca   136740
taaataaaca tcacataacc agggtgtagc tgggtgttga ccccagagcc cactcactgt   136800
ttcctctctc ccaccccat ccacacattt ctaaccacca tcctgcactg ggctcccagt   136860
ctcctctggt ctcacccaca tgtccactga gaaaaggatt ttcagaacac caactagacc   136920
aggaggagcc acatacataa ctcaggcctg cttatcaact ttctacatgt taataatgac   136980
atcagatcaa tgggtgttct cagcttctca gaaggaggtc aaaattctcc ccctctcccc   137040
ttcatgtgtc cagaccttcc cggatttgga tgtaccaagt gcagagtggt gttgaggcca   137100
aggggctcat ccatgtaagt ctcatctgca atcactgggc tgatcccgtg gccctgtctc   137160
cagggcgcca tcagagaggg cttcaatcct caggttacct gtggcccacc ctgccctcag   137220
aggtgccatc tctacattgg ccacgagatg gcagcacata tcatagact gcattaattt   137280 cccagcaact cctggtgggt tttcccttctt atcaggatgt ttgccttgct cagagagcaa   137340
atctgagagc agtgacacct aacttaactt tcagcaaaat attttgagaa gggtgcccct   137400
ttacacatct gtgcagtcca ggtgatgcat cccatgccca atgctcggta gtcaggagga   137460
gcttcctcca tgcagctctg cggaagagac tcttccacgc tgctcatgta aactccagat   137520
```

```
tcggtgtcag ttttctgaca ccgaagacaa tgatctaagt gcagtcaagg gctttgggga  137580
aagcaggaga gagtgcctca gttctagcct gtgccatgct tgcaaagttt tgcaaaattc  137640
taatgagagc tgggcttgca acattggaaa cttggattat ttgtgagagc actgagaaat  137700
ccctgggcat gtccatctgg aaaaacagca tttcctctgg cactttagca gaggttctgt  137760
ttcaatttgg cgaaggaaat taagcagttt ttcacaaaag aagaactaca acgaggagaa  137820
ttgtccctag tatttcttct ccctaattgt caaggaagtg taaattagaa aatgaatcag  137880
gacaatttcc acctactatg ttagctaata tttaaaaaat tgaatatcac aagggtgagg  137940
caaagtaatt gttttccagt gacattttcc actgtcacac cctttagag aataatttgg   138000 caatgttact gtgagataga aatatgtcta tataattatg ggaactgaga cttcagaaag  138060
taataaggaa taagaatgaa atttatgaac aaacatgtgg aaggttggaa gcaagagtgg  138120
ggccaacacg catggggagg aagcatttgg gcagcgactc cgcagaccca gactcaagct  138180
gagctataca acctccttac gcctcagttt cctcaactga agaacaggaa tgacaagtgc  138240
ctgtttcata ggaccgttgt gaggattaag tgagatatac cacattatga gcttgtgcct  138300
ggaaaggttg attcttagta aatgatgact attcttttt attgcaataa aatttataca   138360
acatagagtt actattttaa ccattttgc aggtaccact gagtggcatt cagtacattc    138420
acaatggtgt gcaaccgtca ccatatttcc aggacatttt tctcatcccc aaaggaaacc  138480
tcatgcccat taagcagtca ctcctcatta aaatattagt tatgaagact gtagcatttt  138540
tttaaaaact catgatataa cattgattga aaaaatcagt ataggaaatt gtgcattatg  138600
atgtaatagt aaaagaagca tataaaaatc tgaaaaaagt atataaaaag aatagcaatt  138660
gtatttctca gactctcttt acattgtaaa aatcattttg atagcttcaa aagaaaagca  138720
aaaagtacac aaacaacaac caaccccaaa gcagcatgac aaagcccaga ttgttgaatc  138780
caggtcttgg gaacataaaa tcttatatga catttgcact ttaatgggtc agagagtcca  138840
gtggcattgg gagctgcctt tgttctgca gcctcacgga cagacaggag gtccagctcc   138900
actgctctgt tcttctggaa tttcctcgtg aacaagcttt ggcctcagta accatttctt   138960 tcatctttt aaacacaggt acctttggga ctggccttct caaggaagcc cagctccttg    139020
ttattgagaa tgaagtgtgc aatcactata agtatattg tgctgagcat ttggccagag    139080
gcactgacag ttgccaggta agaaaagatc aatagatcaa agtcttgtgc tctcccgtct  139140
cagtctcagt cccttagacg tcagtcccaa agtggcaaat tcaggaaggt tttgtcagtg  139200
gaagacccca gtcaagtgt tgctcagaaa ctccccagat ctgtccctga atgcatattc    139260
agatcatcta aggagacgtc ttggggcttg agttccagat ccatagcaag ggagccgtaa  139320
gtgccataac tacctcaggc cactcacctt cctggtgtgt gctggtcacc agtgactgaa  139380
gtggtggctt ttccagtaga gaggaaggta gagggtacag gaccgagaca aattacacac  139440
acttaacaat gatgtccagg ctagcccagt ctaaaggaaa caccaagtta ggaagcaatg  139500
catgcaggat tcacaaggga ttattttttt tcccaggaaa aaactaagtg atgtggtttt  139560
gttgaataga ctttgctaag tacttaagca ctgcagatgc ttgagtaata tgctcataag  139620
ttcctttctg atttgaatta ctgggaaaat gtacatatgg ataagagaag gatggcatcc   139680
catattaaaa ggttggcagc ttaaagctca catgaatttt cccctacctc tgtttagggt  139740
gacagtggag ggcctctggt ttgcttcgag aaggacaaat acattttaca aggagtcact  139800
tcttggggtc ttggctgtgc acgccccaat aagcctggtg tctatgctcg tgtttcaagg  139860
```

```
tttgttactt ggattgaggg aatgatgaga aataattaat tggacgggag acagagtgaa   139920
gcatcaacct acttagaagc tgaaacgtgg gtaaggattt agcatgctgg aaataataga   139980
cagcaatcaa acgaagacac tgttcccagc taccagctat gccaaacctt ggcatttttg   140040
gtatttttgt gtataagctt ttaaggtctg actgacaaat tctgtattaa ggtgtcatag   140100
ctatgacatt tgttaaaaat aaactctgca cttatttga tttgaattaa ttttggtttt    140160
ggtcttcaaa atttcatgc tcttttcatc ccatctattt ttattttat tttttagact     140220
ttacgtcctg gggtacatgt gcagaatgtg caggtttgtt acatagatgt acacgtgcca   140280
tggtagtttg ctgcacccat caacctgtca tctaattcgg tatttctttt agttctatcc   140340
ctcccctagc cctccacccc ttgacaggcc caggtgtgtg atgttgccct ccctgtgtcc   140400
atgtgttctc attgttcaac tcacacttat gagtgagaac atgccgtgtt tgttttctg    140460
ttcttgtgtt agtttgctga gaatgatagt ttccagcttc atccatgtcc ctgcaaagga   140520
catgaactca tcctttttta tggctgcata gaattccatg gtgtatatgt gccacatttt   140580
atccaatcta acattgatgg gcaattgggt tggttccaac tctttgctat tgtgaatagt   140640
gccacaataa acatacgtgt gcatgtgttt tcatagcaga atgatttata atcctctggg   140700
tatatcccca gtaatgggat tgcagggtca aatggtgttt ctggtgctag atctttgagg   140760
aatcaccaca ctgtcttcca caatggttga actaatttat gctcccacca acaatatcaa   140820
ggcattccta tttctccaca tcctctccag catctgttgt ttcctgactt tttaatgatc   140880
gccattctaa ctggcatgag atggtatctc attgtggttt tgatttgcat ttctctaatg   140940
atcagtgatg atgagctttt ctcatatgtt tgttggctgc ataaatgcct tttttggaga   141000
agcatctgtt catatccttt gcccactttt tgatggtgtt gttttttct ggtaaatttg    141060
tttaagttct ttgtagattc tggatattag ccttttgtca gatggataga tgcaaaaat    141120
tttatcctat tatgtaggtt gcctgttcac tccgatgata gtttcttttg ctgtgcagaa   141180
gctctttggt ttaattagat ctcatttgtc tattttggct tttgttacca ttgcttttag   141240
tgttttagtc atgaagtctt ctcccatgct atgtcctgaa tggtattgcc taagttttct   141300
tccagggttt ttatggtttt aggttttgca tttaagtctt taatccatct tgagttaatt   141360
tttgtataag taatgcccct cttgtctct tttgatcttt gttggcttaa agtatatttt   141420
atcagagact agaattgcaa tccctgcttt tttttttctt tttgctttcc ttttgcttgg   141480
taaatattct tccatccctt tattttgagc ctatgtatgt ctgcacatga gataggtttc   141540
ctgaatacag cacaccaatg ggtcttgact ctttattcaa tttgccagtc tgtgtctttt   141600
aattgggggc atttagtcca tttacattta aggttaatat tgttatgtgt gaatttgatc   141660
ctgtcattat gatgctagcg ggttattttg cccattagtt gatgcagttt cttcatagtg   141720
tggatggcct ttacaatttg gtagttttg cagtggctgg taccaattgt tcctttccat    141780
gtttagtgct tcgttcagga gctcttgtga ggcaggcctt gtggtgacaa aatctttcag   141840
catttgcttg tctgtaaagg atttatttc tcctttgctt atgaagctta gtttcgctgg    141900
gtatgaaatt ctgggttgaa aattattttc ttttagaatg ttgaatattg gccccactc    141960
tcttcgggct tgtgggttt ctgcagagag atccactgtt agtctgattg gcttccctt     142020
ccgggtaacc caacctttct ctctggctgc ccttagaaat ttttccttca tttcaacctt   142080
ggtgaatctg acgattatgt cttgaggtgg ctccttctcga ggagtatctt tgtggtgttc   142140
tctgtatttc ctgaatttga atgttggtct gtcttgctag gttggggaag ctctccttga   142200
taatatcctg aagagtgttt tccaacttgg ttctattctc cccatcactt tcaggtacat   142260
```

```
caatcaaatg tagatttggt cttttcacat agtcccatat ttcttggagc ctttgtttat  142320
tccttttcat tctttatcct ctattcttgt cttcttgctt tatttcatta agttgatctt  142380
caatctctga tatcctttct tttgcttgat cgatttggct attgatactt gtatatgctt  142440
cacaaagttc ttatgctgtg ttttcagtc agatcaggtc atttatgttc ttctctaaac  142500
tggttattct acttagcaat tcatgtaacc ttttttcaag gttcttagct tctttgcatt  142560
gggttagaac atgctgcttt agctcggagg attttgttat tatacacctt atataatagc  142620
ctgatataac tataagattt ttttgtaagc accatcgtaa ccacaaagca aaaacctaaa  142680
gtagatatac aaaagataaa aaggaatcaa agcataccac tagagaaaat cacttaatca  142740
caaataaaga tacgaagagt ggaataaagg aacgaagggt ctacaaaaca accagaaagc  142800
aattaacaaa atggtgatag cagatcttac ctataaataa ttatcttgaa tggaaatgga  142860
ttaaattttc caataaaaag acatacagtg gccaaataga ttaaaaaata agatccaact  142920
atatgatgcc tataacacac tcacttcacc tgtaaggact caaacagact gaaagtaaag  142980
ggatggaaaa aatattctat gcaaatggaa acaagaagat agagggtag ttatacagat  143040
tgagtatcac taatccaaac atctgaaatc tgaaatactc caaaattaaa aatgtttaag  143100
tgccaacatg atgttcaaag gaatgttct tcggagcatt ttggattttt gtgtttaggg  143160
atgcaaaaac agtaaatata taatttgtat tagtccattc tcacactgct ataaagaata  143220
ctacaaagag actgagtaat tataaggaa agatgtttaa ttaactcaga gttccacagg  143280
cttaacagga agcatggcta aggaggccac aggaaactta taatcatggc ggaagatgaa  143340
ggagaagcag gcaccttctt cacaaggtgg caggacggag tgtgagtgtg tgaaggagga  143400
actgtcaaac acttataaaa ccatcagatc ttgtgggaac tcactcactc tcacaagaac  143460
agcataggga aaaccgcccc catgatccaa tcccctccca ctgggctcct cccttgacac  143520
atggggatca tgagggttac aattcacgat gagatttggg tgggacacag ccaaaccata  143580
tcataatgca aacattgcaa aaacaattca aaattcaaaa catttctggt ttcaggcatt  143640
ttggataagg gaaactcaac tcaacatgag gtaaagcaga cttaagtca aaaactgtaa  143700
aaagagacga agaagaatgt aataataagg agatcagttc attacaaata tatagcaatt  143760
ataaatatat attaatatat atacccaaaa ttgtagtacc tacatatagt aactaaaaca  143820
aacattaata gatctcacag gagagctaca ctgtaatata atcatagtag cacacttgaa  143880
tagctccact ttcactaatg gacagatcat ccagacagag aatcaatatg gaaacacgag  143940
acttaaacta cactttagcc aagtagacct aacagaaata tatagaacat tccatccaac  144000
agcagtagaa tacacattat tctcaagtgc acagggaata ttctccagaa tagatcatat  144060
gttaggtcac aaaactagtc aaaaaatgta agaagattga aatcatatca ggttttttt  144120
ttagatcata atcgtatgaa actagaaatc aataatgggg gaatattgga aaatccacaa  144180
atagatagaa attaatcaat atgctcctga acaatcaatg agtcgaagaa gatattaaaa  144240
gaggaaattt taaaaaatca agacatgagt tcatgtcctt tgcagggaca tgaatgaagc  144300
tggaaaccat cattctcagc aaactatcat aaggacagaa atccaaacac cgcatgttct  144360
cactcatagg taggaattga acaatgagaa cacttggcca cagggcgggg aacatcacac  144420
accagggctt gtcagggggt gggaagctgg tgaagggata gcattaggag aaatatctaa  144480
tgtaaatgac gagttgatgg gtgcagcaaa ccaacacggc acatgtatac ctatgtaaca  144540
aacctgcacg ttgtgcacat gtaccccaga acttaaagta taataataaa aaagaaata  144600
```

```
tttgttttg  atttatatgc  caatcagaca  aaatgtgaaa  agccctactg  aaattaagta   144660
tcaccatgaa  agataaattc  tggataattt  tttcaagttt  taacaatgta  gctttaattg   144720
gagaaagcta  tcatttggaa  tgagttaatc  tatcctatac  taaaataagt  cacttgcttt   144780
aaaacataat  aaatatgatt  ttgaattgaa  aacaaaaaca  actcaagaca  aaggaaaatg   144840
gacacactaa  cataccaata  atttatagta  tgcagcaaaa  gtggttttaa  gagggaagct   144900
tttaccaata  aacacttcca  ttaaaaaaga  agatctcaaa  taagcaacct  aagattacac   144960
ctcaacaaac  tagacaaaga  actaactaac  ccaaaagtta  gtagaaggaa  agaaataata   145020
aagatcacat  cagaaatagt  aaagactaaa  aaactgatac  caaaaagaaa  taaaactact   145080
agttggtttt  caataaaata  acaaaattga  ccaacttta  gctagattaa  gaaaaacaga   145140
gaatactcaa  ataaaaccag  aaagaggaga  cattacaata  gatactacag  aagtacaaac   145200
gatcataaga  gactactatg  aataattaca  tgccaacaaa  ttggataact  tagaagaaat   145260
ggatgaattc  ctagagcaaa  aaacctacaa  agactgactc  agaagaaat  agaaaatctg   145320 aacagaccaa  taatgtgtac  atgattgtat  cagtaataac  aagtctccca  tcaatgaaaa   145380
ggccaggacc  taatggcttc  actgctgaag  cataccaaac  attacaaaga  ctaatatcaa   145440
ccctcctcaa  actcttctta  aaaactaaaa  agaaggaatg  ctttcacatt  cattttatga   145500
ggatagcatt  acactgatac  taaacacaga  aaaataatac  gctaataaaa  gaacattaca   145560
ggcaatatcc  ctgataaaca  tatgtgcaaa  atccgcaac  aaaatactag  aaaactgaat   145620
ccagtagcac  tttaaaaaga  tcattcacca  tgatcaagtg  cgatttgttt  cacgaatgca   145680
agaatagttc  aacttacaca  aataaataaa  tgaaaggatg  gatgataaaa  atgtgtatct   145740
atatatatat  gttttataca  cacacacaca  cacacacaca  cacacacaca  cagaggaata   145800
ttattcagcc  ttaatgaaga  agaaaatcct  gcctttgcat  caacctggag  gacattataa   145860
taagtgaaat  aagccagaca  cagaaaggca  aatactgtgt  gatctcgctt  acatatggaa   145920
tctaagaaag  tcaaattcct  agaaatagag  agtagcttag  tgattgccag  agccgtggaa   145980
gggggaaatg  gagagatgtt  gatcaaagga  tacaactgta  tagctttgca  agataaatag   146040
gttctggaga  tctaatgtgc  agaatggtga  ctagagttaa  taatactgta  ttgcatactt   146100
gaaatttgct  aaaagagttg  atcttaagtg  tcctcaccat  atacacaaaa  gtattatgtg   146160
aggtggtgaa  tattttaatt  agcttatgat  aataatttca  cagtgtacat  ctatattaag   146220
gcattacatt  gtacatctta  aatatatata  attttatttt  gtgaagtgta  cctcaataaa   146280
actggaaaaa  ataattgaaa  agtaatgaaa  aaaattaaaa  gctattatgt  gtcaaatgac   146340
attatcaaga  aagtgaaaag  caacctactg  atgaagcaaa  cctattgaca  aaggcctggt   146400
gtccagaata  tattaagatc  tctaggctgg  gagcagtggc  tcacacctgt  aatcccagca   146460 cttgggagg  ccaaggtggg  aggatcactt  gagcctggga  gttcgacact  gcagtgagct   146520
atgattgggc  cactgccctc  caggctgcgt  gacagagtga  gactgccatc  tcttaaccca   146580
cttcttattt  agaaaaagaa  aatatgtagc  ttgctgcctg  catagtattc  ttggggcaaa   146640
tgggaaatga  gttaaaaaaa  aaaaaagaa  ctcttacaac  tcaacaataa  aagaaaaac   146700 aagaacgtga  atagcatttt  ttccaaaaa  agatatacaa  ataggcaata  agtcacatgaa  146760 atgatggtca  acatcattag  tcattaagaa  aatgccaata  aaatcacaat  gaaataagac   146820
ttcatatcca  ttaaaatgtc  tataatttaa  aaaatggaaa  ataacaagca  tttgtgagga   146880
tgtggagaaa  ttgaatcct  gtatattgct  ggtgggaatg  tacagggaaa  atggtttggc   146940
cactgtggaa  aacaatttga  cagttcctta  aaatgctaaa  catagaatta  ccatgtgatc   147000
```

-continued

```
taacaatttt actcttaggt gtatatatac aagaattgaa aacaagtgcc caaacagata  147060
ccttgcatga gaatgttcat agcagcactg ttacaacagc cacacccaaa tgtcaatcaa  147120
tagatgaggg gataaacaaa ttgtggttta tacagctaca aaaaggaatg aagtactggt  147180
atccgctaca tggctgaaac ttgaaagcaa gggctgggat ggggtcatgg aaagtaccag  147240
cttattgggt actgcattgt gctttggggt catgaaaatg ttttggaact ggatggaggt  147300
ggtggttgcc aatgtgaaca tactaaatac aacgcattgt tcactataag actgctactt  147360
ttcttatgag aatttcactt caattaaaaa ataccttcca tgtatccttt ctaaggatga  147420
tactagaata tttgctttgg caaaatgagg aagtaacttt ttttaaaaag gaagatgtgg  147480
gatccatgaa acgggatcaa atatcagaga ggaaggggg tcttctggat gacagtccat  147540
ggagatccca caactgcaca gcaggccggc tgtgcaccca ggccacacca gagcagagcc  147600
ggtggttccc gaggagctct ctggaagaaa aacgctagat ggcctgattg gtttggggc  147660 atattgaaaa ggtatataac tgagaatttg gagtggaatt aggaaacaga cataaaagct  147720
tacagaaaag aaaataatga attctaggga gaaatataaa aggatactac aggcctcagt  147780
tacataaaca ctgaatattt acttaaccaa aattacaata taattacata attattttag  147840
gtacatatgg caaaaggatg tgtgggtgta tgtagtatgt acggtgtgtg aagtgtatgt  147900
gtgtggtatg tggacggtat gtgtatgctg tgtatgccaa taaaatcaca atgaaataag  147960
acttcatatc cattaaaatg tctataattt aaatgtctat aattttaaaa atggaaaaca  148020
cttctcatat ggcaggagca ggagcaaggg tgggggaggt accacacaca cttaaacaac  148080
cagatctcct gagaactcac tatcaggaga acagcacctg gagaaggtgc taaaccattc  148140
atgagttact gccctatgag ccaatcacct cccatcagac cccgcctcca cactaaggat  148200
tacaatttga cttgaaattt gggcatgaac acagatcgaa accatatcaa taggtaatga  148260
ctaaaactga aaaagaagt accacagtca gaaagttatt tagagagctg aaggtaaatg  148320
ccaataggat cagttgaaag aattggaggt ggccgggtgc ggtggctcag gcctgtaatc  148380
ccagcacttt gggaggcgga ggtgggtgga tcgccctgag gtcaggagtt tgagaccagc  148440
ctggccaaca tggtgaaacc cagtctctac taaaaataca aaaattagcc aggcctggtg  148500
gtggacgccg tagtcccagc tactcaagag gctgaggcag gagaatcgct tgaaccaggg  148560
aggtgaaggt tgcagtgaac cgagatcgtg ccactgcact ccagcctggg tgacagagca  148620
aaactccatc tcaaaaataa atgaaataaa gaattggaag tgtttgcctc tggagagaag  148680
gaaacgcagt aattctgtaa aaacagaact ttttactttt tttctttttt ttttttttt  148740 tgagacagag tctccttctg tcacccaggc tggagtgcag tggtgcagtc ttggctcacc  148800
gcaacctctg cctcttgggt tcaagcaatt cccgtgcctc agcctcccaa gtagctagga  148860
ttacagatat gggctgctat atccagctaa tttttttta tttttattag atgaagtt  148920 tcaccatgtt ggccaatctg gtctcaagct cctggactca tgatcctcct gcctcggcct  148980
tccaaattgc tatgattaca ggtgtgagcc accatgcctg gacagaactt tttgactctt  149040
taaactatgt gcatatataa agctgattta aaaaaaacca agtaaaataa ttttaaaatg  149100
ttccaaaaca gattggatgg gtacacactt catcatgagt ggttgaggga gactgggtta  149160
gagatgagga aattccaggg actggggaaa agttaaaatg acaaactgtt cacaattgtt  149220
aactgcaggt tgtgggaaag ttggtaagtt gctacagtgt ttgttccctc tgtaggtttg  149280
catatattta acatttctta aattagcata ataatgaact gtgtaatcag ctgtagagtt  149340
```

```
gagggtgtgg agctggcaca ggacagctga gctactggtt taaaataaat gacatttaaa   149400
aaaatggcta tttgtagaat taacagatat aagacaccct gatcaaggga tgataagaaa   149460
ggactccagg gctctgtctc agctgtcttg gcaacacctg gaagacatgg gcctctgcaa   149520
ggtctcatac tttcaggagg tgttgatgaa ggatatggac agatctgaag ctctgggcac   149580
tgcatggtct gagaagagaa gctccggaaa cgcgggagct gagtgcagat gcagaagggc   149640
tgtcatccag cagagggta ggtgacaact ggcctagcga gtgacccta tcatggctac     149700 atttgttgat cactttcttt gtatgaggca ctgctgtgat tgcattaaat ttccacttac   149760
ctaaatccaa cgttgtgcac ttgtgaattt ctactcttac aaaaaacaca acggcaacaa   149820
cctcaaacca gtaatctagt caaaaaagca attcccaagg catgacattc agattcatca   149880
gcactcacag agactacagt gattgctgat aacgccaact taatacctgg ccaacagcat   149940
ggatcctgac ctccactttt cttgtgtgtt tacagaacca caaaaggtg cagtgttttc    150000 a                                                                   150001
```

<210> SEQ ID NO 3
<211> LENGTH: 138001
<212> TYPE: DNA
<213> ORGANISM: Homo sapiens

<400> SEQUENCE: 3

```
ctctcccaaa ttgtcaaaga agtataaatt agaaaatgaa tcaggacaat ttcaacctgt      60
tagattagct aatatttaaa aattgaacac tcatacaagt gtggtgaagt gattgttttc     120
tagtgacatt ttacactgtc ataaccttct agaaaataaa ttggcagtgt tattgggaga    180
cagaaatatg tctatataat ttatgggaac ttaggctcag aaaatattaa ggaataagaa    240
tgaactttat gaacaaagat gtggagggt ggaagcaaga ggggggccaa cgcgcacggg     300
gaggaagcat ttgggcagtg actccgcaga cccaggctca ggttgaacta gacaacctcc    360
ttacacctca gttccttaa ctgtagagca ggagtgatgg aactgcctgt ttcataggac     420
tgttgtgagg atgaagtgag atacaccaca ttataagctt gtgcctggaa aggataatgc    480
ttagtaaatg atgactattc tttttttattg caataaaatg tacacagcgt aagagttact   540
attttaacca tttttgcagg gtaccaccaa gtggcattta gtacattcac agtggtgtgc    600
aaccatcatc atatttccag aatattttcc tcatccccaa aggaaacctc atgctcatta    660
atcagtagct ctcctttaaa atattagtta tgaagatcat agcactatac aaaactcatt    720
atgtaatgtt gagtgaaaaa atcagggtgt gaaattttgt gatatgatgt aattagtgaa    780
agaagcatac aaaaagtctg aaaatataaa acaatagca attgcatttc tcagactcta    840
catttaaaca ttattcttta tggttttaaa agcaaagaaa aaggtaaaga aacaacaacc    900
aaccgcaaag caccatgaca aagctcagat tgttaaatcc aggttttgg aacatagact     960 cttatatgac gtttacactc tccagggttc agagagtctg gcagcattgg gagctgcctt   1020
gtgttctaca gcctcacgga cagacaggag gtccatcacc actgctctgt tcttctggag   1080
tttccttgtg aacatgttgt ggacgtagtt accatttctt tcatcttttt aaacacaggt   1140
acctttgggg ctggctttct caaggaagcc cagctccctg tgattgagaa tgaagtgtgc   1200
aatcgctatg agtttctgaa tggaagagtc aaatccactg agctctgtgc tgggcatttg   1260
gctggaggca ttgacagttg caaggtaaga aaagatcaag agaccaaagt tagtcttgtg   1320
ctctcctgtc tcagtctcag tcccttagac ttgagtccca agtagcgaa ttcaagtagg    1380 atttaatcaa tggaagaccc cagtctaagt gttgctcaga aactccctag atctgtccca   1440
```

```
aatgtatatt cagatcatcc aaggggactt cttggggctt gagttccaga tcagcagcaa    1500
gggagccata agtgccataa ctacctcaga ccactcaccc tcctggggtg tcccggtggc    1560
cagggactaa agtggtgatt tttctggtag ggaaggaggt agagggtaca ggacagagac    1620
taactgcaca caatatctga gactggagct cagatattgc tgatgatcag agttggcgtg    1680
tctccccaat tgatttacaa ctggggcttg gatactgttt taaacgggag gagcctccta    1740
accatcttga cacaaccact gacgtgacta cactagagat agactctttc cacttaattc    1800
taccactctt gctttacttc atgagaacga aaatgtaaga ttgcaccatg aattcatttg    1860
cggaaagatt gatactatgc ttttatttta ttttattttta ttttatttta ttttatttta    1920
ttttattgag actctcaccc cggttgaagt gcactgacgt gattttggct cactgcaact    1980
tccacctcct gggttcaagt gaatactcca gcctccctag tagctgggat tacaggtgcc    2040
caccaccacg cctggctaat ttttgtattt ttagtagaga tggggtttca ccacattggc    2100
ctggctggtc tcaaactcct gaccttgtga tccacctgtc ttggcctccc aaagtgctgg    2160
gattacagag ttgagccacc gcactcgacc ctatgtttta ttttaaaaa tatttattta    2220 tttatttaag ccacaactac tagaatagga aggattgata ttttattaat tttatttggt    2280
atttattatt ttttttttctt tcctgagaca ttcttgctct gtcacccagg ctggagtgca    2340
gtggcacatt cttggctcac tgcaacctcc atctcctgtg ttcaagcaat tctagtgcct    2400
cagcctactt agtagctggg atgactggca tgtgcctcca cacccagcta attttttgtat    2460 tttttgtaga gacagggttt tggcatgttg cccaggcttg tctcaaactc ctggcctcag    2520
gtgatccatc tgccgtggcc tcccaaaatg ctgggattat aggcatgagc caccaccccc    2580
tcctggaagg attgatatct tataacataa tttataatta cagaaaacat gtgagttcac    2640
taggaataaa taaattttga agataataaa agattttcac ttatgttgtc atttcggcac    2700
agtttggtat aggatgtgga gatgttaaca tttataccta gcttgctcgt aaactaagac    2760
ctgaaagggt tgtgtctatc agctgcaccc ctgggtagcg acacaacctc gggaaggcct    2820 cagcccctc ctcgtacagc actgcctgtt ggaaagcttg agggaggcta tggatgtgca    2880
gcacttggca gagggtctgg tcatggaagt taccagcaaa tatgagctac ttttatgatt    2940
ttattttatc caaaagaaag agaatgaaag aagaggggag gaaacaagac taatcaggaa    3000
agatgaaggt ctaggggtga gggaaggagt aaggagacat aaaggcaatg tggagcagct    3060 gagggggaa atggctttca ccacttccca gcatctattg acattgcact ctcaaatatt    3120
ttataagact ctatattcaa ggtaatgttt gaaccctgct gagccagtgg catgggtctc    3180
tgagagaatc attaacttaa tttgactatc tggtttgtgg gtgcgtttac tctcatgtaa    3240
gtcaacaatg tcctgggatt gggacacact ttctgggcac tgctggccag tcccaaaatg    3300
gaacataagg aagtggttct tctacttctt ttatttctga aatcaggtaa gacatagttt    3360
ttttaaatta taagaattat ttttctccc acaatgtagt aaaaatacat atgccatggc    3420
tttatgtgca attcatttaa ttttgattc atgaaattcc cagttcaaaa tcttgtatat    3480
gattgaaaaa ttcttaaaaa aataagttta atttccccgt gaagactgtc acggtgctgg    3540
aatgaatggg cagaaaaaat aatggttgat ttttctaatc taaaagagtg tgcctacatg    3600
atggccagtc tggctgaaaa ataaatagcc attgtagcta actatgcaaa ggatggctaa    3660
gctcttcgct tggttctcag tttcattaat ttatatcatc tctgttcagg tgccatgctc    3720
ccctcactag caagttgaaa caatgaaata actctttgaa tatgtttggt tccttgacct    3780
```

-continued

```
gttcatggag tgggactcag catttctctc tttgttatgg cctgagtaag gctttccatc    3840
ggtatacatt tgcttcttat ccctggagaa attatacaca tccatttgcc agatgatata    3900
cgcatataat gattcaacaa atactcaggg tatttgttga gtgggttagg tccccacatt    3960
tttatacata catacacaca tacacaccgt gtgtgattgt gaatgtaagt gtgtgtcctt    4020
tacaaatact agcttattta gctcatggta taggtagggt agcatagtca tccccatttt    4080
ataaacaaag aaatctagac ttaggaaaat catgttattt gtctcgtgac caaattccca    4140
aatcaaggaa ataaagaaac ctggatttaa gccagatttc caagaaaaaa tctagggctc    4200
ttctcacttt ttcatctttg ttccaacatt tgaaaaaata aatctaaaca cattccaatg    4260
taactgaaga gcaggttaat tgtttgccac ttgcagaatc caattaagaa gagagaagtc    4320
tggtataaag aaagtgattt gcttccaaag ctagcttagg ggaagaaatg cagcagtcct    4380
gccgtactac ttcactttag gagcagaaag tggcactttt aaaaggcaac agaggaggcg    4440
agcaaggatt cagggtcca tgctagcttg ggcaccttat ccaccaggta gttgagcagt    4500
tgcctgctgg tgcctttgtg agcagggtgt tgtcccttga ggcaaatctc tggagggtga    4560
gagttttgta gtgggcatgc tttggtttat aaatcacctg tgaactcagg agttccatct    4620
tgaagcacat acatagttag atgaacttgc cctgcaggga gagtctgatg aaagggaggt    4680
agatgcttgc aatttaatct ataaattacc agataaaatt ttacaagttg actttaaagt    4740
caaacacatt tgaatttagt ggaagccatt caagaaaata tcaaagaaaa tacagagcag    4800
gagaagatta agcaaagagt tttttgggga aattggtgtc tatgtctgtg tgtgtaggga    4860
gtgcagggga tatgaatatt ctatttcagc ccatggaaac taggatgtag atcactgtga    4920
acttattcag caggctacac ccaaaggcta gaacaaactt ctctgccaca ggattaacat    4980 atgtttaat cgacctgggg ggcacattct ctgataagct cttttggaaa gccaggcttt    5040
ctgtggacgt gttatctttc caatgtgtgc tggaatgccc ggggagagga aaaagtttct    5100
tttacagcca tgctcagtga gaagcggaga acatcttct attcacaaat tgctaagtct    5160
tttacacatg caaatatgca tacacattca cacaccacag tgaggaagaa attctcacac    5220
cattaataaa atacatttac ttcagtagca atatacatct acattttgcc tataatataa    5280 aagtatttt cctattaaaa gatttgttta atgtttcttc accaacaaat aaaccctatt    5340
aaatccccat tgccatatga gccctggagg tgaatcagag aaacaaaagg attgtggaaa    5400
aatcatcagg ttaaaaaaag aaaaattgat tctgttttgg gatatttcct agcaacatga    5460
gctggggagg ggatctcagc agtgatgctc tatgaagcat aataaaatga cacagttaca    5520
ggtaacttag ttaaaggggg aaataaatgg aagtttcctc tttttgaata tcaattgtag    5580
cctgctctgc tacatttcaa aaacactctt caaaatgttt aactgaactc actgtaggaa    5640
gcaccttatt aatttattgt gtgttttgaa gtcacactgt gagctataga atttacccaa    5700
gcacaactct tcctggaaaa gagagttcaa atgagaaaca gtgcgggtg aagacatgga    5760 tatgggccta aaatatctat ttctcaatga tattttgata tatctatcaa gtgcttttta    5820
gtggattagg ttcagaatgc atcagccaat gcctgttcaa taatccagtt ttccagcata    5880
gagcatatta aattgaggaa ggacaaagtc acagaggtgg ggagcaggtg gactgtggcc    5940
aaggactttg catgaaacag tgagcgtgca tcctcctcct tgccctgccc tcatggtctg    6000
tgtactctca ggaggtcagg acaggccttt ctgagaatga gaatctgttc atctgccttt    6060
ctactggata cttgtcatcg gcatacaaac acatgttctc tgcagtgtgt catctttcag    6120
aacctcccct gaccctgtat tccctagaag tctcgctgct ttcagagcca ggcttctctc    6180
```

```
ctgctgccac ccccactgct cttctagtca ctctttaacc cactccatct gcatgtggcc    6240
cccaccacac ccctcaaagt ggtcaaggtt gtcctgttgc ttaattccat ggaagcttgg    6300
ctatcttcat tttattagcc tcttttggcc tctcaccctg tgaaaatcac tacattttgt    6360
gccagagatg gagctggcat ctccaggctt ggaagagggc tgctgaagct cagccaggtg    6420
tcctaaggag cctcaggaca ggggatgctc agtagccttg caatgggaac acagctgagc    6480
cccacttggc cacccttlgc cacaaccagg cagaaagcag cttttgaaca gatttgttgc    6540
ctcagatttg atctcaaaga aaaatcgtgg gcagtattgg tcccaggttc tgcttttta     6600 caatttcctc tgaaatctgg atgcctatca acaccttgga aaaactgaat tctccccaac    6660
taatagtggt gtgtcactgt agtaagccta gtacaaaaat ggccttcttt gtggaggagc    6720
ttcatatcct ccattttttt tttgcttaat ttttgcccaa gatgagaaca taatttagtt    6780 cacttttat ttattcccaa catcatccat gcaccaacat ttttgtaact aaaggaggga     6840
ccattcagaa gatgcttatc aactgtcaaa gtgacagtgt tacaaccaat gcacatattg    6900
taagaaatca acaatggcc tccaaggttc atttctacac agggattagc agatcaacat      6960
caatcttggc aacacagttg ccactgatgg tgtcttattt tttttatcat gacatggcaa    7020
tcaagagcaa acatgattta ttcttattta agattttatg gttagactag gcagatagct    7080
agatatgagc aggaggtgga agcccctgag agaatggagg tctggagaat ctgaaacccc    7140
agagattacc caagtcctgc atgctagaca tgagtggagg aggggaata cctaggtaga     7200 aaagaatgcc ccttaagatg cccagcagtc gctcactgtg cagttaactt ttcagaatgc    7260
tgctagatac atgctgatag ggagggaaga gggcaaagga gaaattccta agagatacac    7320
ggttgcagtt agtatacatc tgagtgctat acaaccttct ttgggtggtg gcaagaagca    7380
atgcagccat tacgtagaat tcatatcaaa cacctgtatc acaggtgtta aagaaacaag    7440
aaacattgta cttcttgtat tcttaataat gatttgcaat attgtcttta gtatcactgc    7500
aaacctctat aaatatgatt tttaaaaagt atttcttttag gttggaatta cttctacgca   7560
ttgacttatc ttcctgggtt tcattagccg tacccgttgt actttcttcc ttaccactgt    7620
ttatctcaaa ctcttgagat taaagtatgg gctcaggagg gagcgaggag cttcaggact    7680
ctcacggacc tccagcacag tgtagctgcc ttatggaaaa gtggccacac tgttttctgc    7740
actggtccct gccccctacta ttcctcactg ggcagagcac agccaccctg gccctgcctg   7800
aacattttag tcagtgttgg ctctgtgctt ctctggggag gaaatccaag agacaaccca    7860 cagccctct gccatttcag ctgcagcagt accaccgtta atgcccttgg gcttgagaaa     7920
gaagggacct ggccacttcc ctgacacctc cagcacacag cagggaaaga attccagttt    7980
ctctttcttg tgagctttca cctgctactc ttcaccaggc aaggctcctg gcttgggccc    8040
acagtgcagg cacctcgaac tcagttgaac atttccactg gctgcactct gtgttttgt     8100 ggggtgaagc tccagaggt gactgaaagt ccttctgcca ctaacactgc agtcatactg     8160
cccttgctgt acttggacta gggaaggaaa aaagatcctg agtgctttac tcacaccca     8220 gtgtgcccca gccaccctat ggaaaagagg ccagtgtgtc atccctgcaa gcaccctgag    8280 gccctgccc ctgctgcccc caagctgtag agccagaata taaagctggc agaaaaatgt     8340
aaaaaggcta gactggctta gcctcccagc ctacatcttt ctcctgtgct ggatccttcc    8400
tgctcttgaa catcggactc caagttcttc agctgtggga cttggactgt cttccttgct   8460
cctcagattg caggtggcct attatgggac cttgtaatct tgtgagttaa taccacttaa    8520
```

```
taagctcccc tttgtgtgag tatatctata tctatagata gatataggta tactcactat    8580
atatacacat atatacatat actctctctc tctctctctc atatatatat atatataatc    8640
tcctattagt tctgtccctc tagagaaccc cgactaatac agattttcat accagaagtg    8700
gttcttgagg aacagaatat taaggatgga attctttcat tggttttggg acttctggtg    8760
ttggctgatt aatatgatta gaccaaaaaa tgctaaggac tctacttcta atagtatgga    8820
gaacactgat agtacttggc ctgaattgtt tagagagtta tgcaaaataa atgcatttga    8880
cactactgat tcatcactta tgagaggcaa ggagtttagt gactctatac ataatacctt    8940
tgactatatg tggagaacca aggaacataa tgaagttggt tgattgctcc taagttctct    9000
ggagaaagag atgaaagaaa atgatgatct caggggatct gtctcccacc ttcagaagca    9060
gatactgagc cacaaatctg ctaagattgc cctgaatgag agttttaact cctgtagaga    9120
aagagttgaa attgtgaaaa aacagagaca agctgttatc atgcgagtag ctgatctgca    9180
acaagaggtg catgcacagc cttgccaggt gtttactgtt aaagtgaggg cattgactgg    9240
aaaaaaatgg gaccctggaa cttggagtgg ggatgtgtgg gagaaccctg atgaagctga    9300
ggacactgag tttgtgaact ctgatgaaac ttttttgcca gaagaaacag tttccccatc    9360
cccagtagtg gtaacatccc ctccctgacc cgtgctgcca ttagcctttc caccttttgtc   9420
tgaggatgta aaccctgcac tgcttgaggc aacagtgatg gccttccctg aggcagctgc    9480
caggcaagat aatgttgatt ctcctcaaga ggcaccccta atgcccctga atgcttctag    9540
acctataact aggctaaatt ccttgcgggc cccagaggtg aggttcagag tgtgacccat    9600
gaggaggtgc attatactct aaaagaactg cttaagcttt ctaatttata ttggcagaaa    9660
tctggagaac aggcatggga atggatatta agggtaaggg ataatggtgg aagggacata    9720
gagttggatc aagctgaatt tattggtttg gccctactaa gtagggattc tgcatttaat    9780
gttgcagctc ggggacttag aaaaggttct gatagggccg ggagcagtgg ctcacgcctg    9840
taatcccagc accttgggag gcggggggcg gcagatcacg agatcaggag attgagacaa    9900
ttctggctaa aatggtgaaa ccccatctct gctaaaaata caaaaattag ctgggcatgg    9960
tgatgcgtaa ctgtaatctc atctacttgg gaggctgagg caagagaact gcttgaacct   10020
gtgaggcaga gattgcagtg agccaagatc gccccactgc attccagcct ggtaacagag   10080
caagactcca tttccaaaaa aaaaaaaaaa aaagttataa tagtttatttt gcttggttag   10140
ctgaaatatg gattaaaaga tggtccaatg ttagtgagct ggaaatgcct tggtttaatg   10200
tagaggaagt gatccaaagg cttagggaga ttaggatggt ggagtggatt agtcacttta   10260
gacctactca tcccagctgg gagggtccag aagatacacc cttggccgaa gctttgtgaa   10320
atagatttgt gagagcagca cctgtatttt tgaagagccc gtaattgctc ttctctgtat   10380
gtcagatcta acagtaggaa ccacagtcac tcaactacaa aatttaaata caatgggaat   10440
aattggatcc tgaggtggca ggggccaagt gttggcactg aaccatcaaa ggcaaggtgg   10500
gcataactac cataatagac agcagaggca aagcagccat cagaatagtc tgactcatgt   10560
agagctctgg cattggctaa ttaatcatgg tgttcctaga agtgaaattg atgggaaacc   10620
tactgtattc ctacttgatt tatataaaca aaaaactgcc aggtagaatg gactaaagac   10680
taatctgaat tataaaaaca gagaatcatg ggccctcaat caatttccag actcgaacct   10740
gttacagttc cagaacccac tgaatgaagg ggaggctgga tccccttgag gaaggacacc   10800
actaggctac tgcaaactta tgctgttact ctttctccca tccttcccta aggagacctc   10860
tggccttttta ccagggtaac tgtgtgtact ggagaaaggg aagtaatgag acatttcaga   10920
```

| | | | | | |
|---|---|---|---|---|---|
| aagtactgga | cactggctct | gagctgacgt | tgattccagg | gtacccaaaa | cgttattgtg | 10980 |
| gttcccagt | taaagtaggg | gcttatggag | gttaggtaat | taatgagtt | ttagctcatt | 11040 |
| tctgacttac | agtggttcca | gtgggtccct | ggacttatcc | tctggtcatt | ttcccagtgc | 11100 |
| caaaatgcat | aatttgtata | gacatactta | ttagctggca | gaaatgccac | attggctccc | 11160 |
| tgactggtag | gatgagggct | attatggtgg | gaaaggccaa | acagaagcca | ttagagctgt | 11220 |
| ctctacctag | aaaataaaa | aaatcaaaaa | caatatccca | tccctggagg | gactgaagtg | 11280 |
| attagtgtca | ccatcaagga | cttgaaagac | gcaggggtgg | tgattcccac | cacatccctg | 11340 |
| ttcaactctc | ccatttgacc | tgtgcagagg | acagatggat | cttggaaaat | gatggtggat | 11400 |
| tattttaagc | ttaaccaagt | ggtgactcca | attgcagctg | ctctaccagt | tgtggttttg | 11460 |
| ttgcttgagc | aaattaacac | atctcctggt | gcctggtatg | cagccattgg | cttggcaagt | 11520 |
| ggcttttct | ccattcctgt | ccataagacc | caccagaagc | aatttgcctt | cagctgacaa | 11580 |
| ggccagcatt | atacctttac | caccctacct | caggggtgta | tcaactctcc | agctttgtgt | 11640 |
| cataatctta | tttggagaga | ccttgctcgc | ttttcacttc | cacgagatat | aacactggtc | 11700 |
| cattacattc | atgacattat | gatgattgga | tacagtgagc | aagaagtagc | aaacacactg | 11760 |
| aacttattgg | tgagacattt | gtatgccaga | ggatgggaaa | taaatccagc | taaaatttag | 11820 |
| ggactttcta | cctcggtaaa | atttctaggg | ttccagtggc | atgagaccta | tggagatatt | 11880 |
| ccttctaagg | tgaagcataa | cttgctgcgt | ttggcccctc | ttacaaccaa | gaaagaggca | 11940 |
| caatgcctgg | tgggcctatt | tggattttgg | aggcaacaca | ttcctcgttt | gggtgtgtta | 12000 |
| ctctggccca | tttatcgagt | gacctgaaag | gctgccagat | ttaagtgcag | tctagaacaa | 12060 |
| aagaaggctc | tgaaacaggt | ccaggctgct | gtgaaagctg | ctctgccatt | tgggccacat | 12120 |
| gaccccgcag | atccaatggt | gcttgaggtg | tcagtggcag | atagggatgc | tgtttggagc | 12180 |
| ctttggcagg | cccccatagg | tgaatcacag | tggagacctc | taggattttg | gagcaaggcc | 12240 |
| ctgccacttc | tgcagataac | tactctcctt | ttgagagaca | gctattggtc | tgttattggg | 12300 |
| cttttggtggt | aactgaacgt | ttgactgtgg | gtcataaagt | caccatgcta | cctgaacctg | 12360 |
| cctatcatga | actggttgct | ttctgaccca | tctagccatg | aagtgggtca | gcacagcggc | 12420 |
| atttcatcat | caaattgaag | tggtgtgtat | gtgatcgggc | ttgagcaggt | cctgaaggca | 12480 |
| caagtaagtt | acataaggaa | gtggctcaaa | tgcccatgtt | ctccactcat | gccaccctgc | 12540 |
| cttccctccc | ccagcctgca | ccaatggcct | catggggagt | tccctatgat | cagttgacag | 12600 |
| aggaagggaa | gactaaggac | tggttcatag | atggttctgc | acgatatgca | ggcaccaccc | 12660 |
| gaaagtggac | agctgcagca | ctatatccac | tttctaaatg | catgtgtaca | cttgtgctaa | 12720 |
| gaaaatatct | ttattttatt | tcctttattt | ttcctttatc | atgtgacctt | agatttatgg | 12780 |
| acttcacatc | agcatttaag | catttaagtg | ttgttcatat | cagcatttaa | atattgttaa | 12840 |
| ccttatgtaa | taacttttgg | tttggggatt | ggtgcgtttc | tggttgtatg | aggatagttg | 12900 |
| tattatatta | ggcataatta | tgaccttatt | attgtcttta | tttgaagatt | atgtatgatt | 12960 |
| tcaggatgtg | tgtatgggtt | caagttgaca | aggagttgga | cttgtgatgg | ttaatactgt | 13020 |
| caacttgatt | ggattgaaag | atgcaaagta | ttaatctcgg | ttatgtctgt | gagggtgtgg | 13080 |
| caaaaggaga | ttaacatttg | agtcagtggg | ctgggaaggc | agacccaccc | ttaatctggg | 13140 |
| tacacaccat | ctaatcaagt | tccagtgtgg | ccagattgta | aagcagggag | aaaaatgtga | 13200 |
| aaagactaga | ctgaattagc | ttcccagcct | acatctttct | cctgtgccaa | atgcttcctg | 13260 |

```
ctcttgaaca tcggactcca agttcttcag cgttgggagt tggactggct ttcttgctcc    13320
tcagcttgca gagggcctgt tgtggaacct tgtgatccgc tgagttaata ctacttaata    13380
agatcccctt tatatacata taatatatta tattatatat aatatatata atatatatta    13440
tatataatat atataatata ttatatatta tatataatat atattatata ttatatataa    13500
tatatattat atataatata tattatatat tatatattat atataatata tattatatat    13560
aatatatata aaatatatat atatcctatt agttctgtcc ctctagagaa ccctgactaa    13620
tacaatttat gtcattaatc tcatttattg atttgtatac attgaaccaa ccttatatcc    13680
caggaataaa acctacttga ttgtggtgga ttagcttttt gatgtactct tggattcaat    13740
tgctggtatt ttattgagaa ttttttgcatc tgtgttcatc aaggatattg gcttgaagtt    13800
ttctttttt gttgttccat atcagaatga tgacgacctc atagaatgag ttagtctgtc    13860
ctcttttatc ttttggaatt gtttcaggag gcttgatatc agctcttctt tatatgactg    13920
gtatactttg gctaggaatc tctctggtcc aggggttttt ctggtgtagg ttttaatta    13980
ctgattcaac ttcagaactc attactcatt attgagttct aaaactcact ttcatgtact    14040
cttcaaaaga ctgtcttctt ctgttgttga gcggggtgtt ctctcaaggt cgtttaggtg    14100
aaggtggttg ctggtgttct tctgtatcct tactgcttgt cttctctctt ttttattgac    14160
tactgaggat taatggtgat gtgtccaact ttaactctag attagtctat ttctctttta    14220
gattgtaact ctgttttata tattttgaag ctctgttgtt aggcatgtgt atttggattg    14280
ttaggtcttc ttgatgatga cctttatcat tatgtaatgt ttcttcttat ctctggaagt    14340
attcgttgtt ctgaagtcta tttgtgctga tatgaataca gccttcacag ctctattttc    14400
actagtattt gtatatcttt ttctcagctt ttaaattgag atgttcagac catttgcatt    14460
aaagtagttg ttaataggat taaatttaaa tctaccatta agttggttat ttctctttgt    14520
cccatttaaa ctttgttcct tttttcatat ttttctgcct tcatttatat tgagtttatc    14580
tccacgactt acttattaaa ttaattttta atggttttag tattttccac aatgtttata    14640
atatatactt tgattttttc acattccacc ttcaaatgac agaattatac tggatatata    14700
gaaatcttac atcattgcac ttctccttcc tccctctcaa aatgttgtgc tattgctctt    14760
tgtaatagag gcttacttct attatgttat agctctcata atacattgac actattttta    14820
ccctgaataa tcagttgttt tttaaagtga ttatgactac aaatattttg aataatttct    14880
ttatttacc atttctggtg ctccttatct tttacagtag atcccaattt ccatctggag    14940
tcacattctt tctgtgaaaa acaaccttta gcatttctta tagcacggga ctgctgttgc    15000
tgttgtcttt cagcttttct ttgtctgaag aagtcttat tttgccttca gttttaaaa    15060
gtgattttgc tgagtataga tactgggttg agagtttcat tccttgtatc attttaacaa    15120
tgatgttcca ttatattccg ttttgaatag tttctgacta gaaatctgat ctttgtttct    15180
ttgtattcaa tagttccttt ttctctgact gcctttaaga tattctcatc tttgtttttc    15240
aacagtttga ctataatttg tttattatta acttttttgta tttattctgc ttgaggtttc    15300
ctgagctcct tggatttgca gattgttgat ttttattgtt tttgtaaaat tcatagccat    15360
tatctattct actgttttgt tttttttttc acttctctct ctctgtattc ttcttttgg    15420
actgtaagta ttcaaatgtt agatcattca tattgcttca taaaccttat atgcttcttc    15480
tgcttttttt tttttgtcag gaactctttt tttgtatctg tgttggtttg gataagttct    15540
agtagactat gttcaagttt atggattatt ttgttagttg tgtctaattg actcctcagt    15600
gcattcagag aattcttcat ctctgatatt ataaatctct tcctagcatt ttcatgttac    15660
```

```
tcttttctat agtttccatc tctttgctga aattctcccc ctatccatgg atattgtcca    15720
cctttaccac aagattcttt aacatattaa cataggtatc atacaaaccc aaactgatag    15780
tttccagatg gtgtctttc tgagtctgtc tgtcttgatt gctttattat ttaacagtga    15840
cttatcttcc ctcttcagct tttggtgtgt cttgtaattg tttaatcaaa cactgggtat    15900
cataaatgga ggaacagtag agattgcagt aaatattatt tatgctttga atgggcacc    15960
catcttctgt tgaaaatatg ttttgtggtc aattgagtca acctagtaac tggttgaact    16020
gaatttggca tttgtgcttg ttgctttat cttaaatgca ccacaggttt aaattcctcc    16080
agtgatgggt gctgctatc ttttgcttag agtggggcct ggggtgtgga agaattttct    16140
cagtgttcct atctattatt agattttagc agtcactgca tgcctgcact acagagggga    16200
tatcttcata cacataatct aaccccattg aaactgctgt ttcttcttaa tgaatgctca    16260
atctttggtg gaaataaaca aatgctgtat ctcctggagc cacttcagtc ttagtcaggt    16320
tctgcagggc tttgaaggga atgcattctc agtattcttg tgccttattt ggatggaact    16380
tgaacctgtg gtgggtttgg agagaaagag tagcagacgt ctgctatgtt gcaatgcagg    16440
atgctgggca caagaaaatt tccagtctct cctccaagga aataagattt gatcatctac    16500
ctatccctga gaagtgaagg gctttgcctg cggtgctaga tgcaaaacca ttttttctccc    16560
cccattgccc agaaacttaa ggcttttggct tttctgagca gtggtctagg gaattgtgca    16620
aggttttcat atttgacct gacagcccat caccacctac agcttgcagt gccaaatgta    16680
tctccctctg atctctcctg tcctgtggtc ctcatgaaca ttaagaagag atttctaaaa    16740
aagagcttgc acatgagcat agtttctggt gagaagaatt ctgatatgtt aacttcctct    16800
aaacttttaa ataaaatatt tctaagaatt aaataaagtt ctagaatgat atgaatctat    16860
tcctttggtt ttttgcacgt ctgtctgcct gctaatcaag agaagagaat ggtcgtaatt    16920
ctcagagact ttttcctgtt tgtgtcataa atgacttcac attttttct gttctaagaa    16980
ctattcagct tgatttcttc tgtttttaatt ttagcagcac ctgagcaaag ccatgtggtc    17040
caggattgct accatggtga tggacagagt tatcgaggca cgtactccac cactgtcaca    17100
ggaaggacct gccaagcttg gtcatctatg acaccacatc aacataatag gaccacagaa    17160
aactacccaa atgcgtatgt cattaatctt acagtaagca aaacaaggtc caagtaaaat    17220
ttgtcttaga aaaggtgtgc gtcaagctaa cttcttatga ttaaattttt ctcacacata    17280
gaatgcatgg caaaatgtct gagaaacatt actttgagca aagagtatga tagaagagaa    17340
atgttaagct ggctctcttt cctgagagtt tgataaaatc aggagaatat ctggcggtgg    17400
tgaggccaca ataatggaaa atcagaatgt ttagacagag tcagcttcaa caacactcac    17460
taaaggtcaa tgtgatcttt accccttgaa attctataat tctaatctcc aattcctgaa    17520
gtgaaggttg tgttggcctt ttctgtcttg gctcacaagt aaatgatatg tgcatatcta    17580
tggaaaggcg aatctatctt tttctatatc tatgtctatt ccaacgggta gaaacaccct    17640
gggtcctgag caccagtggt ctgaaggaat acgggttgcc aggaagagag aagcaaaggc    17700
aggaaggcag atgaaagtaa gaaatgagac agatgctaaa caataaaaag tgcgggaaga    17760
tagacagaag ctggggtctg accacaccat ggccagtctt tcacacataa gtgactacca    17820
aagacaagaa aaaatgattt ccgcttgttg gacaatagat ggtagaggac caagggaatt    17880
gcgagagaga gaacaatgag atcaactcaa cagatgcact ggttttcttc ctggagaccc    17940
ttcctgcact gaagggcagg agatggagcc caaaaaaaac tgtagccatc ttgctgaaca    18000
```

```
gaggagggac attggagttt gggattattc aggtggctag gattttctag gcctgctaac    18060
aatgagaaca gatttgtgga ggaaaggagt tctagaaata tgcatagaaa tctcctcgag    18120
tcattggcta aacatgaagc tgcatgtaca cagaaaatag atccacaaga aagtagggca    18180
aagaacatct acggaagagc agcaactaca atggaacagt gagctcaata aacatgacag    18240
agctcaaata gcactaaggg atattggagt ttggaccaca cagaggagag agacttcact    18300
gaacatcttg ggcattcagt agagacccag gaaaagccat actttaggag tagaattagt    18360
atattcttag aataaaggca gctccacaca aacaatagca aaactgaaaa ggaagtctcc    18420
aagcatcaga atgatgtcca agtcaatgaa ctgcctctga gaggaaaact caaccatctt    18480
tagaggtaaa catcaaagtc aagtggctca gctatgcagt atccacagtg tgaggcctaa    18540
atataaaact tgactacaca tagaaaacctt ttagtgtgac ccacaagcag gaggaaaatc    18600
agccaataca aacagaccca gaagagacag aaatgattag aatggcataa aaatttgaca    18660
tatcactata taataattga gttctaggat ttaagaaaac atgaatatag aatgcaacag    18720
acaccttatc cagagacagt aagagtataa agagccaaat cgaagaacta ctaagagata    18780
tgtcttaaat gaaaaaatta ctagatggcc tccccatcta gttagacatt tcagaagaaa    18840
ataccaaatg aaaaataatt gcatagaacc tacagaacca gatacacaca tacaaaaacac    18900 acgcatgcat acacacacac tcaaacatgt ataagcttac aaacacacac acacatccac    18960
aaatgctgaa aaatgaaatc aaccgagcca cacagacata aaggaaaaca taaaaagatt    19020
tcctacatgt gggaagcaag tcacagaaag ggggaaggag attggaacag aaatatatac    19080
tgaaagcaag gatggctgaa aattttccaa atataaagaa gattaaaaaa tcacggactc    19140
aagaagctca atggatcaga aaaataattt ctaaaatgac aattataggga tgccactggg    19200 tacatagcag ttcaactgtc agagggcaaa gacataatac acagaaaaat ctcgtaagga    19260
acgggaaaaa caaaaagctg tgtcttgcta gaggaacagt gatacaagtg actaatgtgt    19320
tcccatcaga aacactgcaa cctggacaca aagaataac attaaagtaa taaacgtaag    19380
aaagaagagc tcaactgaga aggctacatc cagcaataaa atgccttgaa gttcatccat    19440
gttggaggaa tgcacattgt gcactcccct aaacaaagaa accggaaaact gtaagacttt    19500 ggaatcagca ggcttatgta acaaaagagg tgaccctaag gaattaagga gaagaagaat    19560
agaacaagaa gggaactttc tgcagcctat ataatgaaga acctagcaat tggcaaatgt    19620
agatgaaaat gctacatgtt ttcttgatca aacgtttata tcttttttaaa tgagagttga    19680 cgagttgaag caaaatgata ccaatatatt taactttacc atatgtagaa gtaaaaattt    19740
gaacatgtag cataaatcat gtagggatta attggaagtg taccactgta agtttcttac    19800
ctcatgcacg atagtatgta atactaataa aaggttaatg tgtgggttca aagggatatt    19860
gcaaatccta gagcaatcac aaagttttta actctgaggt ttgttgtata ataacaatat    19920
tttatgtatt caaagagggg aagccaagga agaaaaaaaa gtctttaaag agctctggct    19980
cttagtacat ccagttgctc attgaatgag cttcctggaa tggagggtct gggactgaga    20040
ctaggccaca tgtgtagagc cactagagac acaatgttgg atccccatgg cccataatac    20100
atttcccatt ttctcaggca gccacaggtc atgaatgtga ggatactgag aggttggagc    20160
aacgttcttg ggaggcataa ggaagagcga atgcttcaag atccccgcag cccaaactcc    20220
tcagctgctt tgcctcctaa ttcattgttt tttgctcctc catagctgtc cgacctcttc    20280
agatctctta gtcttcctgc catcttcctt tatgccatgg gacccactgt tctttcaact    20340
catcccccag ttctggagtg gctgtggaca gcagaggata gactgagagc aggagagaag    20400
```

```
gtcctgccca ggaacccatt ctagagatac tgcattctgc ctgggagcaa gttttccagg   20460
gcagctttga gaagtcttgc agaaacaaac ctacttgacc gacatgatat gggaatgaca   20520
gacagtaata ctatttgcac aatgcttttc catgggaaag gtagagcctt ttcactaggt   20580
tttgagtaca tggagtgtga gagttgacct ggaaaggtta tcctccttga tgccatgttt   20640
tctctgaaga actacatgtt cgttgcaact cccacattag aatatgaagt cctaccgaga   20700
gagatacgga gactagacag atacagatgc atttgcatgt gaatacacaa tcccacaata   20760
cagacgtcaa aacccatacc agttattcca gagagatgga ttgggcagaa ggcagaagga   20820
gaatactctg atcgttttc ggccacgtgt gtgtgttatc tcagtgtttc taagaagcgt   20880
ttgctacttt agatttttta tttaaaaaaa atagtaataa tctattaagt atgagagatg   20940
tgcagagagg attagtgatc gagagccatt tttgctggtg gcaatcatat ggtacttta   21000
atgggaatat tagaaaggca ccggtaatga ccttgttgca gcacaaagga gagagtgtgg   21060
ggtgcccctg catgttgtcc cacctcttgt gacgtgtatc gttttggaat ttccagtggc   21120
ttgatcatga actactgcag gaatccagat gctgtggcag ctccttattg ttatacgagg   21180
gatcccggtg tcaggtggga gtactgcaac ctgacgcaat gctcagacgc agaagggact   21240
gccgtcgcgc ctccgactgt taccccggtt ccaagcctag aggctccttc cgaacaaggt   21300
aaggagtctg tggccagaca tctacacgct tcgatgctgg gatgaaaagc catggaaatt   21360
cccactgatg cagccgcctt caatggtaaa cggatgctcg agtgttgcct gagttctacc   21420
atgtaggagg aagcctccgt gcactctctg ggggagccag cggagtgatt tctggtgcaa   21480
cgtggttggg ctttgtcttt aggatgggca caaaccctcc aggggatcg acttcaaaat   21540
tcaccttgtt gtaaaacggg ctacctcagt gtcccagcca aaattttat tgtaacatgc   21600
tgtcaggtgt gtcactcttt ccaagccagt aagcttttcc ggggatttct tcaagtagcc   21660
agcattcaga gcaatcttca gcattgcaga ttctgagaaa tgtggctctg gagcctgtca   21720
ccctcgagaa acctaagagg gctgcattga ttccatgtgg ccctgggtct atggagcagt   21780
acatgagctc ccagtgctct aaggctcttc agccctaggc tttgaaggga gtgatttctc   21840
agtattctta aacctctttc tgatgacact tgtacctgtg aggggtctag agagaaagag   21900
tagtagactc ctactttact acaattcagg atgcagggca tgagaggatt ccctctctcc   21960
tccaagggaa gaagcttttg gcgtgcacac atccctgaga agcaaagtgt ctttgtcttc   22020
agtcagatac ataggaccgt tttctgcccc atggcccgga agccaaaggc cttggctttc   22080
atgatcaacg gtctagggaa acatgcaaaa tttccatgtc tgtcccaaac tctgcccccg   22140
acagccaatt accacctgca gcccgcattg ccaaatgcgg tgccgtttgc atgaagattc   22200
agtagagttt cctagaaagg tgctacctcg tgagctcact ttccaatgag gaatctgatc   22260
tgttgtgttt ctctaaggtg tcaggtgaaa tatttccaag aacttactac agttctagaa   22320
tgggaggaat ctgttgcttt ggtgtttgtt tgttggtcgg ttttctcaca tccatctgcc   22380
tatggataag gaaaagagaa cggtcgtaat tctcatagac tccttctgg ttgtgtcaca   22440
aatggcttca catgtttctc tatgctcaga gatactcagc ttgatttccc gtgttttcat   22500
ttcagcaccg actgagcaaa ggcctggggt gcaggagtgc taccatggta atggacagag   22560
ttatcgaggc acatactcca ccactgtcac aggaagaacc tgccaagctt ggtcatctat   22620
gacaccacac tcgcatagtc ggaccccaga atactaccca aatgcgtatg tctttgttct   22680
ttaccataag agaagaaagg gccaagtgaa gtttctgtta caagagatgt gtctcaagct   22740
```

```
gagttctccg aactcaactt gtgacagatg cagatggcgt agcaaaatgt ctcaggatga    22800
ttgccttgga gctaagggtc tgagagaagg gaaatgttaa gctccctctc cttcctccta    22860
gttctattga gcagaaggga aatctggagg tgaggagatc acattatgaa gaaagtcaga    22920
atgacaaagg accagacact tagattaccc ttccacaaca ccaactaaac gtcaatggag    22980
actttccagt tggaattccg ttattctggc ttccacttcc tgaagggaag gttgcgtttg    23040
ccttttctct ctgggttcaa gaggaaagaa taggtgctta tttatggaca ggtgaattga    23100
tctgtttcta tatctacgta tattccgatt gtcagaaaaa cactcgttcc taagtaccag    23160
tggcctgaag ggatacaggt tcccagcaag agaagatcca aggaaggaag gcagatgaga    23220
gtcagcacag agagggatgc tgaaaagtaa aagggatggg tggatggaga gaagcccggg    23280
tctgaccacc caatggccaa tattttggcc acaagcgact accagagaca tggaaaaatg    23340
gtttctacat gtgggacaac agatggtaga ggacctagag aattgagaga ggggcaatga    23400
tgggctccac tccgcagatg ccttggcttt cttcctggat acccttcctg cactgaatag    23460
caaggagatg gagcccaagc agactgtagc catcttgctg aatggaggag agggattgga    23520
gtttgggatg actgtggtag ctgaaatttt tctaggtctg ctagaaataa gaactggttt    23580
gtgtggagga aaagagctct acaaatacgc atagaagtct cctccagtcg ttggcctgac    23640
atgacgctgc ctgtgcacag gaaatggttc cacgagaaag tgtggcaaag aacatttact    23700
gagaaacagc aagtacaaga gcacaggaag ctcaataaag aagagagaga tcacatagca    23760
ctctgggata ctggagttct tcccagctag accagagagt cctcacggag cacattgcca    23820
attcagtgga gaccccagaa cagccgtaat ttaaaggtac acttagtata ttactagaat    23880
aaagtcagct gcagacaacc ccttgcacag ctggaaagca agtgtccaag catcaaatcg    23940
gtttccaatc aatgaagtgc ctgtgagagg aaatctcaac tctctttaga agtaaacaac    24000
aaagtcgatt gcctcagcta tgcggtatcc gcagagtgag tcctaaattt aaaatctgac    24060
tacatgtaga aaagcgtttc gtgtgaccca tgaccaggaa ataaatcggg taatacaaac    24120
aggctcagga atgagagaaa tgattagaat tgcgtgaaaa tttgacatat cagtatgata    24180
actgatttca aatatttaaa aaacaacat gcaagaaagc agatatcata tcaagagaaa    24240
ttaacagtac agaatagcca aattaaatta agaggtagt ataaaaaaag tatgtcttaa    24300
ttgaaaaaaa ttactgtatg gccggctgat caatttagac gtttcagagg aaaacattac    24360
ccaacacaca attctagaga acctacagaa tgagctacac acacacacac acacacacac    24420
acacacactg aaaacacacc catactcaca cacacgcaga aactcacaag ttctaacaca    24480
cacagacacg cgcacccctg aagaaacagt gaaatataaa attaagcgag cctcacagac    24540
atgtaggaaa atatgaaaag atttcctgca tgtgggaagc aagtcacagt aaagagcaag    24600
ggagtttata atagaaacaa ataccagaat caaggatggc tgataacttt tcaattacga    24660
agaacattaa aaaaatcac agaatcgtga aactcaaggg atcatatagg gaatttcgga    24720
aaaaaaaccc aacctgtatg atgtactttt gtacatcaca gttcgaaggt aacaaggcaa    24780
agatgtaata agaagaaacc tgtcacgaga aactggagga aaaagagctg tgtcttccta    24840
caagtacact gatacaaatt gccaatgtgt tcacctcaga aacactggaa gccagatacc    24900
agggaatatt gttaaaatga taatcaggaa caaaagaga tcaaccggga atgctgaatc    24960
cagcaataaa atgccttgaa ggtcatccat gtcggataaa tgcatattgt gcactgcccc    25020
aaagaaagaa accggaaact gtaagaattg gaaatcagca ggcttatgta acaagagagg    25080
tgacccgaag gaattaggta gaagaagaat tgaacaagaa aggaactttc tgcagcccac    25140
```

```
gtaatgaaga atccagcaat tggcaaatgt agatagatgt aaatgcaaaa tattttcttg    25200
atcaaatttc tatatctttg taaatgagag ttgactactt gaaacaaaat gatagcaaga    25260
tatttaactt cagcatatgt agaggtaaga atttgaaatg gtagcataaa tcacgaaggg    25320
attaattcga agtgtaccgt tgtaagtttc tttacctcat gcacgatggt gtgtcatatt    25380
aataaaaggg tactgtgcgg gttcgaaggg atattgcaaa tcctagagca atcacaaagg    25440
tttgaactct gaggttttg gtataataag aatagtccat gcattcaaaa gagggaagcc     25500
aaggaagaac tagaagtctt tcaagagctc aggctcttat acatccagtt gctcattgaa    25560
ccagcttcct ggaatggagg gtctggggtt gagactaggc cacaagtcta gagtctctag    25620
agagacagtg ttggaacccc atggcccata atacatttcc cattttctca ggcagccaga    25680
ggtcatgaat gtgaggatac tgggaggttg gagcaacgtt cttgggaggc ataaggaaga    25740
gcgaatgctt caagatcccc gcagcccaaa ctactcgcct gctttgcccc ctaatgcatt    25800
tttctctgct gctccgtagc tgtccgacct cttcagatct cttagtccac cctgccgtct    25860
tcctttatgc catgggtccc actgttcttt caactcatcc cccttttccct cagtcccgga   25920 gtagctgcgg ccagcagagg gtagactgag agcaggagag aaggacctgc ctaggaaccc    25980
cttctagaga tactgcatcc tgcctgggag caagttttcc agggcagctt tgagaagtct    26040
tggagaaaca aacctactaa acctgacaga cagtaatact attttgcacaa tgcttttctg   26100 tgggaaggt agagccttt cactacgtat tgagtacata gagtgtgagg gttgacctgg       26160
aacggctatc ctcctggatg acgtgtgttt tctgaagaac tacatgttcg ttgcaactcc    26220
cacattagaa tatgaagtcc taccgagaga gatacggaga ctagacagat acagatgcat    26280
ttgcatgtga atacacaatc ccacaataca gacgtcaaaa cccataccag ttattccaga    26340
gagatggatt gggcagaagg cagaaggaga atactctgat cgtttttcgg ccacgtgtgt    26400
gtgttatctc agtgtttcta agaagcgttt gctactttag attttttatt taaaaaaata    26460
gtaataatct attaagtatg agagatgtgc agagaggatt agtgatcgag agccattttt    26520
gctggtggca atcatatggt acttttaatg ggaatattag aaaggcaccg gtaatgacct    26580
tgttgcagca caaaggagag agtgtggggt gcccctgcat gttgtcccac ctcttgtgac    26640
gtgtatcgtt ttggaatttc cagtggcttg atcatgaact actgcaggaa tccagatgct    26700
gtggcagctc cttattgtta tacgagggat cccggtgtca ggtgggagta ctgcaacctg    26760
acgcaatgct cagacgcaga agggactgcc gtcgcgcctc cgactgttac cccggttcca    26820
agcctagagg ctccttccga acaaggtaag gagtctgtgg ccagacatct acacgcttcg    26880
atgctgggat gaaaagccat ggaaattccc actgatgcag ccgccttcaa tggtaaacgg    26940
atgctcgagt gttgcctgag ttctaccatg taggaggaag cctccgtgca ctctctgggg    27000
gagccagcgg agtgatttct ggtgcaacgt ggttgggctt tgtctttagg atgggcacaa    27060
accctccagg gggatcgact tcaaaattca ccttgttgta aaacgggcta cctcagtgtc    27120
ccagccaaaa tttttattgt aacatgctgt caggtgtgtc actcttttcca agccagtaag    27180 cttttccggg gatttcttca agtagccagc attcagagca atcttcagca ttgcagattc    27240
tgagaaatgt ggctctggag cctgtcaccc tcgagaaacc taagagggct gcattgattc    27300
catgtggccc tgggtctatg gagcagtaca tgagctccca gtgctctaag gctcttcagc    27360
cctaggcttt gaagggagtg atttctcagt attcttaaac ctctttctga tgacacttgt    27420
acctgtgagg ggtctagaga gaaagagtag tagactccta ctttactaca attcaggatg    27480
```

```
cagggcatga gaggattccc tctctcctcc aagggaagaa gcttttggcg tgcacacatc   27540
cctgagaagc aaagtgtctt tgtcttcagt cagatacata ggaccgtttt ctgccccatg   27600
gcccggaagc caaaggcctt ggctttcatg atcaacggtc tagggaaaca tgcaaaattt   27660
ccatgtctgt cccaaactct gcccccgaca gccaattacc acctgcagcc cgcattgcca   27720
aatgcggtgc cgtttgcatg aagattcagt agagtttcct agaaaggtgc tacctcgtga   27780
gctcactttc caatgaggaa tctgatctgt tgtgtttctc taaggtgtca ggtgaaatat   27840
ttccaagaac ttactacagt tctagaatgg gaggaatctg ttgctttggt gtttgtttgt   27900
tggtcggttt tctcacatcc atctgcctat ggataaggaa aagagaacgg tcgtaattct   27960
catagactcc tttctggttg tgtcacaaat ggcttcacat gtttctctat gctcagagat   28020
actcagcttg atttcccgtg ttttcatttc agcaccgact gagcaaaggc ctggggtgca   28080
ggagtgctac catggtaatg gacagagtta tcgaggcaca tactccacca ctgtcacagg   28140
aagaacctgc caagcttggt catctatgac accacactcg catagtcgga ccccagaata   28200
ctacccaaat gcgtatgtct tgttctttta ccataagaga agaaagggcc aagtgaagtt   28260
tctgttacaa gagatgtgtc tcaagctgag ttctccgaac tcaacttgtg acagatgcag   28320
atggcgtagc aaaatgtctc aggatgattg ccttggagct aagggtctga gagaagggaa   28380
atgttaagct ccctctcctt cctcctagtt ctattgagca aagggaaat ctggaggtga   28440 ggagatcaca ttatgaagaa agtcagaatg acaaggacc agacacttag attacccttc   28500
cacaacacca actaaacgtc aatggagact ttccagttgg aattccgtta ttctggcttc   28560
cacttcctga agggaaggtt gcgtttgcct tttctctctg ggttcaagag gaaagaatag   28620
gtgcttattt atggacaggt gaattgatct gtttctatat ctacgtatat tccgattgtc   28680
agaaaaacac tcgttcctaa gtaccagtgg cctgaaggga tacaggttcc cagcaagaga   28740
agatccaagg aaggaaggca gatgagagtc agcacagaga gggatgctga aaagtaaaag   28800
ggatgggtgg atggagagaa gcccgggtct gaccacccaa tggccaatat tttggccaca   28860
agcgactacc agagacatgg aaaaatggtt tctacatgtg ggacaacaga tggtagagga   28920
cctagagaat tgagagaggg gcaatgatgg gctccactcc gcagatgcct tggctttctt   28980
cctggatacc cttcctgcac tgaatagcaa ggagatggag cccaagcaga ctgtagccat   29040
cttgctgaat ggaggagagg gattggagtt tgggatgact gtggtagctg aaattttcct   29100
aggtctgcta gaaataagaa ctggtttgtg gaggaaaaga gctctacaaa tacgcataga   29160
agtctcctcc agtcgttggc ctgacatgac gctgcctgtg cacaggaaat ggttccacga   29220
gaaagtgtgg caaagaacat ttactgagaa acagcaagta caagagcaca ggaagctcaa   29280
taaagaagag agagatcaca tagcactctg ggatactgga gttcttccca gctagaccag   29340
agagtcctca cggagcacat tgccaattca gtggagaccc cagaacagcc gtaatttaaa   29400
ggtacactta gtatattact agaataaagt cagctgcaga caaccccttg cacagctgga   29460
aagcaagtgt ccaagcatca aatcggtttc caatcaatga agtgcctgtg agaggaaatc   29520
tcaactctct ttagaagtaa acaacaaagt cgattgcctc agctatgcgg tatccgcaga   29580
gtgagtccta aatttaaaat ctgactacat gtagaaaagc gtttcgtgtg acccatgacc   29640
aggaaataaa tcgggtaata caaacaggct caggaatgag agaaatgatt agaattgcgt   29700
gaaaatttga catatcagta tgataactga tttcaaatat ttaaaaaaac aacatgcaag   29760
aaagcagata tcatatcaag agaaattaac agtacagaat agccaaatta aattaaagag   29820
ctagtataaa aaaagtatgt cttaattgaa aaaaattact gtatggccgg ctgatcaatt   29880
```

```
tagacgtttc agaggaaaac attacccaac acacaattct agagaaccta cagaatgagc    29940
tacacacaca cacacacaca cacacacaaa ctgaaaacac acccatactc acacacacgc    30000
agaaactcac aagttctaac acacacagac acgcgcaccc ctgaagaaac agtgaaatat    30060
aaaattaagc gagcctcaca gacatgtagg aaaatatgaa aagatttcct gcatgtggga    30120
agcaagtcac agtaaagagc aagggagttt ggaatagaaa caaataccgg aatcaaggat    30180
ggctgataac ttttcaatta cgaagaacat taaaaaaaat cacagaatcg tgaaactcaa    30240
gggatcacat agggaatttc ggaaaaaaaa cccaacctgt atgatgtact tttgtacatc    30300
acagttcgaa ggtaacaagg caaagatata ataagaagaa acctgtcacg agaaactgga    30360
ggaaaaagag ctgtgtcttc ctacaagtac actgatacaa attgccaatg tgttcacctc    30420
agaaacactg gaagccagat accagggaat attgttaaaa tgataatcag gaacaaaaag    30480
agatcaaccg ggaatgctga atccagcaat aaaatgcctt gaagatcatc catgtcggat    30540
aaatgcatat tgtgcactgc cccaaagaaa gaaaccggaa actgtaagaa ttggaaatca    30600
gcaggcttat gtaacaagag aggtgacccg aaggaattag gtagaagaag aattgaacaa    30660
gaaaggaact ttctgcagcc cacgtaatga agaatccagc aattggcaaa tgtagataga    30720
tgtaaatgca aaatattttc ttgatcaaat ttctatatct ttgtaaatga gagttgacta    30780
cttgaaacaa aatgatagca agatatttaa cttcagcata tgtagaggta agaatttgaa    30840
atggtagcat aaatcacgaa gggattaatt cgaagtgtac cgttgtaagt ttctttacct    30900
catgcacgat ggtgtgtcat attaataaaa gggtactgtg cgggttcgaa gggatattgc    30960
aaatcctaga gcaatcacaa aggtttgaac tctgaggttt ttggtataat aagaatagtc    31020
catgcattca aaagagggaa gccaaggaag aactagaagt ctttcaagag ctcaggctct    31080
tatacatcca gttgctcatt gaaccagctt cctggaatgg agggtctggg gttgagacta    31140
ggccacaagt ctagagtctc tagagagaca gtgttggaac cccatggccc ataatacatt    31200
tcccattttc tcaggcagcc agaggtcatg aatgtgagga tactgggagg ttggagcaac    31260
gttcttggga ggcataagga agagcgaatg cttcaagatc cccgcagccc aaactactcg    31320
cctgctttgc cccctaatgc attttttctct gctgctccgt agctgtccga cctcttcaga    31380
tctcttagtc caccctgccg tcttccttta tgccatgggt cccactgttc tttcaactca    31440
tcccccttc cctcagtccc ggagtagctg cggccagcag agggtagact gagagcagga    31500
gagaaggacc tgcctaggaa ccccttctag agatactgca tcctgcctgg gagcaagttt    31560
tccagggcag ctttgagaag tcttggagaa acaaacctac taaacctgac agacagtaat    31620
actatttgca caatgctttt ctgtgggaaa ggtagagcct tttcactacg tattgagtac    31680
atagagtgtg agggttgacc tggaacggct atcctcctgg atgacgtgtg ttttctgaag    31740
aactacatgt tcgttgcaac tcccacatta gaatatgaag tcctaccgag agagatacgg    31800
agactagaca gatacagatg catttgcatg tgaatacaca atcccacaat acagacgtca    31860
aaacccatac cagttattcc agagagatgg attgggtagg aggcagaagg agaatactct    31920
gatcgttttt cggccacgtg tgtgtgttat ctcagtgttt ctaagaagcg tttgctactt    31980
tagattttt atttaaaaaa aatagtaata atctattaag tatgagagat gtgcagagag    32040
gattagtgat cgagagccat ttttgctggt ggcaatcata tggtacttttt aatgggaata    32100
ttagaaaggc accggtaatg accttgttgc agcacaaagg agagagtgtg gggtgcccct    32160
gcatgttgtc ccacctcttg tgacgtgtat cgttttggaa tttccagtgg cttgatcatg    32220
```

```
aactactgca ggaatccaga tgctgtggca gctccttatt gttatacgag ggatcccggt    32280
gtcaggtggg agtactgcaa cctgacgcaa tgctcagacg cagaagggac tgccgtcgcg    32340
cctccgactg ttaccccggt tccaagccta gaggctcctt ccgaacaagg taaggagtct    32400
gtggccagac atctcacagc ttcgatgctg ggatgaaaag ccatggaaat tcccactgat    32460
gcagccgcct tcaatggtaa acggatgctc gagtgttgcc ggagttctgc catgttgggg    32520
gaagcctccg tgtactctct gggggagcca gcggagtgat ttctggtgca acttgggtgg    32580
gctttgtctt tagaatgggc acaaaccttc cagggtgatg ggcttcacaa ctcacctcct    32640
tctaaaatgg gctatctcag tgtcttagcc aaaattttta ttgtaacgtg ctgtcaggtg    32700
tgtgattctt tctgtcgcag taagcttttc tggggatttc ttcaagtagc cagcagtcag    32760
tgcaatcttc agcattgcag atttcaaaaa atgtggctct ggagcctgtc atcctcgaga    32820
aacctaacag ggctgcatta attccatatg gtcctgggtc tatggagcag tatatgagct    32880
cccaatgctc taaggctctt cagtcctagg ctttgaaggg agtgatttct cagtgttctt    32940
aaacctcttt ctgatggcac ttgtacctgt gaggggtcta gagagaaagg ttagtagact    33000
tctcctttac tgcaattcag gatgcagggc atgagaagat tccctccctc ctccaaggga    33060
agaaggtttt ggcgtgcaca catccttgag aagcaaagtg tctttgcctt cagtcagata    33120
tataggatcg ttttctgccc catggcctgg aagccagagg ccttggcttt catgatcaac    33180
gatctaggga aacatgcaaa atttccatgt ctttcccctc ctctgccctc gacagccaat    33240
taccacctgc atcctgcatt gccaaatgca gtgcccttfg tatgaacatt cagtagagtt    33300
tcatagaaag gtgctacttc gtgagcgcac tttgcagtga aaggagtct gttctgttct    33360 gttttttctaa ggatttcagg tgaaatattt cctagaactt actacagttc tagattggta    33420
ggaatctgta ggtttgctgt atgttttttg gttggttttc tcccatccat ctgcctacag    33480
gtaagggaaa gataacgttc gtaattctca tagactcctt tctggttgtg tcataaatgg    33540
cttcacatat ttcgttattc tcagagatac tcagtttatt tcttgtgttt tcatttcagc    33600
accgactgag cagaggcctg gggtgcagga gtgctaccac ggtaatggac agagttatcg    33660
aggcacatac tccaccactg tcactggaag aacctgccaa gcttggtcat ctatgacacc    33720
acactcgcat agtcggaccc cagaatacta cccaaatgcg tatgtctttg ttcttaccca    33780
taagagaaga aagggccaag tgaagtttct gttacaagag atgtgtctca agctgagttc    33840
tccgaactca acttgtgaca gatgcagatg gcgtagcaaa atgtctcagg atgattgcct    33900
tggagctaag ggtctgagag aagggaaatg ttaagctccc tctccttcct cctagttcta    33960
ttgagcagaa gggaaatctg gaggtgagga gatcacatta tgaagaaagt cagaatgaca    34020
aaggaccaga cacttagatt accottcoac aacaccaact aaacgtcaat ggagactttc    34080
cagttggaat tccgttattc tggcttccac ttcctgaagg gaaggttgcg tttgcctttt    34140
ctctctgggt tcaagaggaa agaataggtg cttatttatg gacaggtgaa ttgatctgtt    34200
tctatatcta cgtatattcc gattgtcaga aaaacactcg ttcctaagta ccagtggcct    34260
gaagggatac aggttcccag caagagaaga tccaaggaag gaaggcagat gagagccagc    34320
acagagaggg atgctgaaaa gtaaaaggga tgggtggatg gagagaagcc cgggtctgac    34380
cacccaatgg ccaatatttt ggccacaagc gactaccaga gacatggaaa aatggtttct    34440
acatgtggga caacagatgg tagaggacct agagaattga gagaggggca atgatgggct    34500
ccactccgca gatgccttgg ctttcttcct ggatacccct cctgcactga atagcaagga    34560
gatggagccc aagcagactg tagccatctt gctgaatgga ggagagggat tggagtttgg    34620
```

```
gatgactgtg gtagctgaaa tttttctagg tctgctagaa ataagaactg gtttgtggag   34680
gaaaagagct ctacaaatac gcatagaagt ctcctccagt cgttggcctg acatgacgct   34740
gcctgtgcac aggaaatggt tccacgagaa agtgtggcaa agaacattta ctgagaaaca   34800
gcaagtacaa gagcacagga agctcaataa agaagagaga gatcacatag cactctggga   34860
tactggagtt cttcccagct agaccagaga gtcctcacgg agcacattgc caattcagtg   34920 gagacccag  aacagccgta atttaaaggt acacttagta tattactaga ataaagtcag   34980
ctgcagacaa ccccttgcac agctggaaag caagtgtcca agcatcaaat cggtttccaa   35040
tcaatgaagt gcctgtggga ggaaatctca actctcttta gaagtaaaca acaaagtcga   35100
ttgcctcagc tatgcggtat ccgcagagtg agtcctaaat ttaaaatctg actacatgta   35160
gaaaagcgtt tcgtgtgacc catgaccagg aaataaatcg ggtaatacaa acaggctcag   35220
gaatgagaga aatgattaga attgcgtgaa aatttgacat atcagtatga taactgattt   35280
caaatattta aaaaacaac atgcaagaaa gcagatatca tatcaagaga aattaacagt    35340
acagaatagc caaattaaat taaagagcta gtataaaaaa agtatgtctt aattgaaaaa   35400
aattactgta tggccggctg atcaaattag acgtttcaga ggaaaacatt acccaacaca   35460
caattctaga gaacctacag aatgagctac acacacacac acacacacac acacacacac   35520
tgaaaacaca cccatactca cacacacgca gaaactcaca agttctaaca cacacagaca   35580
cgcgcacccc tgaagaaaca gtgaaatata aaattaagcg agcctcacag acatgtagga   35640
aaatatgaaa agatttcctg catgtgggaa gcaagtcaca gtaaagagca agggagtttg   35700
gaatagaaac aaataccgga atcaaggatg gctgataact tttcaattac gaagaacatt   35760
aaaaaaaatc acagaatcgt gaaactcaag ggatcatata gggaatttcg gaaaaaaaac   35820
ccaacctgta tgatgtactt tgtacatca  cagttcgaag gtaacaaggc aaagatataa   35880
taagaagaaa cctgtcacga gaaactggag gaaaaagagc tgtgtcttcc tacaagtaca   35940
ctgatacaaa ttgccaatgt gttcacctca gaaacactgg aagccagata ccagggaata   36000
ttgttaaaat gataatcagg aacaaaaaga gatcaaccgg gaatgctgaa tccagcaata   36060
aaatgccttg aagatcatcc atgtcggata aatgcatatt gtgcactgcc ccaaagaaag   36120
aaaccggaaa ctgtcagaat tggaaatcag caggcttatg taacaagaga ggtgacccga   36180
aggaattagg tagaagaaga attgaacaag aaaggaactt tctgcagccc acgtaatgaa   36240
gaatccagca attggcaaat gtagatagat gtaaatgcaa aatattttct tgatcaaatt   36300
tctatatctt tgtaaatgag agttgactac ttgaaacaaa atgatagcaa gatatttaac   36360
ttcagcatat gtagaggtaa gaatttgaaa tggtagcata aatcacgaag ggattaattc   36420
gaagtgtacc gttgtaagtt tctttacctc atgcacgatg gtgtgtcata ttaataaaag   36480
ggtactgtgc gggttcgaag ggatattgca aatcctagag caatcacaaa ggtttgaact   36540
ctgaggtttt tggtataata agaatagtcc atgcattcaa aagagggaag ccaaggaaga   36600
actagaagtc tttcaagagc tcaggctctt atacatccag ttgctcattg aaccagcttc   36660
ctggaatgga gggtctgggg ttgagactag gccacaagtc tagagtctct agagagacag   36720
tgttggaacc ccatggccca taatacattt cccatttcct caggcagcca gaggtcatga   36780
atgtgaggat actgggaggt tggagcaacg ttcttgggag gcataaggaa gagcgaatgc   36840
ttcaagatcc ccgcagccca aactactcgc ctgctttgcc ccctaatgca ttttctctg    36900 ctgctccgta gctgtccgac ctcttcagat ctcttagtcc accctgccgt cttcctttat   36960
```

```
gccatgggtc ccattgttct ttcaactcat cccccttttcc ctcagtcccg gagtagctgc    37020
ggccagcaga gggtagactg agagcaggag agaaggacct gcctaggaac cccttctaga    37080
gatactgcat cctgcctggg agcaagtttt ccagggcagc tttgagaagt cttggagaaa    37140
caaacctact aaacctgaca gacagtaata ctatttgcac aatgcttttc tgtgggaaag    37200
gtagagcctt ttcactacgt attgagtaca tagagtgtga gggttgacct ggaacggcta    37260
tcctcctgga tgacgtgcgt tttctgaaga actacatgtt cgttgcaact cccacattag    37320
aatatgaagt cctaccgaga gagatacgga gactagacag atacagatgc atttgcatgt    37380
gaatacacaa tcccacaata cagacgtcaa aacccatacc agttattcca gagagatgga    37440
ttgggcagaa ggcagaagga gaatactctg atcgtttttc ggccacgtgt gtgtgttatc    37500
tcagtgtttc taagaagcgt ttgctacttt agattttta tttaaaaaaa atagtaataa    37560
tctattaagt atgagagatg tgcagagagg attagtgatc gagagccatt tttgctggtg    37620
gcaatcatat ggtactttta atgggaatat tagaaaggca ccggtaatga ccttgttgca    37680
gcacaaagga gagagtgtgg ggtgcccctg catgttgtcc cacctcttgt gacgtgtatc    37740
gttttggaat ttccagtggc ttgatcatga actactgcag gaatccagat gctgtggcag    37800
ctccttattg ttatacgagg gatcccggtg tcaggtggga gtactgcaac ctgacgcaat    37860
gctcagacgc agaagggact gccgtcgcgc ctccgactgt taccccggtt ccaagcctag    37920
aggctccttc cgaacaaggt aaggagtctg tggccagaca tctacacgct tcgatgctgg    37980
gatgaaaagc catggaaatt cccactgatg cagccgcctt caatggtaaa cggatgctcg    38040
agtgttgcct gagttctacc atgtaggagg aagcctccgt gcactctctg ggggagccag    38100
cggagtgatt tctggtgcaa cgtggttggg cttttgtcttt aggatgggca caaaccctcc    38160 aggggggatcg acttcaaaat tcaccttgtt gtaaaacggg ctacctcagt gtcccagcca    38220
aaatttttat tgtaacatgc tgtcaggtgt gtcactcttt ccaagccagt aagcttttcc    38280
ggggatttct tcaagtagcc agcattcaga gcaatcttca gcattgcaga ttctgagaaa    38340
tgtggctctg gagcctgtca ccctcgagaa acctaagagg gctgcattga ttccatgtgg    38400
ccctgggtct atggagcagt acatgagctc ccagtgctct aaggctcttc agccctaggc    38460
tttgaaggga gtgatttctc agtattctta aacctctttc tgatgacact tgtacctgtg    38520
aggggtctag agagaaagag tagtagactc ctactttact acaattcagg atgcagggca    38580
tgagaggatt ccctctctcc tccaagggaa gaagcttttg gcgtgcacac atccctgaga    38640
agcaaagtgt ctttgtcttc agtcagatac ataggaccgt tttctgcccc atggcccgga    38700
agccaaaggc cttggctttc atgatcaacg gtctagggaa acatgcaaaa tttccatgtc    38760
tgtcccaaac tctgccccccg acagccaatt accacctgca gcccgcattg ccaaatgcgg    38820
tgccgtttgc atgaagattc agtagagttt cctagaaagg tgctacctcg tgagctcact    38880
ttccaatgag gaatctgatc tgttgtgttt ctctaaggtg tcaggtgaaa tatttccaag    38940
aacttactac agttctagaa tgggaggaat ctgttgcttt ggtgtttgtt tgttggtcgg    39000
ttttctcaca tccatctgcc tatggataag gaaaagagaa cggtcgtaat tctcatagac    39060
tcctttctgg ttgtgtcaca aatggcttca catgttctc tatgctcaga gatactcagc    39120
ttgatttccc gtgttttcat ttcagcaccg actgagcaaa ggcctggggt gcaggagtgc    39180
taccatggta atggacagag ttatcgaggc acatactcca ccactgtcac aggaagaacc    39240
tgccaagctt ggtcatctat gacaccacac tcgcatagtc ggaccccaga atactaccca    39300
aatgcgtatg tctttgttct ttaccataag agaagaaagg gccaagtgaa gtttctgtta    39360
```

```
caagagatgt gtctcaagct gagttctccg aactcaactt gtgacagatg cagatggcgt    39420
agcaaaatgt ctcaggatga ttgccttgga gctaagggtc tgagagaagg gaaatgttaa    39480
gctccctctc cttcctccta gttctattga gcagaaggga aatctggagg tgaggagatc    39540
acattatgaa gaaagtcaga atgacaaagg accagacact tagattaccc ttccacaaca    39600
ccaactaaac gtcaatggag actttccagt tggaattccg ttattctggc ttccacttcc    39660
tgaagggaag gttgcgtttg ccttttctct ctgggttcaa gaggaaagaa taggtgctta    39720
tttatggaca ggtgaattga tctgtttcta tatctacgta tattccgatt gtcagaaaaa    39780
cactcgttcc taagtaccag tggcctgaag ggatacaggt tcccagcaag agaagatcca    39840
aggaaggaag gcagatgaga gtcagcacag agagggatgc tgaaaagtaa aagggatggg    39900
tggatggaga gaagcccggg tctgaccacc caatggccaa tattttggcc acaagcgact    39960
accagagaca tggaaaaatg gtttctacat gtgggacaac agatggtaga ggacctagag    40020
aattgagaga ggggcaatga tgggctccac tccgcagatg ccttggcttt cttcctggat    40080
acccttcctg cactgaatag caaggagatg gagcccaagc agactgtagc catcttgctg    40140
aatggaggag agggattgga gtttgggatg actgtggtag ctgaaatttt tctaggtctg    40200
ctagaaataa gaactggttt gtggaggaaa agagctctac aaatacgcat agaagtctcc    40260
tccagtcgtt ggcctgacat gacgctgcct gtgcacagga aatggttcca cgagaaagtg    40320
tggcaaagaa catttactga gaaacagcaa gtacaagagc acaggaagct caataaagaa    40380
gagagagatc acatagcact ctgggatact ggagttcttc ccagctagac cagagagtcc    40440
tcacggagca cattgccaat tcagtggaga ccccagaaca gccgtaattt aaaggtacac    40500
ttagtatatt actagaataa agtcagctgc agacaacccc ttgcacagct ggaaagcaag    40560
tgtccaagca tcaaatcggt ttccaatcaa tgaagtgcct gtgagaggaa atctcaactc    40620
tctttagaag taaacaacaa agtcgattgc ctcagctatg cggtatccgc agagtgagtc    40680
ctaaatttaa aatctgacta catgtagaaa agcgtttcgt gtgacccatg accaggaaat    40740
aaatcgggta atacaaacag gctcaggaat gagagaaatg attagaattg cgtgaaaatt    40800
tgaaatatca gtatgataac tgatttcaaa tatttaaaaa acaacatgc aagaaagcag    40860 atatcatatc aagagaaatt aacagtacag aatagccaaa ttaaattaaa gagctagtat    40920
aaaaaaagta tgtcttaatt gaaaaaaatt actgtatggc cggctgatca atttagacgt    40980
ttcagaggaa acattaccc aacacacaat tctagagaac ctacagaatg agctacacac    41040
acacacacac acacacacac aaactgaaaa cacacccata ctcacacaca cgcagaaact    41100
cacaagttct aacacacaca gacacgcgca cccctgaaga aacagtgaaa tataaaatta    41160
agcgagcctc acagacatgt aggaaaatat gaaaagattt cctgcatgtg ggaagcaagt    41220
cacagtaaag agcaagggag tttggaatag aaacaaatac cagaatcaag gatggctgat    41280
aacttttcaa ttcgaagaa cattaaaaaa aatcacagaa tcgtgaaact caagggatca    41340
catagggaat ttcggaaaaa aaacccaacc tgtatgatgt acttttgtac atcacagttc    41400
gaaggtaaca aggcaaagat ataataagaa gaaacctgtc acgagaaact ggaggaaaaa    41460
gagctgtgtc ttcctacaag tacactgata caaattgcca atgtgttcac ctcagaaaca    41520
ctggaagcca gataccaggg aatattgtta aaatgataat caggaacaaa aagagatcaa    41580
ccgggaatgc tgaatccagc aataaaatgc cttgagatc atccatgtcg gataaatgca    41640
tattgtgcac tgccccaaag aaagaaaccg gaaactgtaa gaattggaaa tcagcaggct    41700
```

```
tatgtaacaa gagaggtgac ccgaaggaat taggtagaag aagaattgaa caagaaagga    41760
actttctgca gcccacgtaa tgaagaatcc agcaattggc aaatgtagat agatgtaaat    41820
gcaaaatatt ttcttgatca aatttctata tctttgtaaa tgagagttga ctacttgaaa    41880
caaaatgata gcaagatatt taacttcagc atatgtagag gtaagaattt gaatggtag     41940 cataaatcac gaagggatta attcgaagtg taccgttgta agtttctta cctcatgcac     42000 gatggtgtgt catattaata aaagggtact gtgcgggttc gaagggatat tgcaaatcct    42060
agagcaatca caaaggtttg aactctgagg ttttggtat aataagaata gtccatgcat     42120
tcaaaagagg gaagccaagg aagaactaga agtctttcaa gagctcaggc tcttatacat    42180
ccagttgctc attgaaccag cttcctggaa tggagggtct ggggttgaga ctaggccaca    42240
agtctagagt ctctagagag acagtgttgg aaccccatgg cccataatac atttcccatt    42300
ttctcaggca gccagaggtc atgaatgtga ggatactggg aggttggagc aacgttcttg    42360
ggaggcataa ggaagagcga atgcttcaag atccccgcag cccaaactac tcgcctgctt    42420 tgcccctaa tgcatttttc tctgctgctc cgtagctgtc cgacctcttc agatctctta     42480
gtccaccctg ccgtcttcct ttatgccatg ggtcccactg ttcttcaac tcatccccct     42540 ttccctcagt cccggagtag ctgcggccag cagagggtag actgagagca ggagagaagg    42600
acctgcctag gaaccccttc tagagatact gcatcctgcc tgggagcaag ttttccaggg    42660
cagctttgag aagtcttgga gaaacaaacc tactaaacct gacagacagt aatactattt    42720
gcacaatgct tttctgtggg aaaggtagag ccttttcact acgtattgag tacatagagt    42780
gtgagggttg acctggaacg gctatcctcc tggatgacgt gtgttttctg aagaactaca    42840
tgttcgttgc aactcccaca ttagaatatg aagtcctacc gagagagata cggagactag    42900
acagatacag atgcatttgc atgtgaatac acaatcccac aatacagacg tcaaaaccca    42960
taccagttat tccagagaga tggattgggc agaaggcaga aggagaatac tctgatcgtt    43020
tttcggccac gtgtgtgtgt tatctcagtg ttttctaagaa gcgtttgcta ctttagattt    43080
tttatttaaa aaaatagta ataatctatt aagtatgaga gatgtgcaga gaggattagt     43140
gatcgagagc cattttgct ggtggcaatc atatggtact tttaatggga atattagaaa     43200
ggcaccggta atgaccttgt tgcagcacaa aggagagagt gtggggtgcc cctgcatgtt    43260
gtcccacctc ttgtgacgtg tatcgttttg gaatttccag tggcttgatc atgaactact    43320
gcaggaatcc agatgctgtg gcagctcctt attgttatac gagggatccc ggtgtcaggt    43380
gggagtactg caacctgacg caatgctcag acgcagaagg gactgccgtc gcgcctccga    43440
ctgttacccc ggttccaagc ctagaggctc cttccgaaca aggtaaggag tctgtggcca    43500
gacatctaca cgcttcgatg ctgggatgaa aagccatgga aattcccact gatgcagccg    43560
ccttcaatgg taaacggatg ctcgagtgtt gcctgagttc taccatgtag gaggaagcct    43620
ccgtgcactc tctgggggag ccagcggagt gatttctggt gcaacgtggt tgggctttgt    43680
ctttaggatg ggcacaaacc ctccaggggg atcgacttca aaattcacct tgttgtaaaa    43740
cgggctacct cagtgtccca gccaaaattt ttattgtaac atgctgtcag gtgtgtcact    43800 cttttccaagc cagtaagctt ttccggggat ttcttcaagt agccagcatt cagagcaatc    43860
ttcagcattg cagattctga gaaatgtggc tctggagcct gtcaccctcg agaaacctaa    43920
gagggctgca ttgattccat gtggccctgg gtctatggag cagtacatga gctcccagtg    43980
ctctaaggct cttcagccct aggctttgaa gggagtgatt tctcagtatt cttaaacctc    44040
tttctgatga cacttgtacc tgtgaggggt ctagagagaa agagtagtag actcctactt    44100
```

```
tactacaatt caggatgcag ggcatgagag gattccctct ctcctccaag ggaagaagct   44160
tttggcgtgc acacatccct gagaagcaaa gtgtctttgt cttcagtcag atacatagga   44220
ccgttttctg ccccatggcc cggaagccaa aggccttggc tttcatgatc aacggtctag   44280
ggaaacatgc aaaatttcca tgtctgtccc aaactcttcc cccgacagcc aattaccacc   44340
tgcagcccgc attgccaaat gcggtgccgt ttgcatgaag attcagtaga gtttcctaga   44400
aaggtgctac ctcgtgagct cactttccaa tgaggaatct gatctgttgt gtttctctaa   44460
ggtgtcaggt gaaatatttc caagaactta ctacagttct agaatgggag gaatctgttg   44520 cttggtgtt tgtttgttgg tcggttttct cacatccatc tgcctatgga taaggaaaag   44580
agaacggtcg taattctcat agactccttt ctggttgtgt cacaaatggc ttcacatgtt   44640
tctctatgct cagagatact cagcttgatt cccgtgttt tcatttcagc accgactgag   44700
caaaggcctg gggtgcagga gtgctaccat ggtaatggac agagttatcg aggcacatac   44760
tccaccactg tcacaggaag aacctgccaa gcttggtcat ctatgacacc acactcgcat   44820
agtcggaccc cagaatacta cccaaatgcg tatgtctttg ttctttacca taagagaaga   44880
aagggccaag tgaagtttct gttacaagag atgtgtctca agctgagttc tccgaactca   44940
acttgtgaca gatgcagatg gcgtagcaaa atgtctcagg atgattgcct tggagctaag   45000
ggtctgagag aagggaaatg ttaagctccc tctccttcct cctagttcta ttgagcagaa   45060
gggaaatctg gaggtgagaa gatcacatta tgaagaaagt cagaatgaca aaggaccaga   45120
cacttagatt acccttccac aacaccaact aaacgtcaat ggagactttc cagttggaat   45180
tccgttattc tggcttccac ttcctgaagg gaaggttgcg tttgccttt ctctctgggt   45240 tcaagaggaa agaataggtg cttatttatg gacaggtgaa ttgatctgtt tctatatcta   45300
cgtatattcc gattgtcaga aaacactcg ttcctaagta ccagtggcct gaagggatac   45360
aggttcccag caagaagaa tccaaggaag gaaggcagat gagagtcagc acagagaggg   45420
atgctgaaaa gtaaagggga tgggtggatg gagagaagcc cgggtctgac cacccaatgg   45480
ccaatatttt ggccacaagc gactaccaga gacatgaaaa aatggtttct acatgtggga   45540
caacagatgg tagaggacct agagaattga gagagggca atgatgggct ccactccgca   45600
gatgccttgg ctttcttcct ggataccctt cctgcactga atagcaagga gatggagccc   45660
aagcagactg tagccatctt gctgaatgga ggagagggat tggagtttgg gatgactgtg   45720
gtagctgaaa ttttttctagg tctgctagaa ataagaactg gtttgtgtgg aggaaaagag   45780
ctctacaaat acgcatagaa gtctcctcca gtcgttggcc tgacatgacg ctgcctgtgc   45840
acaggaaatg gttccacgag aaagtgtggc aaagaacatt tactgagaaa cagcaagtac   45900
aagagcacac gaagctcaat aaagaagaga gagatcacat agcactctgg gatactggag   45960
ttcttcccag ctagaccaga gagtcctcac ggagcacatt gccaattcag tggagacccc   46020
agaacagccg taatttaaag gtacacttag tatattacta gaataaagtc agctgcagac   46080
aaccccttgc acagctggaa agcaagtgtc caagcatcaa atcggtttcc aatcaatgaa   46140
gtgcctgtga gaggaaatct caactctctt tagaagtaaa caacaaagtc gattgcctca   46200
gctatgcggt atccgcagag tgagtcctaa atttaaaatc tgactacatg tagaaaagcg   46260
tttcgtgtga cccatgacca ggaaataaat cgggtaatac aaacaggctc aggaatgaga   46320
gaaatgatta gaattgcgtg aaaatttgac atatcagtat gataactgat ttcaaatatt   46380
taaaaaaaca acatgcaaga aagcagatat catatcaaga gaaattaaca gtacagaata   46440
```

```
gccaaattaa attaaagagg tagtataaaa aaagtatgtc ttaattgaaa aaaattactg    46500
tatggccggc tgatcaattt agacgtttca gaggaaaaca ttacccaaca cacaattcta    46560
gagaacctac agaatgagct acacacacac acacacacac acacacaaac tgaaaacaca    46620
cccatactca cacacacgca gaaactcaca agttctaaca cacacagaca cgcgcacccc    46680
tgaagaaaca gtgaaatata aaattaagcg agcctcacag acatgtagga aaatatgaaa    46740
agatttcctg catgtgggaa gcaagtcaca gtaaagagca agggagtttg aatagaaac    46800 aaataccgga atcaaggatg gctgataact tttcaattac gaagaacatt aaaaaaaatc    46860
acagaatcgt gaaactcaag ggatcacata gggaatttcg gaaaaaaaac ccaacctgta    46920
tgatgtactt ttgtacatca cagttcgaag gtaacaaggc aaagatataa taagaagaaa    46980
cctgtcacga gaaactggag gaaaaagagc tgtgtcttcc tacaagtaca ctgatacaaa    47040
ttgccaatgt gttcacctca gaaacactgg aagccagata ccaggaata ttgttaaaat    47100 gataatcagg aacaaaaaga gatcaaccgg gaatgctgaa tccagcaata aaatgccttg    47160
aaggtcatcc atgtcggata aatgcatatt gtgcactgcc ccaaagaaag aaaccggaaa    47220
ctgtaagaat tggaaatcag caggcttatg taacaagaga ggtgacccga aggaattagg    47280
tagaagaaga attgaacaag aaaggaactt tctgcagccc acgtaatgaa gaatccagca    47340
attggcaaat gtagatagat gtaaatgcaa atatttctc tgatcaaatt tctatatctt    47400
tgtaaatgag agttgactac ttgaaacaaa atgatagcaa gatatttaac ttcagcatat    47460
gtagaggtaa gaatttgaaa tggtagcata aatcacgaag ggattaattc gaagtgtacc    47520
gttgtaagtt tctttacctc atgcacgatg gtgtgtcata ttaataaaag ggtactgtgc    47580
gggttcgaag ggatattgca aatcctagag caatcacaaa ggtttgaact ctgaggtttt    47640
tggtataata agaatagtcc atgcattcaa aagagggaag ccaaggaaga actagaagtc    47700
tttcaagagc tcaggctctt atacatccag ttgctcattg aaccagcttc ctggaatgga    47760
gggtctgggg ttgagactag gccacaagtc tagagtctct agagagacag tgttggaacc    47820
ccatggccca taatacattt cccattttct caggcagcca gaggtcatga atgtgaggat    47880
actgggaggt tggagcaacg ttcttgggag gcataaggaa gagcgaatgc ttcaagatcc    47940
ccgcagccca aactactcgc ctgctttgcc ccctaatgca ttttttctctg ctgctccgta    48000 gctgtccgac ctcttcagat ctcttagtcc accctgccgt cttcctttat gccatgggtc    48060
ccactgttct ttcaactcat ccccctttcc ctcagtcccg gagtagctgc ggccagcaga    48120
gggtagactg agagcaggag agaaggacct gcctaggaac cccttctaga gatactgcat    48180
cctgcctggg agcaagtttt ccagggcagc tttgagaagt cttggagaaa caaacctact    48240
aaacctgaca gacagtaata ctatttgcac aatgcttttc tgtgggaaag gtagagcctt    48300
ttcactacgt attgagtaca tagagtgtga gggttgacct ggaacggcta tcctcctgga    48360
tgacgtgcgt tttctgaaga actacatgtt cgttgcaact cccacattag aatatgaagt    48420
cctaccgaga gagatacgga gactagacag atacagatgc atttgcatgt gaatacacaa    48480
tcccacaata cagacgtcaa aacccatacc agttattcca gagagatgga ttgggcagaa    48540
ggcagaagga gaatactctg atcgtttttc ggccacgtgt gtgtgttatc tcagtgtttc    48600
taagaagcgt ttgctacttt agatttttta tttaaaaaaa atagtaataa tctattaagt    48660
atgagagatg tgcagagagg attagtgatc gagagccatt tttgctggtg gcaatcatat    48720 ggtacttta atgggaatat tagaaaggca ccggtaatga ccttgttgca gcacaaagga    48780
gagagtgtgg ggtgcccctg catgttgtcc cacctcttgt gacgtgtatc gttttggaat    48840
```

```
ttccagtggc ttgatcatga actactgcag gaatccagat gctgtggcag ctccttattg    48900
ttatacgagg gatcccggtg tcaggtggga gtactgcaac ctgacgcaat gctcagacgc    48960
agaagggact gccgtcgcgc ctccgactgt taccccggtt ccaagcctag aggctccttc    49020
cgaacaaggt aaggagtctg tggccagaca tctacacgct tcgatgctgg gatgaaaagc    49080
catggaaatt cccactgatg cagccgcctt caatggtaaa cggatgctcg agtgttgcct    49140
gagttctacc atgtaggagg aagcctccgt gcactctctg ggggagccag cggagtgatt    49200
tctggtgcaa cgtggttggg ctttgtcttt aggatgggca caaaccctcc aggggatcg    49260
acttcaaaat tcaccttgtt gtaaaacggg ctacctcagt gtcccagcca aaattttat    49320
tgtaacatgc tgtcaggtgt gtcactcttt ccaagccagt aagcttttcc ggggatttct    49380
tcaagtagcc agcattcaga gcaatcttca gcattgcaga ttctgagaaa tgtggctctg    49440
gagcctgtca ccctcgagaa acctaagagg gctgcattga ttccatgtgg ccctgggtct    49500
atggagcagt acatgagctc ccagtgctct aaggctcttc agccctaggc tttgaaggga    49560
gtgatttctc agtattctta aacctctttc tgatgacact tgtacctgtg aggggtctag    49620
agagaaagag tagtagactc ctactttact acaattcagg atgcagggca tgagaggatt    49680
ccctctctcc tccaagggaa gaagcttttg gcgtgcacac atccctgaga agcaaagtgt    49740
ctttgtcttc agtcagatac ataggaccgt tttctgcccc atggcccgga agccaaaggc    49800
cttggctttc atgatcaacg gtctagggaa acatgcaaaa tttccatgtc tgtcccaaac    49860
tctgcccccg acagccaatt accacctgca gcccgcattg ccaaatgcgg tgccgtttgc    49920
atgaagattc agtagagttt cctagaaagg tgctacctcg tgagctcact ttccaatgag    49980
gaatctgatc tgttgtgttt ctctaaggtg tcaggtgaaa tatttccaag aacttactac    50040
agttctagaa tgggaggaat ctgttgcttt ggtgtttgtt tgttggtcgg ttttctcaca    50100
tccatctgcc tatggataag gaaaagagaa cggtcgtaat tctcatagac tcctttctgg    50160
ttgtgtcaca aatggcttca catgtttctc tatgctcaga gatactcagc ttgatttccc    50220
gtgttttcat ttcagcaccg actgagcaaa ggcctggggt gcaggagtgc taccatggta    50280
atggacagag ttatcgaggc acatactcca ccactgtcac aggaagaacc tgccaagctt    50340
ggtcatctat gacaccacac tcgcatagtc ggaccccaga atactaccca aatgcgtatg    50400
tctttgttct ttaccataag agaagaaagg gccaagtgaa gttctgttca caagagatgt    50460
gtctcaagct gagttctccg aactcaactt gtgacagatg cagatggcgt agcaaaatgt    50520
ctcaggatga ttgccttgga gctaagggtc tgagagaagg gaaatgttaa gctccctctc    50580
cttcctccta gttctattga gcagaaggga aatctggagg tgaggagatc acattatgaa    50640
gaaagtcaga atgacaaagg accagacact tagattaccc ttccacaaca ccaactaaac    50700
gtcaatggag actttccagt tggaattccg ttattctggc ttccacttcc tgaagggaag    50760
gttgcgtttg ccttttctct ctgggttcaa gaggaaagaa taggtgctta tttatggaca    50820
ggtgaattga tctgtttcta tatctacgta tattccgatt gtcagaaaaa cactcgttcc    50880
taagtaccag tggcctgaag ggatacaggt tcccagcaag agaagatcca aggaaggaag    50940
gcagatgaga gtcagcacag agagggatgc tgaaaagtaa aagggatggg tggatggaga    51000
gaagcccggg tctgaccacc caatggccaa tattttggcc acaagcgact accagagaca    51060
tggaaaaatg gttctacat gtgggacaac agatggtaga ggacctagag aattgagaga    51120
ggggcaatga tgggctccac tccgcagatg ccttggcttt cttcctggat acccttcctg    51180
```

```
cactgaatag caaggagatg gagcccaagc agactgtagc catcttgctg aatggaggag    51240
agggattgga gtttgggatg actgtggtag ctgaaatttt tctaggtctg ctagaaataa    51300
gaactggttt gtgtggagga aaagagctct acaaatacgc atagaagtct cctccagtcg    51360
ttggcctgac atgacgctgc ctgtgcacag gaaatggttc cacgagaaag tgtggcaaag    51420
aacatttact gagaaacagc aagtacaaga gcacaggaag ctcaataaag aagagagaga    51480
tcacatagca ctctgggata ctggagttct tcccagctag accagagagt cctcacggag    51540
cacattgcca attcagtgga gaccccagaa cagccgtaat ttaaaggtac acttagaata    51600
ttactagaat aaagtcagct gcagacaacc ccttgcacag ctggaaagca agtgtccaag    51660
catcaaatcg gtttccaatc aatgaagtgc ctgtgagagg aaatctcaac tctctttaga    51720
agtaaacaac aaagtcgatt gcctcagcta tgcggtatcc gcagagtgag tcctaaattt    51780
aaaatctgac tacatgtaga aaagcgtttc gtgtgaccca tgaccaggaa ataaatcggg    51840
taatacaaac aggctcagga atgagagaaa tgattagaat tgcgtgaaaa tttgacatat    51900
cagtatgata actgatttca aatatttaaa aaaacaacat gcaagaaagc agatatcata    51960
tcaagagaaa ttaacagtac agaatagcca aattaaatta aagagctagt ataaaaaaag    52020
tatgtcttaa ttgaaaaaaa ttactgtatg gccggctgat caaattagac gtttcagagg    52080
aaaacattac ccaacacaca attttagaga acctacagaa tgagctacac acacacacac    52140
acacacacac acacacacaa actgaaaaca cacccatact cacacacacg cagaaactca    52200
caagttctaa cacacacaga cacgcgcacc cctgaagaaa cagtgaaata taaaattaag    52260
cgagcctcac agacatgtag gaaaatatga aaagatttcc tgcatgtggg aagcaagtca    52320
cagtaaagag caagggagtt tataatagaa acaaatacca gaatcaagga tggctgataa    52380
cttttcaatt acgaagaaca ttaaaaaaaa tcacagaatc gtgaaactca agggatcata    52440
tagggaattt cggaaaaaaa acccaacctg tatgatgtac ttttgtacat cacagttcga    52500
aggtaacaag gcaaagatgt aataagaaga aacctgtcac gagaaactgg aggaaaaaga    52560
gctgtgtctt cctacaagta cactgataca aattgccaat gtgttcacct cagaaacact    52620
ggaagccaga taccagggaa tattgttaaa atgataatca ggaacaaaaa gagatcaacc    52680
gggaatgctg aatccagcaa taaatgcct tgaaggtcat ccatgtcgga taaatgcata    52740
ttgtgcactg ccccaaagaa agaaaccgga aactgtaaga attggaaatc agcaggctta    52800
tgtaacaaga gaggtgaccc gaaggaatta ggtagaagaa gaattgaaca agaaaggaac    52860
tttctgcagc ccacgtaatg aagaatccag caattggcaa atgtagatag atgtaaatgc    52920
aaaatatttt cttgatcaaa tttctatatc tttgtaaatg agagttgact acttgaaaca    52980
aaatgatagc aagatattta acttcagcat atgtagaggt aagaatttga aatggtagca    53040
taaatcacga agggattaat tcgaagtgta ccgttgtaag tttctttacc tcatgcacga    53100
tggtgtgtca tattaataaa agggtactgt gcgggttcga agggatattg caaatcctag    53160
agcaatcaca aaggtttgaa ctctgaggtt tttggtataa taagaatagt ccatgcattc    53220
aaaagaggga agccaaggaa gaactagaag tctttcaaga gctcaggctc ttatacatcc    53280
agttgctcat tgaaccagct tcctggaatg gagggtctgg ggttgagact aggccacaag    53340
tctagagtct ctagagagac agtgttggaa ccccatggcc cataatacat ttcccatttt    53400
ctcaggcagc cagaggtcat gaatgtgagg atactgggag gttggagcaa cgttcttggg    53460
aggcataagg aagagcgaat gcttcaagat ccccgcagcc caaactactc gcctgctttg    53520 cccccctaatg catttttctc tgctgctccg tagctgtccg acctcttcag atctcttagt    53580
```

```
ccaccctgcc gtcttccttt atgccatggg tcccactgtt ctttcaactc atccccattt   53640
ccctcagtcc cggagtagct gcggccagca gagggtagac tgagagcagg agagaaggac   53700
ctgcctagga accccttcta gagatactgc atcctgcctg ggagcaagtt ttccagggca   53760
gctttgagaa gtcttggaga aacaaaccta ctaaacctga cagacagtaa tactatttgc   53820
acaatgcttt tctgtgggaa aggtagagcc ttttcactac gtattgagta catagagtgt   53880
gagggttgac ctggaacggc tatcctcctg gatgacgtgc gttttctgaa gaactacatg   53940
ttcgttgcaa ctcccacatt agaatatgaa gtcctaccga gagagatacg gagactagac   54000
agatacagat gcatttgcat gtgaatacac aatcccacaa tacagacgtc aaaacccata   54060
ccagttattc cagagagatg gattgggcag aaggcagaag gagaatactc tgatcgtttt   54120
tcggccacgt gtgtgtgtta tctcagtgtt tctaagaagc gtttgctact ttagattttt   54180
tatttaaaaa aaatagtaat aatctattaa gtatgagaga tgtgcagaga cgattagtga   54240
tcgagagcca tttttgctgg tggcaatcat atggtacttt taatgggaat attagaaagg   54300
caccggtaat gaccttgttg cagcacaaag gagagagtgt ggggtgcccc tgcatgttgt   54360
cccacctctt gtgacgtgta tcgttttgga atttccagtg gcttgatcat gaactactgc   54420
aggaatccag atgctgtggc agctccttat tgttatacga gggatcccgg tgtcaggtgg   54480
gagtactgca acctgacgca atgctcagac gcagaaggga ctgccgtcgc gcctccgact   54540 gttacccegg ttccaagcct agaggctcct tccgaacaag gtaaggagtc tgtggccaga   54600
catctacacg cttcgatgct gggatgaaaa gccatgaaaa ttcccactga tgcagccgcc   54660
ttcaatggta aacggatgct cgagtgttgc ctgagttcta ccatgtagga ggaagcctcc   54720
gtgcactctc tgggggagcc agcggagtga tttctggtgc aacgtggttg ggctttgtct   54780
ttaggatggg cacaaaccct ccaggggat cgacttcaaa attcaccttg ttgtaaaacg   54840
ggctacctca gtgtcccagc caaaattttt attgtaacat gctgtcaggt gtgtcactct   54900
ttccaagcca gtaagctttt ccggggattt cttcaagtag ccagcattca gagcaatctt   54960
cagcattgca gattctgaga aatgtggctc tggagcctgt catcctcgag aaacctaaca   55020
gggctgcatt aattccatat ggtcctgggt ctatggagca gtatatgagc tcccaatgct   55080
ctaaggctct tcagtcctag gctttgaagg gagtgatttc tcagtgttct taaacctctt   55140
tctgatggca cttgtacctg tgaggggtct agagagaaag gttagtagac ttctcctta   55200 ctgcaattca ggatgcaggg catgagaaga ttccctccct cctccaaggg aagaaggttt   55260
tggcgtgcac acatccttga gaagcaaagt gtctttgcct tcagtcagat atataggatc   55320
gttttctgcc ccatggcctg gaagccagag gccttggctt tcatgatcaa cgatctaggg   55380
aaacatgcaa aatttccatg tctttcccct cctctgccct cgacagccaa ttaccacctg   55440
catcctgcat tgccaaatgc agtgcccttt gtatgaacat tcagtagagt ttcatagaaa   55500
ggtgctactt cgtgagcgca ctttgcagtg agaaggagtc tgttctgttc tgttttcta   55560 aggatttcag gtgaaatatt cctagaact tactacagtt ctagattggt aggaatctgt   55620
aggtttgctg tatgtttttt ggttggtttt ctcccatcca tctgcctaca ggtaagggaa   55680
agataacgtt cataattctc atagactcct ttctggttgt gtcataaatg gcttcacata   55740
tttcgttatt ctcagagata ctcagtttat ttcttgtgtt ttcatttcag caccgactga   55800
gcagaggcct ggggtgcagg agtgctacca cggtaatgga cagagttatc gaggcacata   55860
ctccaccact gtcactggaa gaacctgcca agcttggtca tctatgacac cacactcgca   55920
```

```
tagtcggacc ccagaatact acccaaatgc gtatgtcttt gttctttacc ataagagaat   55980
aaagggccaa ctgaagtttc tgtgacaaga gacatgcttc aagctgagtt ctccgaactc   56040
aacttgtgtc agattcagat ggtgtagcaa aatgtctcag gatgatttcc ttggagctaa   56100
gggtctgaga aagagaaat gttaagctgc ctcaccttcc tcctagtttt gtggagcaga   56160
agggaaatga ggaggcgagg agatcacctt atgaagaaag tcagaatgac gaaccaccaa   56220
acacttagat taccccttgcc caacacccac taagcgtcaa tgaagacttt ccagttggaa   56280
ttccgttatt ctgacttcca attcctgaag ggaagattgt gtttgccttt tctgtctggg   56340
ctcatgagga aagtttatgt gcttacttat ggacaggtga attgatctgt ttctatttct   56400
acctgtattc caatagggag aaaatctctt ggtcctaagt accagtggcc tgaaaggata   56460
gaggttccca gcaagagaag atccaaggaa ggaaggcaga tgagagtcag cacagagagg   56520
gatgctgaaa agtaaaaggg atgggtagat ggatagaagc cctggtctga ccaccccatg   56580
gccaatcatt tggccataat caacaaccaa agacatggaa aaatggtttc tacatgtggg   56640
acaacagatg gtagaggacc tagagaattg agagagggcc aatgatgagc tcaactccat   56700
agatgccttg gctttcttcc tggatacct tcctgcactg aatagcaagg agatggagct   56760
caagcagcct gtagccatct agctgagcag aggagaggga ttggagtttg ggatgactct   56820
ggtattttct aggtccgcta caaataagaa ctggtttgtg gaggaaagga gctctacaaa   56880
tacgcataga agtctcctcc agtagttggc ctcacatgac actgcatgtg cacagaaaat   56940
ggttctacag aaagtgtggc aaagaacatt tactgagaaa cagcaactac aagagaacag   57000
caagctcaat taagaagata gagatcacat agcactctgt gttattggag ttcttaccag   57060
ctagatgaga gagtgctcac ggaacacatt gccaattcag tggagacccc agaacagcca   57120
taatttcaaa gtacaattag tatattacta gaataaaggc agctgcagac aaccccttgc   57180
acagctgaaa agcaagtgtc caagcatcaa atgggtttcc aatcaatgaa gtgcctgtga   57240
gaggaaatct caactctctt cagaagtaaa caacaaagtc aattgcctca gctatgcggt   57300
atccccagag tgagtcctaa attaaaaatt tgactacgtg tagaaaagaa tttcgtgtga   57360
tccatgacca gaaaataaat caggcaatac aaacaggctc agaaatgaca tcgataatta   57420
gaattgcatg aaaatttgac atatcagtat gataactgat ttcagatatt taaaaaagt   57480 gcaacaaagc aggtatcata tcaagacaaa ttaatagtat agaatagcca aatcaaatta   57540
aagaactatt atacaaaaag tatgtcttaa atgaagaaat tactgtatgt ccgcctgaaa   57600
aatttagatg tttcagaaga aaaaattaac caaaaacaat tctgcagaac ctacagaatg   57660
agccacacac acacacattc aaaacacacc catacacaca cacatgcaaa aactcacaag   57720
ttctaacaca cacacaaaca cacacacaca tgcacatccc taaagaaata gggaaatata   57780
aaattaaccg accctcagag acatgcagga aaatataaga agatttcctg catgtgggaa   57840
gcaagtcaca gtaaagagca agggagtttg gagtagatac aaataccgga atcacggatg   57900
gctgataact tttcaattat gaagaacgtt agaaaaatca cagattcatg aaactaaagg   57960
gatcaaatag gaaatttcga gaaaaaaaac tacatgatgc acttctctac atcacagttc   58020
aaaggtaaca aggcaaggat ataagaagaa gaaacatctc acgagaaact ggagaaaaaa   58080
gagctgtgtc ttcctagagt acagtgatac aaattgctaa tgcgttcacc tcagaaacac   58140
tggaagccag ataccaggga atattattaa aatgataatg aggaacaaga agagatcaac   58200
cgagaatgct gaatccagca ataaaatgcc ttgaagatca tccatgttgg ataaatgcat   58260
attgtgcact gcccaaaaca aagaaactgg aaagtgtaag actttggaat cagcaggctt   58320
```

```
atgtagcaac agaggtgacc cgaaagaatt aggtataaga agaatagaag aattgcatga    58380
aaatttgaca tatgactaag ataactattt caaatattta aaaaagatg aatatgtaat     58440 aaaacagata aaatatcaaa agaaagtaac agtattgact agccaaatca aattaaagac    58500
ttagtgtaaa aagctatgtc ttaaaagaaa aaattactgg atggctgcct gatcaattta    58560
gacatttctg aataggaaac taaccaaaaa tcaattctac agaaccaact acacacatat    58620
atacacatac aacacaccca tacacaccca cgcaaaaact cacaagttca cacacacaca    58680
cacacacaca caaccctcaa gaaatagtga aatagaaaac caaccgaacc tcacagacat    58740
gttgcaaaat aggaaaagat ttcctgcata tgggaagcaa gtcacagaaa agagaacggg    58800
agattggaaa cagaaacaaa taccggaatc aaggatggcc gaaaactttt cattgatcaa    58860
gaatattaac aaaatcgcaa aaacacgaaa ttcaatgcat caaataggcg tttcgaaaaa    58920
aagaaaaaat ctggtatgat gcactttгgt acttcacatt ttcacggtaa aagacaaag    58980 atataataac aagaaacttc ttatgagaaa ctggggaaaa acaagctgtt tcttgctaga    59040
agaacagtga tacaaattgc taatgcattc tcgtcaaaaa cactggaagc cagataccgg    59100
gaatgttatt aatgtggtaa acaggaacaa gaagagatca accaagaatg ctaaatccag    59160
caataaaatg ccttgaagat catccatgct gcataaatgt atgttgtgca ctgccccaaa    59220
caaagaaacc ggaaactgta agaatttgga atcagcaggc tgatgtaaca agagaggtga    59280
cccaaaggaa ttaggtagaa gaagaatagt acaagaaggg aactttctgc agcccatgta    59340
atgaagaacc cagcaattgg caaatgtaga tgtaaatgca aaatattttc ttgaccaaat    59400
ttctatatat ttttaaatga gcgttgacta ctggaaacaa aatgatagca atatatttaa    59460
ttttagcata tgtagaggta agaatttgaa caagtagcgt aaatcatgta gggaataatt    59520
agaagtgtac cattgtaagt ttcttacctc atgcacaatg gtatgtaata ttaataaaat    59580
gttactgtgt gggttcaagg agatattgca aatcctagag caatcacaaa gttttgaact    59640
ctgaggtata ttgtataata agaatattcc atgtattcaa aagagagaag ccaaggaaga    59700
aagaaatttg tcacgagttt gggctcttag tacatcctgt agctcattga accagcttcc    59760
tggaatggag ggtctgggat tgacactagg ccacatgtat agagtctcta gagagacagt    59820
gtttcatccc catggcccgt aatacatttc ccattttctc aggcagccac aggtcatgaa    59880
tgtgaggata gagagaggtt ggagcaacgt tcttgggagg cataaggaag agcaaatgct    59940
tcaagatccc cgcagcccaa actcctacct gctttgcccc ctaatgcagt gttcctccgt    60000
agctgtccga cctcttcaga tctcttagtc taccctgcca tcttcctta tgccatgggt     60060 cccactgttc tttcaactca tccccctttc cctcagtgca gagtagctgc ggccagcaga    60120
gggtagactg agagcaggag agaaggtcct gcccaggaac ccattctaga gatgctgcat    60180
tctgcctggg agcaagtttt ccagggcagc tttgagaagt cttgcagaaa caaacctatt    60240
tgacccacat gatatgggaa tgacagaaag taatacaatt tgcacagtgc ttttccatgg    60300
gaaaagtaga gccttttcgc gaggttttga gtacatagag agtgaaggtt gacctggaaa    60360
ggttatcctc ctggatccca tgttttttct gaagaactac ctgttagttg caacttgcac    60420
attagaatat gaagtcctac cgagagagat acggagaact agataaatac agatactttt    60480
gtatgtgaat aaacgattcc acaatacaca catcaaaatc cataccagtt attccagaga    60540
gatggattgg gcagaaggca gaaggagaat actctgatcg tttttgccc acgtgtatgt    60600 attatctcag tgtttctaag aagcgtttgc tactтттagat ttttttttat aataataatc    60660
```

```
ttttaagtat gagaaatgtg cagacaggat tagtgattga gagccatttg tgcttgtggc    60720
aatcatatgg tacttttatg ggaatattag aaaggcactg gtaatgacct tgttgcagca    60780
caaaggagag ggtgtggggt gccccctgcat attgtcccac ctcttgtgac gtgtatcgtt   60840
ttggaatttc cagtggcttg atcatgaact actgcaggaa tccagatcct gtggcagccc    60900
cttattgtta tacgagggat cccagtgtca ggtgggagta ctgcaacctg acacaatgct    60960
cagacgcaga agggactgcc gtcgcgcctc caactattac cccgattcca agcctagagg    61020
ctccttctga acaaggtaag gagcctgtgg ccagaaacct acacgtttcg atgctgggat    61080
gaaaagccat ggaaattccc actgatgcag cagcctccaa tggtaaacgg atgctcgagt    61140
gttgactgag ttctgtcatg taggaggaag cctccgtgca ctctctgggg gagccagcgg    61200
attgatttct ggtacaacgt tgggtgggct gtgtctttag aattggcaca aaccctccag    61260
ggtgatcgac ttcacaactc acctcgttga aaaatgggct atctcagtgt cttagccaaa    61320 attttattg taacatgctg tcagatgtgt gactctttcc aagccagtaa gcttttcctg    61380
ggacttcttc aattagccag cattcagtgc aatcttcagc attgcagatt cagagaaatg    61440
tggctctgga gcctgtcacc cttgagaaac agggctaaca gggttgcatt aattccaaat    61500
caccctggtt ctatggagca gtacatgaac tcccaatgat ctatgtttca ggacttcctc    61560
agtcataggt gggctctgca gccctaggtt tttaagtgag tgactgcccc gtgttctggt    61620
ggcagttgta cctgtgagcg gtctggatag aaagagtcgg agacttctgt attattgcaa    61680
ctcaggatgt gggtcatgag aggatttcat ctctcctgca ggggagtaag ctgttcgcct    61740
ccacccatcc ctgataactg aagtgtcttt gtctgcagtc ctagacgaag gactgttgtc    61800
tctcccatgg cccagaagct gaagaccttg ccttttgtta tgaaacgttc attgtttttca   61860 tgtctgtccg tttctctgcc cctaacaccc aatcaccatg tatggcctgt acccccaaat    61920
gcatcgtgct ttgctgtttg ctgccccata gtcctcatga acattcagta gaaattccca    61980
taaatgtgct tgcacgtgag cacagtttcc attgagaagc cctctcattt gtccttttt     62040 tctaagcttt tatgtgaaat atttctaaga acttactaca gttctaaagt gttaggaatt    62100
tgtttctttg gtgttttttgt ttgttggttg gttgttgctt ttctcaagtc catctgccta   62160
caaataaaga aacaagaatg ttacttgtca tattctcctg aggtcataat tctcagagac    62220
ttttttctgg tttgtgccat aagtggcttc acatgtttgt ctcttcttgg aaacactcag    62280
tttgatttct tttcttttca tttcagcacc aactgagcaa aggcctgggg tgcaggagtg    62340
ctaccacgga aatggacaga gttatcaagg cacatacttc attactgtca caggaagaac    62400
ctgccaagct tggtcatcta tgacaccaca ctcgcatagt cggaccccag catactaccc    62460
aaatgcgtat gtctattttc tttaccataa gtgaaggaag ggtcagtgga aatttctgtt    62520
agtagagtca tgcttcaagc tgagtgttca ggactcaagt tgtctcagat gaacagtgca    62580
tagcaaaatg tctcaggaac attgtctttg agcaaagagt ctaagagaag acaaatgtta    62640
atctggctct ccttcctcct agtttaatgg agcagaaagg tatctggagg caaggatatc    62700
acattaagaa acaagtcaag atgacaaatg atgaaactct tagagtaccc ttccacaaca    62760
cccactaagg ttcaatgcag cctttttctcc ttggaattct attaaactaa actccaattc   62820
ctgaagtgaa ggttctgttg gggttttctg ttttggctta caaggaaagt atatatgtat    62880
atctatggag aggcaaatct atctctttct atatctacgt ctattccaat atgtagaaac    62940
acagtcggtt ctgaccacca gtggtctgaa gggatactgg ttgttagaga ataaaaatgg    63000
caggaaggca gatgagagtc agcaaagaga gagatcctgt aaagtaaaag ggtggataga    63060
```

```
tggacagaag cccaggtctg accagcccat ggccaggctt taggccataa gtgacaccaa   63120
agacatggaa aaatggtttc tacatgttgg acaacagaca gtagtggacc aaaagaatag   63180 tgacagggg aacaatgaga tcaactccat agataccttg gctttcttcc tggaggccct    63240
tcttgcactg aagagcaagg tgatggagcc cagatggact gtagccatct tcctgaatgc   63300
aggagagaga ttggaatttg ggactactgt ggtagctagg attttatagg cctgctgaga   63360
atgagaatgg atttgtggat gaaaggagct ccagggcac gcatagtagt ctcctcgaat    63420
ctttggctaa acatgacgtt gcatgtgccc agaaaaaggt tccacaagaa agtagagaaa   63480
agaatatatc ctgaggaata gcaactgcga ttgaacagtg agctcaataa agaggacaga   63540
gccctcatag cattctggga tactggagtt ctgaccagct ggaggagaga cctcactgaa   63600
cctcttggga atacagtaga gactccagaa aagtcatact ttaggagtag aattagtaaa   63660
tttctagaaa aaaaggcagc tctagacaaa ccctggcaaa actgaaaagc aagtctccaa   63720
gcattaaaat catttccaag tcaattaact gcctgggaga ggaaaaccct ctttagaggt   63780
aaacaacaaa gtcaagtggc tcagctatgt ggtgttcaca gtgtgagttc taaatttaaa   63840
acttgactac acatagagaa gcttttagta tgaaccatga ccaggtgaaa aatcagtcaa   63900
tacaaataga cctagaaatg acagaaatga ttagaatggc aaaaaatttg acatatcaat   63960
atgtcaactg agtttaggt tttaagaaaa catgaatacg gaatgaagca gataccatat    64020
caagagacag taacagtata gaagagccaa attaaattaa agaactagta taagaaggta   64080
tgtcttaaat gaaaaaatta ctggatgtat tcccaatgga gtgagatgtt tcagaagtaa   64140
aaactaactg aaaaacaatt ttataccacc tacagaacca gctacacata cacaaatgac   64200
acacacatat acacacatac tcacacatgc acaggcttag aaacatgcac gcacacacac   64260
acacacacac acacacacct ccacaaatac taaaaaatga aatccactga tcctcacaga   64320
caggcgggaa aatataaaaa gatttcctgc atgtgggtag gaagtcacag aaggagagga   64380
aggagagatt gctacaggaa caaatactgg aagcaaggat agctaaaaac ttttcaaata   64440
agaagaatat taaaaaccac agattcaaga agctgaatga atcagacagg gaatttccaa   64500
aaaaaaaaaa aaaaaaactg tatgattcac ttttgtacat caccgttcaa cagtcagaag   64560
gcaaagatat aataacaaga aacatctcat gagaaactgg aggaaaaaga gctgtgtctt   64620
gctagaagaa cagtgataca aattgctaat gcattctcat cagaaacact ggaacccagt   64680
taacagggga tatcattaaa atgataaact agaaaaaaaa gagatcaaat gagaatgcta   64740
catccagcaa taaaatgcct tgaagatcat ccatgttgga taaatgcata ttgtgcactg   64800
ccccaaataa ataaaccaaa aactaataat ttggaatcag caggcttgtg taacaagaga   64860
tgttgcccaa agaaaattag ctagaagaag aatagttcaa gaggagaact ttctgcagcc   64920
cacgtaatga agaacccagc aaatggcaaa tgtagatgta aatgcaaaat attttcttga   64980
tcaaatttct atatcttttt aaatgagagt tgactacttg aagcaaaatg atagcaatat   65040
atttaacttt agcatatgta gaggtaaaaa tttgaacata tagactaaat catgtgggga   65100
ataattggaa gtgtaccatt gtaagtttct taccttatcc acgatggtat gtaatattaa   65160
tgaaaggttg aatttgtggg tccaaaggga tattgtaaat cctaaagcaa tcataaaatt   65220
ttgaattctg agggatatta tataataaga attttccatg tatccaaaag agggaagcca   65280
aggaagaaaa agaagtcttt caagtactca agctctgagc acatccagtt gctcattgaa   65340
ccagcttcct ggaatggagg gtctgggctt gagactaggt cacatgtgta gagtctctag   65400
```

```
agagacagtg ttggatcccc atggcccata atacatttcc cgttttccca ggcagccaca   65460
ggtcacgaat gggaggattc tgagaggttg gagcaatgtt cttaggaggc ataaggagga   65520
gtgaatgctc tgagatttcc ccagcctgag gtcctccata gctgcccgac ctcttcagac   65580
ctcatagtct gcccagctgt ctcccttat gccatgagtg ccactgttct ttcaactcat    65640
cccccattcc ctcagtcccg gaattgctgt ggccagcaga ggatggactg agagcaggag   65700
aggaagtcct gaccaggaac ccatcctaga gatactgcat cctgcctgaa agctaggttt   65760
ccagggcagc tttgagaagt cttgcagaaa gaaacccact tgacccacct gatacggtat   65820
cgacagacag gaatactttt tgtgcaatgg ttttacatgc tgaacataga gccttttggc   65880
tacattttga gtacattgaa tgagactgct ggcctgggaa ggatatcatg ctggatgcca   65940
tttttttctc tggagaacta tgtgttagtt ccaactcgca cattactata tgaagtccta   66000
cacagagaga tacggagagc tagacagata gagatacttt tgtatgtgca taaccaattc   66060
cacaatacac acgtcaaaat ccataccagt tattccagag atggattg ggcagaaggc     66120 agaaggagga tattctgatc cctttttggc cacatgtatg tataatctca gtgtttctag   66180
gaagtgtgtg ctgcattaga ttttttttct ttaaaaaaag tgataatata ttaagtatga   66240
gaaatgtgca gagaggatta gagattgaga gccatttgtc attgtggcaa ttgtatggta   66300
tctcttttgg gaatatttca aaggcaccag taatgacctt gttgtagcaa aatatacagt   66360
gttcctgcat atgtacccat tttttgtgat gtgtattctt ttggaatttc cagtggcttg   66420
atcaagaact actgccgaaa tccagatcct gtggcagccc cttggtgtta caacagat     66480 cccagtgtca ggtgggagta ctgcaacctg acacgatgct cagatgcaga atggactgcc   66540
ttcgtccctc cgaatgttat tctggctcca agcctagagg cttttttga acaaggtaag    66600 aagttgtgcc agacatttac ctgcttggat gctgggatga aaagccatgg ataccccac    66660 tgacgcacaa cccttcagtg ctacactggt tctcgtgtgt tggttctggg tctgccatgt   66720
gggaggaagc cttagcgcac tctctggggg agccagaggt gtgattttg gtgcaacctg    66780 tgcgagctgt gtctttagga tgggcggaaa ccattctggg tgctcgactt caccactccc   66840
ctcattgtaa aagggctat ctcattgtcc tagacaaaat tcttattgta atatgctgtc    66900
agatgtgtgt gtctttccaa gccagtaaac ttttccaggg atttcttcaa gtagacagca   66960
ttcagtgcaa tcttcagcat tgcagattcc gagaaatgtg gctctagatc ctgttatcct   67020
tgagaaacct aactgggttg cattaattcc atatctccct gggtctgtgg agtagtacat   67080
gagctcccga agctctatct ctcaggtctt tttcagtccg aggcaggttg tgcagttctt   67140
agctttgaag ggagtgattt tttcgtgtgc ttttgcctct ttctgatgga acttgtacct   67200 gcgggggtc tggagaaaaa gagtagtaga cttttgcttt attgcaatgc attatgctgg    67260
gcacgagagg attccctatc ttattgtagg tgataagctt ttggcctcca ctcatccctg   67320
agaagtgaag tgttgttgcc tacagtttta gctgcaggac tgttgtctgc cccatcacca   67380
ggagtttaat gctttctttt ttgagcaatc atctaggac acatgcaagg tttttatatg    67440
tccttgcctc ctccccaaaa aaccatttta atgcttggag acttgctttt cagctttgcc   67500
aaatgcatca cccttcttc tatgctgttc catgtcgtca tgaacactct gtagagattc    67560
ctagaaatga gcttccatgt tagtggagtt tccgatgaga agcaatctga tatttctttt   67620
ccactaagtt ttacatgaaa tatttctaag aacttactac agttctagaa tggtaggcat   67680
ctcttacttt cgtgtttgtt tgtgtgtttt ctcatgtcca tttgcctatt aataaagaat   67740
agagaatggt tgtaaatctc agtgactctt ttttggttta tgtcataaat ggcttcctgt   67800
```

```
atttttctgt tctaggaaat aataagcttg atgtcttctg ttttaatttc agcactgact   67860
gaggaaaccc ccggggtaca ggactgctac taccattatg acagagtta ccgaggcaca   67920
tactccacca ctgtcacagg aagaacttgc caagcttggt catctatgac accacaccag   67980
catagtcgga ccccagaaaa ctacccaaat gcgtacgtct ttgttcttta ccataagcga   68040
aggaagggcc aatggaagtt tctgttagaa gagtcatgct tcaaggtgac tgctcaggac   68100
tcaacttggc tcagatgcag aggaacattt cctgtgagca aaagttctta gagaagactt   68160
tgttttttg agacagagtc ttgctttgtt gcccaggctg gagtgcagtg catgatctc    68220
ggctcactgc aagctccgcc tcccgggttc acaccattct cctgcttcag cctctctagc   68280
agctgggact acaggcaccc accaccacac ccggctaatt ttttgtattt ttagtagaga   68340
cagggtttca ctgttctagc caggatggtc ttggtctcct gacctcgtga tccgcctgcc   68400
tcagcctccc aaagtgctgg gattacaggc gtgagccacc gtgcctggct gagaagacat   68460
tttttaagct ggctctcctt cctcctagtt ttatggaagc agaaggatat atggagttga   68520
gaagatctta ttaataaaac agccgggatg acaaatgacc aaagagttag agtatccttc   68580
tacaacatcg gctgagggtt aatacaacct tttcaccttg gaattctatc attctaagct   68640
ctagtccctg aagtgaatgt tgtgttggcc ttttgcatct tgggtcacag ggaattgata   68700
cttgcacatc tatggagagg caaatctttt tctatctact tctttttcaa tgggtacaaa   68760
cacacttggt cctgagcacc agtggtctga agagatacgg tctgcccaga ggagaagaac   68820
aaaggcagga aagcagatga gagtcagcaa aggggcgatg ctgaaaagta aaaggggcgg   68880
gtagatggac agaagccatg atctggccat tctatggcca gtctttcggc cataagtgac   68940
taccaaagac acggcaaaac ggtttccaca tgttgaacaa cagatgctag aggaccaaga   69000
gtattgcaag agggagaaaa tgagatcaac ccatcaatgc cttggctttc ttcaaggaga   69060
cccttcctgc actgaagagc aaggagatgg agcccaagct gactgtagcc atgttgctga   69120
acagaggaga gtgattggac tttgggatta ctcaggtagt taggattttc tagccatgct   69180
aagagtaaga atggacttgt ggaggatagg agctccaggc atagaagtct cctcaagtgt   69240
tagtctaaac ataaagcagc acttgcatag aagattttcc acaagaaaat atggcaaaaa   69300
aacaccatat attgaggaac aacaactaca agggaacagt gagcttaata aaggtgacag   69360
agctcacata gtgctctgga atattggagt tttgaccagc tagagagaag agacctcatt   69420
gaaaatcttg ggcattcagt agagacctca gaaaagtcag actttatgag tagactttgt   69480
atattcctag aataaaggca gctccagaaa aaacctagca aagctgaaaa gcaaatctcc   69540
aagcattaaa atggtgtcct agtcaattaa ctgccttcta gaagaaaact caacactctt   69600
tacaggtgaa caacaaagtt aagttgctga gctatgcaat atccacagtg tgagtcctaa   69660
atttataact ttactacaca taaaaaagca tttagtgtga accataacca ggaaaataat   69720
cagtcaataa aaatagaacc aggaatgata gaaatgattt aaatggcatg agaatttgac   69780
atattagtat cataactgca ttgctggatt taagaaaaca taaacatgga acgtaacaga   69840
tatcatatca agggaaagta aaaggataaa agagtcaaat caaattaaag gactattaaa   69900
aggtatatct taaatgaaaa attcactgga tggtctccca atcaggttag ttgtttccag   69960
ggaaaaaatt aactgaaaaa taattcaata gaatctacag aaatagctgc acatatatac   70020
acacaatggc acacgtgcac acacccacac ccacacaggt gtgaatccta gagccacacg   70080
agcattgaaa catagagaag taaaaattgt tcattgagga atatgtagca atgctcaatg   70140
```

```
tgttttaccc taataagagc ttttgtgatg tatgattgaa aaactgacac aactgaagag    70200
agaaatagat aagcccacac tctgagttag agatttcctt gattctctca ctatggttat    70260
aaatctttcc caaacacaac aggctagaac aaatatgcag aaaattagac atagtatctt    70320
tgttctcaat aaaaacgtcg acctatttaa cattataccg aactaccgag tacacattaa    70380
agtgtgcatg gagcattcac tgaggtgtac tctacacatg accttccagc aagtctccat    70440
agatttaaaa gaattaaagt catacagagt gtgtcacttt attctcccag aataaagtga    70500
gatatgaata atgagaagtt tgccagcttc tcaaatattt gggagtcata cggtgcattt    70560
caaaatactc tttgggacaa agaaaacatc actaaggaat ttagaaaagt tttgaactga    70620
gtaagaatat aacacaattt atccaaactt aggagatgca gtgaatgtct ttaggctttt    70680
acataatttt agatgctctt agggaaaaac agaagcatgt aataatcaag atttcaaact    70740
gcaattctca aagtgtagtc tagagaaacc tgaggacctt tgagtacctt cagagacagt    70800
ccatgaggtt aaaggacttt gctacgtgaa aagtaagatg ctattggccc ttttttacttt    70860 catttttccaa caagagaaga ggggagtttt ccagcagtta cataatatgt aatggcatca    70920
tgtctctgat ggctaagaaa atgggcaatt gttgactttg tgtgttaaaa aaattctcag    70980
tgttggtttc ttatactata aatattcatc ttgtgttttg aaaaagaaaa gctctttgga    71040
atcccctatg aacaaagact ttgacagttg ttgatctaag accacagctt aaatatctac    71100
acaagaaaaa aaaaaaaagc aaataagagc caaggaaagc agatggaagg aagtagtcca    71160
aaccagtgac attcagtgaa caagaaaaga gaccaacaag ggagtaaact cttgaaacag    71220
aaagttgatt ctttgaaaag atccatatga ttgaacacag tctggctaaa caaatgacag    71280
accaatgagg gtgcacaacc atcaccatct ggagtaacag aggagaggtg ccattactat    71340
agcatcttcc agttctgaaa gctgaaaaga agattttgag aacaattgta tgtgaataaa    71400
ttcaggaatg ttaatcatgt gggccaattc ctgaggaaga caacaaatca gcaaaccaga    71460
tgctgaatag ttagtgtagt cctgtagaga gacatacaga gaggctgaca gagaaatatt    71520
tgtatgtgca taaaacaatc tacaagacac acttcaaaat caatctcagt taatctggag    71580
gaacatattt cacagaaggt ggaaggaggg tattctgatc ctcttgtaca ttgtacaaca    71640
ttgtacaatg tacagagtat aattgtacaa gtacaattga agttgtacaa gtacaagtgc    71700
aacttgcaca atgtacagag taaacattga tgtttactct caatttttctt atggagcaca    71760 gatgactttg gatgtgttac aatatgaatg ataatttgtc tttgagatgt tcgcagttgt    71820
ttagaagttg aggaccattt gtgcatatta tgggaccttt agtgaaaata tttcaaagtc    71880 tcttttttaca ctttgttaca gcaaaatgta gagggcgcta agtgcccttg aatcttctcc    71940
catctctggt gacctgtgtt gttttgaaat ttgcagtggc ctgaccagga actactgcag    72000
gaatccagat gctgagattc gcccttggtg ttacaccatg gatcccagtg tcaggtggga    72060
gtactgcaac ctgacacaat gcctggtgac agaatcaagt gtccttgcaa ctctcacggt    72120
ggtcccagat ccaagcacag aggcttcttc tgaagaaggt aggaagtcta tggccagaca    72180
accacaccct aggacgttgg gatgaaaaga gttgcaaaat cttagtgata tagaagcctt    72240
ccatgctcac acaattccaa gtagaatgtg gactcagggt cagccactgg gaaggaacac    72300
tcagcgcctt ctctgggaga accagagctg tgatgtttgg taccctgtga aagggtggta    72360
tctataggaa gggtgcagac cctctagggc actggactta ccactcccct ggttattcaa    72420
aggatcattt tagtgtctta gccagaagaa tattctaaca ttttgccaaa tttgtgaaga    72480
tttaccaagc tcatgataag ccttttcatgg tatttcttca agtagtcagt gttcattgca    72540
```

```
tctttggctt tgcggtttcg gaggaatgcg gttttttgagt ctgtcatcct tgagaaacct    72600
aatatgactt ttcttagttc catatacttc tgggtccagg tagcagtaca tagccaacaa    72660
atgctccatc gttctggcct atctccatct taagccagtc ctgcacaact aggctttgat    72720
gggagggatc tctcagtgtt cttgcccctc cttctcatgg aacatatatc tgtgttggtc    72780
tctgagaaga agagtagtgg atatctactt tgttgcaatg cagaatcctg ggccaaagat    72840
accagccatc cctccaaggg aataaaattt tggccagtag ccctctctga gagacaattt    72900
gtctttgcct acgagtccta gatgcaggac cgcttcctgc cccatcttca agaagctgaa    72960
ggctttggct ttggaggatc agcagtctag ggaaatgtgt gacggtttca tgtctgtccc    73020
cactgacagt caatcaccac ctacaacctg cacagcctga tgcatagcag tctagtttcc    73080
tgccttattc tcaggaacac ccagaagatg tctatattaa agagcatgca catgagtgca    73140
attttgactg ataggcactc tgatctttcc tttggtgcct gtgttttaaa ggaaatcttt    73200
ctaagaactc gttaaagttc tagaatgcta tgaatctttg ggttttatta ttggtatgtc    73260
catctgcctg ctagtacaga acagagcatg gtagtctttc tcagagacaa tgatcctgtt    73320
tcagtcacag atttcttctg atgcttctgt gttctagaaa ttactcagct tgatttctcc    73380
tctttgaatt tcagcaccaa cggagcaaag ccccggggtc caggattgct accatggtga    73440
tggacagagt tatcgaggct cattctctac cactgtcaca ggaaggacat gtcagtcttg    73500
gtcctctatg acaccacact ggcatcagag acaacagaa tattatccaa atgggtacaa    73560
ccttgagttt tcttcaaaga cagacagcag cccccttaca tttctcttgg aagggccatg    73620
cttccaacta acttcttatg acaaatttat ctcagatctg gaatgttggg tagaatgtct    73680
caggcttctt tcttcaggca cagtgtctga aaggagagaa atgtcaggcc agctctcttt    73740
tctcatagtt gacagaagca ggaggatatt tgaaggtggt gagttctcat gaatagaaag    73800
ctcaggacac atggccacgt gcttagaaat agcaccattc cacaatgccc actaaagacc    73860
aatgcaatag ttcaaccagg gatttctgtc attctaatct ccaagtcctg aagtgaaggt    73920
tgtattagcc atgttcatct tgggcaacaa ataaaggata tctatgttga catccagatc    73980
ttccaatcac tttctcctct aacctgtacc tgggttctga aacaaggta tctgaagagc    74040 tatgtgttgc cagcacatga ggggcaaaag taggaaggca gctgagagtc aggaagtata    74100
aagattctga agagttacac atgcaggaag atggacagaa acccagttca gaccacgtca    74160
gcgtttctgc catgaaggac tatcaaatac ataggaaaag tgttttcata ggttggacaa    74220
cagacatgac aggcctgaga aaattcagaa agggaatcaa aggagatcaa ccttatcatg    74280
tccctggcat ccttccttga gacccttgaa gggcaagcag atggagccca gctgaccaca    74340
gcagtcttgc ttaactgagg agagagactg gagtttgtga tgcctcaggc atctgacgta    74400
ttctaggctg gctaagaatg agaggggatt tgtggaggaa aggagctcca agaatacaca    74460
ccgaagtctt ctcaaggctt tggctaaata caaagctgcg tatgcacaag gagagttttc    74520
acaaagaaag aacaataaag aaaagctact ggggaaagaa caactgcaag ggaacagtga    74580
gctcaatgga gatgctagag ctcacatagc actgggggat atttgagttc tgaccactca    74640
gaggagagac acctcactga acatcttggg cattcagtag aggtcaaaga aagccataat    74700
ttgggagtag gatcttcgga ttcctagaaa taaggtgact ccagaaacac tccagcaacc    74760
cttcttccaa gccagtctaa aaggatccaa atgatttcca agtaaattaa ctgccttcca    74820
gaaaaaagta aactcaaccc tccttagagg taaggaacga atacaagttt ctcagttata    74880
```

```
tgacatcccc agagtgcaac ttgcatttaa aaatttacta gacacaaaag aagtttttcac    74940 tgtgatccat aactgggaga aaaatcactc aacacaaata ggcccagaaa taatagaaat    75000
tatggcattg gcaagaacat ttaaaatgca cctctgagaa ctgtgtttca ggaaaatgtc    75060
agcaaaagct gaccatgaga gaaatgaatg cataatatca gaaagaaaaa gaattgaaga    75120
gccaaatgga aatttaaaaa ctgagaaaag ttatatctgt aatgaggaat tcactggatg    75180
gccttataac cagtttagat attatggtag gaaaaggtga acgagaaaat gattcaatta    75240
aagctagaca aaccacaaga cagacagaca gacacaaata cacatacaca caatgactga    75300
accaattaat caacagagcc tcaaggacat ctaggaaaac atccacacat ttaatatatg    75360
tgttaggcaa gtcacagaaa gagaggaaaa agataatgtg acagaagtta tacttgaagc    75420
catgacggct gacaaatttc caaacataca gaaaatgaga aattcatagt catgaagctc    75480
aatgactcag gtatagattt ttaaagagca aaactctgat ttactggggt acatcatagt    75540
taaattgtct gatttcaaag ctaagaagaa aaaaggggg ttcctatgaa caaacatttt    75600
gacagttgat ctaagaccac agcttaaata tctaggcaag gaaaagcaaa taagacacaa    75660
ggaaagggga tggatggaaa tagtccaaac caatgacatt cagtgaacaa gaaaatagac    75720
caacaaagga gtaaatccat gaaacagaaa gttggttctt tgaaaagatt catgtgattg    75780
accacagtct ggctgaacag atgacagacc aaggagggag tacaaccatc accatttgaa    75840
gtaacagggg agaggagcca ttgctatacc atactccagg tctgaaagct gacaagaaga    75900
tatcaagaaa aactgtatgt gaataaattc atgaatgtag atcatgtgga tcaattcctt    75960
aggtaaacaa caaatcagca aaccagatac tgaatagatt gggtactcct atagaaagac    76020
atacagatag ccagacagag aaacatttgt acgtgcataa aacaatctac aagactcact    76080
tcaaaatctc tcagttaatc caaagtaaca tatttggcag aaggtggaag gagggtattc    76140
tgatcctttc ttgtacacat tgatgttttc tctcggtttt cttatggagt atagacgagt    76200
ttggatgtgt tacaataaga atgataatct gtctttgaaa tgttcacagt tgtttagaag    76260
ttgaggacga tttgtgattg ttacaggacc tttagtgaga atatttcaaa gtcacttttt    76320
accactttgt tacaacaaaa tgtagaggat gtctggtgcc cttgtatctt ctcccatctc    76380
tggtgaactg tattgttttg taatttgcag tggcctgacc aggaactact gcaggaatcc    76440
agatgctgag attagtcctt ggtgttatac catggatccc aatgtcagat gggagtactg    76500
caacctgaca caatgtccag tgacagaatc aagtgtcctt gcgacgtcca cggctgtttc    76560
tgaacaaggt aagaagtctc tggccagaca accacaccct tggacgttgg gataaaagag    76620
gttgcaaaat cttagtgata cagaagcctt ccatgctgca cgggaatctg aatgtggact    76680
cagggtcagc caatgggaag gaagcctcag cgccttctct gggggaacca gggctgagat    76740
ttttggcacc ccgtgacagg gtggtgtctt taggaagcgt gcagaccttc tagggcactg    76800
gatttaccac tccctggtt attcaataga ttatttcagt gtcctagtga aaatggatat     76860
tctaacatcc tgccaaattt gtgatgattt accaagctca tcatgagcct ttcctggtat    76920
ttcttcaagt agacagtact cattgcaaac ttcagcttta cagtttcaga ggaatgtggt    76980
ttttgagtct gtcatccttg agaaacctga tatgacttta cttagttcca tatcctcctg    77040
ggtctaggta acagtacata gccagcaaat gctctatctc cctgtctacc ttaatcttag    77100
gcaggtgctg cacacctagg ctttgatgga agggatttct tagtgttctt gcccctcctt    77160
ctcatggaac acgtatctgt gttgctgttt gtgaagaaga gtagtggatg tctactttgt    77220
tgcaatgcag gatcctgggc ccaagatttc ccgccgtccc tccaagggaa taaaattttg    77280
```

-continued

```
gccagtaccc ctctctgaga gacaatgtgt ctttgcctgg aagtcctaga tggaggacca    77340
cttcctgccc catcttccag aaacttaagg ctttggcttt ggaggatcag tgctctggag    77400
aaatgtgtga cggtttcatg tctgcccca ctgacaacca ccacctacag cctgcaccgc    77460
ctgatgcatg gcactctggt ctcctgcctt gttctcagga cacccaaaa gagatctttg    77520
ccaaagaaca ggcacatgag tgcaattttg actgataggc actctgatct gtcctttggt    77580
gcccaggttt taaagaaaat ctttctaaaa actcattgaa gttccagaat gctatgaatc    77640
tttgagcttt gttattggca tgtccatctg cctactaatg tagaacagag catggtcgtc    77700
attttcagag atgatgtcct gtttctatca tggattttt ttctcatgct tctgtgttct    77760
ggaaattact cagtttgttt tctcctcttt gaatttcagc accaacggag caaagcccca    77820
cagtccagga ctgctaccat ggtgatggac agagttatcg aggctcattc tccaccactg    77880
ttacaggaag acatgtcag tcttggtcct ctatgacacc acactggcat cagagaacca    77940
cagaatacta cccaaatggg tatgtctttg agttttctcc caagagaaac agccacccac    78000
ttaaatttct cctggaagag ccatgcttcc agctaacttc ttatgaccca atttctctca    78060
gacccagaat gttggacaga atgtctcagg cttcttgctt tgggcacagg gtctgagagg    78120
agagaaatgt caggccagct ctcttttctc atagttgata gaagtaggag gatacttgga    78180
ggtggtgagg tctcatgaat agaaagctca gaagaacata tgaccatgtg cttagaaata    78240
gcaccattcc acaatgccca ctaaagacca gtgaaatagt tcaaccaggg aattctgtca    78300
ttctaatctc caagccctgg agtgaaggtt gtgtttgcca tgtttgtctt gggtaacaag    78360
tgaaggatat ctatattgac ttcgagatct tccgatcact ttctcctcta acctgtataa    78420
acacattggg ttctgagaac aaggtgtctg aaaagctatg tgttgccagc ccatgagggg    78480
caaaaggagg aaggcagctg agagtcagga agtatagaga tgctgaagag ttacacattc    78540
aggaagatgg acagaaaccc atgtctggct atgccagcct ttctgccatg aaggactatc    78600
aaatacatga gaaaacagtt ttcacaggtt ggacaacaga tatggtaggc ttgagagaac    78660
tgagaaaggg aatcaaagga gatcaacttc atcattaacc tgtcttcctt cctggacaca    78720
gtgttggatt gaaggacaag cagatggagc ccagctgacc acagcagtct tgcttaactg    78780
aggagagaga ctggagtctg cgatgcctca ggcagctgat gtgttctagg ctggctaaga    78840
atgagaaggg atttgtggaa gaaaggagct ccaggaatac acacagaagt ctcctcaagg    78900
ctttggctaa atacaaagct gcgtatgcac agggagagtt ttcataaaga aagaacaaca    78960
aagaaaagct acttgggaaa gaacaactgc aggggaacag taagctcaat ggagatgcca    79020
gagctcacat agcactgggg gatatttgaa ttctgaccac tcagaggaga aacacctcac    79080
tacattttgg gcattcagta gagaccaaag aaagctgtat tttgggattg ggatcatctt    79140
attcctagaa tcaaggtgac tccagaaaaa ctccaacaac ccttcttcca agccagtcta    79200
aaaggatcca aatgatctcc aagtaaatta actgcattcc acaagaaaaa aaaaactcaa    79260
cccccttag aggcaaggga caaatacaag ttgctcagtt atatggcatt cctattgcgt    79320
tacttctatt taaaaattta atagagacac aagaagcttt cactgtgata cataactggg    79380
agaaaaatc actcaacaca aacaggccca gaaattatag aattgatgac attggtgaga    79440
acatttaaaa tgcacctctg agaactgtgt ttcaggaaaa tgtcagcaaa agctgaccat    79500
gagagaaaca aaagcagaat agcaagagaa aagaaaagaa ccggagagcc aaatgaaaat    79560
taaagaactg agaaaaggta catctctaat gaagaactca ctggatggcc ttatcatcac    79620
```

```
tttagacatt acggtaggaa aggtgaccta gaaaataatt caataggagc tacacaaatc    79680
acaggacaga cagacagacc aacagacaga aacacacaca cacacacaca cacacacaca    79740
cacacacaca cacacacaca aagactgaac ctattaatca acagagcctc aagggcatct    79800
aggaaaaatc cacacattta atatatgtgt taggcaagtc acagaaggag aagaaaaaga    79860
tatcatgaca gacattatac ttgaagcgat gatggctcgc aacacgccaa atatacagaa    79920
aacaagaaac tcatagtcaa gaagctaaat gactcaggta tagaattta aagagcaaaa     79980 ctctatgatt tactgggata tatcatagtt aagttgcctc aattcaaagc taaaagaaa     80040 aaaaggggt tcctatgaac aacagctttg acagctgttg atctaagacc acagcttaaa     80100
tatctaggca aggaaaagca aataaggcac aaggaaagag gatggaagga aatagtccaa    80160
accaatgaca ttcagtggaa aagaaaatag accaacaaag gagtaaatcc atgaaacaga    80220
aagttaggtt ctttgaaaag tctatatgat tggccaaagt ctggctaaac agatgacaga    80280
ccaaggaggg agcatatcca tcaccatcat gagtaacagg agagagatgc cattgctata    80340
gcatcctcca ggtgtgaaag ctgagaagta gatattgaga tcaactgtat gtaaataaat    80400
tcatgaatgt agatcatgtg gatggattgc ttaggtaaat aacaaatcag caaatcaaac    80460
actgaataga tcatgcagtt ttatagagac ttacagacag cctgacagat aaacatttgt    80520
atgtacgtga aacaatctcc aagacacact tcaaatccc tctcggttaa tccaaggaa      80580 tgtatttggc agaaggtaga aggagggtat tctgatcctt tctggtacac attgatgttt    80640
tctctcagtt ttcttataaa gcatagatta ctttgaatgt gttacaataa gaatcataag    80700
ctgtctttga aatgttgaca gttgtttaga agttgaggac catttgtgag tgttatggga    80760
ctttagtgag aatatttcaa atttgcttgt ttacacttg ttacaagaaa acatagaggg     80820
tgccaggtgg tgctgtatct tctccaatct ctggtgacct gtattgtttt ggaatttgca    80880
gtggcctgac caggaactac tgcaggaatc cagatgctga gattcgccct tggtgttata    80940
ccatggatcc cagtgtcaga tgggagtact gcaacctgac gcaatgtcca gtgatggaat    81000
caactctcct cacaactccc acggtggtcc cagttccaag cacagagctt ccttctgaag    81060
aaggtaagaa gcctgcagtc agacaaccat accctcggac attgggataa aaagatttgc    81120
aaaatctttg tgatgcagaa aacttccatg ctgcacagga agtcgaaggt gaagtcatgg    81180
acagccaatg ggaaggaagc ttcagtgcct tctctggggg gaccagagct gggatgttga    81240
gtgccttgtg agggatggtg tcttaaaag gggcacagac cctctaggac actggattta    81300
tcacttccct gttatcaaac gaatcatatt agtgtcctag ccaagatgga tattctaaca    81360
tcctgccaaa cttgtgaaga tataccaagc tcctaagcct gtccagccct ttcttcaagt    81420
aggcagtgtt tattgcagtc ttcagcttta ccattttgaa ggaatgccat ttttgaggct    81480
gttgttcttg agaaacctaa catgtcttca ttagatccgt attgtcctga gactttgaag    81540
cagtacatag ccaccaaatt gtttatctcc ccagcctacc ttcatcttgg gcatgccttc    81600
cacacctagg atttgaggga agggatttct cagtgttctc atccctgctt tcatggaac     81660 atttatctcc gttgtttttt gagaagaaga gtagtggatg tcagctttct tgtaatgagg    81720
gatcctgggc ccaagattcc ctgtctcccc tcctaggcta taaattttg gcctgtactc     81780 cttctccctg agaggcaatg tgtctttacc tacaagtcct agatgcaaga tccttttctg    81840
ccccacaccc cagaatctga aggcttttgc tttggaggag cagtggtcta gtgtgcaagg    81900
gtttcatgta tacccccac taacagccaa tcaccaccta tagcctgaac agcttgatgc      81960
atggcaccct ggtctcctgc cttgttctca tgaacaccca gaagaggtgt aagcaaaaga    82020
```

```
ccattcacat gagtgtaatt ttgaagtata ggcactctga tctgtttttt gtttgtttct   82080
ttgtttgttt gttttccagg gttgaattaa aatatttatg actacttatt aaatttctag   82140
aatcctataa gtctatttgt atttttattc tacatttcaa tttgcatgct aatatagaag   82200
agtgtaaatt gttaatcctc agattattcc actttgtgtg tcataatttt tttcacattt   82260
cccttttcta ggcaatactg agcttgattt tctcttttaa tttcagcacc aactgaaaac   82320
agcactgggg tccaggactg ctaccgaggt gatggacaga gttatcgagg cacactctcc   82380
accactatca caggaagaac atgtcagtct tggtcgtcta tgacaccaca ttggcatcgg   82440
aggatcccat tatactatcc aaatgcgtat gtctatcatg ttagccataa aaggaacaat   82500
agtcaactaa aatttctctt agctggccca tgctacaagc tcacttccta ggtccaaatt   82560
tctcatagac tcagagtttg tagcaaaatg tctcaggaaa cttacttttg agcaaaaggt   82620
ctgaatgaag agaagtttta ggattgctat cttttcataac aatttgatgg aagcagcagg   82680
atatatggag gtggtgaagt ctcattaatg taaagctaag gagatcaaat gaccaaatgc   82740
tgagacaaag tatcattcca caatgcccac taaaggtcca tgcagtcttt caaccatgca   82800
attctatcat tctatcctcc attccctgaa gtgaaatttg tgtttgccat ttttgacacg   82860
aatcagaagt aacaaattca ggctgggtgc agtggctcag gcctgtgatc ccaacacttt   82920
gggaggacaa gacgggcaga tcaccagagg tcaggagttc aagaccagcc tggctaacat   82980
ggcaaaaccc catctctacg aaaaattaaa aaattagccg gtcatggtgg tgggtacctg   83040
taattccaac tacttgggag gctgaggcag gagaaacact tgagcctggg attcagagtt   83100
tgctgtgagc cgagaacatg ccactgcact ccagcctggg tgacagagca agactcaatc   83160
tcaaaaaaaa aaaaaaagaa gaagaagaag aaagaagaa gaggaagaag aagaagagga   83220
agaagaagaa gaagaagaag aggaagagga agaggaggag gaggaggagg aggaagaaga   83280
agaagaagaa gaagaagaag aagaagaaga agaagaagaa gaagaagaag aagaagaaga   83340
aaatagaaat gagtgcatat atttatatat gagtactagc ctgtatgaac acactgggtt   83400
ctaagcacca gttttctgaa gggatatggg ttgtcaggca gagtaaaagc aggaatgcag   83460
atgagagtca ggaagtaaac agatgtggtg attaaaatgg gcaggtacat ggacaaaaaa   83520
atgcatgtct gacaaaaact ggcctcttgc cataagtgag tatgaataat atggaaaaac   83580
tgtttgcaca tgttgaacag cagacagtac aacctgagat agtttagaaa gggaaacaaa   83640
taagatcaac cccataatta cccttcctag acttaagggc aaagagtttt aaccaaagca   83700
ttccacagca gtccttgctaa actggggaga gagactggag ttttgtttac taataaaacc   83760
gagattttct aggttaggta ataatgagaa agtatttgtg gagaaaagga gctccaggaa   83820
tacacacaga agtctcttca agtctctggc tgaacagaaa gctgtgtatg cacagaaaga   83880
gtttccagag agaaaggaga acaaagaaca gctactgggg aaagaacaac tgctggggaa   83940
cagtgagctc aatgaagatg ccagagctca catagcactg ggaggtattt gagctctgac   84000
cagcctgagg agagacactt cattgaacat cttgggcatt cagcaaagac cccaaaaaac   84060
catacttcag gagtagaatt aatgcattcc tagaataaag tctactccag aaacacccta   84120
gaaaagctta gaaaccaagt ctaaaaagat ccaaatgatc tccaagtaaa ttaattgcct   84180
gtcagaagaa aacaacctct tcagaggtaa acaacaaaat taaattgctc aattatatag   84240
tatgcacaat gtgtggcata catttaaaaa tttgctaaac atacaaaaag catttagtgt   84300
gacccataac caggagaaaa atcagtcaat acaaatagac ccaaaaatga taaaaataac   84360
```

```
agaattggca aggagattta aaatgtatgt atcataattg tgttcaagga tttaaagaaa    84420
gcgtggacaa gaaataaata aatggataat atcaacagaa agaaaaattg taaaaggacc    84480
aaatggagag tcaagaactg aaaaaaaaga catctcttta atgagaaaat cactacatgg    84540
ccttataatc atattagata gtacagatga taaagctaac tagaaaatat tagggtggtg    84600
caaaccatag cacgcttata caaagcctga gaagataaac agagcctcaa ggacatctat    84660
gaaaatatca aaatatttaa tatttgttta aagcaagtca cagaggaagg gaaagagata    84720
ttggaacaga aaaaatactt gaagcagtga tggctgatga ctttctaaat atggaaaaaa    84780
tgataaactc acatagtcaa gaagctcaat ggatcagata taggatttta aaaagtaaag    84840
ctgtatgatt tatttggaca catcataatt aaattgtcca taatcaaaga tagaaagtaa    84900
aatcttattt gaagcccaag ggaaaaaaca tacctttaca tagagtaaca gtgacacaaa    84960
tgactgatgc cttctcatca gaaacaacac aaatcagaaa caatagaata acacctttag    85020
agtggtaaga agaaaaaaag atcaaatcag aaacaacaaa ataacacgtt tagagtggta    85080
aggaggaaaa caagatcaaa tcagaaacaa tggaataaca cctttagagt gtaagaaaga    85140 aaaaagatc aaatcaggaa caacagaata acgccttcag agtggtaaga aggaaaacaa     85200
gataaaatca gaaacaatga aataacaccct ttagagtagt aagaagaaga aaagatcagg   85260
tcagaaaaaa tggaataata tgctaagaag aaaaaaaaag atcaagtcag aaacaatgga   85320
ataacacctt tagagtgaaa agaaggaaaa aaacccagca agcttaaacg ctatgcacag   85380
caaacaattc cactgaaaat gaatgttacg taagtacata ttctgtcctc ctaaaaacaa   85440
agaacaaata aaagaatgtt tcatcagcag gattatgtaa taaagatgt gaagaatgc    85500 tatgtaagta gaagaaaaat aataccatat gggaattggc atcaaaacca caaaatacta   85560
tcaaaacaaa aaaactttat tgataaattt aacacaatat gcaaaagaac tataccatgt   85620
atactacata acattggtga gaagaaaatt agaagatcta aataaagaca catcatgctt   85680
atagattaaa aaatccaatg tcacttttca caaaactgat ctttagtttc aacccacacc   85740
caagcagaat tcctgcagtc ttttcttgaa aacctaacag aatgtatatg ctagaatcac   85800
caagacaatc tttaaaaaga ataaaaaact tggaataaaa tcacaagttt gtgggataga   85860
tgcatatggt aatatggaaa ttctcataaa gacacagtaa tcaagacatg tggtattggc   85920
tgggacgctt ggctgtaatc ctaacacttt ggaggccaa gatgagagga ttgcctgaga   85980
tgaggagttg cagacaagcc tgggcaacat agcaagaccc tcatctctac aaatatttaa   86040
aaaaattagc caggtttggt gccatgtgcc tgtagtccca gctattcagg aagctgaggt   86100
gggaggatca ctggagccca tgaggtggag gctgaaatga gccatgattg tgctactgaa   86160
ctttagcctg ggagacagat taaaaccttc cctctctctc tcaaacaaac aaacaaaaaa   86220
tacatagtat tgggcaaaac atatgcaaac aaaaacagaa aagggtcagc ataaatttac   86280
atatatggtc aatttatttt caatacaggt agcaaagcaa tttaatgagg aaatttttt    86340 ccaaaattgg tctgaaacaa ctggatagcc atagaaaaaa actataacaa atgtgacgct   86400
tgaatcctac tgtatgactc aaattaaatt aatttgagat agctcttaga cctcaatgta   86460
acagctaatt ctgaggctga aatataagac tgctatgaaa agtatagta tcttataacc    86520 ttggagaagg aaaaattttt tgagggaaga accagaaaac actaactgta aagaaaaca    86580 aatgataatg tggacattca ttgaataaaa acttatgctc accaaatatg actgttaaga   86640
aaataaataa gtaagtaaca cactggaaga aaaacactct catccatata tctgacaaat   86700
ggcctgtatc cagagtatag aaacatttct cccactcact aatcagagga caaacaacct   86760
```

```
aatcaaaatg ggcaacaggc ttgaatagtc atttcttagg agaagatgca cacagagcca    86820
acaatcacct gaaaaagtgc acaacatctt agccatcaaa aatcaagagt tataaccctc    86880
ataagatgac actgaacatc cagtgtacat ggatatcatt aagaagacac aataataagt    86940
ggtgtcaccg atttggagct agaatgtgcc actctctcat atgctggtgg aagttcaaaa    87000
tcatacaaca aattaaaaaa tcagtctgat gctttcttat aaagttcgat aaatatgcat    87060
ctatcctaca aacctgtaat tctattcttg aatatttacc ccccaaaatg aaaacataag    87120
tccacaaaaa tctatataaa tattcatagc agctttatgt tttataaact caaaataaaa    87180
actatttcaa tgtttctcatc aaaagaaaat gaaaactatt taaatggttt catcaaaaga    87240
aaatgaaaaa agaatttcca gtatatttat acaaggaat actattcatc aacaaggaac    87300
aagttactga tagtctcaga agcatgaaca aacctcaaaa atatattaag gaaagaagcc    87360
agacgtcaaa gtgtatagtc tgtatgagtc cattcatgtg agtttataga aaacacaatt    87420
tatggtgaaa gaaaccaata gcatttgaca ctggccgtgg gaagagggta gcagagattg    87480
attgagcagc cacacaaggg agtttctggg gtggtgaaaa tgttctgcat tgtgagggca    87540
gtgtgggcta cacaagtata tgtatttatc aaatctcatc cagctacatt taagatctgt    87600
gcatctcact ctatgtgaaa atatactcaa ctgaaaaaca gagcaggtat ctgtttcagg    87660
tgctacatca cttgatacgt ccagttgtgt taaaaccac tgcctaacat cctcaaatgg    87720
gggatctggg cttgagacta ggtcacatgt gtagagtctc tacagagacc gtgttggatt    87780
cccatgctcc ataatacgtt ccaagttttc tcagacagcc acaggtcatg aatgtgagga    87840
ttctgagagg ttggagcaac gttcttggga ggcataatgg ggaaggcatt ctccaagatt    87900
cctccagcct ggggtcttca cctgctgtgc ctcttactgc attgttttct gactcatcca    87960
tagccacttg accccttcag atcccatagt ctacctagcc gtctcccttt atgccttggg    88020
tcccgctgtt ctttcaactc atcacccatt ccttcagtcc cagagtggct gcagccagca    88080
gaggatggac tgagagcagg agaggaggtc gtgcccatga acccatccta gagaagcagc    88140
atcctgcctg ggagctagtt ttccagggaa gcttttataa gtcctgtaga cccaaaccca    88200
cttgctctac cagatacagt attttatagta atactatttt catgattatt ttatattgca    88260
aatgtagagc atttatgcta cactatgagt aaatagagta aggggctgg catgggaatt    88320 atataatctt ggatgccact tcttccttgg ggaaatgtat ttgagttcca acttacatat    88380
tactatatag tcttatagag agagagacaa agagctagac agacagagat atctttgtat    88440
gtgcattaaa aaatctaaga tacatatttc aaaatctgtg tcatttattc tggaggaaag    88500
tatttggcag aaggtgaaag gaagatattc tgatcctttc ttgtacagac atgtattatc    88560 tcagtttttca tagagagcat atactacttt tgatgtttta aaacaaaaat tataatctgt    88620
gatgtgtcca cagttgttta aaagttgaag ctgaagacca tttgtgcttg tggcaatatt    88680
attgtggtat aatgggaata tttcaaaggc acttgttaac actttgttac agcaaaatgt    88740
agagggcgct aagtgcccct tgaatattctc ccatctctgg tgacctgtgt tgttttgaaa    88800
tttgcagtgg cctgaccagg aactactgca ggaatccaga tgctgagatt cgcccttggt    88860
gttacaccat ggatcccagt gtcaggtggg agtactgcaa cctgacacga tgtccagtga    88920
cagaatcgag tgtcctcaca actcccacag tggccccggt tccaagcaca gaggctcctt    88980
ctgaacaagg taagaaattt gtggttagac atctatatac tgggatgaaa aaccatggaa    89040
aatcttactg atgcagaagc cttcagtggt acactggagg gttggttgag ggtctgcaat    89100
```

```
gtggaggaaa gcctcagcgc cctctctggg ggatccagaa ctgtgatttt tggcacgctg    89160
tgaggaggca gtgtctttag gaagggcacg gtgtctttag gaagggcaca gacccgccag    89220
ggcactggac ttaccactcc cctggttatt aaatgggtca tttcagtgtc ctagccaaaa    89280
tggatattct aacagcctgc caaatatgtg aagatttcca agccaataag cctttccagt    89340
gatttaaagt agacttttt cattgcaatc tacagtttgc agtttcttaa gaacatggcc    89400
tttgagtatg atatcctaga gaaacctaag gagactgcat tatttttcta ttgtcctggg    89460
gctgcatagc aggaggtaac caacgaatgc tgtctctccc tggcctatct cagtctttca    89520
caggctctgt tcacctcagc tttgaagtta gaaatttcta ggtgttcttg cctcttcttc    89580
tcatgaaacc tgcattggca gtgagtctac agaagaagag gaagagaatt ctgctttgtt    89640
acaattcagg actctgggca ctagaagatt ccctatctct cctccaaggg aataagttgt    89700
ttgtctctaa ccctccttga gaaacaatga gtctttgcct gcactcctaa atgtaggatg    89760
atttcctgcc caattttca aaagattaag ccttttgcct tggtatgagc aatggtctag    89820
ggaaatgcgc aagggtcttg tgtcggcccc tgactgacca ccagtcacct cctacagcct    89880
gcaccaagga atgcattgca ttctggtctt ctgccctgtg gttctcatga aaaccagcag    89940
agattcatat gatggagctg cacatgaatg taatttccaa tgtccagcat tctcctctgt    90000
tctttatctt tagatttaaa aataatgttt ctatgaactt attaaaattc tagaatacta    90060
tgaatctact gggtcttttc acatcctttt gctactagta gaaaaagaa tagtaataat    90120 tttcagaggc tactgtccag tatgtgacat aaattgtctc ccatgtttct ctgctcatgc    90180
aattactgag tatgatttat tttatttaa tttcagcacc acctgagaaa agccctgtgg    90240
tccaggattg ctaccatggt gatggacgga gttatcgagg catatcctcc accactgtca    90300
caggaaggac ctgtcaatct tggtcatcta tgataccaca ctggcatcag aggaccccag    90360
aaaactaccc aaatgcgtat gtatttgatt aaaaccataa gaggagcaac agccaactca    90420
aatattggtt agaagaccca tgctttaagc tcacttccta gggacaaatt tctcttagac    90480
tcacattttg gcaaaatgtc tcaggacctt tgcttttgag caaagagtct aagagaagag    90540
aaattttagg cctgctattt ttcctaatag ttttatggaa ggagtagaat atacggaagt    90600
ggcgaagtca tattaatgta aagctcagaa gataaatgac caaagcttaa acacagcacc    90660
attccacaat gcccactaaa aatcaatgtc atctttcact cgtgcaattc tgtcattcta    90720
aatttcaatt cccgaaggtt tgtttgccat ttttgtcatg ggtaataagt aaaaaaaaaa    90780
aaattaagat gtgtatatat atatatatat atatatatat acacacacac acacacacac    90840
aaacatctga atatttatat atatgtctga atatttatat acttgtgtat aaaacttata    90900
tttaaatttt tgcataaatt tatatatttt taatatttca ttaaaaatta tattgtttca    90960
ctatgtatgt ctgagtattt ttatatattt taatataaca ttttaaatat ttatatataa    91020
atattcaggt atgtaactga atattcattt acacacacaa atatatgtgt gcatgtgtgt    91080
atatatatat atacccatat atatatatat atatatatat acatatatat atatatatat    91140
atatgtatat atatatatat atatatatat acacacacac acacacacac atacatacag    91200
gtataaacac actgggcctg aagcaccagt ggtctgaaag gacatgtgtt gccaggactt    91260
gaagagcaaa agcaggaagg cggatgagag tcaggaggta cacaaacgct gaaaagtaaa    91320
atggacaagt acatggacaa aaagcaggta taagcataac agccttttgg aagtaaatga    91380
ctataaaata tatgaaaata ctgttttcac aagttgcaca acagatagta gtgtattgag    91440
ataatttaga acagaaaaca aatgtgatca accccataag tgtgctgtat ttcatcatgg    91500
```

```
attgaaggaa aaagagatgg agcccaagaa gaccacagca gtcttgatga actgagagac    91560
accagagttt gggattacaa aggcagctgg gattttctac acttggtaat aatgagaaag    91620
aatttgtgga gataaagagc tacagtcatg tacctagaag tcacctcagt gtaatataaa    91680
tctgcatatg cacagggagt gattccacaa tgaaagtagg acaaagaaca gctactgggg    91740
aaagaataac tacaagggaa caatgagttc aatggagatg gcagagctca caaagcactg    91800
ggggatattt gagttcttac cagctagaaa agagacctca ttgcaaatct tgggcattca    91860
gtagagaccc cagaaaagcc actctttgga aacagagttg atgtatttta agagcaaaat    91920
ctactccaca aaaatcctag caaaattgaa agcaagtca gaaagaccaa aatcctctca    91980
acataaatta gttgcccatc agaagaaagc ttaacctctt cataggtaaa caataaaatc    92040
aaattgctca gttatctggc atccacaata tgtgacataa atttaaaaat ttactagaca    92100
tacaagaagc atttagtgtg atccataacc aggagaaaaa tcattcaata caaatagacc    92160
cagaaatgac agaaatgata gaattagcaa aaacatttaa aatatacata tgatcatttg    92220
atcttgtgat cagatatcac aagagaagaa agagatactt gaacagaaaa aatgcctgaa    92280
gcaatgatgg ctgaaaactt tccaaatatg aagaaaaaaa agctcacaga ttcaagaaaa    92340
ctaatcaatc agaaatatga ttttgaaaag taaaaatgta tgatttactt tggcaaatct    92400
tcttggttaa attgtctaaa atcaaagaaa gctaggaaaa ttttataagc cagaggaaaa    92460
aagattgttt atataaagga acagttacac aaatgactga tgccttctca tcagaaacaa    92520
tgaaagtcag aaacaataaa gtaacatctt taaagtaata gaagaaaaac ccaagaggtg    92580
agggatcgtg gcagacagga ggcaggacta gattgcagct ctggacagag cagcatgcag    92640
aggctcatat tgtgaatttt agccccatat tgactgcaag aacagaccag caatcctgag    92700
aggacccaca gaccgtgtga aggaagcaga ctgctcctgc aggataaggg agacacccca    92760
aatactgtga gttccccaac tgcagaagtg gaaaagggag gccttactcc ctcaaacaca    92820
ccccacaact ggagaagctg aaagtctgtt tgcaggagaa gttcccaact ttacctgggc    92880
ctcagtaaat ttagagagct gagccaagca aaatataggg gtagaggaag cagcagagaa    92940
gacctcagag cttgctggat ccccaagcag ctcattcctg cctggcacca cagagatcca    93000
tcagaagtgt ggccaaagga acagagggta aaactccaca tggaggactg ctctacctga    93060
actttctaac aatttgaaca gggggagaag cctcctggcc agaacttggg ggagggcatg    93120
aatctggttt gcagacttca caggtggggg aaggactaaa gccctttctc ttcacagctg    93180
ggaggtggaa agcctcaggc aagttttcaa gcctgacttt cccccacct ggaaacagac    93240 ttggagctgt tgcggggttg ggggcatggt gggagtaaga ccagcccttc agtttgcatg    93300
ggtgctgggt gaggcctgtg actgacagct tccctccact tccccgacaa ctcagatgac    93360
tcagcagagg cagccataat cctcctaggt acacaactcc agtgacctgg gaacttcacc    93420
cccacaccat acagaagctt cagtaagacg tgcccaagga aagtctgagc tcagacacgc    93480
ctagtcccac ccccaactga tggtccttcc ctacccaccc tggtagcaga agacaaagag    93540
catataatct ttggagttct agggcccacc cacctctagt ccctctccac actagtatag    93600
ctgatgcagg aggccaacca gcacaaaaat agagcattaa accaccaaag ctaggaaccc    93660
ctatggagtc cattgcaccc tcctccacct ccaccagaac aggcactggt atccacagct    93720
gagagaccca tagatggttc acatcacagg actctgtaca gacagtcccc agtaccagcc    93780
cagagctggg tagacttgct aggtggcaag acccagaaga caggcaataa tcactgcagt    93840
```

```
tcagctcaca ggaagccaca tccataggaa aagagggaga gtactacatc aagggaacac    93900
cccatgggat aaaaacatct gaacaacagc cttcagccct accttccctc tgacacagtc    93960
tacccaaatg agaaggaacc agaaaaccaa ccctggtaat atgacaaaac aaggctcatc    94020
acactcccag ttcaccagca atggatccaa accaagaaga aatccctgat ttacctgaaa    94080
gagaattcag gaggttagtt attaagctaa tcagggaggg accagagaaa ggcaaagccc    94140
aatgcaagga aatccaaaaa aaaaaaggta taagaagtaa aaggtgaaat attcaacaaa    94200
atagatagct taataaaaaa acaataaaaa attcagtaga ctttggacac accttttggaa   94260 atgtgacatg ctctggaaag tctcagcaat agaactgaac aagtagaaaa aataaaattca   94320 gagctcaaag acaaggactt caaattaacc caatccaaca aagacaaaga ataaaggata    94380
agaaaatatg aacaaagcct tcaagatgtc tgggattatg ttaaatgacc aaatataaga    94440
ataatcgtgg ctcctgagga aaaagacaat actaaaagct tggaaaacat atttggggga    94500
ataactgggg aaaacttacc tggccttgct ggacacctag acatgcaaat acaagaaaca    94560
caaagaacat gtaaatacaa gcagcacaaa gaacacctgg gaaattcatc acaaaaagat    94620
cttagcctag gcacattctc atcaggttat gcaaagttaa gacgaaggca agaatcttaa    94680
gagctgtgag acagaagcac caggtaatgt ataaggaaa ccctatcaga ttaacagcca    94740
gtttttcagc aggaactgta caagctataa aggattggag ccctatcata gcctcctcaa    94800
acaaaacaat tatcagtcaa gaattttgta tccagcgaaa gtaagcatca tatatgaagg    94860
aaagatacag tcgtttttgg acaaacaaat gctaagagaa ttcaccatta ccaagtcacc    94920
actagaagaa ctgctaaaag gagctctaaa tcttgaaaca aatcctagaa acacatgaaa    94980
acagaatctc tttaaagcat aaatcacaca ggacctataa aacaaagta caagttaaaa    95040 aacaaaaaca aaaacaaaa ccaaagtacg gaggcaataa agaatatgat gaatgcagtg    95100
gcacctcaca tttcaatgct aaaattgaat ctaaatggcc taaatgctcc acttaaagga    95160
tacaaaaaga gttggtggct ggcaagatgg ctgaatagga acagctccag tctgccgctc    95220
cccgtgagat caacacatag ggtgggtcat ttctgcattt ccaaccaagg tacccggctc    95280
atctcattgg gactggttag acagtggtg cagcccacag agggtgacct gaagcagggt    95340
ggggtgtcac ctcacctggg aagtggaagg ggtcagggaa ctccctcccc tagccaaagg    95400
aagccgtgag ggactgtgcc gtgaagacca gtgcattctg gcacaaatac tatgcttttc    95460
ccacggtctt tgcaacctga agaccaggag attcccttgg gtgcctacac caccagggcc    95520
ctggatttca agcccaaaac tgggctggca tttgggcaga cactaagcta gctgcaggag    95580
ttttttttca taccccagtg gtccctggaa tgccagcaag acagaaccat tcaccccgt    95640 gaagaaaggg ctgaagccag ggagctaagt ggtctttctc agtggatccc accccatgg    95700 agcccagcaa gctaagctcc actggcttga aattcttgct gccagcacag cagtctgaag    95760
ttgacctggg acgctcaagc ttggtgggag gaggggtatc cacaaatact ggggcttgag    95820
taggaggttt tcccctcaca gtgtaagcaa aaccgctagg aagtttgaac tgggcagggt    95880
gcactgcagc ttggcaaagc cattgtagca agagtgcctc tctagattcc tcctctctgg    95940
gcagggcatc tctgaaagaa aggcagcagc cccagtcaga agcttataga taaaactccc    96000
atctccctgg gacagagcaa ctggaggaag gggtggctgt gagtgcagct ccagcagact   96060
tagtttcctg cctgccagct ctgaaaagag caccagatcc cccaacacag cactagagct   96120
ctgataaggg acagactgcc tcctcaagtg ggtcctggtt tcagaagata ataagaaact    96180
cctctgagct aaaggagcat gttctaacac aatgcaagga agctaagaac cttgaaaaag    96240
```

```
gtcagaggaa ttgctaacta cagtaagcag tttagagaag aacataaatg accttaggga   96300
gctgaaaaac acagcacgag aacttcatga cacatacaca agtatcaata gcaaaatcga   96360
tcaagtggaa gaaaggatat cagagattga aaatcaactt aatgaagtaa agcgtgaaaa   96420
caagattaag gaataaagaa tgaaaaggaa tgaacaaatc ctccaagtat gggactatgt   96480
gaaaagattg aacctacgtt tgattggtgt acctgaaagt gatgggagaa tggaaccaag   96540
ttggaaaaca ctcttcagga tattatccag gagaacttcc ccaacctagc aagacaggcc   96600
aacattcaaa ttaaggaaat acagagaata ccacattcaa attcaggaaa tacagagaac   96660
accacaaaga tactcctcaa gaagagcaac ctgaagacac ataatcgtca gattcaccaa   96720
ggttgaaatg aaggaaaaaa atgttgaggg cagccagaga gaaagtttgg gttacccaca   96780
aagggaaccc catcagacta acagtggatc ttcctgcaga aactctacaa gccagaagag   96840
agtgggaggc caatattcaa cattcttttt tactattatt atactttaag ttctagggta   96900
catgtgcaca aggtgcaggt tgttacata tgtatacatg tgccatgttg gtgtgctgca   96960
cccattaact cttcatttac attaggtata tctcctaata ctatccctcc ccactccccc   97020
catcccatga caggccccgg tgtgtgatgt tccccactct gtgtccatgt actctcattg   97080
ttcaattccc acctatgagt gagaacattc ggtgtttgga tttctgtcct tgtgatagtt   97140
tgctgagaat gatggtttcc agcttcatcc acatccctac aaaggacatg aagtcatcct   97200
tctttatggc tgcatagtat tccatggtgt atatgtgcca cattttctta atccagtcta   97260
ccattgatgg acgtttgtgt tggttccaag tctttgctat tgtgaatagt gccgcaataa   97320
acatatgtgt gcatgtgtct ttatagcagc atgatttata atcctttaga tatatatcca   97380
gtaattgtat ggctgtgtca aatggtattt ctagttctaa atccttgagg aatcaccgca   97440
ctgtcttcca caatggttga actagtttac agtcccacca ccagtgtaaa aatgttccta   97500
tttctccaca tcctctctag catctgttgt ttcctgactt tttaatgatc accattctaa   97560
ctggtatgag atggtatctc attgtggttt tgatttgcat ttctctgatg gccagtgatg   97620
gtgagcactt tttcatgtgt ctcttgactg cataaaagtt ttcttttgag aattgtctgt   97680
taatatcctt tgccaacttt ttgatggggt tgtttgattt tttttcttgt aaatttgttt   97740
atgttctttg tagattctgg atattagccc tttgtcagat gggtagattg taaaattttt   97800
ctcccattct gtagcttgcc tgttcattct gagggtagtt tcttttgctg tgcagaagct   97860
ctttagttta attagatccc attggtcaat tttggctttt gttgctattg cttttggtga   97920
tttagtcatg aagtccttgc ccatgcctat gtcctgaatg gtattgctta ggttttcttc   97980
tagggtttat atggttttag gtctaacatt taagtcttta atccatcttg aattaatttt   98040
tatataaggt gtaaggaagg gatccagttt cagctttcta catatggcta ggcagttttc   98100
ccagcaccat gtattaaata gggaaacctt tccctatttc ttgttttgt caggtttgtc   98160 atagatcaga tggttgtaga tgtgtggtat tatttctgag ggctctgttc tgttccattg   98220
gtctatatct ctgttttggt accagtacca tgctgttttg gttactgtag ccttgtaatg   98280
tagtttgaag tcaggcagag tgatgcctcc agctttgctt ttttggctta ggattgtctt   98340
ggcaatgcat gctcttttt gttccatatg aactttaaag tagttttttc caattctgtg   98400
aagaaagtca ttggtagctt gatggggatg gcattgaatc tataaattac cttaggcagt   98460
atggccattt tcacaatatt gattcttcct atccatgagc atggaatgtt cttccatttg   98520
tttgtgtcct cttttatttc attaagcagt ggtttgtagt tctccttgaa gaggtccttc   98580
```

```
ccatcccttg taagttggat tcctaggtat tttattctct ttgaagcaat tgtgaatggg    98640
agttcatcca tgtccctaca aaggacatga agtcatgtat gggaatgctt gtgattttg     98700 cacattgatt ttgtatcttg agactttgct gaagttgctt atcagcttaa ggagattttg    98760
gtctgagaag atggggtttt ctaaatatac aatcatgtca tctgcaaaca gggacaattt    98820
aacttcctct tttcctaact gaataccctt tatttccttc tcctgcctaa ttgccctggc    98880
cagaacttcc aacactatgt tgaataggag tggtgagaga gggcatccct gtcttgtgcc    98940
agttttcaaa gggaatgctt ccagttttg cccattcagt atgatattgg ctatgggttt     99000
gtcataaata gctcttatta ttttgagata tgtcccatca atacatagtt tattgagagt    99060
tcagcatgga gagctgttga attttgtcaa aggcctttc tgcatctatt gagataatca     99120
tgtggttttt gtctttggtt ctgtttatat gatggattac atttattgat ttgcatatgt    99180
tgaaccagcc ttgcatccca gggataaagc caacttgatc atggtggata agcttttga     99240 tgtgctgctg gattcggttt gccagtattt tattgaggat ttttgcatca atgttcatca    99300
tggatgttgg tctaaaattc tcattttgt tgtgtctctg ccaggatttg gtatcaggat      99360
gatgctggcc tcataaaatg agttagggag gattccctct ttttctatga ttggaatagt    99420
ttcagaagaa ttggtaccag ctcctctttg tatctgtggt agaattcggc tatgaatctc    99480
tcctggactt tttttggttg gtaggctctt aattattgcc tcaatttcag agcctgttat    99540
tggtctattc aaggattcaa tttctttctg gtttagtctt ggtagggtgt atgtgtccag    99600
gaatttttcc atttcttcta gattttctag tttatttgca cagaggtgtt tataatattc    99660
tctgatggta gtttgtattt ctgtgggatt ggtagtgata tcccctttat cattttat      99720 tgcatctatt tgattcttct ctcttttctt ctttattagt cttgctagtg gtctatcaat    99780
tttgttgatc ttttcaaaaa accagctcct ggattcattg atgttttgaa ggttttttg     99840 tgtctctatc tccttcagtt ctgctctggt cttagttatt tcttgccttc tgctagcttt    99900
ttaatgtgtt tgctcttgct tctctagttc ttttaatggt gatgttaggg tgtcaatttt    99960
agatctttcc tgcttttctct tgtgggcatt tagtgctgta aatctccccc tacacactgc  100020
tttaaatgtg tcccagagat tctggtatgt tgtgtctttg ttgtcattgg tttcaaagaa  100080
tatctttatt tctgccttca tttcgttaca tacccagtag tcactcaggt gcaggttgtt  100140
cagtttccat atagttgagc agttttaat gagtttctta atcctgagtc ctagtttgat    100200
tgcactgtgg tctgagagac agtttgttat aatttctgtt cttttacatt tgctgaggaa  100260
tgcctcactt ccaactatct ggtcaatttc agaataagtg cgatgtggtg ctgagaagaa  100320
tgtatattct gttgatttgg ggtggagagt tctgtagatg tctattaggt ctgcttggtg  100380
cagagctgag ttcaattcct ggatatccat gttaactttc tgtctcattg atctgtctaa  100440
tgttgacagt ggggtgttaa agtctcccat tattattgtg tgggagtcta agtctctttg  100500
taggtctcta aggacttgct ttatgaatct aggtgctcct gtattgggtg catatatatt  100560
taggatagtt agctcttctt gttaaattgg tcccttacc attatgtaat ggccttcttt    100620
gtctcttttg atctttgtta gtttaaagtc tgttttatca gagactagga ttgcaacccc  100680 tgctttttt gttgttttcc atttgcttgg tagatcttcc tccatccctt tatttgagc     100740 ctatgtgtgt ctctgcacgt gagatgtgtc ttcagaatac agcacactga tggatcttga  100800
ctctttatcc aattttccag tctgtgtctt ttaattggag catttagccc atttacattt  100860
aaggttaata ttttatgtg tgaatttgat cctgtcatca tgatgttcgc tggttatttt    100920
gctcattagt tgatgcagtt tcttcctagc atcgatggtt tttacaattt ggcatgtttg  100980
```

```
tgcagtggct gataccgatt gtttctttcc atgtttagtg cttccttcag gagctcttgt   101040
aaggcaggcc tggtggtgac aaaatctctc agcatttgct tgtctgtaaa ggattttatt   101100
tctccttcac ttatgaagct tagtttggct ggatatgata ttctcagttg aaaattcttt   101160
tctttaagaa tgttgaatat tggctgccac tctcttctgg cttgtagagt ttctgctgag   101220
agatctgctg ttagtctgat gggcttccct ttgtgggtaa cccgaccttt ctggtgaatc   101280
tgacaattat gtgtcttgga gttactcttc tcgaggagta tttttgtggc attctctgta   101340
tttcctgaat ttgaatgttg gcctgccttt gtaggttggg gaagttctcc tggataatat   101400
cctgaagagt gttttccaac ttggttccat tctcctcgtc actttcaggt acaccaagca   101460
gatgtagatt tggtcttttc acatagtccc atatttattg gaggctttgt tcatttcttt   101520
ttactccttt ttttctctaa acttctcttc tcgcttcatt tcattcattt gatctttaat   101580
cactgatacc ctttcttcca cttgattgaa tcaactactg aaacttgttc atgtgtcacg   101640
tagttctcgt gccatggttt tcagctccat tagatcattt aaggtcttct ctatgctgtt   101700
tattttagtc tgccattcat ctaaactttt tcaaggtttt tagcttcttt gcaatgggtt   101760
cgaacatcct tctttagctc ggagaaattt gttattacag atcgtctgaa gccttcttct   101820
ctcaactcat caaagtcatt ctctgtccag ctttgttctg ttgctcgtga ggagctgcgt   101880
tccttcggag gagaagaggc accctgattt ttagaatttt cagctgttct gctctggttt   101940
ctccccatct ttgtggttta tctacctttg gttcttgatg atggtgatgt acagatgggg   102000
ttttggtgtg gatgtctttt ctgtttgtta gttttccttc taacagtcag gaccctcagc   102060
tgcaggtctg ttggagtttg ctggaggtcc actccagtcc ctgtttgcct gggtattacc   102120
agtggaggct gcagaacagc aaatattaca gaacagcaaa tgttgctgcc tgattcttcc   102180 tctgaagct tcatctcaga ggggcaccca gctgtatgag gtgtcagttg gcccctactg   102240
ggaggtgtcc cccagttagg ctactcgggg gtcacggacc cacttgagga ggcagtctgt   102300
ccattctcag atctcaaact ctctgctggg agaaccacta ctctcttcaa agctgtcaga   102360
cagggatgtt taagtctgca gaagtttctg ctgccttttg ttcagctatg ccctgccccc   102420
agaggtggag tctacagagg caggcaggtc tccttgagct gtggtgggct ccacccagtt   102480
tgagcttcct ggtcgctttg tttacctact caagtctcag caatggcaga cgcccctccc   102540
ccagctttgc tgccgccttg cagttcggtc tcagactact gtgctagcag ttcaatctca   102600
gactgctgta ctagcagtga gcaaggctct gtgggcatgg gaccctctga gccatgtgca   102660
ggatataatc tcctggtgtg ccgtttgcta agaccattgg aaaagtgcaa tattagggtg   102720
ggagtgtccc gattttccgg gtacatctgt catggcttcc cttggctagg aaagggaatt   102780
ccctgacccc ttacacttcc cgggtgaggc aatatcccgc cttgcttcgg ctcactctcc   102840
gtgggctgca cccactgtct gacaagcccc ggtgagatga acccagtacc tcagctggaa   102900
atgcagaaac cacccatctt ctgctttgct catgctggga actgtggact ggagctgttc   102960
ctattcggcc atcttgaaac ctcccctctc tcacgatcac aaggtcccac aataggccgt   103020
ctgcaggctg aggagcaaga aaagccagtc tgaattccaa aactgaagaa attggagtct   103080
gatgttcaag ggcaggaaac atccagtgcc aaagaaagat gtagaatatt caacattctt   103140
aaagaaaata attttcaacc tagaatttca tatccagcca aactaagctt tataacaaag   103200
gagaagtaaa atcctttaca aacaagcaaa tgctgaggaa ttttgtcaac accaggcctg   103260
ccttacaaga ggtcctgaag aaaacactaa atatggaaag gaaaaaccag taacagctac   103320
```

```
tgcaaaaaca taccaaattg taaacaccat caacactata aagaaactgc atcaactaat 103380
gggcaaaata gccagctagc atcataatga caggatcaaa ttcacacata acaatattaa 103440
ccttaaatgt aaatgggcta aatgcccccaa ttaaaagaca cagactggga aattgaataa 103500
agagtcaaga cccattggtt tgctgtgttc agaagaccca tctcagggtg aaagacata 103560
catgggctca aaataaagaa atgaaggaat atttaccaag caaatggaaa gaaaaaaaaa 103620
gcagcggttg caatcttagt cttttgatgaa acagacttta aaccatcaaa gatcaaaaga 103680
gacaaaggag ggcattacct aatggtaaaa gtatcaatgc aacaagaaga tctgactgtc 103740
ctacttatat atgcacccaa tacaggagca cccagattaa taaagcaagt tcttagagac 103800
ctacaaagag acttagactt ccacacaaaa atagtgggag actttaacac cccacagcca 103860
atattagatc gacgtgacag aaaattaaca aggatattca ggacgtgaat tcagctctgg 103920
accaagctga cctaatagac atctacagaa ctcgacacca caaatcaaca gaatatacat 103980
tcttctcagc accacattgc acttattcta aaattgacca cataattgga agtaaaacac 104040
ttctcagcaa atgccgtaga atggaaatca taacaaacag tctctcagac caaagtgcaa 104100
tcaaactaga actcaggatt aataaactca ctcaaaacca cacaactata tggaaactga 104160
acaacctgct cctgaattac tactgggtaa ataacaaaat taaggcagaa gtagataagt 104220
tcttagaaac caaagagaac aaagacacaa tgtgccagaa tctctggtac acagctaaag 104280
ccatgtttag agggaaattt atagcactaa atgcccacag gagaaagcgg gaaagatcta 104340
aaatcaacac cctaacatca caattcaaag accagagaa gcaagagcaa acaaatacaa 104400
aagctagcag aagacaagaa ataactaaga tcagagcaga actgaagggg ataaagacac 104460
gaaaacccctt taaaaaatta ataaatccaa gagctggttt tttgaaaaga ttaacaaaat 104520
acatagaagc ctagccagac taataaagaa gaaaatagag aagaatcaaa tagacacaat 104580
aaagaataat aaaggggata tcaccaatga tgccacagaa atacaaacta ccatcagaga 104640
atactttaaa cacctctatg caaataaaat agaaaatcta aaagaaatgg ataaattcct 104700
ggacacatac accctcccaa gactaaacca ggaagaagtc aaatccctga atagaccaat 104760
aacaagttct gaaatcgagg cagtaattaa tagcttacca accaaaaaaa gcccagacca 104820
gagggattaa cagtcaaatc ctaacagagg tacaaagaag agctagtact attccttctg 104880
aaactattcc acacaataga aaagaggga ctcctgccta actcattta tgaggccagc 104940
atcattctga taccaaaacc tggcagagac acaacaagaa aagaaaattt caggccaaca 105000
tccctgatga acatcaatgt gaaaatcctc aataaaatac tggcaaactg aatccagcag 105060
cacatcaaaa agcttatcca ccatgatcaa gttggcttca tccctgggat gcaaggctgg 105120
ttcaacatat tcaaatcaat aaacataatc catcacataa acagaaccaa tgacaaaaac 105180
cgtatgatta tcgcaataga cgcagaaaag gcctttgata aaattcaata cccaatcatg 105240
ctaaaaactc ttaataaact aggtattgat ggagcatgtc tcaaaataat aagagctact 105300
tatgacaaat gcatagccaa tatcatactg aatgagcaga gctggaagc attccctttg 105360
aaaaccagca caagacaagg atgccctctc tcaccactcc tattcaacat agtattggaa 105420
attctgtcca gggcaatcag gcaagagaaa gaaataaagg tattcaagtg ggaagagagg 105480
gagtcaaatt atttctcttt gcagatgaca tgattgtata tttagaaaac tctatcatct 105540
cagcccaaaa tctccttaag ctgataagca acttcagcaa agtctcagga tacaaaatca 105600
atgtgcaaaa atcacaagca ttcctataca ccaataagag acacagagcc aaatcctgag 105660
tgaattccca ttcacaattg ctacaaagag aataaaatat acctaggaat ccaacttaca 105720
```

```
agggatgtga aggacctctt caaggagaac tacaaaccac tgctcaagga aataagatag  105780
gacacaaaca aatggaaaaa cattccatgc taatggattg gaagaatcaa tattgtgaaa  105840
attgccatac tgcccaaagt gatttataga ttcaatgtta tccccatcaa gctaccattg  105900
atttcttcac ataattagaa aaaactactt tcaatttcat atggaataga aaagggcct   105960 gtatatccaa gacaacctaa gcaaaagaa caaagctgga ggcatcatgc tatctgactt   106020
caaaatatac tacaaggcta cagtaacaaa aacagcatgg tatggtactg gtaccaaaac  106080
agatatatag accaatagaa cagaacagag gcctcagaaa taacaccaca catctacaac  106140
tattggatct ttgacaaact ggacaaaaat aagcaatggg gaaggattc cctatttaat   106200 aaatggtgtt gggaaaactg gctagccata tgcagaaaac tgaaactgga tcccttcctt  106260 acacttata cacaaattaa ctcaagatag attaaagaat taaatgtaag acctaaaacc   106320 ataaaaccc tagaagacac tttgggaggc cgaggtggat ggatcacgag gtcaggagat   106380
cgagaccatc ttggctaaca cagtgaaagc ccatctctac taaaaataca aaaaattagc  106440
tgggtgtggt cgtgggcacc tgtagtccca gctacttggg aggctgaggc aggagaatgg  106500
catgagctga ggaggttgag cttgcagcaa gccaagattg tgccactgca ctccagcctg  106560
ggcaacagag tgagactcca tcaaaaaaac aaaaacaaaa acaaaaaatc aaaccctaga  106620
agaaaacata ggcaatacca ttcaggacat aggcatggga gaagacttca tgactaaaac  106680
agcaaaacca atggcaacaa agccaaaat ttacaaatca gatctaatta aataaagag    106740 cttctgcaca gcaaaaaact ctcatcagag tgaaaaagca acctatggag aaaaattctg  106800
tggtctagcc atctgacaaa gggctaatgt ttagaatgta caagcaactt aaacaaatgt  106860
acaagaaaaa aaaacaacc ccatcaaaaa gtgggcaaag gatatgaaca gacacttctg   106920
acaggaagac ctttatgtgg ctgacaaaca tgaaaaaagc tcatcatcac tgttaattag  106980
agaaatgcaa atcgaaacca caatgagata ccatctcatg cccgttagaa tggcgatcat  107040
taaaaagtca ggaaacaaca gatgctgaag aggatgtgtg gagaaagagg aacacattta  107100
cactgttggt gggagtgtaa attagttcaa ccattgtgga agacagtgcg gtgattcctc   107160
aaggatctag aaccagaagt accatttgac ccagcaatcc cattactggg tatatacca   107220 aaggattata aatcattcta caataaagac acatgcacac gtatgtttat tgtagcacta  107280
ttcacaatag caaagacttg gaaccaactg aaatgcccat caatgataga ctggataaag  107340
aaaatgtggc acatatacac tgtggaatac tatgcagcca taaaacagga tgagttcatg  107400
tcttttgcag ggacatggat gaagctgaa accatcattc tcagcaaaact aacacaagaa  107460 cagaaaacca acaccatat gttctcactc ataagtgtga gttgaacaat gagaacacat   107520
ggacacagga agggaacat cacacacagg ggcctgttgg ggagttgagg ctagggagg     107580 gattggatta ggagaaatac ctaatgtaga tgatgggttg ctgggtgcag caaaccacca  107640
tgacacgtgt ataccctatgt aacaaaccca cacattctac acatgtatct cagaacttaa  107700
agtataataa taataagata cagaactgca gaatgaataa gaactcacca accatctgct  107760
gccttcagga gactcatta agacataagg actcacataa acttaaagta aatgggtgga   107820
aataataata agtggtgtca ctgatgtgga ggtagattat aaaactctta tcatatgctg  107880
gtggaagatc aaaatgataa aacgaattaa aaaatcagtc agatggtttc ttaaaaagtt  107940
ccatcaatat gcctctatct tacaaacctg caattctatt cctgaatctt tatcccaagg  108000
aaatgaaaaa gtaagtccac aaagagttct atatgaatat ttataggagc tttatttatt  108060
```

```
ataattcaaa ctgtaaaaat aatttcaatg ttcatcaata acaaaatgaa aaataatttt   108120
gcaacctact ggtacacttg aatactattc agcactgagt atcttaaata gcatggatgg   108180
agctcaaaaa tatactcagg aaagaagcca tgtatattct gtatgagttc atttacatga   108240
gatcatttac atttcctcca aaagaggaaa aactaatttc tgttgaaaga aaccaatgta   108300
tttgcctctg gcagtggtaa gggggtagca cagattaatt gggtagggac tcaagagagt   108360
ttctggggtc acagaaatgt tccgtgtggt gatgggagtt tgggctccac aggtataggt   108420
gttgatccaa aatcatcaaa aaacaacat tgcagatctg tgcatctcac tctgtgggaa   108480
agtatatctc aactgtaaaa agggcagaaa ttgcttttaa acgctcagcc ttttagcaca   108540
tccagttgct tggagaacca gcttactcaa atggggtct aggctggaga ctaggtcaca   108600
ggcatagagt ctctaaactt tcccatggca cataatacgt ttcaggtttt ctcagagagc   108660
tgcaggttag taatctgagg attctgacaa gttgggtcaa cgttcctagg aggcatgaat   108720
gggagtgcat tctctaagat ccctccaccc cagggtcctt gctttctgtg cctcttactc   108780
cattgttttc tgactcctct gtagccactc gacctcttca gatcccattg tctacccagc   108840
catcgccctt tatgacttgg gtcccactgt tctttcatct catcctccat tccctcagtt   108900
tcggagtggc tgccgctagc agaggatgga ctgagagcag gagaggtggt cctgcccagg   108960
aacccatcct agagaaatgg catcctgtct gggagctagt ttttagggc aggttttata   109020 agtcttgtaa agccagacac acttgatcta cctggtatgt tatttacagt aatactattt   109080
tcataattgc ttttcactct aaaagtagag cctttagct acactgtgag taaataaagg   109140
ggctggcctg ggaatggtat catgttggat gttgtttctt ccctgaagta atatatatca   109200
gttacaattt acatgttact gcagagtcct agagagagac acagagaatg agacagatac   109260
caatacattt ttatgtgcat taaaaaaatc taaggccagg cgcagtggct cacacctgta   109320
atcccagcac tttgggaggc cgaggtgggt ggatcacgag gtcaggagat tgagaccatc   109380
ctggctaaca cggtgaaacc ctgtctctac taaaaataca aaaaattagc caggcgtggt   109440
ggcgggcgcc tgtagtccca gctactcagg agactgaggc aggagaatgg cttgaaccca   109500
ggaggcagac cttgcagtga gccgagattg cgccactgca ctccagtctg ggcgacagag   109560
cgagactccg tcacaaaaaa aaaaaaaat ctaaatgca ctcttcaaaa tctatgtcat   109620
ttattctgga ggaatgcagt tggcagaagg aggaagatat tccgaatttt tcttgtatac   109680
atttatgtat gatctcagtt tttttatgga tcatagacca attttgatat tttaaaataa   109740
aaattataat ctatcttgga aatttacatg gttctttaga acttgaggac cgttttgct   109800 tttcggaata ttattgtacc taaaatggga atattacaac gtcactttt aacactttgt   109860 tataacaaag tttagacagc gctgggtgcc cctgaatttt ttcccgcctc ttgtgacctg   109920
tgttgttttg gaatttgcag tggcctgacc gagaactact gcaggaatcc agattctggg   109980
aaacaaccct ggtgttacac aaccgatccg tgtgtgaggt gggagtactg caatctgaca   110040
caatgctcag aaacagaatc aggtgtccta gagactccca ctgttgttcc agttccaagc   110100
atggaggctc attctgaagc aggtaagaag tctgtggcca gatatctaca catttgaaca   110160
ttgggatgaa aagagatgga aaatctgact gatgcagaag ccttccatgc tacacagaaa   110220
cttgagggta tggcaggtgg aaagaagcct cagcactctc tctggtggag caattttgg   110280 cgcaacgtgc gtgggcggtg acttcaggaa tggtgcaaac ccacctgggc acttgactta   110340
ccactcactt tgttatgaaa ggggttatct cggtgttcca gacaaaattc caattctaac   110400
atcaggccaa atttgtgcca aatttcacac tagtgagtgt ttccaggcat ttattaaaat   110460
```

```
ggacagtgtt cattgcaatc ttcagcattg cagttgctga ggtatgtggc cgctgagttt   110520
gtcatcctgg ggaaacctaa tatgatgata tttattccat ctaatcctgg ggctatttgg   110580
cagtaaatac cacagaatac actatttctc tggcttattt cagtcttagg taggctctgc   110640
acacctatgc ttggaaggca ggaatttctt ggtgttcttg tgccttcttc tcatggaacg   110700
tgcatctttg gtgtgtgttg agaggaaggg tagtagactt ctgctttgtt gcaatgcagg   110760
atgctggaac aagaggattc cctgtctcta ctgtaaggga ataagatttt agcctccatc   110820
cttctctaag aagcaatgtg tctttgcctc caagtactag atgcaggacc atgaactgcc   110880
ccgtccacca gaagcttaag gctttggctt ttcaggagca atcatctagg gaactgtgca   110940
gggttttcat gtctgtcccc tactgacagc caatcaccat acagcctgca taacctaatc   111000
catcatcgtc tggtttcctg cctcattgtt ttcatgaaca accagtagag agccatacga   111060
aagagcttgc acatgagtct ttgttccaat tgtaagagca ctgataggtc cttttcccac   111120
caggttttga atataaaatt tctaagaact tattaaaata ttagaatgtt attaatctat   111180
tgttttgct tcagcatgtc cttctgcttg tgagtatact aaagagaaca gtcataattc   111240
tgaaactact gtcctgtttg tgtcataaat tgcttcacat gtttctgcat actagtagtt   111300
actcagcttg attttgtcta ttttcagcac caactgagca aacccctgtg gtccggcagt   111360
gctaccatgg taatgccag agttatcgag gcacattctc caccactgtc acaggaagga    111420
catgtcaatc ttggtcatcc atgacaccac accggcatca gaggaccca gaaaactacc    111480
caaatgagta tgtctttgat gttacttgta agaggagcaa cagccaactt aagttcctcc   111540
tagaagagcc ttgcttcaag ctaacttgtt aggacaaatt tcccttagac ccagaaggtg   111600
tgtcaaaatg tccagacaac tttgcttttg atcaaagagt ctgagagaat aggtatttta   111660
ggcttgctat cttttctaat agtctgatgg aagcagaagg ctacatggag ctgatgaggt   111720
cttttaata taaagctcaa gagatcaaat gatcaaatac ttagagtgcc attctacaag   111780
gctcataaaa gatcaatgca ctcttttcacc catgcaattc tatcattcta acctcccttc   111840
tctgaaatga aggcttttg ccattttgt catgggtcac aagtaaataa ttcacatgta    111900
tatgagtata tatataacca ggtgtgttta ttcagactag tatgtatata tacatata    111960
tatgttcata taagttagta ttcatatata tgttcatata tatgttca tacagactag    112020
tattcatata tatacata tatatataca cacacatata tatatata tatatgttct      112080
agggaaacat gcaaggtttt tatgtctgtc cctgactgat gaccaaatac cctatagcct   112140
gcacagctgc aagctgtata gccatacaat ttgcaggaca cacacacata cacacacaca   112200
cacacacaca cacacactaa catataatat aatataatat aatataatat aatataatat   112260
aatataatat aattaatata tataaacctg tgtgaacaca ctgggttcta agctccagtt   112320
ttctgaaggg atatgggttg ccaggagagg aagagcaaaa gcaagaatgt agatgagaat   112380
taggaagtaa acagatatgg agattaaaat gggcaggtac atggacaaaa aaccaggtct   112440
gacaaaaact ggctttctgc cataaatgac tataaaagat attaaaaaac actttccaca   112500
tgttggacaa gagacagtac aggactgaga taatttagaa aaggaaatga atgagcgcaa   112560
ctccgtaact attatgactt tcttcctgga gaaccttcct ggactgaagg gcaaggaatt   112620
ggagccaaag ccaaccacag cagtcttgct gaactgagga aagagactgg agtttgggat   112680
agctaagaaa atgtgtattt tctatgctag gtaataatga gaaagaattt gtggtgaaaa   112740
ggagctgaag gaatatgcat ggaagtctaa tataaactgc atatgcacag ggagaaattc   112800
```

```
tacaaagtgg gacagagaac cactactggg gaaaggacaa attcagggaa acagtgagct  112860
caatggtgac gccagagctc acgtagcact gggggatacc ggggttctga tcagcccgag  112920
gagagacacc tcattgaaca tctcgggcat tcagtagaga ccccagaaaa gtcatacttt  112980
aggagtagga tttatgcctt cttagaataa agactacccc agaaacaccc tagtaaagct  113040
taaaaaccaa gtctaaaagg acccaaatga tctccaagta aattaactgc ctgacagaag  113100
aaaactcaac catcactgga ggtaaataac atgattacag tgctctgtaa tgttgcattc  113160
acaaggagtg acatcattta aaaatttatg aggcaggaaa aagcaattag tgtgatccat  113220
aactaggaga aaaaccagtc aatacaaata gaccaagaaa tagtagaaac gatggaattg  113280
acaaagaaat taaaactgta tatatgataa ttgtgttcaa agatttaaag aaaacatgaa  113340
catgagggaa acaaatgcag aatataaaaa aaagcaaatg cgtaaaacaa ccaaatggaa  113400
attaaagaac tacaaaaaag tataaccttaa ataaaatact cactggatgg ccttaatatt  113460
agtttataca ttacagaaga aaaagtgaac cagaagataa ctcaatgaaa gccatacaat  113520
ctgtaagaca cacacacacg cacacgcgcg cgcgcgcaca cacacacaca cacagagaga  113580
gagagagaga gaaagagaga gagagaaagg ctgaaaaaaa taaatagaac cttaaggata  113640
tcagtgaaaa tagcaaaaga tttaatatat gggtaaagca agtcacagaa ggacgggaag  113700
gagatattgg gacagaaaaa aatactcaaa gcaatgatgg ctgaagactt tacacgtatg  113760
aagaaaatga taaactcaca gtcaagaagc tcaatgaatc agaaatagta ttttttaaaag  113820
caaaactcta tgatttactt gggtacatta tagataaatc gtccaacatc aaagataaca  113880
aggataatct tataagccag aggaaaaacaa tatcatttac atagagggac agtaatgaaa  113940
gtgaccgatg ccttctcctt ggaaacaatg gcataacatc tttaaagtga taaagagaaa  114000
taaaaacaga tcaacctagg acgacatgtc cagccaaaac aaacaaataa acaaaaaaac  114060
cctttaaaat aaacgtgatg taaatacgta ttctgccacc tccagaggaa acaagcaaaa  114120
aaacaaaaga atgtttccaa ggcaggcttc tgtattaaaa gattttaagg aaagttattc  114180
aggtagaaga aaaataatac cagatgggaa ctttaatcca tactaagtaa tgaagagccc  114240
tggaaatggc aaatggcaat gtcaatataa aatactctta tttatctaat ttttaaatgt  114300
atttaaagga caatttgtga tattaattaa aataatagga atatattgtt gtttcaacgt  114360
atgtagtagt aaaattcata aaaacagtag cacaaataat gcagatgata actgaagta  114420
tactgttaat gagttttttg cattatccat gaagttatat aatattaata gatggttgaa  114480
tgtgatagtt taaggtggga tattataaat cctaggacaa ccaaaaaaat ttaaactgag  114540
aggaatggat agtaagagga atagtccttt tatgcaaaag aaggaagaaa aagaggaata  114600
aagaatataa aagatatggt gtaaacagaa aatacatagc attattgtag acacaaactg  114660
aactaccttg tgagtatatt aaatataaaa ggattaagca ttacaaataa aaggcagaga  114720
ttgtaaattg aataaaaacc acagctaagt gtgttctttt tagaataaat actctttaag  114780
tgtaaagatc tactttaaac accaaaatat gaaaaaggat atataccatg aaaacctgaa  114840
tcataaataa gctggagtgg tgattaatgg atgcaggcac tcctaaagac taataagtga  114900
atgtggtcaa attgaagaaa caaaagtata tacgtgctca atgtgcaaaa acttttttctg  114960
tatacatgct atgatccttt ggaaaattaa agttttaaag caatatcact gacaatagta  115020
tcaaaaccaa aaaatattta gtgataaatt tcacacacta tgctcaagga ctatacacct  115080
tgcactagaa aacaatgttg aggaaagaat taaaagatct aaatatacac catgcttata  115140
gattaaaaga ctccatatca gttctcgtga aattgatctt tggatgaaac ccacacccaa  115200
```

```
gcactattgc aacagtcctt ttttggaaaa aaaaattgga ggacttatat accttaatat    115260
aaagacttat aaaagtacag gaatcaagac atgtggtatt ggcctggccc cttggctcat    115320
gcctgttacc ccaacatttt gggaggctga gtctggagga tggcttgagc ccagatgttc    115380
aagaccagcc ttagcaacag agtgagaccc tctctctaca aaaataaac aattagatcg     115440 atgtgatgac ttgcacatgt agtttcagct actcggaatg ctgaggtgag aggattgctt    115500
gactcaggag gtctagccat gagtgagcat tgatcatgcc tctgcattcc agcctggatg    115560
atggaatgag acactgtctc aaaaaaaaaa aaaaaaaagg atatgtgtta ttggccaaaa    115620
aagtatgcaa acctaaaaag ggatggccca ccaccagacc cacatacata tatggtaaat    115680
ggattttccg tatagatggc aaagcaattc aatggagaca aaaatgtttt acaaaatcat    115740
tctgaaccat ttggatatcc atgatacaaa acaaaagcag aacttgactt ttgcttttca    115800
tctcaaatta ttttgatatc tcttccacct aagtgtcaga gctaaaactg aacctgaaat    115860
atgaaagttc catgaaaaaa tataaaatct tcacaaccct ggagaaggca aacttttttg    115920
aggcaggagt ctgtaaacac tcactataaa ataaaacaaa ttataatgtg gctttcatg    115980 aaaactcatg cttaccaaaa gtcattgtta agaaaataaa taggcaagta acacatgaga    116040
agaaaaatgc tctctgtcca tatatctgac aaatggcttg tgtccagaat ataggaacat    116100
ttctcccact cactaaacag aggacaaaca actaatgggc aacagattga ataggcattt    116160
cttggggata gatagatgta cacatagcca ataagcacct gaaaaaatgt ccagtatctc    116220
agccatgaaa aataaagagt tataatcatc atgagatgtc accaaacacc caatggacat    116280
ggatattatt aagaagacac cacagtaact gatgtcactg atgtagagca aggatgtgaa    116340
actctctcat atgctggtga aagtgcaaaa tgatacaacc acttttgaaa tcagtctgat    116400
agtttctcca aaagttcaat aaatgcactt ttaccctaca aacctgcaat cctgtttgtg    116460
aatatttacc ccacagaaat ggaaacataa gtccacgaag acatctccaa gaatattcat    116520 agcagctta ttttttataa ccccaaactg tagacaattt caatgtcaat caataagaaa     116580
atgaataaat aatttgtgaa ctagtcatac aatggcatac tgttcagcaa taaagggag    116640 catgttttg atactctcaa atagtatgga agatgctcaa aaatattaca ttaaagaaag     116700
atgccagata acaaaaatga acattatgta tgagtctatt gatgtaaggt tccagaaagg    116760
taaaactaat ttctggtgaa agaaaccaat atcatttgcc tctggccatg ggaagagagt    116820
agcagagatt gattgagcag taaaacgaag ttttttttctg gggtgatgta aatgtcctgt    116880
attgtgattg aagtgtgagt tacacaagtg tacatgttca tcagaagtca tcaaactaca    116940
tctaagatct gtgcatttga ctatacatga aaatatacct cagttgaaaa tagatcaata   117000
acctccctca tatactatac ttgctaacac agccagctgc ttggagaacc agcttgctgg    117060
aatggagaat ctgggcttga gactgggtca catgtataga gtctctacag agacaatgtt    117120
gcattcccac ggtacataat acatttcaag gtttctcaga cagccacatg tcatgaatgt    117180
gaggattctg agaggttgga gcaacattcc tgggaggaac gaagggagc acattctcca     117240 agatcccca ccaccggggt cctcaccggc tgtgctttt ttttttttt tcttgacaga       117300 gtctcgctct gtcgccaggc aggagtgtaa tgcccaatc tcggctgatt gcagcctcca    117360
actccagggt tcaagagatt ctcctgcctc agcttcatga gtagctggga ctacagatgt    117420
gcgccactgc gcccagctaa ttttttgtatt tttagtagag acggggtttt gccatgttgg    117480
ccaagatggt ctcgctctgt tgacctcgtg atccacccgc cttggcttcc caaagtgctg     117540
```

-continued

```
ggattacagg cgtgagccaa agcacccagc ctgtgcctct cacttactca attgtttttc 117600
tgaaccctcc atagctggtg gacctttca gatcccatag tctagccagc cctctcactt 117660
tatgccttgg gtcccactgt tccttcatct catccccctt ctgtcagtcc cgcagtggct 117720
gtggccagta gaggatggac tgagagtagg agaggaggtt ctgcccagga acccatccta 117780
gagaaacagc atcctgcctg ggacctagtc ttccaggtca gcttttataa gtcttttaga 117840
ctcaaactca cttgacccac ctgaagtggt attgacaata atgctatttt catggttgtt 117900
tttcactgta aatgcagagc cttttagcta cacgactagt acagagagta agggaggctg 117960
gcctgggaat gatatcatct tggatggcat ttcctccttg gagaaatata tgttagttcc 118020
aactcacatg ttactataca gtcctgtaga aagagataca gagagttaga caggtataga 118080
cgcatttgta tatgcataac aatctataag acacacatca aaatccgtat accggttcct 118140
ctagggtat gtgcttggca gaaggtagaa ggagggtatt ctggttcctt tcttttgcac 118200
atttatgtat gatctcagtt tttatatgga gcattgatag ggtttggcta tgtcccacc 118260
caaaatctca tcttgacttg taatctctat aatcctgata atccccatgt gtcaaggca 118320
ggaccaggtg gaggtaactg gatcatgggg gcagtttctc ccaggctgtt ctcatgacag 118380
tgagagagtc tcctgagatc tgatggtttt gtaagtgtct ggcatttccc ctacttgcac 118440
ttactctgtc ctgccgcctg tgaagaaggt gcctgtttct cccttgcctt ctgccatgac 118500
tgtaaatttc cagaggcctc cccagcaatg tggaactgtg agtcaattaa aactcttttc 118560
tttgtaactt acccagtctg tctcgggtat ttcctcatag caatgtgaga acgggctaat 118620
acaagcatat actactttg atattttaaa ataaaaatta tcatctatct ttgaaaggca 118680
tgcacaaatg ggaagttgag gaacatttgt gttgtggcaa ttgtatgata cctttaatgg 118740
gaatatttca aagacacttg ttaagacttt gttagaacaa aatgtagagg gtgctggatg 118800
tccctgaata ttcttccgcc tcctgtaact tgtattgctt tggaatttcc agtggcctga 118860
caatgaacta ctgcaggaat ccagatgccg atacaggccc ttggtgtttt accatggacc 118920
ccagcatcag gtgggagtac tgcaacctga cgcgatgctc agacacagaa gggactgtgg 118980
tcgctcctcc gactgtcatc caggttccaa gcctagggcc tccttctgaa caaggtaaga 119040
agtctgtgtc ttaccttgtc tagcacatac ctctctatgt gcttggacaa cgggatgaaa 119100
agacatgaaa aaccacactg atgcagaagc ctttagtgct acacgggagc tcgagtgttg 119160
gttgaggttc tgccatgacc aaggaagtct cagtgccgtc cctgggaaag ccagagctgt 119220
gattttggc acaacttgtg ggagtagtga ctttaggact ggcgcaaaac ctccagggtg 119280
ctcaacttaa ccactcacct tattctaaaa tgggttattt cagtgtccca gtcaaattcc 119340
tattctaaca tgctgtcaac tgtgtgatta tttccaagcc aataagcatt tccagtaatt 119400
tcttaaaata gtgttcattg cagtcttcag cgttgtggct cctgagggat gtggcccctg 119460
attctgtcgt cctagagaag cctgacatga ctgcattgat tctgtatcgt cctgggtcta 119520
tgtggctgcc tggctgtctg taatcatctg tttattttt attttttct acagactgta 119580
tgtttgggaa tgggaaagga taccggggca agaaggcaac cactgttact gggacgccat 119640
gccaggaatg ggctgcccag gagccccata gacacagcac gttcattcca gggacaaata 119700
aatgggcagg tctggaaaaa aatgtaagcc actttgattt ggactctttt tccctttgct 119760
gacaaatctt ttcaaacaga agaggggcag aggaaaatac tggaaagact tcaggaggct 119820
aagcgtaatt agccttagca tggaaagtgc aagcagcaca ggccagcaaa gccccacgcg 119880
tgtgggggtt ctcaggcctc ttctcttttg acatttcttt actgtttcca ttgttgggtg 119940
```

```
ctgtttctcg tttctagtgc ttgtcctcta agccaggggt ccccactcca gtactggtac    120000
tggtactggt actggaactg gtaattatct gtggcctgtt aggaactggg ctgcacagca    120060
ggaggtgagc ttcggggggag caaacaaagc ttcatctgta ttttctgctg cttcccatca    120120
ctctcatagc tgcctgagct ctgccagctg tcagatcaga ggcagcatta gattatcata    120180
gcacaaaccc tattgtgaac tgcacatgtg aggaatctag attgcatgct ccttatgaga    120240
atctaatgcc tgatgatctg tcatgcttcc atcaccccca gatgggacca cctacttgca    120300
ggaaaattag ctcagggctc ccactgattt taccttatgg tgagatgcac atttatttca    120360
ttatatatta caatgtaata ataattgaaa taaagtgcac gataaatgga aggtacttga    120420
gtcatccttt aaccatcgcc ccctcacccc aggtgcacag aaaaattgcc ttttatgaaa    120480
ctggtctctg gtgccaaaaa agttggggaa ccacactgct ctgggttcta gtagtcagag    120540
atgccctcta tgaggcttaa gtcagatttt tctagaaaag atttggatgg ccatcaggt     120600 caccatgaga cttcccttag cctcatgcat tctctgtgat ggtttacttt ggggcctatg    120660
aatagggaag actgagatat aggaaaaacc aaagtgtctg tgttccccca ctctcacacc    120720
catgtaacat aacacttctc acaccagata tgggggggatt tctcctcaca ccccaagcga    120780
gtctccagca gataccagct gggtgtccta caatgtaact cggtcctgac actctatctg    120840
gagacagtgt cagatcccac aagttaaggc tcagtcctac aagactgccc cactgcagat    120900
gccaatccca agttgcaggc tgtgacctgt acttctgccc agctggataa agatctgttt    120960
ttctatatga ccctccatgg gtttgattac tttgctagag tggctcacag aactcaggga    121020
aacacgttac ttttatttac ccatttatta taaaagatat taaaaggat cctggtgaac     121080 agccaggtgg aagagatgca cagggcaagg cacgtgggaa ggggctcaga gcctctatgc    121140
cctctccagt gcaccagtcc ccagtaccct aagtgttcag caacccagaa gctctccaag    121200
tgcagtcttg ttgggttttt atggaggctt cattacagag gcacagttga ttacatcatt    121260
ggccatcggt gatcggctca ccttcggccc ctcttccctc cctggaggtt ggagggtggg    121320
gctgaacagt tccaaccctc aagtcacatg gttggttccc ttggcaacca gccctgggg    121380 ctatccagga acccaccaag agttgcttca ttgcagctcc cttcacccag gaaactccaa    121440
gggatttagg agctctgtgt taagaactgg ggggcagaga cccaatatac atttcttatt    121500
ctatcacaat atcacaggaa gctaaggatg atactgcctt tgtgtgtctt ggctgtggat    121560
ggtgcataat gcatggaagt aagcatttct gaatcaacag caaacaggct ttatcaggta    121620
gaagacccct cagcgcccca gggacaaagc tcatcaatga tgtcccactg tcctctgagg    121680
ctctagctct aagacctcca gtgggtcaag ctcctggaga agtggcacat tctccaaaga    121740
cccttcaggg tcaccacacc ctggttaagg gtgtggcctc ataactcctt ttgactatga    121800
ctgatggctt acagcataga aagaaataac tttgtcaaaa aatataataa tgatagaaag    121860
gaagaaggaa cgctcccttt tgtcttctaa gaatagatgt gaaatgtgtg tgccttagaa    121920
tatcttctcc ctctcctgct ccacgtgagc tggagcttac atgcctgctt gttttcagta    121980
ctgccgtaac cctgatggtg acatcaatgg tccctggtgc tacacaatga atccaagaaa    122040 acttttgac tactgtgata tccctctctg tggtaagttg ccttctgttt tggtaaggaa     122100
actgcttcct taatatggat ttggaaaaaa aaagcaaaa aaacagaaa atggcttttg       122160 agctgagtgc ttctggggag gagatggctg ccctctccac cagagcctgc ttttcatcat    122220
ggccaccttg aacctgccct actattggcc ccatttgtta ggaaaacacc cgcccctccc    122280
```

```
accacacaca cataaataaa ataaatgtca aatteccaaa gggcaaactt agaggtgatc  122340
taatcagccc gggatagtcc caccgaaccc ttctttgtct agcgtgggat gcatgaaaaa  122400
caaatttaga gtcattatga tgaaaaactg tcctcttctg cagctgagaa gaaaaaaaaa  122460
atacgagcag caggaaacag ctaagcatgt aatgcacatt gtaaacctca gatggccatc  122520
ctaggaaatc aatgaagggt agtgcagctc tttagcccca gatggccttt ctcgtaagat  122580
tactactcat gagtcccatt agcgacattg cttagagact gcttgttagg ttccttcctc  122640
attgctctga gactcttatt gggagtatga ggcttggatc aggggaaggg gaattgacat  122700
tagatcttaa atgattgggg taacaaatcc atgggggaaa aaaagccact tgtacttgtt  122760
ccctattttc ttcctgctga ccaatcaact tgtctgtccg agttacagaa caccaccctg  122820
gacttttctt ttgtgtaatt tggttgcttg tggttgggtc tgccatgtga agggaccttg  122880
agctggggga agaaggttgg cctccaagtc cactgaagac cagcatcctg agattgcctg  122940
gggaggtggt acagggcagt gatgaagatc atgggagcca cactgcccat cgtcacattt  123000
gggccactcc tggggagagc aagagggaag aaggagaggt tagggtgata ggaaagattc  123060
tacttggcca atattattat aatgtggcat tgtggtctct ggatttagtg tgagttgata  123120
gctgactttt ttctcgagtg ggtgcttttg ttctattttg tcggtgctat tgcagaagca  123180
tcttggtggt tcctctacct caaagtctct tgatggggtc agttccagtt ctccgcttct  123240
ggccccatct agtacacgcc actgcctctc actgcctggg ctctctatcc ttgacaggct  123300
gccttgaatt taagcccagt ctgacttacc tgcctcaaac acccacagta gtgcctggga  123360
ctcatgcacc tttgactccc atggaaggga agtgcagtag cttcccaggt gcaattctgc  123420
tgtcctcacc cacattgagg atgtatgaga atcaggttct tagagattgg agaaagaagg  123480
aagaatggga acaagatttc ttccaatgga ctgtgaggtt ccccacctta ctttgatgta  123540
agacaagtga ggttaacccc aagcctggtg aggagggttc ccatcagaca cttggaaatc  123600
ctgaggactg tttcctgcag aaggatgtgg ttggtgggat attcaggttt gactcatgat  123660
tgagaaagtt agagcctctg gttggagaaa gagtttaata actatttcat ttccaccaac  123720
acattcagta cgaataataa ataagtaaaa ataaatagaa acattcagtt ttattttgaa  123780
tagtaggagt agggtataat ttctgtagtt actcttttag tacaatgatg catgtttact  123840
gtatgtaagg catactagca gaaattgagc tcagcactag aaaagatgat tgcattccat  123900
gccatgcttc ttttttacaa aagacttcta tagatagatt ctcaaaacaa cccacagcaa  123960
atgaaaagtt atttggaaaa ctcaggttcc agattcactg gagtgtagaa tctctggttg  124020
gttggggagg aatttcctct tgcagttgtt attaataatt atatgaataa ttattaacta  124080
tattaatatt tatagttttg aagaccttga agggctggag acaacagaga agcatttttg  124140
aacaccctct gtagcccctg cactgttgta ggcattgatg ggtggtacca agatgggac  124200
actttcccta cctccagaga ccttgtgggc ttgctgcaga gagaaggcag ggaggaggaa  124260
aagaagaata gaggcacatg tgtgtaaatt accccacag cagtcagtta gtcatgggag  124320
gctccccaga agaactgtcc tgaagctggc tgagagaagg caacatttca acataggaca  124380
gttatccttg ctacataaaa tcacatacac acatgcacat atgtccacac acagagactc  124440
acatgcaaaa gaatcctttg tgcctttcag taaactttac atggtttaga aagaacttat  124500
atttccttga aaggagagtg tcctttgttg tttactacca cttttaaaac ttagaaagaa  124560
aaatctaaag agtgttatg attttaccat ttaatttcac ctttgagatg tgaaaaacta  124620
gtgcttggaa ttcgtcctga attaaacgac acaattgcta acttggactc aaatgcgact  124680
```

```
tcttttccca ccttgtgcca cagcatcctc ttcatttgat tgtgggaagc ctcaagtgga 124740
gccgaagaaa tgtcctggaa gcattgtagg ggggtgtgtg gcccaccCac attcctggcc 124800
ctggcaagtc agtctcagaa caaggtaaga acaggcccag aaaccatcta tactgtcctt 124860
ccatgtaagc cccacaaaac ccttctacat ttacacagaa cccacacagc tgatgcatca 124920
atacctgcct ctctgttttc tgaaggagga aaaatatag aaaaattaaa aaaagttata 124980
ttattatagg ttctctactt ggaaaatagc caaaatacaa atcttttttct tgatctgggc 125040 agttccatca aaatctgtag gcacagtgat ttgcaccaag ttccaatact tttggaaaat 125100
attgaagatg ctctgagggt ttctatggat atccattgtc tcactgtcag atgaaaagaa 125160
agggaagttt ttagaaatgt gacactttgc agtgagggag acaagagca aacttaccta 125220 cagtctatca caggcacaga ttttttttta cacttttgtg aatcattgaa ttcaatgccg 125280
aggctattca tctattcaca aacacatgaa caaattatgg gttgtgatcc ccataaatga 125340
agagtaatca gtccgaaccc acagaacctg gacattttgg gtatcgtttc agtggaacat 125400
gcaattcgta agttcagttt gcttgggtgt ctcttaggaa gaacacatag gacacagacc 125460
catctgcctg catgttttgc ttcctcatct cctttctaca ccagggcacc tgtgctcaat 125520
tgctgttctc ctctaaagag acttccttct gtaagtttgt gaaatgccat cgacaaacct 125580
gatcgcatcg catttcactc tgctgttgag ttgatttttc tttactttat cgtttgtaac 125640
ttcttgctct acagagcttt caccttccac atatttcaga ttcattcttt cctaaactgt 125700
gtggtggtct atgtcctcac tgactatcaa catactgcca tcatgcactt cctatctcta 125760
ttcctcttcg ttgcaatctg gctccaagtg gctcacacca ttattctgat ctatcaactg 125820
cctacacagt cctagaaagt aagtgagtca agaaacatcc cccaaaagta aacttttcag 125880
gtaagatcag aagaccctca tgagtcactg ctgctcagga tcgtatctgg ctccttgaag 125940
agtgaccttg catagatctt gtcataaaaa atgaaagaga ccttgggaag gtcttgggct 126000
ggtcactttt gtcagagtcc agggctgtgg ggtgaaagcc acagctatag agcttcattc 126060
tggagtcact tagctttgct ctcctgggga caggctgtgc ctattcttgc ctcaggcatc 126120
aaaaaaagtg gcacagatgg gcccttctga aaaatctcac tactggagca cagctcgaag 126180
tttctactat cctgacgttg ggcggtagtc ctttgctttg ggaatatgaa catgatcaaa 126240
actgagtgaa cttgtcttcc tggctttctg tacaatgaag tagaacaaac catccaattt 126300
gaccaaagcc ttggcatgtt ttcttttctag gtttggaaag cacttctgtg gaggcacctt 126360
aatatcccca gagtgggtgc tgactgctgc tcactgcttg aagaagtacg tttaagggaa 126420
aactgacatg gggtcttatc ttcaagactt ttttcctccc tctcttcctc catcccttct 126480
ttcttcccac cctccccttc cttcctcccc acctctcttc cttttctgga aggaacacta 126540
ggaaccaggg aatgcatgca gaatcctgag gcagaatttc cagggcaatt ggatgagaga 126600
ggagggaagt gtttctagag ggaatctgca gagggaagac ccagtgcaag tgatttttg 126660 gacctgtata aaccgcagga cagagctgtt cactaccaga ggcatcaatc tgtattgcat 126720
tgctctagag caatatctga ggctgaataa tttataaaga aaagagttta attggcacat 126780
gtttctgcag gctttacagg aagcaggatg ctgtcatctc ctctgcttct gtgtgggcct 126840
aaggaagatt acaatcatgg tggagggcaa agtgggagca ggcatgtcac atggccagag 126900
caggagcaag agacagagag agatggggtg ggggtgctgc acaataccaa atgaccagac 126960
tttgcaagaa ctaagagtga gagctcactg atcaccatga agatgtggcc caagccattc 127020
```

```
aagagggatg cacctctatg atccaaaccc ctttcacagg ccatagctcc atcactgggg   127080
actacagttg aacacgagat ttaggtgggg acaaatatac aaactatatc acagtctctg   127140
atgaaacaga ttgagaacag accttaactg tcagtttcca gcaaattgtg aattttgttt   127200
cttgccactc ataagtcact gattctgggt ggccgagggt gtcagaggga cagcgccaag   127260
ttcatggcac agaggatacc tgaaggggct ggaccatatt tttctcttga catcctcatc   127320
ttttctaggt cctcaaggcc ttcatcctac aaggtcatcc tgggtgcaca ccaagaagtg   127380
aacctcgaat ctcatgttca ggaaatagaa gtgtctaggc tgttcttgga gcccacacaa   127440
gcagatattg ccttgctaaa gctaagcagg tactcgctca cctgtggtct tcacccacg    127500 ctggtgaaga tatttgcttt atgtctgggt tttatgggcc atggccactg catggcagtg   127560
gggaggaact gtctatcaca tgaaaggctc aagggctttg gggacagcat caatcttcaa   127620
ccccagccct gccacatgtt agttgtgctc tttaaaaagg cagaaggatt cgtttcctca   127680
cgtggaaaaa gagataccct gttacccgta aaacttactt aatgttcacc agttcatcca   127740
cattcatgat cagggaaagg ttgttattcc aggctaacta ttctcctttc ataataatat   127800
gctggagaga atcaaatgag attgcatttc aaagcgcttg aaaaaccacc atatcgagcc   127860
atgcttagtg tgggcgcctc taatcactgc tattcaggag gctgacgagg aagaattgct   127920
tgagcccagg acttcaaggc tgtaggcagc tatgattgtg ccactgcact ccaggctggg   127980
tgacagatca agaccctgtc tcaacaaaag aaaagaaaac aaaacaaatg aacagaaata   128040
ttccacaatg tcaaaaaaaa aaaaaaccca cacaacatac aatttacaaa tgcaaataat   128100
aatattattg ttgtcttctt tgattttctc tttcctggtg aaattttgtt ttattaagcc   128160
tgacaaagtg ataccttgc  ttacatcact taaagttagt ctatttggac ctaggtgaca   128220
gtacaatcag ctaagaaaca gtatttgtag gagaggcagg tttgggacag gtgacaaggc   128280
atgtggggtg ctcgctgtgc tggtggctct ggaaggcagg gtgtcaatgc agacagggat   128340
gagcatggcc tggttgggaa ggcatggggc aggcaggagc tgagctgct  ctcctggcc    128400 tggtcacaag cccatggcag cttctctggg tctgtgaact gaggggtgat gtcctggaat   128460
cctctgacac tctaggaagg agagaagggc ctttctggct cagcctttat aaacagtagc   128520
tgatctccct cttgctcccc agggtcctcc ccaccatccc agcaaatgtg caaatacaag   128580
atctctgctc ctcatggtcc tcagagagct ggggtgttct gatggcttga acaagtcact   128640
taggaaatgt ggggttttgg aggcattctc tgataggctg atacgttttg agtttagagt   128700
tcccaccgca catccccaca cccctagagt ctagggcatt tagtgctcca tgagggaacc   128760
tgtagagtga ggacatctgc atcacaggct gggccttcta gtgtccagaa gcagaaagtg   128820
tgtctgcttc aaagttggtg ctaatgatga ttttggtca  gaatacggca tttctcattt   128880
ccattccttt atcccttga  acttactaaa gtagaatcag gtctaaaaac cagagttcta   128940
atctttaaga gtccctggga ttctaaggta tatgaatgtc cttggaaaac aataccattt   129000
agttcatgca aggtgcttat ttcccatcct ctttcatttg atgtctagca ttttactgca   129060
ttcttaccac cacggtttag taacattcac gaggaggaag tggaggatcc agatggagca   129120
acttgctctg ggcacacaag gcatttgcaa ttttataccc tcttgatgat gtctcagcca   129180
gacattctgc ccagtcatca atgccctctt caattaatat gaaggacac  acttggcatg   129240 agattccaat cgtgcacaga atatacatga gaagtgtgcc tttgtcatcc ctactttcaa   129300
aggctaaggc caccctcagt ttcttgcatg caactgatgc ctttcaaatg aaaccttaca   129360
tctgtgtagt ccataggcaa ccacaggcaa atgtgagggt gaaacgctgt gttctacatt   129420
```

```
gttctgtgtc agtgaagcaa ggcagtgcca gctcagaggg ctctggggct tcaaggcagg  129480
gatgcctggt tgtaggtact gccacttcca gctgggcagt gaaacataac tgctaatact  129540
ttccttacag gcctgccgtc atcactgaca aagtaatgcc agcttgtctg ccatcccag   129600 actacatggt caccgccagg actgaatgtt acatcactgg ctggggagaa acccaaggtg  129660
agatcaattc cattgcccac gtaacaaatt gttttgacc ttcagtgcat gttacaaaat    129720
gagcattttg gagatagttg tacaaattcc tacccatgaa tgtggtctac ccactcctga  129780
ctttgcctgg acacctgtct atgtctccat aatcagtctt caagggactt gggcaagggg  129840
agcggtgcca tttccttgag tctctctctt ttttgttttc agaatctttt aatttttttt  129900
gtaatgattg tatgtttccc ttacaacaaa acaaacacc agtagaggtc tttgagtctc   129960
ttaatcataa tttcagcatt catattgctt ccccaggtaa gtggggtttt gacccagccc  130020
tcaagttaag ggtgttagat tatttttcat gtgaaattag acagactgcg tttctaaaca  130080
tggtgcaaaa cagtaacgac aaaagttgta attaaactat tcttcttccc aaatacccac  130140
atgtctaatg tgtgtgtgag ggtgttaggc aggggacctg aagctggggg agaggcagac  130200
agttcccatg gccccaagtc taggatggca tttggtattg gttgatgggt gagagcaaga  130260
gagggaatat ttttgtgcat gatgtggtat cagcacctgt actacatttt atggattcct  130320
tcttctcttt gcggtatgcc ctgacaataa ttatatccgt cagccttacc cccttggcag  130380
taggaaaact gaaactgtct taaagtctca gctctacttt ctcagaggtg caggcaaggg  130440
cactgggagt ctggggccct ggaaaactgt tctgactctg ccacttgcca gatagacctg  130500
aactagacac gttacctctt tgtaccactt ggctctaatc ccttatctgt aaaaccagca  130560
ttttcaaatg gtgctttgca catcagcctt ttgcataagc tttgatttga taaatgttt    130620 tttgtgtttt taaaagatt aaaaaccaca ggtttagata atttcaaagt aggcttccct    130680
ttttctgtca ttttcctatt attttttaaaa cctcacctcc ttgactcctt gttcccttt   130740 tctgcactgc tgagtctggg agcactgagg ccaggtaaaa ggaaacttgg caaatgaggg  130800
gcacctatgg gtgtgggagg ctgctcctgg tgtttgcata ttttaaaatt taaatgctac  130860
aaaccactgt gagttaggta ttattgttcc tattttacca ttgaggaagc tggggctcag  130920
agaaggtgga gggtggtaca gacaaacctg aattggaacc ctggctcctg cctatgggct  130980
gtcaggactt agaaaagtcg tgagctctcg ctgattgttt cctcagctga tgtgggctgc  131040
agggctgtta tgggggaaat aataagaaag tgcatcaagt gctgagcaca tcctaagcac  131100
tccatcatgg cagctcctac tactaataaa gaatagaatt atatctaaca tgattctttc  131160
ttgcaagtga cagaaaatcc aactcaaatt ggattaagca aaacaaggga aattcttagt  131220
gagctgcaaa gttttcaggc tcacatgatg gccccaaatc ccaggtcctc ccaatcatgg  131280
agtaggcact atttggggc acaaaggtga cattcccatg gctgcagatg ctgtggtgct   131340
gtggctgtac cgggaaagaa taagaaaggc cactctccca attatgtgaa caatagtctg  131400
cccactctga gaagtcaaac ttgggtcaca gtcctgcccc tgaacccatc actgactggc  131460
tctgacctgc accaattgtt ccatgttgga ggtgaaggca agaccccact aatacccata  131520 agggggcaaaa gttagataga tccttcaaga ggattatggg aggtagggca aaagctgct   131580 gggcagccag aaagcaaaca gagcctctat gatacctcaa ctgatgaaag catgaagcta  131640
aaatcataag gatctgggtg tgagttctgg ctctcccatc ttccatgtga cattgggcag  131700
ttatttaatc tctttagcc tccgctttct catcttacat atgagataat tgtgaggatt   131760
```

```
aagattacac ataatcatca tcatcaccgt ccaccactac caccatcatc cccatcaaca    131820
tcatcgccac cactatcatc attcttactg gcactaccat caccatcacc accattccac    131880
caccatcacc aatatcatca ctgtcaacat cattaccacc atcaccatca ccaccaccat    131940
catcattact accactacca ctactaccac catcaccatc accaccattc caccaccatc    132000
accaatatca tcactctcaa catcatcacc atcaccatca ccaccaccat catcatcatt    132060
actaccacta ccactactac caccatcacc atcaccactg tcccactact atcagcatga    132120
catcaccatc accaccacca tcatcattac caccgctact accaacatca ccatcaccac    132180
aattctactg ccatcaccat taacattacc accaccatca tcactatcac catcaccacc    132240
atcatcacca ctgccattat cactgccacc atcatcacta tcctctatat ttcctcatct    132300
gtattatcat tactaccacc atcactatca ccaccatcgt caccatcata atcaccatca    132360
acaccatctc caataccacc atcactgtaa ccatcatcac caccaccatg atcactatca    132420
ccatcatcac aatgatcact gtaaccatca ttactaccca ccaccatcac cactactcca    132480
ccaccatcac cattatcatt accatcacca ttataccacc catcatcatc accagcacca    132540
ccatcatcac cagcaccacc atcaccatca ccatcattaa caccatcact atcaccattg    132600
gtttaatcat caccaccatc atcataaata aacatcacat aaccagggtg tagctgggtg    132660
ttgaccccag agcccactca ctgtttcctc tctcccaccc ccatccacac atttctaacc    132720
accatcctgc actgggctcc cagtctcctc tggtctcacc cacatgtcca ctgagaaaag    132780
gattttcaga acaccaacta gaccaggagg agccacatac ataactcagg cctgcttatc    132840
aactttctac atgttaataa tgacatcaga tcaatgggtg ttctcagctt ctcagaagga    132900
ggtcaaaatt ctcccctct ccccttcatg tgtccagacc ttcccggatt tggatgtacc     132960
aagtgcagag tggtgttgag gccaaggggc tcatccatgt aagtctcatc tgcaatcact    133020
gggctgatcc cgtggccctg tctccagggc gccatcagag agggcttcaa tcctcaggtt    133080
acctgtggcc caccctgccc tcagaggtgc catctctaca ttggccacga gatggcagca    133140
catactcata gactgcatta atttcccagc aactcctggt gggttttccc tcttatcagg    133200
atgtttgcct tgctcagaga gcaaatctga gagcagtgac acctaactta actttcagca    133260
aaatattttg agaagggtgc ccctttacac atctgtgcag tccaggtgat gcatcccatg    133320
cccaatgctc ggtagtcagg aggagcttcc tccatgcagc tctgcggaag agactcttcc    133380
acgctgctca tgtaaactcc agattcggtg tcagttttct gacaccgaag acaatgatct    133440
aagtgcagtc aagggctttg gggaaagcag gagagagtgc ctcagttcta gcctgtgcca    133500
tgcttgcaaa gttttgcaaa attctaatga gagctgggct tgcaacattg gaaacttgga    133560
ttatttgtga gagcactgag aaatccctgg gcatgtccat ctggaaaaac agcatttcct    133620
ctggcacttt agcagaggtt ctgtttcaat ttggcgaagg aaattaagca gttttcaca    133680 aaagaagaac tacaacgagg agaattgtcc ctagtatttc ttctccctaa ttgtcaagga    133740
agtgtaaatt agaaaatgaa tcaggacaat ttccacctac tatgttagct aatatttaa    133800 aaattgaata tcacaagggt gaggcaaagt aattgttttc cagtgacatt ttccactgtc    133860
acaccctttt agagaataat ttggcaatgt tactgtgaga tagaaatatg tctatataat    133920
tatgggaact gagacttcag aaagtaataa ggaataagaa tgaaatttat gaacaaacat    133980
gtggaaggtt ggaagcaaga gtggggccaa cacgcatggg gaggaagcat ttgggcagcg    134040
actccgcaga cccagactca agctgagcta tacaacctcc ttacgcctca gtttcctcaa    134100
ctgaagaaca ggaatgacaa gtgcctgttt cataggaccg ttgtgaggat taagtgagat    134160
```

```
ataccacatt atgagcttgt gcctggaaag gttgattctt agtaaatgat gactattctt  134220
ttttattgca ataaaattta tacaacatag agttactatt ttaaccattt ttgcaggtac  134280
cactgagtgg cattcagtac attcacaatg gtgtgcaacc gtcaccatat ttccaggaca  134340
tttttctcat ccccaaagga aacctcatgc ccattaagca gtcactcctc attaaaatat  134400
tagttatgaa gactgtagca ttttttttaaa aactcatgat ataacattga ttgaaaaaat  134460
cagtatagga aattgtgcat tatgatgtaa tagtaaaaga agcatataaa aatctgaaaa  134520
aagtatataa aaagaatagc aattgtattt ctcagactct ctttacattg taaaaatcat  134580
tttgatagct tcaaaagaaa agcaaaaagt acacaaacaa caaccaaccc caaagcagca  134640
tgacaaagcc cagattgttg aatccaggtc ttgggaacat aaaatcttat atgacatttg  134700
cactttaatg ggtcagagag tccagtggca ttgggagctg ccttgtgttc tgcagcctca  134760
cggacagaca ggaggtccag ctccactgct ctgttcttct ggaatttcct cgtgaacaag  134820
ctttggcctc agtaaccatt tctttcatct tttttaaacac aggtaccttt gggactggcc  134880
ttctcaagga agcccagctc cttgttattg agaatgaagt gtgcaatcac tataagtata  134940
tttgtgctga gcatttggcc agaggcactg acagttgcca ggtaagaaaa gatcaataga  135000
tcaaagtctt gtgctctccc gtctcagtct cagtcccttt gacgtcagtc ccaaagtggc  135060
aaattcagga aggttttgtc agtggaagac cccagtctaa gtgttgctca gaaactcccc  135120
agatctgtcc ctgaatgcat attcagatca tctaaggaga cgtcttgggg cttgagttcc  135180
agatccatag caagggagcc gtaagtgcca taactacctc aggccactca ccttcctggt  135240
gtgtgctggt caccagtgac tgaagtggtg cttttccag tagagaggaa ggtagagggt  135300
acaggaccga gacaaattac acacacttaa caatgatgtc caggctagcc cagtctaaag  135360
gaaacaccaa gttaggaagc aatgcatgca ggattcacaa gggattattt ttttttcccag  135420 gaaaaaacta agtgatgtgg ttttgttgaa tagactttgc taagtactta agcactgcag  135480
atgcttgagt aatatgctca taagttcctt tctgatttga attactggga aaatgtacat  135540
atggataaga gaaggatggc atcccatatt aaaaggttgg cagcttaaag ctcacatgaa  135600 ttttcccta cctctgttta gggtgacagt ggagggcctc tggtttgctt cgagaaggac  135660
aaatacattt tacaaggagt cacttcttgg ggtcttggct gtgcacgccc caataagcct  135720
ggtgtctatg ctcgtgtttc aaggtttgtt acttggattg agggaatgat gagaaataat  135780
taattggacg ggagacagag tgaagcatca acctacttag aagctgaaac gtgggtaagg  135840 attttagcatg ctggaaataa tagacagcaa tcaaacgaag acactgttcc cagctaccag  135900
ctatgccaaa ccttggcatt tttggtattt ttgtgtataa gcttttaagg tctgactgac  135960
aaattctgta ttaaggtgtc atagctatga catttgttaa aaataaactc tgcacttatt  136020
ttgatttgaa ttaattttgg ttttggtctt caaaatttttc atgctctttt catcccatct  136080 attttttattt ttatttttta gactttacgt cctggggtac atgtgcagaa tgtgcaggtt  136140
tgttacatag atgtacacgt gccatggtag tttgctgcac ccatcaacct gtcatctaat  136200
tcggtatttc ttttagttct atccctcccc tagccctcca cccccttgaca ggcccaggtg  136260 tgtgatgttg ccctccctgt gtccatgtgt tctcattgtt caactcacac ttatgagtga  136320
gaacatgccg tgtttgtttt tctgttcttg tgttagtttg ctgagaatga tagtttccag  136380
cttcatccat gtccctgcaa aggacatgaa ctcatccttt tttatggctg catagaattc  136440
catggtgtat atgtgccaca ttttatccaa tctaacattg atgggcaatt gggttggttc  136500
```

-continued

```
caactctttg ctattgtgaa tagtgccaca ataaacatac gtgtgcatgt gttttcatag    136560
cagaatgatt tataatcctc tgggtatata cccagtaatg ggattgcagg gtcaaatggt    136620
gtttctggtg ctagatcttt gaggaatcac cacactgtct tccacaatgg ttgaactaat    136680
ttatgctccc accaacaata tcaaggcatt cctatttctc cacatcctct ccagcatctg    136740
ttgtttcctg acttttaat gatcgccatt ctaactggca tgagatggta tctcattgtg     136800
gttttgattt gcatttctct aatgatcagt gatgatgagc ttttctcata tgttgttgg     136860
ctgcataaat gccttttttg gagaagcatc tgttcatatc ctttgcccac tttttgatgg    136920
tgttgttttt ttctggtaaa tttgtttaag ttctttgtag attctggata ttagcctttt    136980
gtcagatgga tagatggcaa aaattttatc ctattatgta ggttgcctgt tcactccgat    137040
gatagtttct tttgctgtgc agaagctctt tggtttaatt agatctcatt tgtctatttt    137100
ggcttttgtt accattgctt ttagtgtttt agtcatgaag tcttctccca tgctatgtcc    137160
tgaatggtat tgcctaagtt ttcttccagg gtttttatgg ttttaggttt tgcatttaag    137220
tctttaatcc atcttgagtt aattttgta taagtaatgc ccttctttgt ctcttttgat     137280
ctttgttggc ttaaagtata ttttatcaga gactagaatt gcaatccctg ctttttttt     137340
tcttttgct ttccttttgc ttggtaaata ttcttccatc cctttatttt gagcctatgt     137400
atgtctgcac atgagatagg tttcctgaat acagcacacc aatgggtctt gactcttat    137460
tcaatttgcc agtctgtgtc ttttaattgg gggcatttag tccatttaca tttaaggtta    137520
atattgttat gtgtgaattt gatcctgtca ttatgatgct agcgggttat tttgcccatt    137580
agttgatgca gtttcttcat agtgtggatg gcctttacaa tttggtagtt tttgcagtgg    137640
ctggtaccaa ttgttccttt ccatgtttag tgcttcgttc aggagctctt gtgaggcagg    137700
ccttgtggtg acaaaatctt tcagcatttg cttgtctgta aaggatttta tttctccttt    137760
gcttatgaag cttagtttcg ctgggtatga aattctgggt tgaaaattat tttcttttag    137820
aatgttgaat attggccccc actctcttcg ggcttgttgg gtttctgcag agagatccac    137880
tgttagtctg attggcttcc ctttccgggt aacccaacct ttctctctgg ctgcccttag    137940
aaatttttcc ttcatttcaa ccttggtgaa tctgacgatt atgtcttgag gtggctcttc    138000
t                                                                    138001
```

<210> SEQ ID NO 4
<211> LENGTH: 13938
<212> TYPE: DNA
<213> ORGANISM: Homo sapiens

<400> SEQUENCE: 4

```
ctgggattgg gacacacttt ctggacactg ctggccagtc ccaaaatgga acataaggaa      60
gtggttcttc tacttctttt atttctgaaa tcagcagcac ctgagcaaag ccatgtggtc     120
caggattgct accatggtga tggacagagt tatcgaggca cgtactccac cactgtcaca     180
ggaaggacct gccaagcttg gtcatctatg acaccacatc aacataatag gaccacagaa     240
aactacccaa atgctggctt gatcatgaac tactgcagga tccagatgc tgtggcagct     300
cctattgtt atacgaggga tcccggtgtc aggtgggagt actgcaacct gacgcaatgc     360
tcagacgcag aagggactgc cgtcgcgcct ccgactgtta ccccggttcc aagcctagag    420
gctccttccg aacaagcacc gactgagcaa aggcctgggg tgcaggagtg ctaccatggt    480
aatggacaga gttatcgagg cacatactcc accactgtca caggaagaac ctgccaagct    540
tggtcatcta tgacaccaca ctcgcatagt cggaccccag aatactaccc aaatgctggc    600
```

```
ttgatcatga actactgcag gaatccagat gctgtggcag ctccttattg ttatacgagg    660
gatcccggtg tcaggtggga gtactgcaac ctgacgcaat gctcagacgc agaagggact    720
gccgtcgcgc ctccgactgt taccccggtt ccaagcctag aggctccttc cgaacaagca    780
ccgactgagc aaaggcctgg ggtgcaggag tgctaccatg gtaatggaca gagttatcga    840
ggcacatact ccaccactgt cacaggaaga acctgccaag cttggtcatc tatgacacca    900
cactcgcata gtcggacccc agaatactac ccaaatgctg gcttgatcat gaactactgc    960
aggaatccag atgctgtggc agctccttat tgttatacga gggatcccgg tgtcaggtgg   1020
gagtactgca acctgacgca atgctcagac gcagaaggga ctgccgtcgc gcctccgact   1080
gttaccccgg ttccaagcct agaggctcct tccgaacaag caccgactga gcaaaggcct   1140
ggggtgcagg agtgctacca tggtaatgga cagagttatc gaggcacata ctccaccact   1200
gtcacaggaa gaacctgcca agcttggtca tctatgacac cacactcgca tagtcggacc   1260
ccagaatact acccaaatgc tggcttgatc atgaactact gcaggaatcc agatgctgtg   1320
gcagctcctt attgttatac gagggatccc ggtgtcaggt gggagtactg caacctgacg   1380
caatgctcag acgcagaagg gactgccgtc gcgcctccga ctgttacccc ggttccaagc   1440
ctagaggctc cttccgaaca agcaccgact gagcaaaggc ctggggtgca ggagtgctac   1500
catggtaatg acagagtta tcgaggcaca tactccacca ctgtcacagg aagaacctgc   1560
caagcttggt catctatgac accacactcg catagtcgga ccccagaata ctacccaaat   1620
gctggcttga tcatgaacta ctgcaggaat ccagatgctg tggcagctcc ttattgttat   1680
acgagggatc ccggtgtcag gtgggagtac tgcaacctga cgcaatgctc agacgcagaa   1740
gggactgccg tcgcgcctcc gactgttacc ccggttccaa gcctagaggc tccttccgaa   1800
caagcaccga ctgagcaaag gcctggggtg caggagtgct accatggtaa tggacagagt   1860
tatcgaggca catactccac cactgtcaca ggaagaacct gccaagcttg gtcatctatg   1920
acaccacact cgcatagtcg accccagaa tactacccaa atgctggctt gatcatgaac   1980
tactgcagga atccagatgc tgtggcagct ccttattgtt atacgaggga tcccggtgtc   2040
aggtgggagt actgcaacct gacgcaatgc tcagacgcag aagggactgc cgtcgcgcct   2100
ccgactgtta ccccggttcc aagcctagag gctccttccg aacaagcacc gactgagcaa   2160
aggcctgggg tgcaggagtg ctaccatggt aatggacaga gttatcgagg cacatactcc   2220
accactgtca caggaagaac ctgccaagct tggtcatcta tgacaccaca ctcgcatagt   2280
cggaccccag aatactaccc aaatgctggc ttgatcatga actactgcag gaatccagat   2340
gctgtggcag ctccttattg ttatacgagg gatcccggtg tcaggtggga gtactgcaac   2400
ctgacgcaat gctcagacgc agaagggact gccgtcgcgc ctccgactgt taccccggtt   2460
ccaagcctag aggctccttc cgaacaagca ccgactgagc aaaggcctgg ggtgcaggag   2520
tgctaccatg gtaatggaca gagttatcga ggcacatact ccaccactgt cacaggaaga   2580
acctgccaag cttggtcatc tatgacacca cactcgcata gtcggacccc agaatactac   2640
ccaaatgctg gcttgatcat gaactactgc aggaatccag atgctgtggc agctccttat   2700
tgttatacga gggatcccgg tgtcaggtgg gagtactgca acctgacgca atgctcagac   2760
gcagaaggga ctgccgtcgc gcctccgact gttaccccgg ttccaagcct agaggctcct   2820
tccgaacaag caccgactga gcaaaggcct ggggtgcagg agtgctacca tggtaatgga   2880
cagagttatc gaggcacata ctccaccact gtcacaggaa gaacctgcca agcttggtca   2940
```

```
tctatgacac cacactcgca tagtcggacc ccagaatact acccaaatgc tggcttgatc    3000
atgaactact gcaggaatcc agatgctgtg gcagctcctt attgttatac gagggatccc    3060
ggtgtcaggt gggagtactg caacctgacg caatgctcag acgcagaagg gactgccgtc    3120
gcgcctccga ctgttacccc ggttccaagc ctagaggctc cttccgaaca agcaccgact    3180
gagcaaaggc ctggggtgca ggagtgctac catggtaatg gacagagtta tcgaggcaca    3240
tactccacca ctgtcacagg aagaacctgc caagcttggt catctatgac accacactcg    3300
catagtcgga ccccagaata ctacccaaat gctggcttga tcatgaacta ctgcaggaat    3360
ccagatgctg tggcagctcc ttattgttat acgagggatc ccggtgtcag gtgggagtac    3420
tgcaacctga cgcaatgctc agacgcagaa gggactgccg tcgcgcctcc gactgttacc    3480
ccggttccaa gcctagaggc tccttccgaa caagcaccga ctgagcaaag gcctggggtg    3540
caggagtgct accatggtaa tggacagagt tatcgaggca catactccac cactgtcaca    3600
ggaagaacct gccaagcttg gtcatctatg acaccacact cgcatagtcg gaccccagaa    3660
tactacccaa atgctggctt gatcatgaac tactgcagga atccagatgc tgtggcagct    3720
ccttattgtt atacgaggga tcccggtgtc aggtgggagt actgcaacct gacgcaatgc    3780
tcagacgcag aagggactgc cgtcgcgcct ccgactgtta ccccggttcc aagcctagag    3840
gctccttccg aacaagcacc gactgagcaa aggcctgggg tgcaggagtg ctaccatggt    3900
aatggacaga gttatcgagg cacatactcc accactgtca caggaagaac ctgccaagct    3960
tggtcatcta tgacaccaca ctcgcatagt cggaccccag aatactaccc aaatgctggc    4020
ttgatcatga actactgcag gaatccagat gctgtggcag ctccttattg ttatacgagg    4080
gatcccggtg tcaggtggga gtactgcaac ctgacgcaat gctcagacgc agaagggact    4140
gccgtcgcgc tccgactgt tacccggtt ccaagcctag aggctccttc gaacaagca    4200 ccgactgagc aaaggcctgg ggtgcaggag tgctaccatg gtaatggaca gagttatcga    4260
ggcacatact ccaccactgt cacaggaaga acctgccaag cttggtcatc tatgacacca    4320
cactcgcata gtcggacccc agaatactac caaatgctg cttgatcat gaactactgc    4380 aggaatccag atgctgtggc agctccttat tgttatacga gggatcccgg tgtcaggtgg    4440
gagtactgca acctgacgca atgctcagac gcagaaggga ctgccgtcgc gcctccgact    4500
gttaccccgg ttccaagcct agaggctcct tccgaacaag caccgactga gcaaaggcct    4560
ggggtgcagg agtgctacca tggtaatgga cagagttatc gaggcacata ctccaccact    4620
gtcacaggaa gaacctgcca agcttggtca tctatgacac cacactcgca tagtcggacc    4680
ccagaatact acccaaatgc tggcttgatc atgaactact gcaggaatcc agatgctgtg    4740
gcagctcctt attgttatac gagggatccc ggtgtcaggt gggagtactg caacctgacg    4800
caatgctcag acgcagaagg gactgccgtc gcgcctccga ctgttacccc ggttccaagc    4860
ctagaggctc cttccgaaca agcaccgact gagcaaaggc ctggggtgca ggagtgctac    4920
catggtaatg gacagagtta tcgaggcaca tactccacca ctgtcacagg aagaacctgc    4980
caagcttggt catctatgac accacactcg catagtcgga ccccagaata ctacccaaat    5040
gctggcttga tcatgaacta ctgcaggaat ccagatgctg tggcagctcc ttattgttat    5100
acgagggatc ccggtgtcag gtgggagtac tgcaacctga cgcaatgctc agacgcagaa    5160
gggactgccg tcgcgcctcc gactgttacc ccggttccaa gcctagaggc tccttccgaa    5220
caagcaccga ctgagcaaag gcctggggtg caggagtgct accatggtaa tggacagagt    5280
tatcgaggca catactccac cactgtcaca ggaagaacct gccaagcttg gtcatctatg    5340
```

```
acaccacact cgcatagtcg gaccccagaa tactacccaa atgctggctt gatcatgaac    5400
tactgcagga atccagatgc tgtggcagct ccttattgtt atacgaggga tcccggtgtc    5460
aggtgggagt actgcaacct gacgcaatgc tcagacgcag aagggactgc cgtcgcgcct    5520
ccgactgtta ccccggttcc aagcctagag gctccttccg aacaagcacc gactgagcaa    5580
aggcctgggg tgcaggagtg ctaccatggt aatggacaga gttatcgagg cacatactcc    5640
accactgtca caggaagaac ctgccaagct tggtcatcta tgacaccaca ctcgcatagt    5700
cggaccccag aatactaccc aaatgctggc ttgatcatga actactgcag gaatccagat    5760
gctgtggcag ctccttattg ttatacgagg gatcccggtg tcaggtggga gtactgcaac    5820
ctgacgcaat gctcagacgc agaagggact gccgtcgcgc tccgactgta ccccggtt     5880 ccaagcctag aggctccttc cgaacaagca ccgactgagc aaaggcctgg ggtgcaggag    5940
tgctaccatg gtaatggaca gagttatcga ggcacatact ccaccactgt cacaggaaga    6000
acctgccaag cttggtcatc tatgacacca cactcgcata gtcggacccc agaatactac    6060
ccaaatgctg gcttgatcat gaactactgc aggaatccag atgctgtggc agctccttat    6120
tgttatacga gggatcccgg tgtcaggtgg gagtactgca acctgacgca atgctcagac    6180
gcagaaggga ctgccgtcgc gcctccgact gttaccccgg ttccaagcct agaggctcct    6240
tccgaacaag caccgactga gcaaaggcct ggggtgcagg agtgctacca tggtaatgga    6300
cagagttatc gaggcacata ctccaccact gtcacaggaa gaacctgcca agcttggtca    6360
tctatgacac cacactcgca tagtcggacc ccagaatact acccaaatgc tggcttgatc    6420
atgaactact gcaggaatcc agatgctgtg gcagctcctt attgttatac gagggatccc    6480
ggtgtcaggt gggagtactg caacctgacg caatgctcag acgcagaagg gactgccgtc    6540
gcgcctccga ctgttacccc ggttccaagc ctagaggctc cttccgaaca agcaccgact    6600
gagcaaaggc ctggggtgca ggagtgctac catggtaatg gacagagtta tcgaggcaca    6660
tactccacca ctgtcacagg aagaacctgc caagcttggt catctatgac accacactcg    6720
catagtcgga ccccagaata ctacccaaat gctggcttga tcatgaacta ctgcaggaat    6780
ccagatgctg tggcagctcc ttattgttat acgagggatc cggtgtcag gtgggagtac    6840 tgcaacctga cgcaatgctc agacgcagaa gggactgccg tcgcgcctcc gactgttacc    6900
ccggttccaa gcctagaggc tccttccgaa caagcaccga ctgagcaaag gcctggggtg    6960
caggagtgct accatggtaa tggacagagt tatcgaggca catactccac cactgtcaca    7020
ggaagaacct gccaagcttg gtcatctatg acaccacact cgcatagtcg gaccccagaa    7080
tactacccaa atgctggctt gatcatgaac tactgcagga atccagatgc tgtggcagct    7140
ccttattgtt atacgaggga tcccggtgtc aggtgggagt actgcaacct gacgcaatgc    7200
tcagacgcag aagggactgc cgtcgcgcct ccgactgtta ccccggttcc aagcctagag    7260
gctccttccg aacaagcacc gactgagcaa aggcctgggg tgcaggagtg ctaccatggt    7320
aatggacaga gttatcgagg cacatactcc accactgtca caggaagaac ctgccaagct    7380
tggtcatcta tgacaccaca ctcgcatagt cggaccccag aatactaccc aaatgctggc    7440
ttgatcatga actactgcag gaatccagat gctgtggcag ctccttattg ttatacgagg    7500
gatcccggtg tcaggtggga gtactgcaac ctgacgcaat gctcagacgc agaagggact    7560
gccgtcgcgc tccgactgt  accccggtt  ccaagcctag aggctccttc cgaacaagca    7620
ccgactgagc aaaggcctgg ggtgcaggag tgctaccatg gtaatggaca gagttatcga    7680
```

-continued

```
ggcacatact ccaccactgt cacaggaaga acctgccaag cttggtcatc tatgacacca   7740
cactcgcata gtcggacccc agaatactac ccaaatgctg gcttgatcat gaactactgc   7800
aggaatccag atgctgtggc agctccttat tgttatacga gggatcccgg tgtcaggtgg   7860
gagtactgca acctgacgca atgctcagac gcagaaggga ctgccgtcgc gcctccgact   7920
gttaccccgg ttccaagcct agaggctcct tccgaacaag caccgactga gcagaggcct   7980
ggggtgcagg agtgctacca cggtaatgga cagagttatc gaggcacata ctccaccact   8040
gtcactggaa gaacctgcca agcttggtca tctatgacac cacactcgca tagtcggacc   8100
ccagaatact acccaaatgc tggcttgatc atgaactact gcaggaatcc agatgctgtg   8160
gcagctcctt attgttatac gagggatccc ggtgtcaggt gggagtactg caacctgacg   8220
caatgctcag acgcagaagg gactgccgtc gcgcctccga ctgttacccc ggttccaagc   8280
ctagaggctc cttccgaaca agcaccgact gagcaaaggc ctggggtgca ggagtgctac   8340
catggtaatg acagagtta tcgaggcaca tactccacca ctgtcacagg aagaacctgc   8400
caagcttggt catctatgac accacactcg catagtcgga ccccagaata ctacccaaat   8460
gctggcttga tcatgaacta ctgcaggaat ccagatgctg tggcagctcc ttattgttat   8520
acgagggatc ccggtgtcag gtgggagtac tgcaacctga cgcaatgctc agacgcagaa   8580
gggactgccg tcgcgcctcc gactgttacc ccggttccaa gcctagaggc tccttccgaa   8640
caagcaccga ctgagcaaag gcctggggtg caggagtgct accatggtaa tgacagagt   8700 tatcgaggca catactccac cactgtcaca ggaagaacct gccaagcttg gtcatctatg   8760
acaccacact cgcatagtcg daccccagaa tactacccaa atgctggctt gatcatgaac   8820
tactgcagga atccagatgc tgtggcagct ccttattgtt atacgaggga tcccggtgtc   8880
aggtgggagt actgcaacct gacgcaatgc tcagacgcag aagggactgc cgtcgcgcct   8940
ccgactgtta ccccggttcc aagcctagag gctccttccg aacaagcacc gactgagcag   9000
aggcctgggg tgcaggagtg ctaccacggt aatggacaga gttatcgagg cacatactcc   9060
accactgtca ctggaagaac ctgccaagct tggtcatcta tgacaccaca ctcgcatagt   9120
cggaccccag aatactaccc aaatgctggc ttgatcatga actactgcag gaatccagat   9180
gctgtggcag ctccttattg ttatacgagg gatcccggtg tcaggtggga gtactgcaac   9240
ctgacgcaat gctcagacgc agaagggact gccgtcgcgc tccgactgt taccccggtt   9300 ccaagcctag aggctccttc cgaacaagca ccgactgagc agaggcctgg ggtgcaggag   9360
tgctaccacg gtaatggaca gagttatcga ggcacatact ccaccactgt cactggaaga   9420
acctgccaag cttggtcatc tatgacacca cactcgcata gtcggacccc agaatactac   9480
ccaaatgctg gcttgatcat gaactactgc aggaatccag atgctgtggc agctccttat   9540
tgttatacga gggatcccgg tgtcaggtgg gagtactgca acctgacgca atgctcagac   9600
gcagaaggga ctgccgtcgc gcctccgact gttaccccgg ttccaagcct agaggctcct   9660
tccgaacaag caccgactga gcagaggcct ggggtgcagg agtgctacca cggtaatgga   9720
cagagttatc gaggcacata ctccaccact gtcactggaa gaacctgcca agcttggtca   9780
tctatgacac cacactcgca tagtcggacc ccagaatact acccaaatgc tggcttgatc   9840
atgaactact gcaggaatcc agatgctgtg gcagctcctt attgttatac gagggatccc   9900
ggtgtcaggt gggagtactg caacctgacg caatgctcag acgcagaagg gactgccgtc   9960
gcgcctccga ctgttacccc ggttccaagc ctagaggctc cttccgaaca agcaccgact  10020
gagcagaggc ctggggtgca ggagtgctac cacggtaatg acagagtta tcgaggcaca  10080
```

```
tactccacca ctgtcactgg aagaacctgc caagcttggt catctatgac accacactcg   10140
catagtcgga ccccagaata ctacccaaat gctggcttga tcatgaacta ctgcaggaat   10200
ccagatcctg tggcagcccc ttattgttat acgagggatc ccagtgtcag gtgggagtac   10260
tgcaacctga cacaatgctc agacgcagaa gggactgccg tcgcgcctcc aactattacc   10320
ccgattccaa gcctagaggc tccttctgaa caagcaccaa ctgagcaaag gcctggggtg   10380
caggagtgct accacggaaa tggacagagt tatcaaggca catacttcat tactgtcaca   10440
ggaagaacct gccaagcttg gtcatctatg acaccacact cgcatagtcg gaccccagca   10500
tactacccaa atgctggctt gatcaagaac tactgccgaa atccagatcc tgtggcagcc   10560
ccttggtgtt atacaacaga tcccagtgtc aggtgggagt actgcaacct gacacgatgc   10620
tcagatgcag aatggactgc cttcgtccct ccgaatgtta ttctggctcc aagcctagag   10680 gcttttttg aacaagcact gactgaggaa accccgggg tacaggactg ctactaccat   10740
tatggacaga gttaccgagg cacatactcc accactgtca caggaagaac ttgccaagct   10800
tggtcatcta tgacaccaca ccagcatagt cggaccccag aaaactaccc aaatgctggc   10860
ctgaccagga actactgcag gaatccagat gctgagattc gcccttggtg ttacaccatg   10920
gatcccagtg tcaggtggga gtactgcaac ctgacacaat gcctggtgac agaatcaagt   10980
gtccttgcaa ctctcacggt ggtcccagat ccaagcacag aggcttcttc tgaagaagca   11040
ccaacggagc aaagccccgg ggtccaggat tgctaccatg gtgatggaca gagttatcga   11100
ggctcattct ctaccactgt cacaggaagg acatgtcagt cttggtcctc tatgacacca   11160
cactggcatc agaggacaac agaatattat ccaaatggtg gcctgaccag gaactactgc   11220
aggaatccag atgctgagat tagtccttgg tgttatacca tggatcccaa tgtcagatgg   11280
gagtactgca acctgacaca atgtccagtg acagaatcaa gtgtccttgc gacgtccacg   11340
gctgtttctg aacaagcacc aacggagcaa agccccacag tccaggactg ctaccatggt   11400
gatggacaga gttatcgagg ctcattctcc accactgtta caggaaggac atgtcagtct   11460
tggtcctcta tgacaccaca ctggcatcag agaaccacag aatactaccc aaatggtggc   11520
ctgaccagga actactgcag gaatccagat gctgagattc gcccttggtg ttataccatg   11580
gatcccagtg tcagatggga gtactgcaac ctgacgcaat gtccagtgat ggaatcaact   11640
ctcctcacaa ctcccacggt ggtcccagtt ccaagcacag agcttccttc tgaagaagca   11700
ccaactgaaa acagcactgg ggtccaggac tgctaccgag gtgatggaca gagttatcga   11760
ggcacactct ccaccactat cacaggaaga acatgtcagt cttggtcgtc tatgacacca   11820
cattggcatc ggaggatccc attatactat ccaaatgctg gcctgaccag gaactactgc   11880
aggaatccag atgctgagat tcgcccttgg tgttacacca tggatcccag tgtcaggtgg   11940
gagtactgca acctgacacg atgtccagtg acagaatcga gtgtcctcac aactcccaca   12000
gtggccccgg ttccaagcac agaggctcct tctgaacaag caccacctga gaaagccct   12060 gtggtccagg attgctacca tggtgatgga cggagttatc gaggcatatc ctccaccact   12120
gtcacaggaa ggacctgtca atcttggtca tctatgatac cacactgcca tcagaggacc   12180
ccagaaaact acccaaatgc tggcctgacc gagaactact gcaggaatcc agattctggg   12240
aaacaaccct ggtgttacac aaccgatccg tgtgtgaggt gggagtactg caatctgaca   12300
caatgctcag aaacagaatc aggtgtccta gagactccca ctgttgttcc agttccaagc   12360
atggaggctc attctgaagc agcaccaact gagcaaaccc ctgtggtccg gcagtgctac   12420
```

| | | | | | |
|---|---|---|---|---|---|
|catggtaatg|gccagagtta|tcgaggcaca|ttctccacca|ctgtcacagg|aaggacatgt|12480|
|caatcttggt|catccatgac|accacaccgg|catcagagga|ccccagaaaa|ctacccaaat|12540|
|gatggcctga|caatgaacta|ctgcaggaat|ccagatgccg|atacaggccc|ttggtgtttt|12600|
|accatggacc|ccagcatcag|gtgggagtac|tgcaacctga|cgcgatgctc|agacacagaa|12660|
|gggactgtgg|tcgctcctcc|gactgtcatc|caggttccaa|gcctagggcc|tccttctgaa|12720|
|caagactgta|tgtttgggaa|tgggaaagga|taccggggca|agaaggcaac|cactgttact|12780|
|gggacgccat|gccaggaatg|ggctgcccag|gagccccata|gacacagcac|gttcattcca|12840|
|gggacaaata|aatgggcagg|tctggaaaaa|aattactgcc|gtaaccctga|tggtgacatc|12900|
|aatggtccct|ggtgctacac|aatgaatcca|agaaaacttt|ttgactactg|tgatatccct|12960|
|ctctgtgcat|cctcttcatt|tgattgtggg|aagcctcaag|tggagccgaa|gaaatgtcct|13020|
|ggaagcattg|taggggggtg|tgtggcccac|ccacattcct|ggccctggca|agtcagtctc|13080|
|agaacaaggt|ttggaaagca|cttctgtgga|ggcaccttaa|tatccccaga|gtgggtgctg|13140|
|actgctgctc|actgcttgaa|gaagtcctca|aggccttcat|cctacaaggt|catcctgggt|13200|
|gcacaccaag|aagtgaacct|cgaatctcat|gttcaggaaa|tagaagtgtc|taggctgttc|13260|
|ttggagccca|cacaagcaga|tattgccttg|ctaaagctaa|gcaggcctgc|cgtcatcact|13320|
|gacaaagtaa|tgccagcttg|tctgccatcc|ccagactaca|tggtcaccgc|caggactgaa|13380|
|tgttacatca|ctggctgggg|agaaacccaa|ggtacctttg|ggactggcct|tctcaaggaa|13440|
|gcccagctcc|ttgttattga|gaatgaagtg|tgcaatcact|ataagtatat|ttgtgctgag|13500|
|catttggcca|gaggcactga|cagttgccag|ggtgacagtg|gagggcctct|ggtttgcttc|13560|
|gagaaggaca|aatacatttt|acaaggagtc|acttcttggg|gtcttggctg|tgcacgcccc|13620|
|aataagcctg|gtgtctatgc|tcgtgtttca|aggtttgtta|cttggattga|gggaatgatg|13680|
|agaaataatt|aattggacgg|gagacagagt|gaagcatcaa|cctacttaga|agctgaaacg|13740|
|tgggtaagga|tttagcatgc|tggaaataat|agacagcaat|caaacgaaga|cactgttccc|13800|
|agctaccagc|tatgccaaac|cttggcattt|ttggtatttt|tgtgtataag|cttttaaggt|13860|
|ctgactgaca|aattctgtat|taaggtgtca|tagctatgac|atttgttaaa|ataaactct|13920|
|gcacttattt|tgatttga| | | | |13938|

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
acagcaatca aacgaagaca ctg              23

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
agcttataca caaaaatacc aaaaatgc           28

<210> SEQ ID NO 7
<211> LENGTH: 27

-continued

```
<212> TYPE: DNA
<213> ORGANISM: Artificial Sequence
<220> FEATURE:
<223> OTHER INFORMATION: Probe

<400> SEQUENCE: 7
tcccagctac cagctatgcc aaaccTt                                          27

<210> SEQ ID NO 8
<211> LENGTH: 16
<212> TYPE: DNA
<213> ORGANISM: Artificial Sequence
<220> FEATURE:
<223> OTHER INFORMATION: Primer

<400> SEQUENCE: 8
ccacagtggc cccggt                                                      16

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acagggcttt tctcaggtgg t                                                21

<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10
ccaagcacag aggctccttc tgaacaag                                         28

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ggcaggtcct tcctgtgaca                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cctgtgacag tggtggagta                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
```
tcctgtgaca gtggtggagt                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cttcctgtga cagtggtgga                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccttcctgtg acagtggtgg                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tccttcctgt gacagtggtg                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gtccttcctg tgacagtggt                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ggtccttcct gtgacagtgg                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aggtccttcc tgtgacagtg                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
caggtccttc ctgtgacagt                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gcaggtcctt cctgtgacag                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tggcaggtcc ttcctgtgac                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ttggcaggtc cttcctgtga                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cttggcaggt ccttcctgtg                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcttggcagg tccttcctgt                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tcttcctgtg acagtggtgg                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ttcttcctgt gacagtggtg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gttcttcctg tgacagtggt                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ggttcttcct gtgacagtgg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
aggttcttcc tgtgacagtg                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
caggttcttc ctgtgacagt                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tggcaggttc ttcctgtgac                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ttggcaggtt cttcctgtga                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cttggcaggt tcttcctgtg                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agcttggcag gttcttcctg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
actatgcgag tgtggtgtca                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gactatgcga gtgtggtgtc                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
cgactatgcg agtgtggtgt                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ccgactatgc gagtgtggtg                                          20

<210> SEQ ID NO 40

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tccgactatg cgagtgtggt                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gtccgactat gcgagtgtgg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ggtccgacta tgcgagtgtg                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gggtccgact atgcgagtgt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ctgctcagtc ggtgcttgtt                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cctctgctca gtcggtgctt                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
```
gcctctgctc agtcggtgct                                                 20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
cttccagtga cagtggtgga                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ttcttccagt gacagtggtg                                                 20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gttcttccag tgacagtggt                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggttcttcca gtgacagtgg                                                 20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gaccttaaaa gcttatacac                                                 20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gtcagacctt aaaagcttat                                                 20

<210> SEQ ID NO 53
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 53
tgtcagtcag accttaaaag                                                    20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gaatttgtca gtcagacctt                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agaatttgtc agtcagacct                                                    20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ccttaataca gaatttgtca                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gctccgttgg tgcttgttca                                                    20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tgctccgttg gtgcttgttc                                                    20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ttgctccgtt ggtgcttgtt                                                    20
```

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tttgctccgt tggtgcttgt                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ctttgctccg ttggtgcttg                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tcctgtaaca gtggtggaga                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ttcctgtaac agtggtggag                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
cttcctgtaa cagtggtgga                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ccttcctgta acagtggtgg                                              20

<210> SEQ ID NO 66
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 66
tccttcctgt aacagtggtg                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gtccttcctg taacagtggt                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tgtccttcct gtaacagtgg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tggagccaga ataacattcg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cctctaggct tggagccaga                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
agttcttcct gtgacagtgg                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
gtccgactat gctggtgtgg                                              20

```
<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
ggtccgacta tgctggtgtg                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
gggtccgact atgctggtgt                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cctctaggct tggaatcggg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gttcagaagg agcctctagg                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tgttcagaag gagcctctag                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gcttgttcag aaggagcctc                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 79
tgcttgttca gaaggagcct                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gtgcttgttc agaaggagcc                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ggtgcttgtt cagaaggagc                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tggtgcttgt tcagaaggag                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gctcagttgg tgcttgttca                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tgctcagttg gtgcttgttc                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gcttggatct gggaccaccg                                              20

<210> SEQ ID NO 86
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 86
gcctccatgc ttggaactgg                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
gctcagttgg tgctgcttca                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
cctcgataac tctggccatt                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tcctgtgaca gtggtggaga                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gtaggttgat gcttcactct                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
cgtttgattg ctgtctatta                                              20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
```
ctctgtgctt ggatctggga                          20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cctctgtgct tggatctggg                          20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
gcctctgtgc ttggatctgg                          20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
agaagcctct gtgcttggat                          20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
ttcagaagaa gcctctgtgc                          20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
gctccgttgg tgcttcttca                          20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tttgctccgt tggtgcttct                          20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
gctttgctcc gttggtgctt    20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ggctttgctc cgttggtgct    20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gggctttgct ccgttggtgc    20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ccttcctgtg acagtggtag    20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tccttcctgt gacagtggta    20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tgtccttcct gtgacagtgg    20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
cctctaggct tggaaccggg    20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
tgcttgttcg gaaggagcct                                                 20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gtgcttgttc ggaaggagcc                                                 20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcttggaact gggaccaccg                                                 20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
ctgtgcttgg aactgggacc                                                 20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
ctctgtgctt ggaactggga                                                 20

<210> SEQ ID NO 111
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 111
cctgtgacag tggtgga                                                    17

<210> SEQ ID NO 112
<211> LENGTH: 17
<212> TYPE: DNA
<213> ORGANISM: Artificial Sequence
<220> FEATURE:
<223> OTHER INFORMATION: Synthetic oligonucleotide

```
<400> SEQUENCE: 112
tcctgtgaca gtggtgg                                                  17

<210> SEQ ID NO 113
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 113
ttcctgtgac agtggtg                                                  17

<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 114
cttcctgtga cagtggt                                                  17

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 115
ccttcctgtg acagtgg                                                  17

<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 116
tccttcctgt gacagtg                                                  17

<210> SEQ ID NO 117
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 117
gtccttcctg tgacagt                                                  17

<210> SEQ ID NO 118
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 118
ggtccttcct gtgacag                                                  17

<210> SEQ ID NO 119
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 119
ccgactatgc gagtgtg                                               17

<210> SEQ ID NO 120
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 120
gtccgactat gcgagtg                                               17

<210> SEQ ID NO 121
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 121
ggtccgacta tgcgagt                                               17

<210> SEQ ID NO 122
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 122
gtcagacctt aaaagct                                               17

<210> SEQ ID NO 123
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 123
aagcctctgt gcttgga                                               17

<210> SEQ ID NO 124
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 124
agcctctgtg cttggat                                               17

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 125
```
gcctctgtgc ttggatc                                                17

<210> SEQ ID NO 126
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 126
gctccgttgg tgcttct                                                17

<210> SEQ ID NO 127
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 127
ctctgtgctt ggaactg                                                17

<210> SEQ ID NO 128
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 128
tgcctcgata actctgt                                                17

<210> SEQ ID NO 129
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 129
tgtgcctcga taactct                                                17

<210> SEQ ID NO 130
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 130
gctcagttgg tgctgct                                                17

<210> SEQ ID NO 131
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 131
gcgtttgctc ttcttcttgc gtttttt                                     27

<210> SEQ ID NO 132
<211> LENGTH: 3987
<212> TYPE: DNA

<213> ORGANISM: Macaca mulatta

<400> SEQUENCE: 132

| | |
|---|---|
| atgtatcgtt ttggaatttc cagtggcttg atcaggaact actgcaggaa tccagatcct | 60 |
| gtggcagccc cttattgtta tacgatggat cccaatgtca ggtgggagta ctgcaacctg | 120 |
| acacaatgct cagatgcaga agggactgcc gtcgcacctc cgaatgtcac cctggttcca | 180 |
| agcctagagg ctccttccga caatcaccg actgagcaaa ggcctggggt gcaggagtgc | 240 |
| taccacggta atggacagag ttatcgaggc acatacttca ccactgtgac aggaagaacc | 300 |
| tgccaagctt ggtcatctat gacaccgcac tctcatagtc ggaccccgga aaactaccca | 360 |
| aatggtggct tgatcaggaa ctactgcagg aatccagatc ctgtggcagc cccttattgt | 420 |
| tataccatgg atcccaatgt caggtgggag tactgcaacc taacacaatg ctcagacgca | 480 |
| gaagggattg ccgtcacacc tctgactgtt accccggttc aagcctaga ggctccttcc | 540 |
| aagcaagcac caactgagca aaggcctggt gtccaggagt gctaccatgg taatggacag | 600 |
| agttatcgag gcacatactt caccactgtg acaggaagaa cctgccaagc ttggtcatct | 660 |
| atgacaccac attctcatag tcgtacccca gaaaactacc caaatggcag tccgacctct | 720 |
| tcagatctct tagtctaccc tgccgtcttc cttgatgcca tgggtcccac tgttctttca | 780 |
| actcatccgc tttccctcag tcccggagtg gctgcgacca gcaggagata tattgagagc | 840 |
| aagagagaag caccgactga gcaaaggcct ggggtgcagg agtgctacca cggtaatgga | 900 |
| cagagttatc gaggcacata cttcaccact gtgacaggaa gaacctgcca agcttggtca | 960 |
| tctatgacac cgcactctca gtcggacc ccggaaaact acccaaatgg tggcttgatc | 1020 |
| aggaactact gcaggaatcc agatcctgtg gcagcccctt attgttatac catggatccc | 1080 |
| agtgtcaggt gggagtactg caacctgaca caatgctcag acgcagaagg gactgccgtc | 1140 |
| gcacctccga atgtcacccc ggttccaagc ctagaggctc cttctgagca agcaccaact | 1200 |
| gagcaaaggc ttggggtgca ggagtgctac cacagtaatg gacagagtta tcgaggcaca | 1260 |
| tacttcacca ctgtgacagg aagaacctgc caagcttggt catctatgac accacactct | 1320 |
| catagtcgga ccccagaaaa ctacccaaat gctggcttgg tcaagaacta ctgccgaaat | 1380 |
| ccagatcctg tggcagcccc ttggtgttat acaacggatc ccagtgtcag gtgggagtac | 1440 |
| tgcaacctga cacgatgctc agatgcagaa gggactgctg tcgtgcctcc aaatattatt | 1500 |
| ccggttccaa gcctagaggc ttttcttgaa caagaaccga ctgaggaaac ccccggggta | 1560 |
| caggagtgct actaccatta tggacagagt tatagaggca catactccac cactgttaca | 1620 |
| ggaagaactt gccaagcttg gtcatctatg acaccacacc agcatagtcg accccaaaa | 1680 |
| aactatccaa atgctggcct gaccaggaac tactgcagga atccagatgc tgagattcgc | 1740 |
| ccttggtgtt ataccatgga tcccagtgtc aggtgggagt actgcaacct gacacaatgt | 1800 |
| ctggtgacag aatcaagtgt ccttgaaact ctcacagtgg tcccagatcc aagcacacag | 1860 |
| gcttcttctg aagaagcacc aacgagcaa agtcccgagg tccaggactg ctaccatggt | 1920 |
| gatggacaga gttatcgagg ctcattctcc accactgtca caggaaggac atgtcagtct | 1980 |
| tggtcctcta tgcaccaca ctggcatcag aggacaacag aatattatcc agatggtggc | 2040 |
| ctgaccagga actactgcag gaatccagat gctgagattc gcccttggtg ttataccatg | 2100 |
| gatcccagtg tcaggtggga gtactgcaac ctgacacaat gtccagtgac agaatcaagt | 2160 |

```
gtcctcgcaa cgtccatggc tgtttctgaa caagcaccaa tggagcaaag ccccggggtc    2220
caggactgct accatggtga tggacagagt tatcgaggtt cattctccac cactgtcaca    2280
ggaaggacat gtcagtcttg gtcctctatg acaccacact ggcatcagag gaccatagaa    2340
tactacccaa atggtggcct gaccaagaac tactgcagga atccagatgc tgagattcgc    2400
ccttggtgtt ataccatgga tcccagagtc agatgggagt actgcaacct gacacaatgt    2460
gtggtgatgg aatcaagtgt ccttgcaact cccatggtgg tcccagttcc aagcagagag    2520
gttccttctg aagaagcacc aactgaaaac agccctgggg tccaggactg ctaccaaggt    2580
gatggacaga gttatcgagg cacattctcc accactatca caggaagaac atgtcagtct    2640
tggttgtcta tgacaccaca tcggcatcgg aggatcccat tacgctatcc aaatgctggc    2700
ctgaccagga actattgcag aaatccagat gctgagattc gcccttggtg ttacaccatg    2760
gatcccagtg tcaggtggga gtactgcaac ctgacacaat gtccagtgac agaatcaagt    2820
gtcctcacaa ctcccacggt ggtcccggtt ccaagcacag aggctccttc tgaacaagca    2880
ccacctgaga aaagccctgt ggtccaggat tgctaccatg gtgatggaca gagttatcga    2940
ggcacatcct ccaccactgt cacaggaagg aactgtcagt cttggtcatc tatgatacca    3000
cactggcatc agaggacccc agaaaactac ccaaatgctg gcctgaccag gaactactgc    3060
aggaatccag attctgggaa acaaccctgg tgttacacga ctgatccatg tgtgaggtgg    3120
gagtactgca acctgacaca atgctcagaa acagaatcag gtgtcctaga gactcccact    3180
gttgttccgg ttccaagcat ggaagctcat tctgaagcag caccaactga gcaaacccct    3240
gtggtccagc agtgctacca tggtaatgga cagagttatc gaggcacatt ctccaccact    3300
gtcacaggaa ggacatgtca atcttggtca tccatgacac cacaccagca taagaggacc    3360
ccggaaaacc acccaaatga tggcttgaca atgaactact gcaggaatcc agatgctgac    3420
acaggccctt ggtgttttac catggacccc agcgtcaggc gggagtactg caacctgacg    3480
cgatgctcag acacagaagg gactgtggtc acacctccga ctgttatccc ggttccaagc    3540
ctagaggctc cttctgaaca agtgcttgga attcatcctg aattaaacga cacaattgct    3600
aacttggact caaaggtgaa ttctttccca ccttgtgcca cagcatcctc ttcatttgat    3660
tgtgggaagc tcaagtggag gccaaagaaa tgtcctggaa gcattgtagg tgggtgtgtg    3720
gcccacccac attcctggcc ctggcaagtc agtcttagaa caaggtttgg aaagcacttc    3780
tgtggaggca ccttaatatc cccagagtgg gtgctgactg ctgcttgctg cttggagacg    3840
ttctcaaggc cttccttcta caaggtcatc ctgggtgcac accaagaagt gaatctcgaa    3900
tctcatgttc aagaaataga agtgtctagg ttgttcttgg agcccatagg agcagatatt    3960
gccttgctaa agctaagcag gtactaa                                       3987
```

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
ggttcttcca gtgacagtgg                                               20

<210> SEQ ID NO 134
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 134
atgcctcgat aactccgtcc                                               20
```